US011572570B2

(12) United States Patent
Brutnell et al.

(10) Patent No.: US 11,572,570 B2
(45) Date of Patent: Feb. 7, 2023

(54) EXPRESSION OF DICARBOXYLATE TRANSPORTER FROM SETARIA ITALICA IN TRANSGENIC PLANTS TO INCREASE YIELD

(71) Applicant: Donald Danforth Plant Science Center, St. Louis, MO (US)

(72) Inventors: Thomas P. Brutnell, St. Louis, MO (US); Huang Pu, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 183 days.

(21) Appl. No.: 17/166,516

(22) Filed: Feb. 3, 2021

(65) Prior Publication Data

US 2021/0238624 A1  Aug. 5, 2021

Related U.S. Application Data

(63) Continuation of application No. 15/769,870, filed as application No. PCT/US2016/058091 on Oct. 21, 2016, now Pat. No. 10,947,554.

(60) Provisional application No. 62/245,348, filed on Oct. 23, 2015.

(51) Int. Cl.
*C12N 15/82* (2006.01)
*C07K 14/415* (2006.01)

(52) U.S. Cl.
CPC ........ *C12N 15/8269* (2013.01); *C07K 14/415* (2013.01); *C12N 15/8261* (2013.01); *Y02A 40/146* (2018.01)

(58) Field of Classification Search
None
See application file for complete search history.

(56) References Cited

U.S. PATENT DOCUMENTS

2012/0102591 A1  4/2012  Xiong et al.

FOREIGN PATENT DOCUMENTS

| CN | 101 538 573 A | 9/2009 |
| WO | WO 2010/118635 A1 | 10/2010 |
| WO | WO 2016/104916 A1 | 6/2016 |

OTHER PUBLICATIONS

Karki et al. Improvement of photosynthesis in rice (*Oryza sativa* L.) by inserting the C4 pathway. (2013) Rice; vol. 6; pp. 1-8 (Year: 2013).*

Database Geneseq ANM27969, "*Oryza sativa* amiono acid sequence SEQ ID No. 141970," 2007, 1 page.
Database Geneseq, AXS65121, *Zeas mays* Na+/H+ antiporter protein sequence, 2010, 1 page.
Furumoto, T., et al., "Aplastidial sodium-dependent pyruvate transporter," *Nature*, 2011, vol. 476 (7361), pp. 472-475.
GenBank Accession XM 004984057; "Predicted: Setaria italic dicarboxylates transporter 2.1, chloroplastic-like (LOC101759872), mRNA," 2013, pp. 1-2.
GenPept Accession XP 004969305, Predicted: probable sodium/metabolite cotransporter BASS@, chloroplastic-like [Setaria italic], 2013, pp. 1-2.
Häusler, R., et al., "Overexpression of C4-cycle enzymes in transgenic C3 plants: a biotechnological approach to improve C3-photosynthesis," *Journal of Experimental Botany*, 2002, vol. 53(369), pp. 591-607.
He, C., et al., "Expression of an *Arabidopsis* Vacuolar Sodium/Proton Antiporter Gene in Cotton Improves Photosynthetic Performance Under Salt Conditions and Increases Fiber Yield in the Field," *Plant Cell Physiol.*, 2005, vol. 46(11), pp. 1848-1854.
Karki, S., et al., "Improvement of photosynthesis in rice (*Oryza sativa* L.) by inserting the C4 pathway," *Rice*, 2013, vol. 6(28), pp. 1-8.
Müller, M., et al., "Decreased capacity for sodium export out of *Arabidopsis* chloroplasts impairs salt tolerance, photosynthesis and plant performance," *The Plant Journal*, 2014, vol. 78(4), pp. 646-658.
Qin, F., et al., "Co-suppression of Si401, a maize pollen specific Zm401 homologous gene, results in aberrant anther development in foxtail millet," *Euphytica*, 2008, vol. 163, pp. 103-111.
Renne, P., et al., "The *Arabidopsis* mutant dct is deficient in the plastidic glutamate/malate translocator DiT2," *The Plant Journal*, 2003, vol. 35, pp. 316-331.
Sage, R., et anon., "Exploiting the engine of $C_4$ photosynthesis," *Journal of Experimental Botany*, 2011, vol. 62(9), pp. 2989-3000.

* cited by examiner

*Primary Examiner* — Cathy Kingdon Worley
(74) *Attorney, Agent, or Firm* — Womble Bond Dickinson (US) LLP

(57) ABSTRACT

Compositions and methods for increasing plant growth for higher crop yield are provided. The methods involve the expression in a plant of interest of at least one C4 transporter coding sequence. Plants showing increased expression of one or more C4 transporter coding sequence of interest are encompassed by the invention. It is recognized that any method for increasing the expression of the C4 transporter coding sequences in a plant of interest can be used in the practice of the methods disclosed herein. Such methods include transformation, breeding and the like. Increased expression of the C4 transporter coding sequences in the plant of interest results in yield gains. Expression cassettes and vectors comprising the C4 transporter sequences disclosed herein are also provided herein. Methods for identifying genes under positive selection in plants that use C4 photosynthesis are disclosed and provided herein.

14 Claims, No Drawings
Specification includes a Sequence Listing.

SEQUENCE LISTING

```
<160> NUMBER OF SEQ ID NOS: 96

<210> SEQ ID NO 1
<211> LENGTH: 570
<212> TYPE: PRT
<213> ORGANISM: Setaria italica
<220> FEATURE:
<221> NAME/KEY: MISC_FEATURE
<222> LOCATION: (1)..(570)
<223> OTHER INFORMATION: NHD

<400> SEQUENCE: 1

Met Ala Leu Ser Cys Gly Leu Leu Ala Gly Ala Arg Ala Ala Ala Phe
1               5                   10                  15

Pro Ser Leu Pro Ser Ser Ala Ala Leu Leu Arg Arg Arg Arg Cys Pro
            20                  25                  30

Pro Ala Val Ala Val Gly Pro Leu Pro His Ala Glu Arg Trp Arg Arg
        35                  40                  45
```

```
Gly Leu Arg Phe Cys Cys Ala Ser Ser Ser Ser Ser Pro Pro Leu
 50                  55                  60

Pro Pro Ala Pro Glu Glu Pro Glu Asp Tyr Glu Leu Leu Asp Thr
 65              70                  75                  80

Thr Gly Asn Cys Asp Pro Leu Cys Ser Val Asp Glu Val Ser Ser Gln
             85                  90                  95

Tyr Leu Gly Glu Asn Tyr Lys Pro Lys Asn Asp Leu Leu Lys Ala Phe
            100                 105                 110

Thr Ile Phe Ala Thr Ala Leu Ala Gly Ala Ala Ile Asn His Ser
         115                 120                 125

Trp Val Ala Ala Asn Gln Asp Ala Ala Met Val Leu Val Phe Ala Ile
130                 135                 140

Gly Tyr Ala Gly Ile Ile Phe Glu Glu Ser Leu Ala Phe Asn Lys Ser
145                 150                 155                 160

Gly Val Ala Leu Leu Met Ala Ala Cys Leu Trp Val Ile Arg Ser Ile
                165                 170                 175

Gly Ala Pro Ser Ile Asp Ile Ala Val Glu Glu Leu Asn His Thr Thr
                180                 185                 190

Thr Glu Val Ser Glu Ile Val Phe Phe Leu Leu Gly Ala Met Thr Ile
            195                 200                 205

Val Glu Ile Val Asp Ala His Gln Gly Phe Lys Leu Val Thr Asp Asn
210                 215                 220

Ile Ser Thr Arg Ser Pro Lys Thr Leu Val Trp Val Ile Gly Ile Val
225                 230                 235                 240

Thr Phe Phe Val Ser Ala Ile Leu Asp Asn Leu Thr Ser Thr Ile Val
                245                 250                 255

Met Val Ser Leu Leu Arg Lys Leu Val Pro Pro Ser Glu Tyr Arg Lys
            260                 265                 270

Leu Leu Gly Ala Val Val Ile Ala Ala Asn Ala Gly Gly Ala Trp
            275                 280                 285

Thr Pro Ile Gly Asp Val Thr Thr Met Leu Trp Ile His Gly Gln
290                 295                 300

Leu Thr Thr Leu Lys Ile Met Gln Gly Leu Phe Ile Pro Ser Val Val
305                 310                 315                 320

Ser Leu Ala Val Pro Leu Ala Leu Met Ser Leu Thr Ser Glu Ala Asn
                325                 330                 335

Gly Ser Ser Gln Lys Ser Ser Ser Leu Ser Ser Glu Gln Met Ala Pro
            340                 345                 350

Arg Gly Gln Leu Val Leu Ala Val Gly Val Gly Ala Leu Val Phe Val
            355                 360                 365

Pro Val Phe Lys Ser Leu Thr Gly Leu Pro Pro Phe Met Gly Met Leu
370                 375                 380

Leu Gly Leu Gly Ile Leu Trp Ile Leu Thr Asp Ala Ile His Tyr Gly
385                 390                 395                 400

Asp Ser Glu Arg Gln Arg Leu Lys Val Pro Gln Ala Leu Ser Arg Ile
                405                 410                 415

Asp Ser Gln Gly Ile Leu Phe Phe Leu Gly Ile Leu Leu Ser Val Gly
            420                 425                 430

Ser Leu Glu Ser Ala Gly Ile Leu Arg Gln Leu Ala Asn Tyr Leu Asp
            435                 440                 445

Ala Asn Ile Pro Asn Ala Asp Leu Ile Ala Ser Ala Ile Gly Val Ala
450                 455                 460

Ser Ala Leu Ile Asp Asn Val Pro Leu Val Ala Ala Thr Met Gly Met
```

```
                465                 470                 475                 480
Tyr Asp Leu Thr Ala Tyr Pro Gln Asp Ser Asp Phe Trp Gln Leu Ile
                    485                 490                 495

Ala Phe Cys Ala Gly Thr Gly Gly Ser Met Leu Ile Ile Gly Ser Ala
                    500                 505                 510

Ala Gly Val Ala Phe Met Gly Met Glu Lys Val Asp Phe Phe Trp Tyr
                    515                 520                 525

Ile Arg Lys Val Ser Gly Phe Ala Leu Ala Gly Tyr Ala Ala Gly Ile
                    530                 535                 540

Ile Ser Tyr Leu Val Gly Gln Asn Leu Asn Phe Ser Leu Pro Thr Ser
545                 550                 555                 560

Leu Ala Glu Ile Pro Phe Ile Pro Gly Ser
                    565                 570

<210> SEQ ID NO 2
<211> LENGTH: 421
<212> TYPE: PRT
<213> ORGANISM: Setaria italica
<220> FEATURE:
<221> NAME/KEY: MISC_FEATURE
<222> LOCATION: (1)..(421)
<223> OTHER INFORMATION: BASS2

<400> SEQUENCE: 2

Met Ala Pro Ser Ala Thr Ser Ser Met Ala Ser Val Ser Arg Ala Leu
1               5                   10                  15

Arg Pro Arg Pro Arg Ala Ala Ala Cys Ser Ala Pro Arg Leu Gly Cys
                20                  25                  30

Gly Leu Gly Ile Ala Cys Ser Met Pro Ser Leu Gly Leu Ala Val Val
            35                  40                  45

Thr Ala Pro Ser Ala Thr Val Thr Pro Ala Leu Arg Arg Arg Gln Ile
        50                  55                  60

Leu Cys Gln Ala Glu Ala Asn Ile Ser Asn Asn Leu Pro Glu Lys Leu
65                  70                  75                  80

Pro Ala Lys Val Ser Gln Pro Ala Lys Val Ser Gln Pro Ala Glu Val
                85                  90                  95

Ser Gln Pro Ala Glu Val Ser Gln Tyr Glu Lys Ile Val Glu Leu Leu
                100                 105                 110

Thr Thr Leu Phe Pro Val Trp Val Ile Gly Thr Val Ile Gly Ile
            115                 120                 125

Tyr Lys Pro Ala Met Val Thr Trp Leu Asp Thr Asp Leu Phe Thr Ile
        130                 135                 140

Gly Leu Gly Leu Leu Met Leu Ser Met Gly Leu Thr Leu Thr Phe Glu
145                 150                 155                 160

Asp Phe Arg Arg Cys Leu Arg Asn Pro Trp Thr Val Gly Ile Gly Phe
                165                 170                 175

Leu Ala Gln Tyr Cys Val Lys Pro Leu Leu Gly Leu Ala Ile Ala Thr
                180                 185                 190

Thr Leu Lys Leu Pro Ala Pro Leu Ala Thr Gly Leu Ile Leu Val Ser
            195                 200                 205

Cys Cys Pro Gly Gly Gln Ala Ser Asn Val Ala Thr Tyr Ile Ser Lys
        210                 215                 220

Gly Asn Val Ala Leu Ser Val Leu Met Thr Thr Cys Ser Thr Ile Gly
225                 230                 235                 240

Ala Ile Ile Met Thr Pro Leu Leu Thr Lys Leu Leu Ala Gly Gln Leu
                245                 250                 255
```

```
Val Pro Val Asp Ala Ala Gly Leu Ala Ile Ser Thr Phe Gln Val Val
            260                 265                 270

Leu Leu Pro Thr Val Leu Gly Val Ala His Glu Tyr Phe Pro Lys
        275                 280                 285

Phe Thr Glu Arg Ile Ile Thr Val Ala Pro Leu Phe Gly Val Leu Leu
290                 295                 300

Thr Thr Leu Leu Cys Ala Ser Pro Ile Gly Gln Val Ala Glu Val Leu
305                 310                 315                 320

Lys Thr Gln Gly Ala Gln Leu Ile Ile Pro Val Ala Leu Leu His Val
                325                 330                 335

Ala Ala Phe Ala Leu Gly Tyr Trp Leu Ser Arg Phe Ser Ser Phe Gly
            340                 345                 350

Glu Ser Thr Ser Arg Thr Ile Ser Ile Glu Cys Gly Met Gln Ser Ser
        355                 360                 365

Ala Leu Gly Phe Leu Leu Ala Gln Lys His Phe Thr Asn Pro Leu Val
    370                 375                 380

Ala Val Pro Ser Ala Val Ser Val Val Ala Met Ala Leu Gly Gly Ser
385                 390                 395                 400

Ala Leu Ala Val Phe Trp Arg Ser Ile Gly Leu Pro Ala Asn Asp Lys
                405                 410                 415

Asp Asp Phe Lys Glu
            420

<210> SEQ ID NO 3
<211> LENGTH: 567
<212> TYPE: PRT
<213> ORGANISM: Setaria italica
<220> FEATURE:
<221> NAME/KEY: MISC_FEATURE
<222> LOCATION: (1)..(567)
<223> OTHER INFORMATION: OMT

<400> SEQUENCE: 3

Met Ala Ser Ser Thr Ala Ala Ser Pro Leu Thr Cys His His Leu Gly
1               5                   10                  15

Ser Ser Ala Val Pro Arg Ser Arg Leu Pro Ser Leu Ser Phe Ser Leu
            20                  25                  30

Arg Arg Arg Ser Ser Lys Pro His Leu Pro Ser Pro Thr Arg Leu Ser
        35                  40                  45

Leu Pro Pro Ser Lys Pro Leu Phe Thr Pro Pro Thr Ala Ala Ala
    50                  55                  60

Ala Ser Thr Ser Thr Ser Arg Ser Gly Val Leu Pro Pro Val Ser Ala
65                  70                  75                  80

Ser Ala Ser Ala Arg Ala Ala Pro Ala Pro Pro Lys Pro Ala
                85                  90                  95

Leu Gln Gly Ala Ala Ile Thr Pro Leu Leu Ala Thr Val Ala Thr Gly
            100                 105                 110

Val Leu Ile Arg Leu Gly Pro Ala Pro Ser Gly Val Pro Arg Lys Ala
        115                 120                 125

Trp Gln Leu Leu Ala Ile Phe Leu Ser Thr Ile Val Gly Ile Ile Thr
    130                 135                 140

Gln Pro Leu Pro Leu Gly Ala Val Ala Leu Leu Gly Leu Gly Ala Ala
145                 150                 155                 160

Val Leu Thr Arg Thr Leu Thr Phe Ala Ala Ala Phe Ser Ala Phe Gly
                165                 170                 175
```

Asp Pro Ile Pro Trp Leu Ile Ala Leu Ala Phe Phe Ala Arg Gly
            180                 185                 190

Phe Ile Lys Thr Gly Leu Gly Ser Arg Val Ala Tyr Ala Phe Val Ala
        195                 200                 205

Ala Phe Gly Ser Ser Ser Leu Gly Leu Gly Tyr Ser Leu Val Phe Ala
210                 215                 220

Glu Ala Leu Leu Ala Pro Ala Ile Pro Ser Val Ser Ala Arg Ala Gly
225                 230                 235                 240

Gly Ile Phe Leu Pro Leu Val Lys Ala Leu Cys Glu Ala Cys Gly Ser
                245                 250                 255

Arg Ala Gly Asp Gly Thr Glu Arg Arg Leu Gly Ala Trp Leu Met Leu
            260                 265                 270

Thr Cys Phe Gln Thr Ser Val Val Ser Ser Ala Met Phe Leu Thr Ala
        275                 280                 285

Met Ala Ala Asn Pro Leu Ser Ala Asn Leu Thr Ala Ala Thr Ile Gly
    290                 295                 300

Glu Gly Ile Gly Trp Thr Leu Trp Ala Lys Ala Ala Ile Val Pro Gly
305                 310                 315                 320

Met Leu Ser Leu Val Leu Val Pro Leu Ile Leu Tyr Val Ile Tyr Pro
                325                 330                 335

Pro Glu Val Lys Ser Ser Pro Asp Ala Pro Arg Leu Ala Lys Glu Arg
            340                 345                 350

Leu Ala Lys Met Gly Pro Met Ser Lys Glu Lys Ile Met Ala Gly
        355                 360                 365

Thr Leu Leu Leu Thr Val Gly Leu Trp Ile Phe Gly Gly Met Ile Ser
    370                 375                 380

Val Asp Ala Val Ser Ala Ala Ile Leu Gly Leu Gly Val Leu Leu Ile
385                 390                 395                 400

Thr Gly Val Val Thr Trp Lys Glu Cys Leu Ala Glu Ser Val Ala Trp
                405                 410                 415

Asp Thr Leu Thr Trp Phe Ala Ala Leu Ile Ala Met Ala Gly Tyr Leu
            420                 425                 430

Asn Lys Tyr Gly Leu Ile Ala Trp Phe Ser Glu Thr Val Val Lys Phe
        435                 440                 445

Val Gly Gly Leu Gly Leu Ser Trp Gln Leu Ser Phe Ser Val Leu Val
    450                 455                 460

Leu Leu Tyr Phe Tyr Ser His Tyr Phe Phe Ala Ser Gly Ala Ala His
465                 470                 475                 480

Ile Gly Ala Met Phe Ala Ala Phe Leu Ser Val Ala Lys Ala Leu Gly
                485                 490                 495

Thr Pro Ser Leu Phe Ala Ala Met Val Leu Ser Phe Leu Ser Asn Leu
            500                 505                 510

Met Gly Gly Ile Thr His Tyr Gly Ile Gly Ser Ala Pro Val Phe Tyr
        515                 520                 525

Gly Ala Gly Tyr Val Pro Leu Ala Gln Trp Trp Gly Tyr Gly Phe Val
    530                 535                 540

Ile Ser Val Val Asn Ile Ile Trp Leu Gly Val Gly Gly Phe Trp
545                 550                 555                 560

Trp Lys Met Ile Gly Leu Trp
                565

<210> SEQ ID NO 4
<211> LENGTH: 421
<212> TYPE: PRT

<213> ORGANISM: Setaria italica
<220> FEATURE:
<221> NAME/KEY: MISC_FEATURE
<222> LOCATION: (1)..(421)
<223> OTHER INFORMATION: MEP3a

<400> SEQUENCE: 4

```
Met Ala Phe Pro Ser Pro Thr Ser Leu Ser Ser Gly Tyr Pro Ala
 1               5                  10                  15

Pro Ile His Leu Arg Leu Gln Pro Leu Pro Ser Ile Pro Pro Leu Leu
             20                  25                  30

Pro Phe Arg Arg Thr Leu Pro Leu Leu Pro Ser Leu Arg Leu Ala
             35                  40                  45

Arg Pro His Leu Leu Pro Leu Pro Val Ala Ser Ser Gly Ser Gly Ser
 50                  55                  60

Ile Gly Gly Gly Gly Asp Asp Glu Leu Pro Ser Gly Gly Gly Gly Asp
 65                  70                  75                  80

Asp Glu Leu Pro Ser Gly Asp Gly Ser Gly Glu Gly Gly Asp Glu
             85                  90                  95

Gly Asp Gly Gly Ser Gly Gly Gly Asp Glu Gly Asp Gly Gly Ser
            100                 105                 110

Gly Gly Gly Gly Asp Glu Gly Asp Gly Gly Ser Ala Asp Gly Ser Gly
            115                 120                 125

Asp Gly Asp Asp Ala Ser Gly Asn Arg Arg Glu Ala Leu Phe Val Leu
130                 135                 140

Ala Gln Leu Gly Arg Lys Leu Glu Ser Leu Pro Ala Asp Leu Ala Ala
145                 150                 155                 160

Ala Val Glu Gly Gly Arg Val Thr Gly Asp Ile Val Arg Arg Tyr Val
                165                 170                 175

Asp Leu Glu Ala Ser Pro Leu Ser Arg Trp Leu Leu Gln Phe Gly Gly
            180                 185                 190

Phe Lys Glu Arg Leu Leu Ala Asp Asp Leu Phe Leu Thr Lys Val Gly
            195                 200                 205

Ile Glu Cys Gly Ile Gly Val Phe Thr Lys Ser Ala Ala Glu Tyr Glu
210                 215                 220

Lys Arg Lys Glu Asn Phe Val Lys Glu Leu Asp Phe Val Leu Ala Asn
225                 230                 235                 240

Val Ile Met Ala Ile Val Ala Asp Phe Met Leu Ala Trp Leu Pro Ala
                245                 250                 255

Pro Thr Val Ser Leu Arg Pro Pro Leu Ala Met Asn Ser Gly Ala Ile
            260                 265                 270

Ser Lys Phe Phe Tyr Asn Cys Pro Asp Asn Ala Phe Gln Val Ala Leu
            275                 280                 285

Ala Gly Arg Ser Tyr Thr Leu Leu Gln Arg Ala Gly Ala Ile Val Arg
            290                 295                 300

Asn Gly Ala Lys Leu Phe Ala Val Gly Thr Ser Ala Ser Leu Ile Gly
305                 310                 315                 320

Thr Thr Ala Thr Asn Ala Leu Ile Lys Ala Arg Gln Ala Val Ser Ser
                325                 330                 335

Asp Ser Ala Gly Glu Val Lys Glu Ala Lys Asn Ile Pro Ile Val Glu
            340                 345                 350

Thr Ser Ile Ala Tyr Gly Val Tyr Met Ser Ile Ser Ser Asn Leu Arg
            355                 360                 365

Tyr Gln Ile Val Ala Gly Val Ile Glu Gln Arg Leu Leu Glu Pro Leu
            370                 375                 380
```

```
Leu His Arg His Lys Leu Ala Leu Thr Ala Met Ser Phe Ala Val Arg
385                 390                 395                 400

Thr Gly Asn Thr Phe Leu Gly Ser Cys Leu Trp Val Asp Tyr Ala Arg
            405                 410                 415

Leu Ile Gly Ile Gln
            420

<210> SEQ ID NO 5
<211> LENGTH: 405
<212> TYPE: PRT
<213> ORGANISM: Setaria italica
<220> FEATURE:
<221> NAME/KEY: MISC_FEATURE
<222> LOCATION: (1)..(405)
<223> OTHER INFORMATION: TPT isoform 1

<400> SEQUENCE: 5

Met Ser Ala Leu Gly Ala Leu Ser Gly Gly Ala Ala Gly Val Ala Gly
1               5                   10                  15

Leu Leu Ser Leu Arg Arg Arg Ala Ala Ala Pro Pro Pro Pro Ser Ala
            20                  25                  30

Leu Ala Ser Ser Ser His Leu Pro Pro Leu Lys Cys Ala Ala Val Pro
        35                  40                  45

Asp Ala Gly His Leu Val Trp Gly Arg Gln Leu Arg Pro Ala Leu Ala
    50                  55                  60

Leu Leu Pro Phe Pro Ser Gln Ala Ala Arg Lys Gln Thr Pro Arg Pro
65                  70                  75                  80

Pro Ala Ala Ala Ser Ala Gly Glu Ala Lys Pro Ala Gly Phe Leu Ser
                85                  90                  95

Lys Tyr Pro Ala Leu Val Thr Gly Phe Phe Phe Phe Met Trp Tyr Phe
            100                 105                 110

Leu Asn Val Ile Phe Asn Ile Leu Asn Lys Lys Ile Tyr Asn Tyr Phe
        115                 120                 125

Pro Tyr Pro Tyr Phe Val Ser Ala Ile His Leu Leu Val Gly Val Val
    130                 135                 140

Tyr Cys Leu Ile Ser Trp Ser Leu Gly Leu Pro Lys Arg Ala Pro Val
145                 150                 155                 160

Asn Ala Asn Leu Leu Lys Leu Leu Phe Pro Val Ala Leu Cys His Ala
                165                 170                 175

Leu Gly His Val Thr Ser Asn Val Ser Phe Ala Ala Val Ala Val Ser
            180                 185                 190

Phe Ala His Thr Ile Lys Ala Leu Glu Pro Phe Phe Asn Ala Ala Ala
        195                 200                 205

Thr Gln Phe Ile Leu Gly Gln Gln Val Pro Leu Ser Leu Trp Leu Ser
    210                 215                 220

Leu Ala Pro Val Val Ile Gly Val Ser Met Ala Ser Leu Thr Glu Leu
225                 230                 235                 240

Ser Phe Asn Trp Thr Gly Phe Ile Asn Ala Met Ile Ser Asn Ile Ser
                245                 250                 255

Phe Thr Tyr Arg Ser Ile Tyr Ser Lys Lys Ala Met Thr Asp Met Asp
            260                 265                 270

Ser Thr Asn Val Tyr Ala Tyr Ile Ser Ile Ile Ser Leu Ile Val Cys
        275                 280                 285

Ile Pro Pro Ala Leu Met Phe Glu Gly Pro Lys Leu Met Gln His Gly
    290                 295                 300
```

```
Phe Asn Asp Ala Ile Ala Lys Val Gly Leu Gln Lys Phe Val Thr Asp
305                 310                 315                 320

Leu Phe Leu Val Gly Leu Phe Tyr His Leu Tyr Asn Gln Val Ala Thr
            325                 330                 335

Asn Thr Leu Glu Arg Val Ala Pro Leu Thr His Ala Val Gly Asn Val
            340                 345                 350

Leu Lys Arg Val Phe Val Ile Gly Phe Ser Ile Ile Val Phe Gly Asn
            355                 360                 365

Arg Ile Thr Thr Gln Thr Gly Ile Gly Thr Ser Ile Ala Ile Ala Gly
            370                 375                 380

Val Ala Met Tyr Ser Tyr Ile Lys Ala Lys Ile Glu Glu Glu Lys Arg
385                 390                 395                 400

Lys Lys Lys Ser Ala
            405

<210> SEQ ID NO 6
<211> LENGTH: 343
<212> TYPE: PRT
<213> ORGANISM: Setaria italica
<220> FEATURE:
<221> NAME/KEY: MISC_FEATURE
<222> LOCATION: (1)..(343)
<223> OTHER INFORMATION: TPT isoform 2

<400> SEQUENCE: 6

Met Ser Ala Leu Gly Ala Leu Ser Gly Gly Ala Ala Gly Val Ala Gly
1               5                   10                  15

Leu Leu Ser Leu Arg Arg Arg Ala Ala Ala Pro Pro Pro Pro Ser Ala
            20                  25                  30

Leu Ala Ser Ser Ser His Leu Pro Pro Leu Lys Cys Ala Ala Val Pro
            35                  40                  45

Asp Ala Gly His Leu Val Trp Gly Arg Gln Leu Arg Pro Ala Leu Ala
        50                  55                  60

Leu Leu Pro Phe Pro Ser Gln Ala Ala Arg Lys Gln Thr Pro Arg Pro
65                  70                  75                  80

Pro Ala Ala Ala Ser Ala Gly Glu Ala Lys Pro Ala Gly Phe Leu Ser
                85                  90                  95

Lys Tyr Pro Ala Leu Val Thr Gly Phe Phe Phe Phe Met Trp Tyr Phe
            100                 105                 110

Leu Asn Val Ile Phe Asn Ile Leu Asn Lys Lys Ile Tyr Asn Tyr Phe
            115                 120                 125

Pro Tyr Pro Tyr Phe Val Ser Ala Ile His Leu Leu Val Gly Val Val
            130                 135                 140

Tyr Cys Leu Ile Ser Trp Ser Leu Gly Leu Pro Lys Arg Ala Pro Val
145                 150                 155                 160

Asn Ala Asn Leu Leu Lys Leu Leu Phe Pro Val Ala Leu Cys His Ala
                165                 170                 175

Leu Gly His Val Thr Ser Asn Val Ser Phe Ala Ala Val Ala Val Ser
            180                 185                 190

Phe Ala His Thr Ile Lys Ala Leu Glu Pro Phe Phe Asn Ala Ala Ala
            195                 200                 205

Thr Gln Phe Ile Leu Gly Gln Gln Val Pro Leu Ser Leu Trp Leu Ser
            210                 215                 220

Leu Ala Pro Val Val Ile Gly Val Ser Met Ala Ser Leu Thr Glu Leu
225                 230                 235                 240

Ser Phe Asn Trp Thr Gly Phe Ile Asn Ala Met Ile Ser Asn Ile Ser
```

```
            245                 250                 255
Phe Thr Tyr Arg Ser Ile Tyr Ser Lys Lys Ala Met Thr Asp Met Asp
            260                 265                 270

Ser Thr Asn Val Tyr Ala Tyr Ile Ser Ile Ile Ser Leu Ile Val Cys
        275                 280                 285

Ile Pro Pro Ala Leu Met Phe Glu Gly Pro Lys Leu Met Gln His Gly
    290                 295                 300

Phe Asn Asp Ala Ile Ala Lys Val Gly Leu Gln Lys Phe Val Thr Asp
305                 310                 315                 320

Leu Phe Leu Val Gly Leu Phe Tyr His Leu Tyr Asn Gln Val Thr Gly
                325                 330                 335

Ser Ser Ile Ser Cys Lys Ser
            340

<210> SEQ ID NO 7
<211> LENGTH: 554
<212> TYPE: PRT
<213> ORGANISM: Setaria italica
<220> FEATURE:
<221> NAME/KEY: MISC_FEATURE
<222> LOCATION: (1)..(554)
<223> OTHER INFORMATION: DCT2

<400> SEQUENCE: 7

Met Glu Ser Leu Arg Leu Ala Val Ser His Arg Pro Ala Leu Pro Leu
1               5                   10                  15

Pro Ile Pro His Gly His Leu Arg Arg Gly His Leu Gln Leu Gln Pro
            20                  25                  30

Ser Pro Asn Ser Leu Ser Leu Ser Leu Pro Ile Ser Pro His Leu Thr
        35                  40                  45

Leu Phe Pro Thr Thr Arg Arg His Leu Pro Pro Ile Leu Ala Ser Ala
    50                  55                  60

Ser Ala Ser Ala Val Ala Lys Pro Ser Pro Asp Pro Lys Pro Ala Ala
65                  70                  75                  80

Ala Ala Gly Gly Ala Lys Pro Leu Pro Leu Leu Ile Ser Leu Ala Ala
                85                  90                  95

Gly Leu Ala Val Arg Phe Leu Val Pro Arg Pro Ala Glu Val Thr Pro
            100                 105                 110

Gln Ala Trp Gln Leu Leu Ser Ile Phe Leu Ser Thr Ile Ala Gly Leu
        115                 120                 125

Val Leu Gly Pro Leu Pro Val Gly Ala Trp Ala Phe Leu Gly Leu Thr
    130                 135                 140

Ala Thr Val Ala Thr Arg Thr Leu Pro Phe Thr Ala Ala Phe Gly Ala
145                 150                 155                 160

Phe Thr Asn Glu Val Ile Trp Leu Ile Val Ile Ser Phe Phe Ala
                165                 170                 175

Arg Gly Phe Val Lys Thr Gly Leu Gly Asp Arg Val Ala Thr Tyr Phe
            180                 185                 190

Val Lys Trp Leu Gly Arg Ser Thr Leu Gly Leu Ser Tyr Gly Leu Ala
        195                 200                 205

Ile Ser Glu Ala Phe Ile Ala Pro Ala Met Pro Ser Thr Thr Ala Arg
    210                 215                 220

Ala Gly Gly Val Phe Leu Pro Ile Val Lys Ser Leu Ser Leu Ala Ser
225                 230                 235                 240

Gly Ser Lys Pro Asn Asp Pro Ser Ala Lys Lys Leu Gly Ser Tyr Leu
                245                 250                 255
```

Val Gln Ser Gln Leu Gln Ala Ser Ser Asn Ser Ser Ala Leu Phe Leu
            260                 265                 270

Thr Ala Ala Ala Gln Asn Leu Leu Cys Leu Lys Leu Ala Glu Glu Leu
        275                 280                 285

Gly Val Lys Ile Ala Asn Pro Trp Val Thr Trp Leu Lys Val Ala Ser
    290                 295                 300

Leu Pro Ala Ile Val Gly Leu Val Thr Pro Tyr Leu Leu Tyr Lys
305                 310                 315                 320

Ile Phe Pro Pro Glu Ile Lys Asp Thr Pro Asp Ala Pro Ala Leu Ala
                325                 330                 335

Ala Gln Lys Leu Lys Asn Met Gly Pro Val Thr Arg Asn Glu Trp Val
            340                 345                 350

Met Ile Gly Thr Met Ile Leu Ala Val Ser Leu Trp Ile Phe Gly Glu
        355                 360                 365

Ala Ile Gly Val Ser Ser Val Val Ala Ala Met Ile Gly Leu Ser Ile
    370                 375                 380

Leu Leu Leu Leu Gly Val Leu Asn Trp Glu Asp Cys Leu Asn Glu Lys
385                 390                 395                 400

Ser Ala Trp Asp Thr Leu Ala Trp Phe Ala Ile Leu Val Gly Leu Ala
                405                 410                 415

Gly Gln Leu Thr Ser Val Gly Ile Val Ser Trp Met Ser Asn Cys Val
            420                 425                 430

Ala Asn Val Leu Gln Ser Phe Ser Leu Ser Trp Pro Ala Ala Phe Gly
        435                 440                 445

Val Leu Gln Ala Ser Tyr Phe Phe Ile His Tyr Leu Phe Ala Ser Gln
    450                 455                 460

Thr Ala His Val Gly Ala Leu Phe Ser Ala Phe Leu Ala Met His Leu
465                 470                 475                 480

Ala Ala Gly Val Pro Gly Gln Leu Ala Ala Leu Ala Leu Thr Tyr Asn
                485                 490                 495

Ala Asn Leu Phe Gly Ala Leu Thr His Tyr Ser Ser Gly Gln Ala Ala
            500                 505                 510

Val Tyr Tyr Gly Ala Gly Tyr Val Asp Leu Pro Asp Val Phe Lys Leu
        515                 520                 525

Gly Phe Thr Thr Ala Ala Leu Asn Ala Val Ile Trp Gly Val Val Gly
    530                 535                 540

Ala Phe Trp Trp Lys Phe Leu Gly Leu Tyr
545                 550

<210> SEQ ID NO 8
<211> LENGTH: 551
<212> TYPE: PRT
<213> ORGANISM: Setaria italica
<220> FEATURE:
<221> NAME/KEY: MISC_FEATURE
<222> LOCATION: (1)..(551)
<223> OTHER INFORMATION: DCT4

<400> SEQUENCE: 8

Met Glu Ile Gly Leu Val Val Ala His Arg Pro Ser Leu Pro Val Ala
1               5                   10                  15

Ala Val Pro Ala Pro Ala Tyr Leu Arg Arg His Leu Pro Gly Leu
            20                  25                  30

Ile Ser Leu Pro Arg Thr Ser Pro Ser Leu Phe Ser Pro His His Gln
        35                  40                  45

```
Arg Leu Ser Pro Thr Pro Arg His Asp Leu Leu Gln Pro Leu Arg Ala
     50                  55                  60
Ser Pro Ala Pro Asp Ser Ser Pro Lys Pro Glu Pro Pro Ala Ala Ser
 65                  70                  75                  80
Gly Ala Lys Leu Val Pro Leu Val Ile Ser Ile Ala Val Gly Leu Ala
                 85                  90                  95
Val Arg Phe Leu Ala Pro Arg Pro Ala Glu Val Ser Pro Asn Ala Trp
            100                 105                 110
Gln Met Leu Ser Ile Phe Leu Ser Thr Ile Ala Gly Leu Val Leu Gly
            115                 120                 125
Pro Leu Pro Val Gly Ala Val Ala Phe Leu Gly Leu Thr Thr Val Val
        130                 135                 140
Ala Thr Lys Thr Leu Pro Phe Ala Ala Ala Phe Ala Ala Phe Thr Asn
145                 150                 155                 160
Glu Ile Ile Trp Leu Ile Val Ile Ser Phe Phe Ala Arg Gly Phe
                165                 170                 175
Val Lys Thr Gly Leu Gly Asp Arg Ile Ala Thr Tyr Phe Val Lys Trp
            180                 185                 190
Leu Gly Ser Ser Thr Leu Gly Leu Ser Tyr Gly Leu Thr Leu Gly Glu
        195                 200                 205
Ala Cys Ile Ala Pro Ala Met Pro Ser Thr Ala Ala Arg Ala Gly Gly
210                 215                 220
Ile Phe Leu Pro Ile Ile Lys Ser Leu Ser Ile Ser Ala Gly Ser Lys
225                 230                 235                 240
Pro Asn His Pro Ser Ser Arg Lys Leu Gly Ser Tyr Leu Val Met Thr
            245                 250                 255
Gln Phe Gln Ala Ala Ser Ser Ser Ser Ala Leu Phe Leu Thr Ala Gly
        260                 265                 270
Ala Gln Asn Leu Leu Cys Leu Asn Leu Ala Glu Glu Leu Gly Val Ile
        275                 280                 285
Ile Ala Asn Pro Trp Val Ser Trp Phe Lys Ala Ser Leu Pro Ala
        290                 295                 300
Ile Val Ser Leu Leu Ala Thr Pro Tyr Leu Leu Tyr Lys Ile Tyr Pro
305                 310                 315                 320
Pro Glu Thr Lys Asp Thr Pro Glu Ala Pro Ala Leu Ala Ala Glu Lys
            325                 330                 335
Gln Lys Arg Met Gly Pro Val Thr Lys Asn Glu Trp Val Met Val Gly
        340                 345                 350
Thr Met Ile Phe Ala Val Ser Leu Trp Ile Leu Gly Asp Ala Ile Gly
        355                 360                 365
Val Pro Ser Val Val Ala Ala Met Leu Gly Leu Ser Ile Leu Leu Leu
370                 375                 380
Leu Gly Val Leu Asp Trp Gly Asp Ile Leu Asn Glu Lys Ser Ala Trp
385                 390                 395                 400
Asp Thr Leu Ala Trp Phe Ser Val Leu Val Gly Met Ala Ala Gln Leu
            405                 410                 415
Thr Asn Leu Gly Ile Val Ser Trp Met Ser Asn Cys Ile Ala Lys Leu
        420                 425                 430
Leu Gln Ser Phe Ser Leu Ser Trp Pro Ala Ala Phe Cys Val Leu Gln
        435                 440                 445
Ala Ser Tyr Phe Leu Ile His Tyr Leu Phe Ala Ser Gln Thr Gly His
450                 455                 460
Ile Gly Ala Leu Tyr Ser Ala Phe Leu Ala Met His Val Ala Ala Gly
```

```
                465                 470                 475                 480
Val Pro Arg Val Leu Ser Ala Leu Ala Leu Ala Phe Asn Thr Asp Leu
                485                 490                 495

Phe Gly Gly Ile Thr His Tyr Ser Ser Gly Gln Ala Ala Val Tyr Phe
            500                 505                 510

Gly Ala Gly Tyr Leu Asp Leu Pro Asp Val Phe Arg Ile Gly Phe Val
            515                 520                 525

Ile Thr Met Ile Asn Ala Cys Ile Trp Gly Val Ile Gly Thr Ile Trp
        530                 535                 540

Trp Lys Phe Leu Gly Leu Tyr
545                 550

<210> SEQ ID NO 9
<211> LENGTH: 79
<212> TYPE: PRT
<213> ORGANISM: Setaria italica
<220> FEATURE:
<221> NAME/KEY: MISC_FEATURE
<222> LOCATION: (1)..(79)
<223> OTHER INFORMATION: MEP3c isoform 1

<400> SEQUENCE: 9

Met Glu Leu Gly Val Gly Val Ile Ala Lys Thr Ala Ala Glu Tyr Glu
1               5                   10                  15

Lys Arg Arg Glu Asn Phe Val Lys Glu Ile Asp Ile Val Ile Ala Asp
                20                  25                  30

Val Ile Met Ala Ile Val Ala Asp Phe Met Leu Val Tyr Leu Pro Ala
            35                  40                  45

Pro Thr Val Ser Leu Gln Pro Pro Leu Ala Arg Asn Ala Gly Ala Ile
        50                  55                  60

Ala Asn Phe Phe His Asn Cys Pro Asp Asn Ala Phe Gln Val Asn
65                  70                  75

<210> SEQ ID NO 10
<211> LENGTH: 215
<212> TYPE: PRT
<213> ORGANISM: Setaria italica
<220> FEATURE:
<221> NAME/KEY: MISC_FEATURE
<222> LOCATION: (1)..(215)
<223> OTHER INFORMATION: MEP3c isoform 2

<400> SEQUENCE: 10

Met Glu Leu Gly Val Gly Val Ile Ala Lys Thr Ala Ala Glu Tyr Glu
1               5                   10                  15

Lys Arg Arg Glu Asn Phe Val Lys Glu Ile Asp Ile Val Ile Ala Asp
                20                  25                  30

Val Ile Met Ala Ile Val Ala Asp Phe Met Leu Val Tyr Leu Pro Ala
            35                  40                  45

Pro Thr Val Ser Leu Gln Pro Pro Leu Ala Arg Asn Ala Gly Ala Ile
        50                  55                  60

Ala Asn Phe Phe His Asn Cys Pro Asp Asn Ala Phe Gln Ile Ala Leu
65                  70                  75                  80

Ala Gly Arg Ser Phe Ser Leu Leu Gln Arg Leu Gly Ala Ile Leu Arg
                85                  90                  95

Asn Gly Ala Lys Leu Phe Ala Val Gly Thr Ser Ala Ser Leu Ile Gly
            100                 105                 110

Thr Gly Val Thr Asn Ala Leu Ile Lys Ala Arg Lys Ala Val Asp Lys
        115                 120                 125
```

```
Asp Leu Glu Gly Glu Val Glu Asp Ile Pro Val Val Ser Thr Ser Val
    130                 135                 140
Ala Tyr Gly Val Tyr Met Ala Ile Ser Ser Asn Leu Arg Tyr Gln Ile
145                 150                 155                 160
Leu Ala Gly Val Ile Glu Gln Arg Met Leu Glu Pro Leu Leu His Asn
                165                 170                 175
Gln Lys Leu Leu Leu Ser Ala Met Cys Phe Ala Val Arg Thr Gly Asn
            180                 185                 190
Thr Phe Leu Gly Ser Leu Leu Trp Val Asp Tyr Ala Arg Leu Val Gly
        195                 200                 205
Val Gln Lys Val Gln Glu Ala
    210                 215

<210> SEQ ID NO 11
<211> LENGTH: 398
<212> TYPE: PRT
<213> ORGANISM: Setaria italica
<220> FEATURE:
<221> NAME/KEY: MISC_FEATURE
<222> LOCATION: (1)..(398)
<223> OTHER INFORMATION: PPT1

<400> SEQUENCE: 11

Met Gln Ser Ala Ala Ala Phe Arg Pro Cys Pro Ala Arg Pro Leu Val
1               5                   10                  15
Ser Arg Asn Pro Ser Arg Pro Leu Leu Pro Ala Arg Pro Leu Arg Val
            20                  25                  30
Gly Ala Ala Ala Ala Thr Thr Ser Thr Arg Cys Gly Ala Val Gly
        35                  40                  45
Pro Arg Gly His Gly Leu Gly Leu Gln Pro Val Ser Pro Asp Arg Glu
    50                  55                  60
Gly Lys Ala Arg Gln Arg Gln Val Ala Cys Gly Ala Ala Gly Ala Ala
65                  70                  75                  80
Gly Lys Val Glu Glu Glu Gly Gly Leu Met Lys Thr Leu Gln Leu
                85                  90                  95
Gly Leu Phe Phe Gly Leu Trp Tyr Leu Phe Asn Ile Tyr Phe Asn Ile
            100                 105                 110
Tyr Asn Lys Gln Val Leu Lys Val Phe Pro Tyr Pro Ile Asn Ile Thr
        115                 120                 125
Glu Ile Gln Phe Ala Val Gly Ala Ala Val Ala Leu Phe Met Trp Ile
    130                 135                 140
Thr Gly Ile Ile Lys Arg Pro Lys Ile Ser Gly Ala Gln Leu Val Ala
145                 150                 155                 160
Ile Leu Pro Leu Ala Ile Val His Thr Met Gly Asn Leu Phe Thr Asn
                165                 170                 175
Met Ser Leu Gly Lys Val Ala Val Ser Phe Thr His Thr Ile Lys Ala
            180                 185                 190
Met Glu Pro Phe Phe Ser Val Leu Leu Ser Ala Ile Phe Leu Gly Glu
        195                 200                 205
Leu Pro Thr Val Trp Val Leu Ser Leu Pro Ile Val Gly Gly
    210                 215                 220
Val Gly Leu Ala Ser Leu Thr Glu Ala Ser Phe Asn Trp Ala Gly Phe
225                 230                 235                 240
Trp Ser Ala Met Ala Ser Asn Val Thr Phe Gln Ser Arg Asn Val Leu
                245                 250                 255
```

```
Ser Lys Lys Val Met Val Lys Lys Glu Asn Glu Ser Leu Asp Asn
            260                 265                 270

Ile Asn Leu Phe Ser Ile Ile Thr Val Met Ser Phe Phe Leu Leu Ala
            275                 280                 285

Pro Val Thr Phe Phe Thr Glu Gly Val Lys Ile Thr Pro Thr Phe Leu
            290                 295                 300

Gln Ser Ala Gly Leu Asp Val Lys Leu Val Leu Thr Arg Ser Leu Leu
305                 310                 315                 320

Ala Ala Leu Cys Phe His Ala Tyr Gln Gln Val Ser Tyr Met Ile Leu
                325                 330                 335

Glu Arg Val Ser Pro Val Thr His Ser Val Gly Asn Cys Val Lys Arg
                340                 345                 350

Val Val Val Ile Val Thr Ser Val Leu Phe Phe Arg Thr Pro Val Ser
                355                 360                 365

Pro Ile Asn Ser Leu Gly Thr Ala Ile Ala Leu Ala Gly Val Phe Leu
                370                 375                 380

Tyr Ser Gln Leu Lys Arg Leu Lys Pro Lys Pro Lys Thr Ala
385                 390                 395

<210> SEQ ID NO 12
<211> LENGTH: 549
<212> TYPE: PRT
<213> ORGANISM: Setaria italica
<220> FEATURE:
<221> NAME/KEY: MISC_FEATURE
<222> LOCATION: (1)..(549)
<223> OTHER INFORMATION: DCT1

<400> SEQUENCE: 12

Met Glu Ser Leu Arg Leu Ala Val Ala His Arg Pro Leu Pro Val
1               5                   10                  15

Pro Ala Pro Gly His Leu Arg Arg His Leu His Arg Leu Pro Ala
                20                  25                  30

Ser Leu Ser Leu Pro Thr Thr Ser Leu Ser Leu Pro Ser Pro His His
            35                  40                  45

His Arg Leu Ser Ala Ala Pro Arg Arg Gly Leu Pro Leu Pro Leu Leu
        50                  55                  60

Ala Ser Gln Ala Ser His Ser Asn Pro Glu Pro Glu Ser Ala Gly Ala
65                  70                  75                  80

Lys Leu Val Pro Leu Val Ile Ser Val Ala Ile Gly Leu Ala Val Arg
                85                  90                  95

Phe Leu Ala Pro Arg Pro Ala Glu Val Ser Leu Gln Gly Trp Gln Leu
                100                 105                 110

Leu Ser Ile Phe Leu Ser Thr Ile Ala Gly Leu Val Leu Gly Pro Leu
            115                 120                 125

Pro Val Gly Ala Trp Ala Phe Leu Gly Leu Thr Ala Ala Val Ala Thr
            130                 135                 140

Arg Thr Leu Pro Phe Thr Ala Ala Phe Ser Ala Phe Thr Asn Glu Val
145                 150                 155                 160

Ile Trp Leu Ile Val Ile Ser Phe Phe Ala Arg Gly Phe Val Lys
                165                 170                 175

Thr Gly Leu Gly Asp Arg Ile Ala Thr Tyr Phe Val Lys Trp Leu Gly
                180                 185                 190

Ser Ser Thr Leu Gly Leu Ser Tyr Gly Leu Thr Ile Ser Glu Ala Cys
            195                 200                 205

Ile Ala Pro Ala Met Pro Ser Thr Thr Ala Arg Ala Gly Gly Val Phe
```

```
                210                 215                 220
Leu Pro Ile Ile Lys Ser Leu Ser Leu Ser Ala Glu Ser Lys Pro Asn
225                 230                 235                 240

His Pro Ser Ser Arg Lys Leu Gly Ser Tyr Leu Val Met Thr Gln Phe
                245                 250                 255

Gln Ala Ala Gly Asn Ser Ser Ala Leu Phe Leu Thr Ala Ala Ala Gln
                260                 265                 270

Asn Leu Leu Cys Leu Lys Leu Ala Glu Glu Leu Gly Val Ile Ile Ala
                275                 280                 285

Asn Pro Trp Val Ser Trp Phe Lys Ala Ala Ser Leu Pro Ala Ile Val
290                 295                 300

Ser Leu Leu Ala Thr Pro Tyr Leu Leu Tyr Lys Ile Phe Pro Pro Glu
305                 310                 315                 320

Thr Lys Asp Thr Pro Asp Ala Pro Ala Leu Ala Ala Glu Lys Leu Lys
                325                 330                 335

Arg Met Gly Pro Val Thr Lys Asn Glu Trp Val Met Ile Ser Thr Met
                340                 345                 350

Ile Leu Ala Val Ser Leu Trp Val Phe Gly Asp Ala Ile Gly Val Ser
                355                 360                 365

Ser Val Val Ala Ala Met Leu Gly Leu Ser Ile Leu Leu Leu Leu Gly
                370                 375                 380

Val Leu Asp Trp Asp Asp Cys Leu Asn Glu Lys Ser Ala Trp Asp Thr
385                 390                 395                 400

Leu Ala Trp Phe Ala Val Leu Val Gly Met Ala Ala Gln Leu Thr Asn
                405                 410                 415

Leu Gly Ile Val Ser Trp Met Ser Ser Cys Val Ala Lys Leu Leu Gln
                420                 425                 430

Ser Phe Ser Leu Ser Trp Pro Ala Ala Phe Cys Val Leu Glu Ala Ser
                435                 440                 445

Tyr Phe Leu Ile His Tyr Leu Phe Ala Ser Gln Thr Gly His Val Gly
                450                 455                 460

Ala Leu Tyr Ser Ala Phe Leu Ala Met His Ile Ala Ala Gly Val Pro
465                 470                 475                 480

Arg Ala Leu Ser Ala Leu Ala Leu Ala Phe Asn Thr Asn Leu Phe Gly
                485                 490                 495

Ala Leu Thr His Tyr Ser Ser Gly Gln Ala Ala Val Tyr Phe Gly Ala
                500                 505                 510

Gly Tyr Leu Asp Leu Pro Asp Val Phe Arg Leu Gly Phe Val Thr Ala
                515                 520                 525

Leu Val Asn Thr Leu Ile Trp Gly Val Ile Gly Thr Ile Trp Trp Lys
                530                 535                 540

Phe Leu Gly Leu Tyr
545

<210> SEQ ID NO 13
<211> LENGTH: 132
<212> TYPE: PRT
<213> ORGANISM: Setaria italica
<220> FEATURE:
<221> NAME/KEY: MISC_FEATURE
<222> LOCATION: (1)..(132)
<223> OTHER INFORMATION: PPT2 isoform 1

<400> SEQUENCE: 13

Met Gln Asp Ala Met Asp Asp Ile Asn Leu Phe Ser Val Ile Thr Val
1               5                   10                  15
```

```
Leu Ser Phe Leu Leu Ser Cys Pro Leu Met Leu Phe Ala Glu Gly Val
            20                  25                  30

Lys Phe Thr Pro Gly Tyr Leu Gln Ser Ser Gly Leu Asn Leu Gln Glu
        35                  40                  45

Leu Cys Ile Arg Ala Ala Leu Ala Gly Phe Cys Phe His Gly Tyr Gln
    50                  55                  60

Lys Leu Ser Tyr Leu Ile Leu Ser Arg Val Ser Pro Val Thr His Ser
65                  70                  75                  80

Val Ala Asn Cys Val Lys Arg Val Val Ile Val Ser Ser Val Ile
                85                  90                  95

Phe Phe Ser Thr Pro Ile Ser Pro Val Asn Ala Leu Gly Thr Gly Ala
            100                 105                 110

Ala Leu Gly Gly Val Phe Leu Tyr Ser Lys Leu Thr Arg Thr Lys Lys
        115                 120                 125

Pro Lys Asn Ala
    130
```

<210> SEQ ID NO 14
<211> LENGTH: 152
<212> TYPE: PRT
<213> ORGANISM: Setaria italica
<220> FEATURE:
<221> NAME/KEY: MISC_FEATURE
<222> LOCATION: (1)..(152)
<223> OTHER INFORMATION: PPT2 isoform 2

<400> SEQUENCE: 14

```
Met Ala Ser Asn Leu Thr Asn Gln Ser Arg Asn Val Leu Ser Lys Lys
1               5                   10                  15

Leu Leu Ala Gly Asp Lys Asp Ala Met Asp Asp Ile Asn Leu Phe Ser
            20                  25                  30

Val Ile Thr Val Leu Ser Phe Leu Leu Ser Cys Pro Leu Met Leu Phe
        35                  40                  45

Ala Glu Gly Val Lys Phe Thr Pro Gly Tyr Leu Gln Ser Ser Gly Leu
    50                  55                  60

Asn Leu Gln Glu Leu Cys Ile Arg Ala Ala Leu Ala Gly Phe Cys Phe
65                  70                  75                  80

His Gly Tyr Gln Lys Leu Ser Tyr Leu Ile Leu Ser Arg Val Ser Pro
                85                  90                  95

Val Thr His Ser Val Ala Asn Cys Val Lys Arg Val Val Ile Val
            100                 105                 110

Ser Ser Val Ile Phe Phe Ser Thr Pro Ile Ser Pro Val Asn Ala Leu
        115                 120                 125

Gly Thr Gly Ala Ala Leu Gly Gly Val Phe Leu Tyr Ser Lys Leu Thr
    130                 135                 140

Arg Thr Lys Lys Pro Lys Asn Ala
145                 150
```

<210> SEQ ID NO 15
<211> LENGTH: 578
<212> TYPE: PRT
<213> ORGANISM: Zea mays
<220> FEATURE:
<221> NAME/KEY: MISC_FEATURE
<222> LOCATION: (1)..(578)
<223> OTHER INFORMATION: OMT

<400> SEQUENCE: 15

```
Met Ala Ser Ser Thr Ala Ala Ser Pro Leu Thr Cys His His Leu Gly
1               5                  10                 15

Ser Val Gly Ala Arg Pro Arg Leu Pro Ser Leu Ser Ile Ser Leu Arg
            20                  25                 30

Arg Arg Ser Ser Ser Ser Lys Pro Thr Ser Leu Ser His Ser Leu
        35                  40                  45

Pro Ser Lys His Ser Leu Ala Pro Pro Ala Ala Ser Ala Ser Ser
50                  55                  60

Arg Arg Gly Leu Thr Pro Val Pro Ala Ser Ser Ala Ala Ala Ala
65                  70                  75                  80

Pro Ala Pro Asp Pro Val Pro Val Pro Ala Pro Ala Pro Ala
                85                  90                  95

Pro Ala Pro Ala Ala Pro Pro Lys Lys Pro Ala Leu Gln Gly Ala Ala
                100                 105                 110

Ile Lys Pro Leu Leu Ala Ser Ile Ala Thr Gly Val Leu Ile Trp Leu
            115                 120                 125

Ile Pro Pro Pro Ala Gly Val Pro Arg Asn Ala Trp Gln Leu Leu Ala
    130                 135                 140

Ile Phe Leu Ser Thr Ile Val Gly Ile Ile Thr Gln Pro Leu Pro Leu
145                 150                 155                 160

Gly Ala Val Ala Leu Leu Gly Leu Gly Ala Ala Val Leu Ser Arg Thr
                165                 170                 175

Leu Thr Phe Ala Ala Ala Phe Ser Ala Phe Gly Asp Pro Ile Pro Trp
                180                 185                 190

Leu Ile Ala Leu Ala Phe Phe Ala Arg Gly Phe Ile Lys Thr Gly
    195                 200                 205

Leu Gly Ser Arg Val Ala Tyr Ala Phe Val Ala Phe Gly Ser Ser
    210                 215                 220

Ser Leu Gly Leu Gly Tyr Ser Leu Val Phe Ala Glu Ala Leu Leu Ala
225                 230                 235                 240

Pro Ala Ile Pro Ser Val Ser Ala Arg Ala Gly Gly Ile Phe Leu Pro
                245                 250                 255

Leu Val Lys Ser Leu Cys Glu Ala Cys Gly Ser Arg Ala Gly Asp Gly
                260                 265                 270

Thr Glu Arg Arg Leu Gly Ala Trp Leu Met Leu Thr Cys Phe Gln Thr
            275                 280                 285

Ser Val Val Ser Ser Ala Met Phe Leu Thr Ala Met Ala Asn Pro
        290                 295                 300

Leu Ser Ala Asn Leu Thr Ala Thr Ile Gly Glu Gly Ile Gly Trp
305                 310                 315                 320

Thr Leu Trp Ala Lys Ala Ala Ile Val Pro Gly Leu Leu Ser Leu Val
                325                 330                 335

Leu Val Pro Leu Ile Leu Tyr Val Ile Tyr Pro Pro Glu Val Lys Ala
            340                 345                 350

Ser Pro Asp Ala Pro Arg Leu Ala Lys Glu Arg Leu Ala Lys Met Gly
        355                 360                 365

Pro Met Ser Lys Glu Glu Thr Ile Met Ala Gly Thr Leu Leu Leu Thr
    370                 375                 380

Val Gly Leu Trp Ile Phe Gly Gly Met Leu Asn Val Asp Ala Val Ser
385                 390                 395                 400

Ala Ala Ile Leu Gly Leu Ala Val Leu Leu Ile Ser Gly Val Val Thr
                405                 410                 415

Trp Lys Glu Cys Leu Ala Glu Ser Val Ala Trp Asp Thr Leu Thr Trp
```

```
                420             425             430
Phe Ala Ala Leu Ile Ala Met Ala Gly Tyr Leu Asn Lys Phe Gly Leu
            435                 440                 445
Ile Ser Trp Phe Ser Glu Thr Val Val Lys Phe Val Gly Gly Leu Gly
        450                 455                 460
Met Ser Trp Gln Leu Ser Phe Gly Val Leu Val Leu Leu Tyr Phe Tyr
465                 470                 475                 480
Ser His Tyr Phe Phe Ala Ser Gly Ala Ala His Ile Gly Ala Met Phe
                485                 490                 495
Thr Ala Phe Leu Ser Val Ala Ser Ala Leu Gly Thr Pro Ser Leu Phe
            500                 505                 510
Ala Ala Met Val Leu Ser Phe Leu Ser Asn Leu Met Gly Gly Thr Thr
        515                 520                 525
His Tyr Gly Ile Gly Ser Ala Pro Val Phe Tyr Gly Ala Gly Tyr Val
    530                 535                 540
Pro Leu Ala Gln Trp Trp Gly Tyr Gly Phe Val Ile Ser Val Val Asn
545                 550                 555                 560
Ile Ile Ile Trp Leu Gly Val Gly Gly Phe Trp Trp Lys Ile Ile Gly
                565                 570                 575
Leu Trp

<210> SEQ ID NO 16
<211> LENGTH: 554
<212> TYPE: PRT
<213> ORGANISM: Zea mays
<220> FEATURE:
<221> NAME/KEY: MISC_FEATURE
<222> LOCATION: (1)..(554)
<223> OTHER INFORMATION: DCT1 isoform 1

<400> SEQUENCE: 16

Met Glu Leu His Leu Ala Thr Ile Ala His Arg Pro Leu Pro Val
1               5                   10                  15
Pro Ala Arg Gly His His Leu Arg Arg Arg Leu His His Leu Pro Ala
                20                  25                  30
Pro Leu Ser Phe Gln Asn Thr Tyr Ser Pro Ser Leu Ser Pro His
            35                  40                  45
His His Arg Leu Ser Pro Thr Leu Arg Arg His Leu Arg Leu Pro Leu
        50                  55                  60
Leu Ala Ser Gln Ala Pro Asn Ser Asn Pro Glu Pro Glu Pro Glu Pro
65                  70                  75                  80
Glu Pro Thr Gly Ala Lys Leu Leu Pro Leu Val Ile Ser Ile Ala Ile
                85                  90                  95
Gly Leu Ala Val Arg Phe Leu Ala Pro Arg Pro Val Glu Val Ser Pro
            100                 105                 110
Gln Ala Trp Gln Leu Leu Ser Ile Phe Leu Ser Thr Ile Ala Gly Leu
        115                 120                 125
Val Leu Gly Pro Leu Pro Val Gly Ala Trp Ala Phe Leu Gly Leu Thr
    130                 135                 140
Ala Ala Val Ala Thr Arg Thr Leu Pro Phe Thr Ala Ala Phe Ser Ala
145                 150                 155                 160
Phe Thr Asn Glu Val Ile Trp Leu Ile Val Ile Ser Phe Phe Phe Ala
                165                 170                 175
Arg Gly Phe Val Lys Thr Gly Leu Gly Asp Arg Ile Ala Thr Tyr Phe
            180                 185                 190
```

```
Val Lys Trp Leu Gly Ser Ser Thr Leu Gly Leu Ser Tyr Gly Leu Thr
            195                 200                 205

Leu Ser Glu Ala Cys Ile Ala Pro Ala Met Pro Ser Thr Thr Ala Arg
210                 215                 220

Ala Gly Gly Val Phe Leu Pro Ile Ile Lys Ser Leu Ser Leu Ser Ala
225                 230                 235                 240

Glu Ser Lys Pro Asn His Pro Ser Ser Arg Lys Leu Gly Ser Tyr Leu
                245                 250                 255

Val Met Thr Gln Phe Gln Ala Ser Gly Asn Ser Ser Ala Leu Phe Leu
            260                 265                 270

Thr Ala Ala Gln Asn Leu Leu Cys Leu Lys Leu Ala Glu Glu Leu
        275                 280                 285

Gly Val Ile Ile Ala Asn Pro Trp Val Ser Trp Phe Lys Ala Ala Ser
290                 295                 300

Leu Pro Ala Leu Val Ser Leu Ala Thr Pro Tyr Leu Leu Tyr Lys
305                 310                 315                 320

Ile Phe Pro Pro Glu Thr Lys Asp Thr Pro Asp Ala Pro Ala Leu Ala
                325                 330                 335

Glu Lys Lys Leu Lys Leu Met Gly Pro Val Thr Lys Asn Glu Ser Val
            340                 345                 350

Met Ile Gly Thr Met Ile Leu Ala Val Ser Leu Trp Val Phe Gly Asp
        355                 360                 365

Ala Ile Gly Val Ser Ser Val Val Ala Ala Met Leu Gly Leu Ser Ile
370                 375                 380

Leu Leu Val Leu Gly Val Leu Asp Trp Asp Asp Cys Leu Asn Glu Lys
385                 390                 395                 400

Ser Ala Trp Asp Thr Leu Ala Trp Phe Ala Val Leu Val Gly Met Ala
                405                 410                 415

Gly Gln Leu Thr Asn Leu Gly Ile Val Ser Trp Met Ser Asn Cys Val
            420                 425                 430

Ala Lys Leu Leu Gln Ser Phe Ser Leu Ser Trp Pro Val Ala Phe Cys
        435                 440                 445

Val Leu Glu Ala Ser Tyr Phe Leu Ile His Tyr Leu Phe Ala Ser Gln
450                 455                 460

Thr Gly His Val Gly Ala Leu Tyr Ser Ala Phe Leu Ala Met His Ile
465                 470                 475                 480

Ala Ala Gly Val Pro Ser Val Leu Ser Ala Leu Ala Leu Ala Phe Asn
                485                 490                 495

Thr Asn Leu Phe Gly Ala Ile Thr His Tyr Ser Ser Gly Gln Ala Ala
            500                 505                 510

Val Tyr Phe Gly Ala Gly Tyr Met Glu Leu Pro Asp Val Phe Arg Leu
        515                 520                 525

Gly Phe Ile Thr Ala Leu Ala Asn Thr Leu Ile Trp Gly Val Val Gly
530                 535                 540

Thr Ile Trp Trp Lys Phe Leu Gly Leu Tyr
545                 550

<210> SEQ ID NO 17
<211> LENGTH: 422
<212> TYPE: PRT
<213> ORGANISM: Zea mays
<220> FEATURE:
<221> NAME/KEY: MISC_FEATURE
<222> LOCATION: (1)..(422)
<223> OTHER INFORMATION: DCT1 isoform 2
```

<400> SEQUENCE: 17

```
Met Ala Asp Gly Ser Ser Thr Trp Gly Arg Arg Asp Pro Ser Trp Ala
1               5                   10                  15

Ser Asp Ala Ala Ala Gly Arg Ser Arg Gly Gly Arg Pro Arg Gln Arg
            20                  25                  30

Lys Glu Gly Thr Thr Leu Val Ser Val Leu Gly Arg Ser Thr Arg Pro
        35                  40                  45

Asn Cys Ile Leu Glu Trp Arg Met Thr Thr Ser Ala Gly Glu Met Ser
50                  55                  60

Glu Leu Ala Ala Ala Leu Gln Val Glu Tyr Glu Ala Phe Glu Gly Phe
65                  70                  75                  80

Gln Lys Ala Ser Ala His His Arg Gln Cys Arg Gly Thr Asn Pro Ser
                85                  90                  95

His Lys Phe Gly Asp Asp Met Leu Gln Lys Ala Lys Arg Met Glu
            100                 105                 110

Ala Thr Arg Gly Gln Lys Pro Ser Asp Ile Glu Val Tyr Gln Glu Gly
            115                 120                 125

His Lys Gly Pro Asn Pro Thr Asn Ser Asp Gln Leu Cys Ser Gln Thr
        130                 135                 140

Ala Met Asp Arg Leu Glu Leu Glu Ile Met Arg Met Arg Glu Glu Met
145                 150                 155                 160

Arg Gln Gln Arg Glu Phe Met Glu Ala Cys Asn Ala His Asn Gln Ala
                165                 170                 175

Met Tyr Gln Ala Thr Gly Asn Ser Ser Ala Leu Phe Leu Thr Ala Ala
            180                 185                 190

Ala Gln Asn Leu Ser Cys Leu Lys Leu Ala Glu Glu Phe Gly Val Ile
        195                 200                 205

Ile Ala Asn Pro Trp Val Ser Trp Leu Lys Ala Ser Leu Pro Ala
210                 215                 220

Phe Val Ser Leu Ile Ala Thr Pro Tyr Leu Leu Lys Leu Phe Pro Pro
225                 230                 235                 240

Glu Thr Lys Asp Ala Pro Asp Ala Leu Glu Leu Ala Glu Asn Leu
                245                 250                 255

Lys Arg Met Gly Pro Asp Ser Asp Phe Leu Ile His Tyr Leu Ile Ala
            260                 265                 270

Ser Gln Thr Arg His Val Gly Ala Leu Tyr Ser Ala Phe Leu Ala Met
        275                 280                 285

His Ile Thr Ala Gly Val Pro Arg Ala Leu Ser Ala Leu Ala Leu Ala
290                 295                 300

Phe Asn Thr Asn Leu Phe Gly Ala Ile Thr His Tyr Ser Ser Gly Gln
305                 310                 315                 320

Ala Ala Val Tyr Phe Gly Ala Gly Tyr Ser Cys Trp Ala Ser Gly Leu
                325                 330                 335

Pro Asp Val Phe Gln Ala Gly Phe Tyr Asn Ser Pro Asp Gln His Val
            340                 345                 350

Asn Leu Gly Ser Cys Trp Asn His Ser Val Glu Asn Phe Gly Glu Asn
        355                 360                 365

Ser Trp Tyr Ala Ile Arg Phe Tyr Thr His Pro Leu Cys Ala Thr Glu
370                 375                 380

Trp His Ile Gly Ile Phe Phe Gly Val Tyr Asp Met Trp Gly Gln Trp
385                 390                 395                 400

His Thr Arg Asn Glu Tyr Ile Phe Gln Trp His Thr Gly Asn Trp Pro
                405                 410                 415
```

Lys Ile Leu Gly Leu Tyr
            420

<210> SEQ ID NO 18
<211> LENGTH: 513
<212> TYPE: PRT
<213> ORGANISM: Zea mays
<220> FEATURE:
<221> NAME/KEY: MISC_FEATURE
<222> LOCATION: (1)..(513)
<223> OTHER INFORMATION: DCT2

<400> SEQUENCE: 18

Met Glu Ser Leu Arg Leu Ala Val Thr His Arg Pro Ala Leu Pro Leu
1               5                   10                  15

Pro Thr Ser His Ser His Leu Arg Arg Arg His Leu His Leu His Leu
            20                  25                  30

His Ser Tyr Pro Asn Pro Leu Ser Leu Ser Pro Pro Ile Ala Ser His
        35                  40                  45

Leu Ser Pro Ile Pro Arg Arg His Leu Pro Pro Leu Leu Ala Ser Ala
    50                  55                  60

Ser Ala Ser Gln Ala Ser Ser Lys Pro Ala Ala Ser Ala Ala Ser Gly
65                  70                  75                  80

Gly Ala Lys Pro Leu Pro Leu Phe Leu Ser Leu Ala Ala Gly Leu Ala
                85                  90                  95

Val Arg Phe Leu Val Pro Arg Pro Ala Glu Val Thr Pro Glu Ala Trp
            100                 105                 110

Gln Leu Leu Ser Ile Phe Leu Ser Thr Ile Ala Gly Leu Val Leu Gly
        115                 120                 125

Pro Leu Pro Val Gly Ala Trp Ala Phe Leu Gly Leu Thr Ala Thr Val
    130                 135                 140

Ala Thr Arg Thr Leu Pro Phe Thr Ala Ala Phe Gly Ala Phe Thr Asn
145                 150                 155                 160

Glu Val Ile Trp Leu Ile Val Ile Ser Phe Phe Ala Arg Gly Phe
                165                 170                 175

Val Lys Thr Gly Leu Gly Asp Arg Val Ala Thr Tyr Phe Val Lys Trp
            180                 185                 190

Leu Gly Arg Ser Thr Leu Gly Leu Ser Tyr Gly Leu Ala Ile Ser Glu
        195                 200                 205

Ala Leu Ile Ser Pro Ala Met Pro Ser Thr Thr Ala Arg Ala Gly Gly
    210                 215                 220

Val Phe Leu Pro Ile Val Lys Ser Leu Ser Leu Ser Ser Gly Ser Lys
225                 230                 235                 240

Pro Asn Asp Pro Ser Ala Lys Lys Leu Gly Ser Tyr Leu Val Gln Ser
                245                 250                 255

Gln Leu Gln Ala Ala Ala Asn Ser Ser Ala Leu Phe Leu Thr Ala Ala
            260                 265                 270

Ala Gln Asn Leu Leu Cys Leu Lys Leu Ala Glu Glu Ile Gly Asp Thr
        275                 280                 285

Pro Glu Ala Pro Ala Leu Ala Ala Glu Lys Leu Lys Asn Met Gly Pro
    290                 295                 300

Val Thr Lys Asn Glu Trp Val Met Ile Gly Thr Met Leu Leu Ala Val
305                 310                 315                 320

Ser Leu Trp Ile Phe Gly Glu Thr Ile Gly Val Ser Val Val Ala
                325                 330                 335

```
Ala Met Ile Gly Leu Ser Ile Leu Leu Val Leu Gly Val Leu Asn Trp
            340                 345                 350

Glu Asp Cys Leu Asn Glu Lys Ser Ala Trp Asp Thr Leu Ala Trp Phe
        355                 360                 365

Ala Ile Leu Val Gly Leu Ala Gly Gln Leu Thr Asn Leu Gly Ile Val
    370                 375                 380

Ser Trp Met Ser Asn Cys Val Ala Lys Val Leu Gln Ser Phe Ser Leu
385                 390                 395                 400

Ser Trp Pro Ala Ala Phe Val Val Leu Gln Ala Ser Tyr Phe Phe Ile
                405                 410                 415

His Tyr Ile Phe Ala Ser Gln Thr Ala His Val Gly Ala Leu Tyr Ser
            420                 425                 430

Ala Phe Leu Ala Met His Leu Ala Ala Gly Val Pro Ala Leu Met Ser
        435                 440                 445

Ala Leu Ala Leu Ala Tyr Asn Ala Asn Leu Phe Gly Ala Leu Thr His
    450                 455                 460

Tyr Ser Ser Gly Gln Ser Ala Val Tyr Phe Gly Ala Gly Tyr Val Asp
465                 470                 475                 480

Leu Pro Asp Val Phe Lys Leu Gly Phe Ile Thr Ala Ala Ile Asn Ala
                485                 490                 495

Val Ile Trp Gly Val Ala Gly Ala Leu Trp Trp Lys Phe Leu Gly Leu
            500                 505                 510

Tyr

<210> SEQ ID NO 19
<211> LENGTH: 387
<212> TYPE: PRT
<213> ORGANISM: Zea mays
<220> FEATURE:
<221> NAME/KEY: MISC_FEATURE
<222> LOCATION: (1)..(387)
<223> OTHER INFORMATION: MEP3a

<400> SEQUENCE: 19

Met Ala Ser Pro Pro Thr Ser Leu Ser Pro His Leu Ile His
1               5                   10                  15

Leu Arg Leu Gln Pro Leu Pro Ser Val Pro Leu His Leu Thr Thr
            20                  25                  30

Leu Pro Phe Leu Arg Ser Leu Pro Leu His Leu His Ser Leu Arg Leu
        35                  40                  45

Asn Arg Pro His Leu Pro Pro Leu Pro Leu Ala Ser Ser Gly Ser Gly
    50                  55                  60

Ser Asp Ile Thr Gly Ser Gly Gly Glu Asp Leu Pro Pro Ser Gly
65                  70                  75                  80

Gly Gly Gly Gly Gly Gly Gly Gly Glu Gly Asp Gly Glu Gly Glu Gly
                85                  90                  95

Asp Gly Ser Glu Gly Asp Ser Val Asn Arg Arg Glu Ala Leu Phe Val
            100                 105                 110

Leu Ala Gln Leu Gly Arg Lys Leu Glu Ser Leu Pro Ala Asp Leu Ala
        115                 120                 125

Ala Ala Val Glu Gly Gly Arg Ile Pro Gly Glu Ile Val Arg Arg Phe
    130                 135                 140

Val Asp Leu Glu Ala Ser Pro Val Phe Arg Trp Leu Leu Gln Phe Gly
145                 150                 155                 160

Gly Phe Lys Glu Arg Leu Leu Ala Asp Asp Leu Phe Leu Thr Lys Val
                165                 170                 175
```

-continued

Ala Ile Glu Cys Gly Val Gly Ile Phe Thr Lys Thr Ala Ala Glu Tyr
            180                 185                 190

Glu Lys Arg Arg Glu Asn Phe Val Lys Glu Leu Asp Phe Val Ile Ala
        195                 200                 205

Asp Val Val Met Ala Ile Val Ala Asp Phe Met Leu Val Trp Leu Pro
210                 215                 220

Ala Pro Thr Val Ser Leu Gln Pro Pro Leu Ala Met Asn Ser Gly Ala
225                 230                 235                 240

Ile Ala Lys Phe Phe Tyr Asn Cys Pro Asp Asn Ala Phe Gln Val Ala
                245                 250                 255

Leu Ser Gly Thr Ser Tyr Ser Leu Leu Gln Arg Val Gly Ala Ile Leu
            260                 265                 270

Arg Asn Gly Ala Lys Leu Phe Ala Val Gly Thr Ser Ala Ser Leu Ile
        275                 280                 285

Gly Thr Gly Val Thr Asn Ala Leu Ile Lys Ala Arg Gln Ala Ala Ser
    290                 295                 300

Lys Asp Phe Ala Gly Glu Val Glu Asn Ile Pro Ile Leu Ser Thr Ser
305                 310                 315                 320

Val Ala Tyr Gly Val Tyr Met Ala Val Ser Ser Asn Leu Arg Tyr Gln
                325                 330                 335

Val Leu Ala Gly Val Ile Glu Gln Arg Met Leu Glu Pro Leu Leu His
            340                 345                 350

Gln His Lys Leu Val Leu Ser Ala Ala Cys Phe Ala Val Arg Thr Gly
        355                 360                 365

Asn Thr Phe Leu Gly Ser Leu Leu Trp Ile Asp Tyr Ala Arg Trp Ile
    370                 375                 380

Gly Val Gln
385

<210> SEQ ID NO 20
<211> LENGTH: 738
<212> TYPE: PRT
<213> ORGANISM: Zea mays
<220> FEATURE:
<221> NAME/KEY: MISC_FEATURE
<222> LOCATION: (1)..(738)
<223> OTHER INFORMATION: MEP3b

<400> SEQUENCE: 20

Met Leu Pro His Ala Pro Ser Arg Thr Ser Gly Ala Leu Arg Phe Lys
1               5                   10                  15

Pro His Leu Pro Thr Lys Pro Pro Leu Thr Ser Ser Ser Thr Ala
            20                  25                  30

Thr Pro Ala Ser Ala Ser Ala Ser Thr Arg Gly Arg Leu Cys Ala Ala
        35                  40                  45

Ala Ala Ala Ala Ala Thr Arg Arg Asp Leu Leu Val Leu Val Pro Ser
    50                  55                  60

Leu Val Ala Ala Ser Thr Val Leu Gln Ser Leu Pro Leu Ala Ala Ser
65                  70                  75                  80

Ala Ala Ala Gly Asp Asp Lys Pro Ala Pro Thr Pro Ala Gln Ala
                85                  90                  95

Gln Ala Pro Ala Ser Pro Ala Ser Pro Pro Pro Pro Pro Ala Asp
            100                 105                 110

Glu Pro Ala Leu Ser Arg Val Tyr Asp Ala Thr Val Ile Gly Glu Pro
        115                 120                 125

-continued

```
Gln Ala Val Gly Lys Glu Ala Arg Arg Val Trp Glu Lys Leu Ile
130                 135                 140
Ala Ala Arg Val Val Tyr Leu Gly Glu Ser Glu Leu Val Pro Asp Arg
145                 150                 155                 160
Asp Asp Arg Val Leu Glu Leu Glu Ile Val Arg Lys Leu Ala Ala Gly
                165                 170                 175
Cys Ala Glu Ala Gly Arg Ser Ile Ser Leu Ala Leu Glu Ala Phe Pro
            180                 185                 190
Cys Asp Leu Gln Glu Gln Leu Asn Arg Phe Met Asp Gly Arg Ile Asp
        195                 200                 205
Gly Asn Thr Leu Arg Leu Tyr Thr Ser His Trp Ala Pro Glu Arg Trp
    210                 215                 220
Gln Glu Tyr Glu Pro Leu Leu Asn Tyr Cys Arg Asp Asn Gly Ile Lys
225                 230                 235                 240
Leu Val Ala Cys Gly Thr Pro Leu Glu Val Val Arg Thr Val Gln Ala
                245                 250                 255
Glu Gly Ile Arg Ser Leu Ser Lys Ala Gln Arg Lys Leu Tyr Ala Pro
                260                 265                 270
Pro Ala Gly Ser Gly Phe Val Ser Gly Phe Thr Ser Ile Ser Gly Arg
            275                 280                 285
Ser Leu Ile Asp Lys Ile Ser Ser Thr Arg Gly Ser Pro Phe Gly Pro
        290                 295                 300
Ser Ser Tyr Leu Ser Ala Gln Ala Arg Val Val Asp Asp Tyr Thr Met
305                 310                 315                 320
Ser Gln Thr Ile Met Lys Glu Ile Ser Asn Gly Asp Pro Ser Gly Met
                325                 330                 335
Leu Val Val Val Thr Gly Ala Ser His Val Met Tyr Gly Pro Arg Gly
                340                 345                 350
Ile Gly Val Pro Ala Arg Ile Ser Lys Lys Met Gln Lys Lys Asn Gln
            355                 360                 365
Val Val Ile Leu Leu Asp Pro Glu Arg Gln Ser Ile Arg Arg Glu Gly
        370                 375                 380
Glu Ile Pro Val Ala Asp Phe Leu Trp Tyr Ser Ala Ala Lys Pro Cys
385                 390                 395                 400
Ser Arg Asn Cys Phe Asp Arg Ala Glu Ile Ala Arg Val Met Asn Ala
                405                 410                 415
Ala Gly Arg Arg Arg Glu Ala Leu Pro Gln Asp Leu Gln Lys Gly Ile
                420                 425                 430
Asp Leu Gly Val Val Ser Pro Glu Ile Leu Gln Asn Phe Phe Asp Leu
            435                 440                 445
Glu Lys Tyr Pro Val Met Ala Glu Leu Ile His Arg Phe Gln Gly Phe
        450                 455                 460
Arg Glu Arg Leu Leu Ala Asp Pro Lys Phe Leu Asn Arg Leu Ala Ile
465                 470                 475                 480
Glu Glu Ala Ile Ser Ile Thr Thr Thr Leu Leu Ala Gln Tyr Glu Lys
                485                 490                 495
Arg Lys Gly Arg Phe Phe Glu Glu Ile Asp Tyr Val Leu Thr Asp Thr
            500                 505                 510
Ile Arg Gly Ser Val Val Asp Phe Phe Thr Val Trp Leu Pro Ala Pro
        515                 520                 525
Thr Ile Ser Leu Leu Ser Phe Ala Asp Asp Gly Ser Gly Glu Ser Val
    530                 535                 540
Glu Leu Leu Lys Gly Ile Leu Gly Ser Leu Pro Asp Asn Ala Phe Gln
```

```
545                 550                 555                 560
Lys Gly Ile Val Gly Gln Asn Trp Asn Ile Asn Gln Arg Phe Ala Ser
                565                 570                 575

Val Leu Met Gly Gly Leu Lys Leu Ala Gly Val Gly Phe Ile Ser Ser
                580                 585                 590

Ile Gly Ala Gly Val Ala Ser Asp Val Leu Tyr Gly Ala Arg Arg Ile
                595                 600                 605

Leu Lys Pro Ser Ala Asn Met Glu Val Gly Arg Lys Arg Ser Pro Ile
        610                 615                 620

Trp Lys Ser Ala Ala Val Tyr Ser Cys Phe Leu Gly Thr Ser Ala Asn
625                 630                 635                 640

Leu Arg Tyr Gln Val Ile Ala Gly Leu Ile Glu His Arg Leu Gly Glu
                645                 650                 655

Asn Leu Met Ala Tyr Tyr Asp Gln Pro Leu Ile Ala Asn Leu Leu Ser
                660                 665                 670

Phe Val Ser Arg Thr Val Asn Ser Tyr Trp Gly Thr Gln Gln Trp Ile
        675                 680                 685

Asp Leu Ala Arg Val Thr Gly Val Gln Arg Thr Asn Lys Glu Leu Pro
        690                 695                 700

Ser Pro Glu Val Ser Ser Ala Ser Glu Met Pro Leu Leu Glu Cys Gly
705                 710                 715                 720

Thr Ala Glu Val Gln Asn Ala Asp Asp Ser Ser Asn Gln Ser Asn Asp
                725                 730                 735

Leu Thr

<210> SEQ ID NO 21
<211> LENGTH: 415
<212> TYPE: PRT
<213> ORGANISM: Zea mays
<220> FEATURE:
<221> NAME/KEY: MISC_FEATURE
<222> LOCATION: (1)..(415)
<223> OTHER INFORMATION: MEP3c

<400> SEQUENCE: 21

Met Ala Leu Pro Pro Ser Ser Pro Ser Ser Leu Ser Ala Ala Ser
1               5                   10                  15

Ala Gln Pro Thr Pro Leu His Leu His Leu Pro Thr Lys Ala Pro Gly
                20                  25                  30

Arg Leu Pro Leu Leu Pro Phe Ser Arg Ala Ala Leu Pro Pro Pro Leu
        35                  40                  45

Arg Leu Arg Ile Ala Arg Thr Ser Leu Ser Pro Gly Thr Pro Leu Pro
        50                  55                  60

Arg Ala Leu Leu Pro Pro Pro Ser Ala Ser Ala Asp Ala Ala Ala Ser
65                  70                  75                  80

Asp Val Gly Gly Gly Gly Ala Gly Phe Gly Gly His Asp Asp Asp Gly
                85                  90                  95

His Asn His His Gly Gly Glu Gly Gly Gly Asp Gly His Gly
                100                 105                 110

Asp Asp Ala Gly His Gly Asp Asp Ala Pro Gly Gly Gly Asp Ala Arg
        115                 120                 125

Gly Glu Ala Leu Phe Val Leu Ala Gln Leu Gly Arg Lys Leu Asp Ser
        130                 135                 140

Leu Pro Ser Asp Leu Ala Ala Ala Val Asp Ser Gly Arg Ile Gly Ala
145                 150                 155                 160
```

```
Asp Ile Val Arg Arg Phe Thr Glu Leu Glu Ala Asn Gly Phe Phe Arg
            165                 170                 175

Trp Leu Leu Gln Phe Gln Gly Phe Arg Glu Arg Leu Leu Ala Asp Glu
        180                 185                 190

Leu Phe Leu Thr Lys Leu Gly Ile Glu Cys Gly Ile Gly Leu Val Ala
    195                 200                 205

Lys Thr Val Ala Glu Phe Gln Lys Arg Gly Asp Asn Phe Phe Lys Glu
210                 215                 220

Ile Glu Val Val Ile Ser Asp Val Val Met Ala Ile Val Ala Asp Val
225                 230                 235                 240

Met Leu Val Tyr Leu Pro Ala Pro Thr Ile Gly Leu Gln Pro Pro Leu
                245                 250                 255

Ala Arg Asn Ala Gly Ala Ile Ala Asn Phe Phe Tyr Asn Cys Pro Asp
            260                 265                 270

Asn Thr Phe Gln Ile Ala Met Ala Gly Arg Ser Phe Ser Leu Leu Gln
        275                 280                 285

Arg Ile Gly Ala Phe Val Arg Asn Gly Ile Lys Leu Leu Ala Val Gly
    290                 295                 300

Thr Thr Ala Ser Leu Ile Gly Thr Ser Val Thr Asn Ala Ala Leu Lys
305                 310                 315                 320

Ala Lys Arg Ala Val Asp Lys Asp Leu Glu Asp Val Met Glu Ile
                325                 330                 335

Pro Val Val Ser Thr Ser Val Ala Tyr Gly Val Tyr Met Ser Ile Ser
                340                 345                 350

Ser Asn Leu Arg Tyr Gln Leu Leu Ala Gly Val Ile Glu Gln Arg Met
            355                 360                 365

Leu Glu Pro Leu Leu His Asn Gln Lys Leu Leu Ser Ala Met Cys
        370                 375                 380

Phe Ile Val Arg Thr Gly Asn Thr Phe Leu Gly Ser Leu Leu Trp Val
385                 390                 395                 400

Asp Tyr Ala Arg Trp Ile Gly Val Gln Lys Ser His Glu Glu Ala
                405                 410                 415

<210> SEQ ID NO 22
<211> LENGTH: 274
<212> TYPE: PRT
<213> ORGANISM: Zea mays
<220> FEATURE:
<221> NAME/KEY: MISC_FEATURE
<222> LOCATION: (1)..(274)
<223> OTHER INFORMATION: NHD

<400> SEQUENCE: 22

Met Ala Leu Ser Cys Tyr Leu Leu Ala Gly Ala Arg Ala Ala Ser
1               5                   10                  15

Pro Ser Phe Ser Ser Ala Ala Ile Arg Arg Arg Asp His Arg Leu
            20                  25                  30

Leu Thr Leu Ser Val Val Pro Leu Ser Leu Ser Gln Arg Cys Arg His
        35                  40                  45

Gly Leu Arg Val Cys Cys Ala Ser Ser Thr Ser Ser Ser Pro Pro
    50                  55                  60

Pro Ala Thr Pro Glu Glu Pro Asp Asp Tyr Glu Leu Leu Asp Thr Ala
65                  70                  75                  80

Gly Asn Cys Asp Pro Leu Cys Ser Ala Asp Glu Val Ser Ser Gln Tyr
                85                  90                  95

Phe Glu Ala Asn Tyr Lys Pro Lys Asn Asp Leu Leu Lys Ala Leu Thr
```

```
            100                 105                 110
Ile Ile Gly Thr Ala Leu Thr Gly Ala Ala Ile Asn His Ser Trp
            115                 120                 125

Val Ala Ala Asn Gln Asp Ile Ala Met Val Leu Val Phe Ala Ile Gly
130                 135                 140

Tyr Ala Gly Ile Val Phe Glu Glu Ser Leu Ala Phe Asn Lys Ser Gly
145                 150                 155                 160

Val Ala Leu Leu Met Ala Val Cys Leu Trp Val Ile Arg Gly Ile Gly
                165                 170                 175

Ala Pro Ser Thr Asp Val Ala Val Gln Glu Leu Ser Gln Ser Thr Ser
                180                 185                 190

Glu Val Ser Glu Ile Val Phe Phe Leu Leu Gly Ala Met Thr Ile Val
                195                 200                 205

Glu Ile Val Asp Ala His Gln Gly Phe Lys Leu Val Thr Asp Asn Ile
                210                 215                 220

Ser Thr Arg Asn Pro Lys Thr Leu Leu Trp Val Ile Gly Ile Val Thr
225                 230                 235                 240

Phe Phe Leu Ser Ser Ile Leu Asp Asn Leu Thr Ser Thr Ile Val Met
                245                 250                 255

Val Ser Leu Leu Arg Lys Leu Val Pro Pro Ser Glu Tyr Arg Lys Tyr
                260                 265                 270

Ala Phe

<210> SEQ ID NO 23
<211> LENGTH: 395
<212> TYPE: PRT
<213> ORGANISM: Zea mays
<220> FEATURE:
<221> NAME/KEY: MISC_FEATURE
<222> LOCATION: (1)..(395)
<223> OTHER INFORMATION: PPT1

<400> SEQUENCE: 23

Met Gln Ser Ala Ala Ala Phe Arg Pro Cys Pro Thr Arg Leu Leu Val
1               5                   10                  15

Ser Ser Pro Cys Arg Pro Leu Leu Ser Ala Arg Pro Leu Arg Ala Ser
                20                  25                  30

Ala Ala Gly Ala Val Ala Thr Arg Ser Ser Ala Val Gly Pro Arg Gly
            35                  40                  45

Leu Gly Leu Gly Leu Leu Pro Ala Ser Pro Asp Arg Asp Gly Lys Cys
50                  55                  60

Arg Gln Arg Gln Val Ser Cys Ser Ala Ala Gly Asp Ala Val Ala Ala
65                  70                  75                  80

Pro Lys Ala Glu Glu Gly Gly Gly Leu Met Lys Thr Leu Trp Leu Gly
                85                  90                  95

Ser Leu Phe Gly Leu Trp Tyr Leu Phe Asn Ile Tyr Phe Asn Ile Tyr
                100                 105                 110

Asn Lys Gln Val Leu Lys Val Phe Pro Tyr Pro Ile Asn Ile Thr Glu
            115                 120                 125

Val Gln Phe Ala Val Gly Thr Val Ala Ala Leu Phe Met Trp Ile Thr
130                 135                 140

Gly Ile Ile Lys Arg Pro Lys Ile Ser Gly Ala Gln Leu Val Ala Ile
145                 150                 155                 160

Leu Pro Leu Ala Ile Val His Thr Met Gly Asn Leu Phe Thr Asn Met
                165                 170                 175
```

```
Ser Leu Gly Lys Val Ala Val Ser Phe Thr His Thr Ile Lys Ala Met
            180                 185                 190

Glu Pro Phe Phe Ser Val Ile Leu Ser Ala Ile Phe Leu Gly Glu Leu
            195                 200                 205

Pro Thr Ile Trp Val Val Ser Ser Leu Leu Pro Ile Val Gly Gly Val
        210                 215                 220

Ala Leu Ala Ser Leu Thr Glu Ala Ser Phe Asn Trp Ala Gly Phe Trp
225                 230                 235                 240

Ser Ala Met Ala Ser Asn Val Thr Phe Gln Ser Arg Asn Val Leu Ser
                245                 250                 255

Lys Lys Leu Met Val Lys Lys Glu Glu Ser Leu Asp Asn Leu Asn Leu
            260                 265                 270

Phe Ser Ile Ile Thr Val Met Ser Phe Phe Leu Leu Ala Pro Val Thr
        275                 280                 285

Phe Phe Thr Glu Gly Val Lys Ile Thr Pro Thr Phe Leu Gln Ser Ala
290                 295                 300

Gly Leu Asn Val Asn Gln Val Leu Thr Arg Cys Leu Phe Ala Gly Leu
305                 310                 315                 320

Cys Phe His Ala Tyr Gln Gln Val Ser Tyr Met Ile Leu Ala Met Val
                325                 330                 335

Ser Pro Val Thr His Ser Val Gly Asn Cys Val Lys Arg Val Val Val
            340                 345                 350

Ile Val Thr Ser Val Leu Phe Phe Arg Thr Pro Val Ser Pro Ile Asn
        355                 360                 365

Ser Leu Gly Thr Ala Ile Ala Leu Ala Gly Val Phe Leu Tyr Ser Gln
370                 375                 380

Leu Lys Arg Leu Lys Pro Lys Pro Lys Thr Ala
385                 390                 395

<210> SEQ ID NO 24
<211> LENGTH: 415
<212> TYPE: PRT
<213> ORGANISM: Zea mays
<220> FEATURE:
<221> NAME/KEY: MISC_FEATURE
<222> LOCATION: (1)..(415)
<223> OTHER INFORMATION: PPT2

<400> SEQUENCE: 24

Met Met Gln Gly Ala Ala Ala Gly Gly Thr Ser Val Ser Gly Ala Ser
1               5                   10                  15

Trp Ala Arg Ala Thr Arg Gly Arg Ala Ala Val Leu Ala Ser Arg His
            20                  25                  30

Val Gly Val Gly Ala Ser Ser Ser Asp Tyr Tyr Asn His Phe Gly
        35                  40                  45

Pro Arg Gly Ala Thr Ala Ala Pro Leu Leu Arg Ala Arg Gly Gly Gly
    50                  55                  60

Arg Leu Arg Pro Leu Pro Leu Ser Gly Ser Gly Lys Asn Gly Glu
65                  70                  75                  80

Val Ala Lys Ala Ala Ala Ala Ala Ser Val Pro Ala Asp Asp Ala
                85                  90                  95

Ser Ala Ala Ala Val Thr Thr Asp Gly Gly Ile Ala Ala Thr Ala
            100                 105                 110

Gln Leu Gly Ala Met Ile Val Ala Trp Tyr Leu Leu Asn Ile Tyr Phe
        115                 120                 125

Asn Ile Tyr Asn Lys Gln Val Leu Gly Ala Leu Pro Leu Pro Leu Pro
```

```
                130               135                140
Tyr Thr Ile Thr Ala Phe Gln Leu Ala Phe Gly Ser Leu Leu Ile Phe
145                 150                 155                 160

Leu Met Trp Ala Thr Arg Leu His Pro Ala Pro Arg Leu Ser Ala Ala
                165                 170                 175

Gln Leu Gly Lys Ile Ala Pro Leu Ala Val Gly His Met Leu Gly Thr
                180                 185                 190

Val Phe Thr Asn Met Ser Leu Gly Lys Val Ala Val Ser Phe Thr His
                195                 200                 205

Thr Ile Lys Ala Ser Glu Pro Phe Phe Thr Val Val Leu Ser Ala Leu
210                 215                 220

Phe Leu Gly Glu Val Pro Ser Leu Pro Val Leu Gly Ser Leu Val Pro
225                 230                 235                 240

Ile Val Gly Gly Val Ala Leu Ala Ser Phe Thr Glu Val Ser Phe Asn
                245                 250                 255

Trp Thr Gly Phe Trp Ser Ala Met Ala Ser Asn Leu Thr Asn Gln Ser
                260                 265                 270

Arg Asn Val Leu Ser Lys Lys Leu Leu Ala Gly Asp Lys Asp Val Met
                275                 280                 285

Asp Asp Ile Asn Leu Phe Ser Val Ile Thr Val Leu Ser Phe Leu Leu
290                 295                 300

Ser Cys Pro Leu Met Ile Phe Ala Glu Gly Ile Lys Phe Thr Pro Gly
305                 310                 315                 320

Tyr Leu Gln Ser Thr Gly Leu Asn Leu Gln Glu Leu Cys Val Arg Ala
                325                 330                 335

Ala Leu Ala Gly Leu Cys Phe His Gly Tyr Gln Lys Leu Ser Tyr Leu
                340                 345                 350

Ile Leu Ser Arg Val Ser Pro Val Thr His Ser Val Ala Asn Cys Val
                355                 360                 365

Lys Arg Val Val Val Ile Val Ser Ser Val Leu Phe Phe Ser Thr Pro
                370                 375                 380

Ile Ser Pro Val Asn Ala Leu Gly Thr Gly Ala Ala Leu Ala Gly Val
385                 390                 395                 400

Phe Leu Tyr Ser Arg Leu Thr Arg Thr Lys Lys Pro Lys Asp Ala
                405                 410                 415

<210> SEQ ID NO 25
<211> LENGTH: 404
<212> TYPE: PRT
<213> ORGANISM: Zea mays
<220> FEATURE:
<221> NAME/KEY: MISC_FEATURE
<222> LOCATION: (1)..(404)
<223> OTHER INFORMATION: TPT

<400> SEQUENCE: 25

Met Ser Ala Leu Gly Thr Leu Ser Gly Gly Ala Ala Gly Val Ser Gly
1               5                   10                  15

Leu Ile Arg Leu Arg Arg Arg Val Ala Pro Ala Leu Ala Ala Pro Ser
                20                  25                  30

His His Ala Ala Gly Thr Leu Asn Cys Ala Ala Leu Pro Asp Ala Ala
                35                  40                  45

Pro Leu Val Trp Gly Arg Gln Leu Arg Pro Ser Leu Leu Leu Pro Ala
                50                  55                  60

Thr Leu Leu Pro Ser Ser Ser Gln Gly Ala Arg Arg His Thr Pro Arg
65                  70                  75                  80
```

Arg Pro Ala Ala Ala Ala Gly Glu Ala Lys Ser Val Gly Phe Leu Glu
                85                  90                  95

Lys Tyr Pro Ala Leu Val Thr Gly Phe Phe Phe Met Trp Tyr Phe
            100                 105                 110

Leu Asn Val Ile Phe Asn Ile Leu Asn Lys Lys Ile Tyr Asn Tyr Phe
            115                 120                 125

Pro Tyr Pro Tyr Phe Val Ser Leu Ile His Leu Val Gly Val Val
            130                 135                 140

Tyr Cys Leu Ile Ser Trp Ser Val Gly Leu Pro Lys Arg Ala Pro Ile
145                 150                 155                 160

Asn Gly Thr Leu Leu Lys Leu Leu Phe Pro Val Ala Leu Cys His Gly
            165                 170                 175

Ile Gly His Ile Thr Ser Asn Val Ser Phe Ala Ala Val Ala Val Ser
            180                 185                 190

Phe Ala His Thr Ile Lys Ala Leu Glu Pro Phe Phe Ser Ala Ala Ala
            195                 200                 205

Thr Gln Phe Ile Leu Gly Gln Gln Val Pro Phe Ser Leu Trp Leu Ser
210                 215                 220

Leu Ala Pro Val Val Ile Gly Val Ser Met Ala Ser Leu Thr Glu Leu
225                 230                 235                 240

Ser Phe Asn Trp Thr Gly Phe Ile Asn Ala Met Ile Ser Asn Ile Ser
            245                 250                 255

Phe Thr Tyr Arg Ser Ile Tyr Ser Lys Lys Ala Met Thr Asp Met Asp
            260                 265                 270

Ser Thr Asn Val Tyr Ala Tyr Ile Ser Ile Ala Leu Ile Val Cys
            275                 280                 285

Ile Pro Pro Ala Val Ile Phe Glu Gly Pro Arg Leu Met Gln His Gly
290                 295                 300

Phe Ser Asp Ala Ile Ala Lys Val Gly Leu Thr Lys Phe Val Ser Asp
305                 310                 315                 320

Leu Phe Leu Val Gly Leu Phe Tyr His Leu Tyr Asn Gln Ile Ala Thr
            325                 330                 335

Asn Thr Leu Glu Arg Val Ala Pro Leu Thr His Ala Val Gly Asn Val
            340                 345                 350

Leu Lys Arg Val Phe Val Ile Gly Phe Ser Ile Val Val Phe Gly Asn
            355                 360                 365

Lys Ile Ser Thr Gln Thr Gly Ile Gly Thr Ser Ile Ala Ile Ala Gly
            370                 375                 380

Val Ala Met Tyr Ser Tyr Ile Lys Ala Lys Ile Glu Glu Glu Lys Arg
385                 390                 395                 400

Lys Lys Ser Ala

<210> SEQ ID NO 26
<211> LENGTH: 584
<212> TYPE: PRT
<213> ORGANISM: Sorghum bicolor
<220> FEATURE:
<221> NAME/KEY: MISC_FEATURE
<222> LOCATION: (1)..(584)
<223> OTHER INFORMATION: OMT

<400> SEQUENCE: 26

Met Ala Ser Ser Thr Ala Ala Ser Pro Leu Thr Cys His His Leu Gly
1               5                   10                  15

Ser Val Gly Ala Arg Pro Ser Leu Pro Ser Leu Ser Phe Gly Pro Leu

```
                20                  25                  30
Arg Arg Arg Ser Ser Ser Lys Pro Ile Ser Leu Ser His Ser Leu Pro
            35                  40                  45
Ser Lys Pro Ser Ser Leu Ala Pro Pro Ala Ala Ser Ser Ser Ala
50                  55                  60
Ser Ala Ser Ser Ser Ser Arg Arg Gly Leu Thr Pro Val Ser Ala Ser
65                  70                  75                  80
Ala Ser Ala Ala Ala Pro Ala Pro Asp Pro Val Pro Ala Pro Ala
            85                  90                  95
Pro Ala Pro Ala Pro Ala Pro Ala Ala Pro Pro Lys Lys Pro
            100                 105                 110
Ala Leu Gln Gly Ala Ala Ile Lys Pro Leu Leu Ala Ser Leu Ala Ile
            115                 120                 125
Gly Val Leu Ile Trp Phe Leu Pro Ala Pro Ala Gly Val Pro Arg Asn
            130                 135                 140
Ala Trp Gln Leu Leu Ala Ile Phe Leu Ser Thr Ile Val Gly Ile Ile
145                 150                 155                 160
Thr Gln Pro Leu Pro Leu Gly Ala Val Ala Leu Leu Gly Leu Gly Ala
            165                 170                 175
Ala Val Leu Thr Lys Thr Leu Thr Phe Ala Ala Ala Phe Ser Ala Phe
            180                 185                 190
Gly Asp Pro Ile Pro Trp Leu Ile Ala Leu Ala Phe Phe Ala Arg
            195                 200                 205
Gly Phe Ile Lys Thr Gly Leu Gly Ser Arg Val Ala Tyr Ala Phe Val
            210                 215                 220
Ala Ala Phe Gly Ser Ser Ser Leu Gly Leu Gly Tyr Ser Leu Val Phe
225                 230                 235                 240
Ala Glu Ala Leu Leu Ala Pro Ala Ile Pro Ser Val Ser Ala Arg Ala
            245                 250                 255
Gly Gly Ile Phe Leu Pro Leu Val Lys Ser Leu Cys Glu Ala Cys Gly
            260                 265                 270
Ser Arg Ala Gly Asp Gly Thr Glu Arg Lys Leu Gly Ala Trp Leu Met
            275                 280                 285
Leu Thr Cys Phe Gln Thr Ser Val Val Ser Ser Ala Met Phe Leu Thr
            290                 295                 300
Ala Met Ala Ala Asn Pro Leu Ser Ala Asn Leu Thr Ala Ala Thr Ile
305                 310                 315                 320
Gly Gln Gly Ile Gly Trp Thr Leu Trp Ala Lys Ala Ala Ile Val Pro
            325                 330                 335
Gly Leu Leu Ser Leu Val Leu Pro Leu Ile Leu Tyr Val Ile Tyr
            340                 345                 350
Pro Pro Glu Val Lys Ala Ser Pro Asp Ala Pro Arg Leu Ala Lys Glu
            355                 360                 365
Arg Leu Ala Lys Met Gly Pro Met Ser Thr Glu Glu Lys Ile Met Ala
            370                 375                 380
Gly Thr Leu Leu Leu Thr Val Gly Leu Trp Ile Phe Gly Gly Met Leu
385                 390                 395                 400
Ser Val Asp Ala Val Ser Ala Ala Ile Leu Gly Leu Gly Val Leu Leu
            405                 410                 415
Ile Thr Gly Val Val Thr Trp Lys Glu Cys Leu Ala Glu Ser Val Ala
            420                 425                 430
Trp Asp Thr Leu Thr Trp Phe Ala Ala Leu Ile Ala Met Ala Gly Tyr
            435                 440                 445
```

```
Leu Asn Lys Tyr Gly Phe Ile Ser Trp Phe Ser Glu Thr Val Val Lys
    450                 455                 460

Phe Val Gly Gly Leu Gly Leu Ser Trp Gln Ala Ser Phe Gly Val Leu
465                 470                 475                 480

Val Leu Leu Tyr Phe Tyr Ser His Tyr Phe Ala Ser Gly Ala Ala
            485                 490                 495

His Ile Gly Ala Met Phe Ala Ala Phe Leu Ser Val Ala Ser Ala Leu
            500                 505                 510

Gly Thr Pro Ser Leu Phe Ala Ala Met Val Leu Ser Phe Leu Ser Asn
            515                 520                 525

Leu Met Gly Gly Thr Thr His Tyr Gly Ile Gly Ser Ala Pro Val Phe
    530                 535                 540

Tyr Gly Ala Gly Tyr Val Pro Leu Ala Gln Trp Trp Gly Tyr Gly Phe
545                 550                 555                 560

Val Ile Ser Ile Val Asn Ile Ile Ile Trp Leu Gly Ala Gly Gly Phe
                565                 570                 575

Trp Trp Lys Met Ile Gly Leu Trp
            580

<210> SEQ ID NO 27
<211> LENGTH: 557
<212> TYPE: PRT
<213> ORGANISM: Sorghum bicolor
<220> FEATURE:
<221> NAME/KEY: MISC_FEATURE
<222> LOCATION: (1)..(557)
<223> OTHER INFORMATION: DCT1

<400> SEQUENCE: 27

Met Glu Asn Leu His Leu Ala Ile Ala His Arg Pro Pro Leu Pro Val
1               5                   10                  15

Pro Ala Ala Gly His Leu Arg Arg His Leu His Leu His His Leu
            20                  25                  30

Pro Ala Pro Leu Ser Leu Pro Ser Thr Ser His Ser Leu Ser Ser Pro
            35                  40                  45

His His His Arg Leu Thr Pro Thr Leu Arg Arg His Leu Arg Pro Pro
    50                  55                  60

Leu Arg Val Ser Gln Thr Pro Asp Ala Asn Pro Glu Pro Glu Pro Glu
65                  70                  75                  80

Pro Glu Ser Glu Pro Thr Gly Ala Lys Leu Val Pro Phe Val Ile Ser
                85                  90                  95

Val Ala Val Gly Leu Ala Val Arg Phe Leu Ala Pro Arg Pro Val Glu
            100                 105                 110

Val Ser Pro Gln Ala Trp Gln Leu Leu Ser Ile Phe Leu Ser Thr Ile
            115                 120                 125

Ala Gly Leu Val Leu Gly Pro Leu Pro Val Gly Ala Trp Ala Phe Leu
    130                 135                 140

Gly Leu Thr Ala Ala Val Ala Thr Arg Thr Leu Pro Phe Ala Ala Ala
145                 150                 155                 160

Phe Ser Ala Phe Thr Asn Glu Val Ile Trp Leu Ile Val Ile Ser Phe
                165                 170                 175

Phe Phe Ala Arg Gly Phe Val Lys Thr Gly Leu Gly Asp Arg Ile Ala
            180                 185                 190

Thr Tyr Phe Val Lys Trp Leu Gly Ser Ser Thr Leu Gly Leu Ser Tyr
            195                 200                 205
```

Gly Leu Thr Ile Ser Glu Ala Cys Ile Ala Pro Ala Met Pro Ser Thr
210                 215                 220

Thr Ala Arg Ala Gly Gly Val Phe Leu Pro Ile Ile Lys Ser Leu Ser
225                 230                 235                 240

Leu Ser Ala Glu Ser Lys Pro Asn His Pro Ser Ser Arg Lys Leu Gly
            245                 250                 255

Ser Tyr Leu Val Met Thr Gln Phe Gln Ala Ser Gly Asn Ser Ser Ala
            260                 265                 270

Leu Phe Leu Thr Ala Ala Ala Gln Asn Leu Leu Cys Leu Lys Leu Ala
        275                 280                 285

Glu Glu Leu Gly Val Phe Ile Ala Asn Pro Trp Val Ser Trp Phe Lys
290                 295                 300

Ala Ala Ser Leu Pro Ala Leu Ala Ala Leu Leu Ala Thr Pro Tyr Leu
305                 310                 315                 320

Leu Tyr Lys Ile Phe Pro Pro Glu Thr Lys Asp Thr Pro Asp Ala Pro
                325                 330                 335

Ala Leu Ala Glu Glu Lys Leu Lys Arg Met Gly Pro Val Thr Lys Asn
                340                 345                 350

Glu Trp Val Met Ile Gly Thr Met Ile Leu Ala Val Ser Leu Trp Val
            355                 360                 365

Phe Gly Asp Ala Ile Gly Val Pro Ser Val Val Ala Ala Met Leu Gly
370                 375                 380

Leu Ser Ile Leu Leu Leu Gly Val Leu Asp Trp Asp Asp Cys Leu
385                 390                 395                 400

Asn Glu Lys Ser Ala Trp Asp Thr Leu Ala Trp Phe Ala Val Leu Val
                405                 410                 415

Gly Met Ala Ala Gln Leu Thr Asn Leu Gly Ile Val Ser Trp Met Ser
            420                 425                 430

Ser Cys Val Ala Lys Leu Leu Gln Ser Phe Ser Leu Ser Trp Pro Val
        435                 440                 445

Ala Phe Cys Ile Leu Glu Gly Ser Tyr Phe Leu Ile His Tyr Leu Phe
        450                 455                 460

Ala Ser Gln Thr Gly His Val Gly Ala Leu Tyr Ser Ala Phe Leu Ala
465                 470                 475                 480

Met His Ile Ala Ala Gly Val Pro Arg Ala Leu Ser Ala Leu Ala Leu
                485                 490                 495

Ala Phe Asn Thr Asn Leu Phe Gly Ala Ile Thr His Tyr Ser Ser Gly
            500                 505                 510

Gln Ala Ala Val Tyr Phe Gly Ala Gly Tyr Ile Glu Leu Pro Asp Val
        515                 520                 525

Phe Arg Leu Gly Phe Ile Thr Ala Leu Ile Asn Thr Phe Ile Trp Gly
530                 535                 540

Val Val Gly Thr Ile Trp Trp Lys Phe Leu Gly Leu Tyr
545                 550                 555

<210> SEQ ID NO 28
<211> LENGTH: 563
<212> TYPE: PRT
<213> ORGANISM: Sorghum bicolor
<220> FEATURE:
<221> NAME/KEY: MISC_FEATURE
<222> LOCATION: (1)..(563)
<223> OTHER INFORMATION: DCT4

<400> SEQUENCE: 28

Met Glu Ser Ser Ile Arg Leu Ala Asp Thr Leu Arg Pro Ser Ser Leu

-continued

```
1               5                   10                  15
Pro Ala Pro Ala Ser Ala His Leu Arg Arg His Leu Tyr Leu His
                20                  25                  30
Arg Leu Pro Arg Thr Ser Ser Ser Ser Leu Phe Phe Ser Pro Ser
                35                  40                  45
His His His Arg Leu Cys Pro Thr Pro Arg His Asp Leu Leu Gln Pro
    50                      55                  60
Leu Ala Ala Ala Ala Ser Gly Ala Ala Lys Leu Val Pro Ala Ser Pro
65                  70                  75                  80
Ala Pro Ala Asp Ser Ser Pro Glu Pro Lys Pro Ser Gly Ala Lys Leu
                    85                  90                  95
Val Pro Leu Val Ile Ser Leu Ala Val Gly Leu Ala Val Arg Phe Leu
                100                 105                 110
Ala Pro Arg Pro Ala Glu Val Ser Pro Arg Ala Trp Gln Leu Leu Ser
                115                 120                 125
Ile Phe Leu Ser Thr Ile Ala Gly Leu Val Leu Gly Pro Leu Pro Val
                130                 135                 140
Gly Ala Trp Ala Phe Leu Gly Leu Thr Ala Ala Val Ala Thr His Thr
145                 150                 155                 160
Leu Pro Phe Ala Ala Ala Phe Ala Ala Phe Thr Asn Glu Ile Ile Trp
                    165                 170                 175
Leu Ile Val Ile Ser Phe Phe Ala Arg Gly Phe Val Lys Thr Gly
                180                 185                 190
Leu Gly Asp Arg Val Ala Thr Tyr Phe Val Lys Trp Leu Gly Lys Ser
                195                 200                 205
Thr Leu Gly Leu Ser Tyr Gly Leu Ala Leu Gly Glu Ala Cys Ile Ala
    210                 215                 220
Pro Ala Met Pro Ser Thr Ala Arg Ala Gly Gly Ile Phe Leu Pro
225                 230                 235                 240
Ile Ile Lys Ser Leu Ser Leu Ser Ala Gly Ser Lys Pro Asn His Pro
                245                 250                 255
Ser Ser Arg Lys Leu Gly Thr Tyr Leu Val Met Ser Gln Phe Gln Ala
                260                 265                 270
Ala Ser Ser Ser Ala Leu Phe Leu Thr Ala Gly Ala Gln Asn Leu
                275                 280                 285
Leu Cys Leu Asn Leu Ala Glu Lys Phe Gly Val Ile Ile Ala Asn Pro
                290                 295                 300
Trp Val Thr Trp Phe Lys Ala Ala Ser Leu Pro Ala Ile Val Ser Leu
305                 310                 315                 320
Leu Ala Thr Pro Tyr Leu Leu Tyr Lys Ile Phe Pro Pro Glu Ile Lys
                325                 330                 335
Asp Thr Pro Glu Ala Pro Ala Leu Ala Ala Glu Lys Gln Lys Gln Met
                340                 345                 350
Gly Pro Val Thr Lys Asn Glu Trp Ala Met Ile Gly Thr Met Ile Leu
                355                 360                 365
Ala Val Ala Leu Trp Ile Phe Gly Asp Ala Ile Gly Val Ser Ser Val
                370                 375                 380
Val Ala Ala Met Leu Gly Leu Ser Ile Leu Leu Leu Gly Val Leu
385                 390                 395                 400
Asp Trp Ala Asp Ile Leu Asn Glu Lys Ser Ala Trp Asp Thr Leu Ala
                    405                 410                 415
Trp Phe Ser Val Leu Val Gly Met Ala Ala Gln Leu Thr Ser Leu Gly
                420                 425                 430
```

Ile Val Ser Trp Met Ser Ser Cys Ile Ala Asn Leu Leu Gln Ser Phe
            435                 440                 445

Ser Leu Ser Trp Pro Ala Ala Phe Cys Val Leu Gln Ala Ser Tyr Leu
    450                 455                 460

Val Ile His Tyr Leu Phe Ala Ser Gln Thr Gly His Val Gly Ala Leu
465                 470                 475                 480

Tyr Ser Ala Phe Leu Ala Met His Val Ala Ala Gly Val Pro Ser Val
                485                 490                 495

Leu Ser Ala Leu Ala Leu Ala Phe Asn Thr Asp Leu Phe Gly Gly Ile
                500                 505                 510

Thr His Tyr Ser Ser Gly Gln Ala Ala Val Tyr Phe Gly Ala Gly Tyr
                515                 520                 525

Leu Asp Leu Pro Asp Val Phe Arg Ile Gly Phe Ile Ser Thr Leu Ile
                530                 535                 540

Asn Thr Leu Ile Trp Gly Gly Ile Gly Thr Phe Trp Trp Lys Phe Leu
545                 550                 555                 560

Gly Leu Tyr

<210> SEQ ID NO 29
<211> LENGTH: 551
<212> TYPE: PRT
<213> ORGANISM: Sorghum bicolor
<220> FEATURE:
<221> NAME/KEY: MISC_FEATURE
<222> LOCATION: (1)..(551)
<223> OTHER INFORMATION: DCT2

<400> SEQUENCE: 29

Met Ala Ser Leu Arg Leu Ala Val Thr His Cys Pro Ala Leu Pro Leu
1               5                   10                  15

Pro Thr Pro His Ser His Leu Arg Arg Gln Leu Gln Leu His Pro
                20                  25                  30

Tyr Pro Asn Pro Leu Ser Leu Ser Pro Arg Ile Ser Ser His Leu Ser
                35                  40                  45

Pro Ile Pro Arg Arg His Leu Pro Pro Leu Phe Ala Ser Ala Ser Ala
    50                  55                  60

Ser Gln Ala Glu Thr Lys Pro Pro Pro Pro Thr Glu Ala Ser Gly
65                  70                  75                  80

Gly Ala Lys Pro Leu Pro Leu Leu Ile Ser Leu Ala Ala Gly Leu Ala
                85                  90                  95

Val Arg Phe Leu Val Pro Arg Pro Ala Glu Val Thr Pro Glu Ala Trp
                100                 105                 110

Gln Leu Leu Ser Ile Phe Leu Ser Thr Ile Ala Gly Leu Val Leu Gly
                115                 120                 125

Pro Leu Pro Val Gly Ala Trp Ala Phe Leu Gly Leu Thr Ala Thr Val
                130                 135                 140

Ala Thr Arg Thr Leu Pro Phe Thr Ala Ala Phe Gly Ala Phe Thr Asn
145                 150                 155                 160

Glu Val Ile Trp Leu Ile Val Ile Ser Phe Phe Ala Arg Gly Phe
                165                 170                 175

Val Lys Thr Gly Leu Gly Asp Arg Val Ala Thr Tyr Phe Val Lys Trp
                180                 185                 190

Leu Gly Arg Ser Thr Leu Gly Leu Ser Tyr Gly Leu Ala Ile Ser Glu
                195                 200                 205

Ala Phe Ile Ser Pro Ala Met Pro Ser Thr Thr Ala Arg Ala Gly Gly

```
                210                 215                 220
Val Phe Leu Pro Ile Val Lys Ser Leu Ser Leu Ser Ser Gly Ser Lys
225                 230                 235                 240

Pro Asn Asp Pro Ser Ala Lys Lys Leu Gly Ser Tyr Leu Val Gln Ser
                245                 250                 255

Gln Leu Gln Ala Ala Asn Ser Ser Ala Leu Phe Leu Thr Ala Ala
            260                 265                 270

Ala Gln Asn Leu Leu Cys Leu Lys Leu Ala Glu Glu Ile Gly Val Asn
            275                 280                 285

Ile Gly Asn Pro Trp Ile Thr Trp Phe Lys Val Ala Ser Val Pro Ala
    290                 295                 300

Leu Leu Gly Leu Leu Val Thr Pro Tyr Leu Ile Tyr Lys Ile Phe Pro
305                 310                 315                 320

Pro Glu Ile Lys Asp Thr Pro Glu Ala Pro Ala Leu Ala Ala Glu Lys
                325                 330                 335

Leu Lys Leu Met Gly Pro Val Thr Lys Asn Glu Trp Val Met Ile Ala
            340                 345                 350

Thr Met Leu Leu Ala Val Ser Leu Trp Ile Phe Gly Glu Ala Ile Gly
            355                 360                 365

Val Ser Ser Val Val Ala Ala Met Ile Gly Leu Ser Ile Leu Leu Leu
    370                 375                 380

Leu Gly Val Leu Asn Trp Glu Asp Cys Leu Asn Glu Lys Ser Ala Trp
385                 390                 395                 400

Asp Thr Leu Ala Trp Phe Ala Ile Leu Val Gly Leu Ala Gly Gln Leu
                405                 410                 415

Thr Asn Leu Gly Ile Val Ser Trp Met Ser Asn Cys Val Ala Lys Val
            420                 425                 430

Leu Gln Ser Phe Ser Leu Ser Trp Pro Ala Ala Phe Gly Val Leu Gln
            435                 440                 445

Ala Ser Tyr Phe Leu Ile His Tyr Ile Phe Ala Ser Gln Thr Ala His
    450                 455                 460

Val Gly Ala Leu Tyr Ser Ala Phe Leu Ala Met His Leu Ala Ala Gly
465                 470                 475                 480

Val Pro Ala Val Met Ser Ala Leu Ala Leu Ala Tyr Asn Ala Asn Leu
                485                 490                 495

Phe Gly Ala Leu Thr His Tyr Ser Ser Gly Gln Ser Ala Val Tyr Phe
            500                 505                 510

Gly Ala Gly Tyr Val Asp Leu Pro Asp Val Phe Lys Leu Gly Phe Ile
            515                 520                 525

Thr Ala Ala Leu Asn Ala Val Val Trp Gly Val Ala Gly Ala Phe Trp
    530                 535                 540

Trp Lys Phe Leu Gly Leu Tyr
545                 550

<210> SEQ ID NO 30
<211> LENGTH: 413
<212> TYPE: PRT
<213> ORGANISM: Sorghum bicolor
<220> FEATURE:
<221> NAME/KEY: MISC_FEATURE
<222> LOCATION: (1)..(413)
<223> OTHER INFORMATION: MEP3a

<400> SEQUENCE: 30

Met Ala Ser Pro Arg Pro Thr Ser Leu Ser Ser Pro Ala Ala Leu Ile
1               5                   10                  15
```

His Leu Arg Leu Gln Pro Leu Pro Ser Ile Pro Pro Leu His Pro Thr
            20                  25                  30

Thr Leu Pro Phe Pro Arg Ser Leu Pro Leu His Leu Pro Ser Leu Arg
        35                  40                  45

Leu Asn Gly Pro His Leu Pro Pro Leu Pro Leu Ala Ser Ser Gly Ser
 50                  55                  60

Gly Ser Ala Ile Thr Gly Thr Gly Glu Ala Asp Leu Pro Pro Leu
 65                  70                  75                  80

Pro Leu Asp Ser Ser Asp Ser Gly Ser Gly Ile Thr Gly Thr Gly Gly
                 85                  90                  95

Glu Asp Gly Leu Pro Pro Ser Gly Gly Gly Gly Gly Gly Gly
            100                 105                 110

Asp Gly Glu Gly Glu Gly Glu Gly Asp Gly Glu Gly Ser Asp Asp Ala
            115                 120                 125

Ser Val Asn Arg Arg Glu Ala Leu Phe Val Leu Ala Gln Leu Gly Arg
130                 135                 140

Lys Leu Glu Ser Leu Pro Ala Asp Leu Ala Ala Ala Val Glu Gly Gly
145                 150                 155                 160

Arg Ile Pro Ala Glu Ile Val Arg Arg Phe Val Asp Leu Glu Ala Ser
                165                 170                 175

Pro Val Phe Arg Trp Leu Leu Gln Phe Gly Phe Lys Glu Arg Leu
                180                 185                 190

Leu Ala Asp Asp Leu Phe Leu Thr Lys Val Ala Ile Glu Cys Gly Val
                195                 200                 205

Gly Ile Phe Thr Lys Thr Ala Ala Glu Tyr Glu Lys Arg Arg Glu Asn
        210                 215                 220

Phe Val Lys Glu Leu Asp Phe Val Ile Ala Asp Val Val Met Ala Ile
225                 230                 235                 240

Val Ala Asp Phe Met Leu Val Trp Leu Pro Ala Pro Thr Val Ser Leu
                245                 250                 255

Gln Pro Pro Leu Ala Val Asn Ser Gly Ala Ile Ala Lys Phe Phe Tyr
                260                 265                 270

Asn Cys Pro Asp Asn Ala Phe Gln Val Ala Leu Ser Gly Thr Ser Tyr
                275                 280                 285

Ser Leu Leu Gln Arg Ala Gly Ala Ile Leu Arg Asn Gly Ala Lys Leu
        290                 295                 300

Phe Ala Val Gly Thr Ser Ala Ser Leu Val Gly Thr Gly Val Thr Asn
305                 310                 315                 320

Ala Leu Ile Lys Ala Arg Gln Ala Ala Ser Lys Asp Phe Asp Gly Glu
                325                 330                 335

Val Glu Asn Leu Pro Ile Val Ser Thr Ser Val Ala Tyr Gly Val Tyr
                340                 345                 350

Met Ala Val Ser Ser Asn Leu Arg Tyr Gln Val Leu Ala Gly Val Ile
                355                 360                 365

Glu Gln Arg Met Leu Glu Pro Leu Leu His Gln His Lys Leu Val Leu
        370                 375                 380

Ser Ala Ala Ser Phe Ala Val Arg Thr Gly Asn Thr Phe Leu Gly Ser
385                 390                 395                 400

Leu Leu Trp Ile Asp Tyr Ala Arg Trp Val Gly Val Gln
                405                 410

<210> SEQ ID NO 31
<211> LENGTH: 734

<212> TYPE: PRT
<213> ORGANISM: Sorghum bicolor
<220> FEATURE:
<221> NAME/KEY: MISC_FEATURE
<222> LOCATION: (1)..(734)
<223> OTHER INFORMATION: MEP3b

<400> SEQUENCE: 31

Met Leu Pro His Ala Pro Cys Arg Thr Leu Gly Ala Phe Arg Cys Lys
1               5                   10                  15

Pro His Leu Pro Thr Lys Pro Pro Leu Leu Thr Ser Thr Pro Thr Ser
                20                  25                  30

Ala Ser Thr Arg Gly Arg Leu Cys Ala Thr Ala Ala Ala Ala Ala Thr
            35                  40                  45

Arg Arg Gly Leu Leu Val Leu Val Pro Ser Leu Val Ala Ala Ser Thr
    50                  55                  60

Val Leu Gln Ser Leu Pro Leu Ala Ala Ser Ala Ala Ala Gly Asp Asp
65                  70                  75                  80

Lys Pro Ser Pro Pro Pro Ala Gln Ala Gln Ala Ala Pro Ala Ala
                85                  90                  95

Pro Ala Ser Pro Pro Pro Pro Ala Glu Glu Pro Ala Leu Ser
                100                 105                 110

Arg Val Tyr Asp Ala Thr Val Ile Gly Glu Pro Gln Ala Val Gly Lys
            115                 120                 125

Asp Ala Arg Arg Val Trp Glu Lys Leu Met Ala Ala Arg Val Val
    130                 135                 140

Tyr Leu Gly Glu Ala Glu Leu Val Pro Asp Arg Asp Asp Arg Val Leu
145                 150                 155                 160

Glu Leu Glu Ile Val Arg Lys Leu Ala Ala Gly Cys Ala Glu Ala Gly
                165                 170                 175

Arg Ser Ile Ser Leu Ala Leu Glu Ala Phe Pro Cys Asp Leu Gln Glu
            180                 185                 190

Gln Leu Asn Gln Phe Met Asp Gly Arg Ile Asp Gly Asn Ser Leu Arg
    195                 200                 205

Leu Tyr Thr Ser His Trp Ala Pro Glu Arg Trp Gln Glu Tyr Glu Pro
210                 215                 220

Ile Leu Asn Tyr Cys Arg Asp Asn Gly Ile Lys Leu Val Ala Cys Gly
225                 230                 235                 240

Thr Pro Leu Glu Val Val Arg Thr Val Gln Ala Glu Gly Ile Arg Ser
                245                 250                 255

Leu Ser Lys Ala Gln Arg Lys Leu Tyr Ala Pro Pro Ala Gly Ser Gly
            260                 265                 270

Phe Ile Ser Gly Phe Thr Ser Ile Ser Gly Arg Ser Leu Ile Asp Lys
    275                 280                 285

Ile Ser Ser Asn Arg Gly Ser Pro Phe Gly Pro Ser Ser Tyr Leu Ser
290                 295                 300

Ala Gln Ala Arg Val Val Asp Asp Tyr Thr Met Ser Gln Thr Ile Met
305                 310                 315                 320

Lys Glu Ile Thr Asn Gly Asp Pro Ser Gly Met Leu Val Val Thr
                325                 330                 335

Gly Ala Ser His Val Met Tyr Gly Ser Arg Gly Ile Gly Val Pro Ala
            340                 345                 350

Arg Ile Ser Lys Lys Met Gln Lys Lys Gln Val Val Ile Leu Leu
    355                 360                 365

Asp Pro Glu Arg Gln Ser Ile Arg Arg Glu Gly Glu Ile Pro Val Ala

```
                370                 375                 380
Asp Phe Leu Trp Tyr Ser Ala Ala Lys Pro Cys Ser Arg Asn Cys Phe
385                 390                 395                 400

Asp Arg Ala Glu Ile Ala Arg Val Met Asn Ala Ala Gly Arg Arg Arg
            405                 410                 415

Glu Ala Leu Pro Gln Asp Leu Gln Lys Gly Ile Asp Leu Gly Val Val
        420                 425                 430

Ser Pro Glu Ile Leu Gln Asn Phe Phe Asp Leu Glu Lys Tyr Pro Val
    435                 440                 445

Met Ala Glu Leu Ile His Arg Phe Gln Gly Phe Arg Glu Arg Leu Leu
450                 455                 460

Ala Asp Pro Lys Phe Leu His Arg Leu Ala Ile Glu Glu Gly Ile Ser
465                 470                 475                 480

Ile Thr Thr Thr Leu Leu Ala Gln Tyr Glu Lys Arg Lys Gly Arg Phe
                485                 490                 495

Phe Glu Glu Ile Asp Tyr Val Leu Thr Asp Thr Ile Arg Gly Ser Val
            500                 505                 510

Val Asp Phe Phe Thr Val Trp Leu Pro Ala Pro Thr Ile Ser Leu Leu
        515                 520                 525

Ser Phe Ala Asp Asp Gly Ser Gly Glu Ser Val Glu Leu Leu Lys Gly
    530                 535                 540

Ile Leu Gly Ser Val Pro Asp Asn Ala Phe Gln Lys Gly Ile Val Gly
545                 550                 555                 560

Gln Asn Trp Asn Ile Asn Gln Arg Phe Ala Ser Val Leu Met Gly Gly
                565                 570                 575

Leu Lys Leu Ala Gly Val Gly Phe Ile Ser Ser Ile Gly Ala Gly Val
            580                 585                 590

Ala Ser Asp Val Leu Tyr Gly Ala Arg Gln Ile Leu Lys Pro Ser Ala
        595                 600                 605

Ser Met Glu Val Ala Arg Lys Arg Thr Pro Ile Trp Lys Ala Ala Thr
    610                 615                 620

Val Tyr Ser Cys Phe Leu Gly Thr Ser Ala Asn Leu Arg Tyr Gln Val
625                 630                 635                 640

Ile Ala Gly Leu Ile Glu His Arg Leu Gly Glu Asp Leu Met Thr Tyr
                645                 650                 655

Tyr Asn Gln Pro Leu Leu Ala Ser Leu Val Ser Phe Val Ser Arg Thr
            660                 665                 670

Val Asn Ser Tyr Trp Gly Thr Gln Gln Trp Ile Asp Leu Ala Arg Ala
        675                 680                 685

Thr Gly Val Gln Ser Thr Lys Lys Glu Leu Pro Ser Pro Glu Val Ser
    690                 695                 700

Ser Ala Thr Glu Met Pro Leu Leu Glu Cys Gly Thr Thr Glu Val Gln
705                 710                 715                 720

Lys Val Asp Asp Ser Ser Asn Asn Gln Ser Asn Asp Leu Thr
                725                 730
```

<210> SEQ ID NO 32
<211> LENGTH: 418
<212> TYPE: PRT
<213> ORGANISM: Sorghum bicolor
<220> FEATURE:
<221> NAME/KEY: MISC_FEATURE
<222> LOCATION: (1)..(418)
<223> OTHER INFORMATION: MEP3c

<400> SEQUENCE: 32

```
Met Ala Leu Pro Pro Ser Ser Ala Ser Ser Leu Ser Ala Ala Ser
1               5                   10                  15

Ala Gln Pro Thr Pro Leu His Leu His Leu Thr Ser Arg Ala Pro Gly
            20                  25                  30

Arg Leu Pro Leu Leu His Phe Ser Arg Ala Ala Leu Pro Leu Pro Leu
        35                  40                  45

Arg Ala Arg Ile Pro Arg Thr Asn Asn Pro Gly Thr Pro Leu His
50                  55                  60

Arg Gly Leu Pro Pro Pro Ser Ala Ser Ser Pro Ser Ile Ala
65              70                  75                  80

Gly Gly Gly Phe Gly Ser Asp Asp Ala Glu Glu Asn His Gly Gly Asp
                85                  90                  95

Gly Gly Ser Gly Ser Gly Ala Gly Gly Asp Glu Gly Gly Gly Asp Asp
            100                 105                 110

Gly Gly His Asn Asp His Gly Gly Glu Asp Ala Gly Asp Gly Ser Leu
            115                 120                 125

Gly Asp Pro Arg Gly Glu Ala Leu Phe Val Leu Ala Gln Leu Gly Arg
        130                 135                 140

Lys Leu Asp Ser Leu Pro Ser Asp Leu Ala Ala Ala Ile Glu Ser Gly
145                 150                 155                 160

Arg Ile Gly Gly Asp Ile Val Ala Arg Phe Asn Glu Leu Glu Ala Asn
                165                 170                 175

Gly Phe Ile Lys Trp Leu Leu Thr Phe Lys Gly Phe Arg Glu Arg Leu
                180                 185                 190

Leu Ala Asp Glu Leu Phe Leu Thr Lys Leu Gly Ile Glu Cys Gly Ile
            195                 200                 205

Gly Leu Val Ala Lys Thr Ala Ala Glu Leu Gln Lys Arg Gly Asp Asn
        210                 215                 220

Phe Phe Lys Glu Ile Glu Val Val Ile Ser Asp Val Val Met Ala Ile
225                 230                 235                 240

Val Ala Asp Val Met Leu Val Tyr Leu Pro Ala Pro Thr Ile Gly Leu
                245                 250                 255

Gln Pro Pro Ile Ala Arg Asn Ala Ser Ala Ile Ala Ser Phe Phe Ser
                260                 265                 270

Ser Cys Pro Asp Asn Ala Phe Gln Ile Ala Leu Ala Gly Arg Ser Phe
        275                 280                 285

Thr Leu Val Gln Arg Ile Gly Ala Phe Val Arg Asn Ala Ala Lys Leu
    290                 295                 300

Leu Val Val Gly Thr Thr Ala Ser Leu Val Gly Thr Ser Val Thr Ser
305                 310                 315                 320

Ala Ala Leu Lys Ala Lys Ala Val Asn Lys Asp Glu Ala Val Glu
                325                 330                 335

Ile Pro Val Leu Gln Thr Ser Ile Ala Tyr Gly Ile Tyr Met Ser Ile
            340                 345                 350

Ser Ser Asn Leu Arg Tyr Gln Leu Leu Ala Gly Val Leu Glu Gln Arg
        355                 360                 365

Ile Leu Glu Pro Leu Leu His Asn Gln Lys Leu Leu Leu Ser Ala Met
    370                 375                 380

Cys Phe Met Val Arg Ser Gly Asn Thr Phe Leu Gly Ser Leu Leu Trp
385                 390                 395                 400

Ile Asp Tyr Ala Arg Trp Ile Gly Val Gln Lys Gly His Asp His Glu
                405                 410                 415
```

Glu Ala

<210> SEQ ID NO 33
<211> LENGTH: 597
<212> TYPE: PRT
<213> ORGANISM: Sorghum bicolor
<220> FEATURE:
<221> NAME/KEY: MISC_FEATURE
<222> LOCATION: (1)..(597)
<223> OTHER INFORMATION: NHD

<400> SEQUENCE: 33

Met Thr Thr Arg Phe Thr Val Leu Ile Arg Asp Pro Phe Asp Tyr Ser
1               5                   10                  15

Ser Ser Ala Ser Gly Pro Gln Ile Leu Pro Ala Ala Met Ser Leu
            20                  25                  30

Ser Ser Cys Leu Leu Ala Gly Thr Arg Ala Ala Ser Pro Ser Phe
        35                  40                  45

Pro Ser Ala Ala Ile Arg Arg Arg Asp His Arg Pro Leu Thr Val
    50                  55                  60

Ser Val Val Pro Leu Ser Pro Ser Gln Gln Trp Arg His Gly Leu Arg
65                  70                  75                  80

Phe Cys Cys Ala Ser Ser Thr Ser Ser Ser Pro Pro Pro Ala Pro
                85                  90                  95

Pro Glu Glu Pro Asp Asp Tyr Glu Leu Leu Asp Thr Thr Gly Asn Cys
                100                 105                 110

Asp Pro Leu Cys Ser Val Asp Glu Val Ser Ser Gln Tyr Phe Glu Ala
            115                 120                 125

Asn Tyr Lys Pro Lys Asn Asp Leu Leu Lys Ala Leu Thr Ile Ile Gly
        130                 135                 140

Thr Ala Leu Ala Gly Ala Ala Ala Ile Asn His Ser Trp Val Ala Ala
145                 150                 155                 160

Asn Gln Asp Ile Ala Met Val Leu Val Phe Ala Ile Gly Tyr Ala Gly
                165                 170                 175

Ile Ile Phe Glu Glu Ser Leu Ala Phe Asn Lys Ser Gly Val Ala Leu
            180                 185                 190

Leu Met Ala Val Cys Leu Trp Val Ile Arg Ser Ile Gly Ala Pro Ser
        195                 200                 205

Thr Asp Val Ala Val Gln Glu Leu Ser His Thr Thr Ser Glu Val Ser
210                 215                 220

Glu Ile Val Phe Phe Leu Leu Gly Ala Met Thr Ile Val Glu Ile Val
225                 230                 235                 240

Asp Ala His Gln Gly Phe Lys Leu Val Thr Asp Asn Ile Ser Thr Arg
                245                 250                 255

Asn Pro Lys Thr Leu Leu Trp Val Ile Gly Ile Val Thr Phe Phe Leu
            260                 265                 270

Ser Ser Ile Leu Asp Asn Leu Thr Ser Thr Ile Val Met Val Ser Leu
        275                 280                 285

Leu Arg Lys Leu Val Pro Pro Ser Glu Tyr Arg Lys Leu Leu Gly Ala
    290                 295                 300

Val Val Val Ile Ala Ala Asn Ala Gly Gly Ala Trp Thr Pro Ile Gly
305                 310                 315                 320

Asp Val Thr Thr Thr Met Leu Trp Ile His Gly Gln Ile Thr Thr Leu
                325                 330                 335

Lys Ile Met Gln Gly Leu Phe Ile Pro Ser Ala Val Ser Leu Ala Val
            340                 345                 350

-continued

Pro Leu Ala Leu Met Ser Leu Thr Ser Glu Ala Asn Gly Ser Ser Gln
        355                 360                 365

Lys Ser Ser Ser Leu Leu Ser Ser Glu Gln Met Ala Pro Arg Gly Gln
    370                 375                 380

Leu Val Leu Gly Val Gly Val Gly Ala Leu Val Phe Val Pro Ile Phe
385                 390                 395                 400

Lys Ala Leu Thr Gly Leu Pro Pro Phe Met Gly Met Leu Leu Gly Leu
                405                 410                 415

Gly Ile Leu Trp Ile Leu Thr Asp Ala Ile His Tyr Gly Asp Ala Glu
                420                 425                 430

Arg Gln Arg Leu Lys Val Pro Gln Ala Leu Ser Arg Ile Asp Thr Gln
                435                 440                 445

Gly Ile Leu Phe Phe Leu Gly Ile Leu Leu Ser Val Gly Ser Leu Glu
                450                 455                 460

Ser Ala Gly Ile Leu Arg Gln Leu Ala Asn Tyr Leu Asp Ala Asn Ile
465                 470                 475                 480

Pro Asn Ala Asp Leu Ile Ala Ser Ala Ile Gly Val Ala Ser Ala Val
                485                 490                 495

Ile Asp Asn Val Pro Leu Val Ala Ala Thr Met Gly Met Tyr Asp Leu
                500                 505                 510

Thr Ser Phe Pro Pro Asp Ser Asp Phe Trp Gln Leu Val Ala Phe Cys
                515                 520                 525

Ala Gly Thr Gly Gly Ser Met Leu Ile Ile Gly Ser Ala Ala Gly Val
                530                 535                 540

Ala Phe Met Gly Met Glu Lys Val Asp Phe Phe Trp Tyr Phe Arg Lys
545                 550                 555                 560

Val Ser Gly Phe Ala Leu Ala Gly Tyr Ala Ala Gly Ile Ile Ser Tyr
                565                 570                 575

Leu Ala Ala Gln Asn Leu His Leu Ser Leu Pro Thr Ser Leu Ala Glu
                580                 585                 590

Ile Pro Phe Ile Ser
                595

<210> SEQ ID NO 34
<211> LENGTH: 414
<212> TYPE: PRT
<213> ORGANISM: Sorghum bicolor
<220> FEATURE:
<221> NAME/KEY: MISC_FEATURE
<222> LOCATION: (1)..(414)
<223> OTHER INFORMATION: BASS2

<400> SEQUENCE: 34

Met Ala Pro Ser Ala Ala Cys Ser Met Ala Ser Val Ser Arg Ala Leu
1               5                   10                  15

Arg Pro Arg Pro Arg Pro Arg Ala Ala Val Cys Ser Ala Ala Arg Leu
                20                  25                  30

Gly Cys Gly Leu Gly Ile Ala Cys Ser Met Pro Ser His Gly Met Gly
                35                  40                  45

Asn Glu Lys His Glu Leu Gly Leu Ala Val Ala Ser Ala Pro Ala Ala
        50                  55                  60

Thr Ile Thr Pro Val Leu Arg Ser Arg Gln Ile Leu Cys Lys Ala Glu
65                  70                  75                  80

Ala Asn Val Ser Ser Asn Leu Pro Asp Thr Leu Pro Thr Gly Val Ser
                85                  90                  95

```
Gln Tyr Glu Lys Ile Val Glu Leu Leu Thr Thr Leu Phe Pro Val Trp
                100                 105                 110

Val Ile Leu Gly Thr Ile Ile Gly Ile Tyr Lys Pro Ser Met Val Thr
            115                 120                 125

Trp Leu Glu Thr Asp Leu Phe Thr Met Gly Leu Gly Phe Leu Met Leu
        130                 135                 140

Ser Met Gly Leu Thr Leu Thr Phe Glu Asp Phe Arg Arg Cys Leu Arg
145                 150                 155                 160

Asn Pro Trp Thr Val Gly Val Gly Phe Leu Ala Gln Tyr Leu Ile Lys
                165                 170                 175

Pro Met Leu Gly Phe Ser Ile Ala Leu Ala Leu Lys Leu Ser Ala Pro
            180                 185                 190

Leu Ala Thr Gly Leu Ile Leu Val Ser Cys Cys Pro Gly Gly Gln Ala
        195                 200                 205

Ser Asn Val Ala Thr Tyr Ile Ser Lys Gly Asn Val Ala Leu Ser Val
210                 215                 220

Leu Met Thr Thr Cys Ser Thr Val Gly Ala Ile Val Met Thr Pro Leu
225                 230                 235                 240

Leu Thr Lys Leu Leu Ala Gly Gln Leu Val Pro Val Asp Ala Ala Gly
                245                 250                 255

Leu Ala Ile Ser Thr Phe Gln Val Val Leu Val Pro Thr Val Val Gly
            260                 265                 270

Val Leu Ala His Glu Tyr Phe Pro Lys Phe Thr Glu His Ile Ile Thr
        275                 280                 285

Val Thr Pro Leu Ile Gly Val Leu Leu Thr Thr Leu Leu Cys Ala Ser
290                 295                 300

Pro Ile Gly Gln Val Ala Glu Val Leu Lys Thr Gln Gly Gly Gln Leu
305                 310                 315                 320

Ile Ile Pro Val Ala Leu Leu His Val Ala Ala Phe Ala Leu Gly Tyr
                325                 330                 335

Trp Leu Ser Arg Leu Ser Thr Phe Gly Glu Ser Thr Ser Arg Thr Ile
            340                 345                 350

Ala Ile Glu Cys Gly Met Gln Ser Ser Ala Leu Gly Phe Leu Leu Ala
        355                 360                 365

Gln Lys His Phe Thr Asn Pro Leu Val Ala Val Pro Ser Ala Val Ser
370                 375                 380

Val Val Cys Met Ala Leu Gly Gly Ser Ala Leu Ala Val Tyr Trp Arg
385                 390                 395                 400

Asn Lys Gly Leu Pro Thr Asp Asp Lys Asp Asp Phe Lys Glu
                405                 410
```

<210> SEQ ID NO 35
<211> LENGTH: 418
<212> TYPE: PRT
<213> ORGANISM: Sorghum bicolor
<220> FEATURE:
<221> NAME/KEY: MISC_FEATURE
<222> LOCATION: (1)..(418)
<223> OTHER INFORMATION: PPT2

<400> SEQUENCE: 35

```
Met Gln Arg Gly Ala Ala Ala Gly Thr Thr Ser Val Ser Gly Ala
1               5                   10                  15

Ser Ser Trp Thr Arg Ala Ala Thr Arg Gly Leu Ala Ser Arg His Val
            20                  25                  30

Gly Val Ala Ser Ser Ser Ser Phe Phe Gly Pro Arg Gly Ala Thr
```

```
                35                  40                  45
Ala Ala Ala Gln Arg Leu Pro Leu Leu Arg Val Arg Gly Gly Asp Gly
 50                  55                  60

Arg Leu Arg Pro Leu Ser Leu Leu Ser Asp Ser Gly Gly Lys Asn Gly
 65                  70                  75                  80

Glu Val Ala Lys Ala Val Ala Ala Ala Ala Ser Val Pro Ala
                 85                  90                  95

Asp Asp Ala Ser Ala Ala Val Thr Gly Asp Arg Gly Gly Ile Ala
                100                 105                 110

Ala Thr Ala Gln Leu Gly Ala Met Ile Val Ala Trp Tyr Leu Leu Asn
                115                 120                 125

Ile Tyr Phe Asn Ile Tyr Asn Lys Gln Val Leu Gly Ala Leu Pro Leu
    130                 135                 140

Pro Leu Pro Tyr Thr Ile Thr Ala Phe Gln Leu Ala Phe Gly Ser Leu
145                 150                 155                 160

Leu Ile Phe Leu Met Trp Ala Thr Arg Leu His Pro Val Pro Arg Leu
                165                 170                 175

Ser Ala Ala Gln Leu Gly Lys Ile Ala Pro Leu Ala Val Gly His Met
                180                 185                 190

Leu Gly Thr Val Phe Thr Asn Met Ser Leu Gly Lys Val Ala Val Ser
                195                 200                 205

Phe Thr His Thr Ile Lys Ala Ser Glu Pro Phe Phe Thr Val Val Leu
    210                 215                 220

Ser Ala Leu Phe Leu Gly Glu Val Pro Ser Leu Pro Val Leu Gly Ser
225                 230                 235                 240

Leu Val Pro Ile Val Gly Gly Val Ala Leu Ala Ser Phe Thr Glu Val
                245                 250                 255

Ser Phe Asn Trp Thr Gly Phe Trp Ser Ala Met Ala Ser Asn Leu Thr
                260                 265                 270

Asn Gln Ser Arg Asn Val Leu Ser Lys Lys Leu Leu Ala Gly Asp Lys
    275                 280                 285

Asp Val Met Asp Asp Ile Asn Leu Phe Ser Val Ile Thr Val Leu Ser
290                 295                 300

Phe Leu Leu Ser Cys Pro Leu Met Phe Phe Ala Glu Gly Ile Lys Phe
305                 310                 315                 320

Thr Pro Gly Tyr Leu Gln Ser Thr Gly Leu Asn Leu Gln Glu Leu Cys
                325                 330                 335

Val Arg Ala Ala Leu Ala Gly Leu Cys Phe His Gly Tyr Gln Lys Leu
                340                 345                 350

Ser Tyr Leu Ile Leu Ser Arg Val Ser Pro Val Thr His Ser Val Ala
    355                 360                 365

Asn Cys Val Lys Arg Val Val Ile Val Ser Val Leu Phe Phe
    370                 375                 380

Ser Thr Pro Ile Ser Pro Val Asn Ala Leu Gly Thr Gly Ala Ala Leu
385                 390                 395                 400

Ala Gly Val Phe Leu Tyr Ser Arg Leu Thr Arg Thr Lys Lys Pro Lys
                405                 410                 415

Asp Ala

<210> SEQ ID NO 36
<211> LENGTH: 406
<212> TYPE: PRT
<213> ORGANISM: Sorghum bicolor
<220> FEATURE:
```

```
<221> NAME/KEY: MISC_FEATURE
<222> LOCATION: (1)..(406)
<223> OTHER INFORMATION: TPT

<400> SEQUENCE: 36

Met Ser Ala Ala Gly Thr Leu Ser Gly Ala Ala Gly Leu Ser Gly
1               5                   10                  15

Leu Leu Arg Leu Arg Arg Ala Ala Pro Ala Pro Ala Ile Ala Ala
                20                  25                  30

Pro Ser Leu His Pro Ala Gly Thr Ile Lys Cys Thr Ala Val Pro Asp
            35                  40                  45

Ala Ala Pro Ile Val Trp Gly Arg Gln Leu Arg Pro Ala Leu Leu Leu
        50                  55                  60

Pro Ala Ala Leu Leu Pro Ser Ser Gln Pro Ala Lys Lys His Asn Leu
65                  70                  75                  80

Arg Pro Ala Ala Ala Ala Glu Ser Ala Gly Glu Ala Lys Gly Phe
                85                  90                  95

Leu Glu Lys Tyr Pro Ala Leu Val Thr Gly Phe Phe Phe Met Trp
            100                 105                 110

Tyr Phe Leu Asn Val Ile Phe Asn Ile Leu Asn Lys Lys Ile Tyr Asn
        115                 120                 125

Tyr Phe Pro Tyr Pro Tyr Phe Val Ser Leu Ile His Leu Val Val Gly
        130                 135                 140

Val Ala Tyr Cys Leu Val Gly Trp Ser Val Gly Leu Pro Lys Arg Ala
145                 150                 155                 160

Pro Ile Asn Ala Asn Leu Leu Lys Leu Leu Phe Pro Val Ala Leu Cys
                165                 170                 175

His Gly Ile Gly His Val Thr Ser Asn Val Ser Phe Ala Ala Val Ala
                180                 185                 190

Val Ser Phe Ala His Thr Ile Lys Ala Leu Glu Pro Phe Phe Ser Ala
        195                 200                 205

Ala Ala Thr Gln Phe Ile Leu Gly Gln Gln Val Pro Leu Ser Leu Trp
        210                 215                 220

Met Ser Leu Ala Pro Val Val Ile Gly Val Ser Met Ala Ser Leu Thr
225                 230                 235                 240

Glu Leu Ser Phe Asn Trp Thr Gly Phe Ile Asn Ala Met Ile Ser Asn
                245                 250                 255

Ile Ser Phe Thr Tyr Arg Ser Ile Tyr Ser Lys Lys Ala Met Thr Asp
                260                 265                 270

Met Asp Ser Thr Asn Val Tyr Ala Tyr Ile Ser Ile Ile Ala Leu Ile
            275                 280                 285

Val Cys Ile Pro Pro Ala Ile Ile Phe Glu Gly Pro Gln Leu Met Ser
        290                 295                 300

His Gly Phe Ser Asp Ala Ile Ala Lys Val Gly Leu Thr Lys Phe Val
305                 310                 315                 320

Ser Asp Leu Val Leu Val Gly Leu Phe Tyr His Leu Tyr Asn Gln Ile
                325                 330                 335

Ala Thr Asn Thr Leu Glu Arg Val Ala Pro Leu Thr His Ala Val Gly
            340                 345                 350

Asn Val Leu Lys Arg Val Phe Val Ile Gly Phe Ser Ile Val Val Phe
                355                 360                 365

Gly Asn Lys Ile Ser Thr Gln Thr Gly Ile Gly Thr Ser Ile Ala Ile
            370                 375                 380

Ala Gly Val Ala Leu Tyr Ser Tyr Ile Lys Ala Lys Ile Glu Glu Glu
```

Lys Arg Lys Lys Ser Ala
            405

<210> SEQ ID NO 37
<211> LENGTH: 548
<212> TYPE: PRT
<213> ORGANISM: Oryza sativa
<220> FEATURE:
<221> NAME/KEY: MISC_FEATURE
<222> LOCATION: (1)..(548)
<223> OTHER INFORMATION: OMT

<400> SEQUENCE: 37

Met Ala Thr Ser Thr Ser Ala Ala Thr Ala Pro Leu Thr Cys His His
1               5                   10                  15

Leu Gly Leu Arg Leu Arg Pro Arg Leu Pro Ser Leu Pro Leu Arg Pro
            20                  25                  30

Leu Ser Pro Ser Pro Ser Leu Ser Leu Ser Arg Pro Thr Pro Leu Thr
        35                  40                  45

Pro Ser Pro Pro Pro Arg His Arg Ala Leu His Ala Ser Ala Ser Ala
    50                  55                  60

Ala Pro Ala Ala Pro Pro Ser Gln Pro Pro Lys Pro Val Leu Gln Gly
65                  70                  75                  80

Ala Ala Ile Lys Pro Leu Val Ala Thr Ile Gly Thr Gly Val Leu Ile
                85                  90                  95

Trp Leu Val Pro Pro Ala Gly Val Ala Arg Asn Ala Trp Gln Leu
            100                 105                 110

Leu Ser Ile Phe Leu Ala Thr Ile Val Gly Ile Ile Thr Gln Pro Leu
        115                 120                 125

Pro Leu Gly Ala Val Ala Leu Leu Gly Leu Gly Ala Ala Val Leu Thr
    130                 135                 140

Arg Thr Leu Thr Phe Ala Ala Phe Ser Ala Phe Gly Asp Pro Ile
145                 150                 155                 160

Pro Trp Leu Ile Ala Leu Ala Phe Phe Ala Arg Gly Phe Ile Lys
                165                 170                 175

Thr Gly Leu Gly Ser Arg Val Ala Tyr Ala Phe Val Ser Ala Phe Gly
            180                 185                 190

Gly Ser Ser Leu Gly Leu Gly Tyr Ala Leu Val Phe Ala Glu Ala Leu
        195                 200                 205

Leu Ala Pro Ala Ile Pro Ser Val Ser Ala Arg Ala Gly Gly Ile Phe
    210                 215                 220

Leu Pro Leu Val Lys Ser Leu Cys Glu Ala Cys Gly Ser Arg Ala Gly
225                 230                 235                 240

Asp Gly Thr Glu Arg Arg Leu Gly Ser Trp Leu Met Leu Thr Cys Phe
                245                 250                 255

Gln Thr Ser Val Ile Ser Ser Ala Met Phe Leu Thr Ala Met Ala Ala
            260                 265                 270

Asn Pro Leu Ala Ala Asn Leu Thr Ala Gly Thr Ile Gly Gln Gly Ile
        275                 280                 285

Gly Trp Thr Leu Trp Ala Lys Ala Ala Ile Val Pro Gly Leu Leu Ser
    290                 295                 300

Leu Val Phe Val Pro Leu Ile Leu Tyr Leu Ile Tyr Pro Pro Glu Val
305                 310                 315                 320

Lys Thr Ser Pro Asp Ala Pro Arg Leu Ala Lys Glu Arg Leu Glu Lys
                325                 330                 335

```
Met Gly Pro Met Ser Lys Glu Glu Lys Ile Met Ala Gly Thr Leu Phe
                340                 345                 350

Leu Thr Val Gly Leu Trp Ile Phe Gly Gly Met Leu Asn Val Asp Ala
            355                 360                 365

Val Ser Ala Ala Ile Leu Gly Leu Ser Val Leu Ile Ser Gly Val
370                 375                 380

Val Thr Trp Lys Glu Cys Leu Gly Glu Ala Val Ala Trp Asp Thr Leu
385                 390                 395                 400

Thr Trp Phe Ala Ala Leu Ile Ala Met Ala Gly Tyr Leu Asn Lys Tyr
                405                 410                 415

Gly Leu Ile Ser Trp Phe Ser Glu Thr Val Val Lys Phe Val Gly Gly
            420                 425                 430

Leu Gly Leu Ser Trp Gln Leu Ser Phe Gly Val Leu Leu Leu Tyr
                435                 440                 445

Phe Tyr Ser His Tyr Phe Phe Ala Ser Gly Ala Ala His Ile Gly Ala
                450                 455                 460

Met Phe Thr Ala Phe Leu Ser Val Ser Ser Ala Leu Gly Thr Pro Pro
465                 470                 475                 480

Leu Ile Ala Ala Met Val Leu Ser Phe Leu Ser Asn Ile Met Gly Gly
                485                 490                 495

Leu Thr His Tyr Gly Ile Gly Ser Ala Pro Val Phe Tyr Gly Ala Gly
                500                 505                 510

Tyr Val Pro Leu Ala Gln Trp Trp Gly Tyr Gly Phe Val Ile Ser Ile
                515                 520                 525

Val Asn Ile Ile Ile Trp Leu Gly Ala Gly Gly Phe Trp Trp Lys Met
530                 535                 540

Leu Gly Leu Trp
545

<210> SEQ ID NO 38
<211> LENGTH: 550
<212> TYPE: PRT
<213> ORGANISM: Oryza sativa
<220> FEATURE:
<221> NAME/KEY: MISC_FEATURE
<222> LOCATION: (1)..(550)
<223> OTHER INFORMATION: DCT1

<400> SEQUENCE: 38

Met Glu Ser Leu Arg Ile Ala Ala Ser His Arg Pro Pro Leu Leu
1               5                   10                  15

Pro Ser Pro His Gln Leu Arg Arg His Ile Ala Ala Val Ser Leu
                20                  25                  30

Ser Leu Pro His Thr Ser Leu Ser Leu Ser Ser His His His His
            35                  40                  45

His Arg Leu Ala Pro Thr Pro Leu Arg Arg Ile Pro Pro Leu Leu
50                  55                  60

Ala Ser Gln Thr Pro Asn Pro Glu Ala Asp Ser Pro Ala Pro Ala Gly
65                  70                  75                  80

Thr Lys Leu Ala Pro Leu Leu Val Ser Leu Ala Val Gly Leu Ala Val
                85                  90                  95

Arg Phe Leu Ala Pro Arg Pro Glu Val Ser Pro Gln Ala Trp Gln
                100                 105                 110

Leu Leu Ser Ile Phe Leu Ser Thr Ile Ala Gly Leu Val Leu Gly Pro
                115                 120                 125
```

```
Leu Pro Val Gly Ala Trp Ala Phe Leu Gly Leu Thr Ala Ala Val Ala
            130                 135                 140

Thr His Thr Leu Pro Phe Ala Ala Ala Phe Ser Ala Phe Thr Asn Glu
145                 150                 155                 160

Val Ile Trp Leu Ile Val Ile Ser Phe Phe Phe Ala Arg Gly Phe Val
                165                 170                 175

Lys Thr Gly Leu Gly Asp Arg Ile Ala Thr Tyr Phe Val Lys Trp Leu
                180                 185                 190

Gly Gly Ser Thr Leu Gly Leu Ser Tyr Gly Leu Thr Ile Ser Glu Ala
            195                 200                 205

Phe Ile Ser Pro Ala Met Pro Ser Thr Thr Ala Arg Ala Gly Gly Val
210                 215                 220

Phe Leu Pro Ile Ile Lys Ser Leu Ser Leu Ser Ala Gly Ser Lys Pro
225                 230                 235                 240

Asn His Pro Ser Ser Arg Lys Leu Gly Ser Tyr Leu Val Met Ser Gln
                245                 250                 255

Phe Gln Ala Ala Gly Asn Ser Ser Ala Leu Phe Leu Thr Ala Ala Ala
            260                 265                 270

Gln Asn Leu Leu Cys Leu Lys Leu Ala Glu Glu Leu Gly Ile Ile Val
    275                 280                 285

Ala Asn Pro Trp Val Ala Trp Phe Lys Ala Ala Ser Leu Pro Ala Ile
290                 295                 300

Ala Ser Leu Leu Ala Thr Pro Tyr Leu Leu Tyr Lys Ile Phe Pro Pro
305                 310                 315                 320

Glu Thr Lys Asp Thr Pro Asp Ala Pro Ala Leu Ala Ala Glu Lys Leu
                325                 330                 335

Glu Arg Met Gly Pro Val Thr Lys Asn Glu Trp Val Met Ile Gly Thr
            340                 345                 350

Met Leu Leu Ala Val Ser Leu Trp Val Phe Gly Asp Ala Ile Gly Val
            355                 360                 365

Ser Ser Val Val Ala Ala Met Leu Gly Leu Ser Ile Leu Leu Leu Leu
    370                 375                 380

Gly Val Leu Asp Trp Asp Asp Cys Leu Asn Glu Lys Ser Ala Trp Asp
385                 390                 395                 400

Thr Leu Ala Trp Phe Ala Val Leu Val Gly Met Ala Gly Gln Leu Thr
                405                 410                 415

Asn Leu Gly Ile Val Ser Trp Met Ser Ser Cys Val Ala Lys Leu Leu
            420                 425                 430

Glu Ser Phe Ser Leu Ser Trp Pro Ala Ala Phe Cys Val Leu Glu Ala
    435                 440                 445

Ser Tyr Phe Leu Ile His Tyr Leu Phe Ala Ser Gln Thr Gly His Val
450                 455                 460

Gly Ala Leu Tyr Ser Ala Phe Leu Ala Met His Val Ala Ala Gly Val
465                 470                 475                 480

Pro Arg Val Leu Ser Ala Leu Ala Leu Ala Phe Asn Thr Asn Leu Phe
                485                 490                 495

Gly Ala Leu Thr His Tyr Ser Ser Gly Gln Ala Ala Val Tyr Phe Gly
            500                 505                 510

Ala Gly Tyr Leu Glu Leu Pro Asp Val Phe Arg Met Gly Phe Val Thr
            515                 520                 525

Ala Leu Ile Asn Ile Leu Ile Trp Gly Val Val Gly Thr Phe Trp Trp
530                 535                 540

Lys Leu Leu Gly Leu Tyr
```

<210> SEQ ID NO 39
<211> LENGTH: 555
<212> TYPE: PRT
<213> ORGANISM: Oryza sativa
<220> FEATURE:
<221> NAME/KEY: MISC_FEATURE
<222> LOCATION: (1)..(555)
<223> OTHER INFORMATION: DCT2

<400> SEQUENCE: 39

```
Met Glu Arg Leu Arg Val Ala Ile Ser His Arg Ala Ala Leu Pro
1               5                   10                  15

Leu Pro Thr His His Asn His Phe Arg Arg His Leu Gln Leu Gln
                20                  25                  30

Pro Phe Pro Ser Ser Leu Ser Leu Ser Leu Pro Ile Ser Pro Gln Leu
            35                  40                  45

Ser Pro Ala Pro Pro Arg Arg His Leu Leu Pro Pro Leu Leu Ala Ser
50                  55                  60

Ala Ser Ala Ala Gln Ala Ala Gly Pro Ala Pro Ala Arg Ala Ala Gly
65                  70                  75                  80

Gly Gly Gly Gly Gly Ala Lys Pro Val Pro Leu Leu Val Ser Leu Ala
                85                  90                  95

Val Gly Leu Ala Val Arg Phe Leu Ala Pro Arg Pro Ala Glu Val Thr
            100                 105                 110

Pro Gln Ala Trp Gln Leu Leu Ser Ile Phe Leu Thr Thr Ile Ala Gly
            115                 120                 125

Leu Val Leu Gly Pro Leu Pro Val Gly Ala Trp Ala Phe Leu Gly Leu
130                 135                 140

Thr Ala Thr Val Ala Thr Arg Thr Leu Pro Phe Thr Ala Ala Phe Gly
145                 150                 155                 160

Ala Phe Thr Asn Glu Val Ile Trp Leu Ile Val Ile Ser Phe Phe Phe
                165                 170                 175

Ala Arg Gly Phe Val Lys Thr Gly Leu Gly Asp Arg Val Ala Thr Tyr
            180                 185                 190

Phe Val Lys Trp Leu Gly Arg Ser Thr Leu Gly Leu Ser Tyr Gly Leu
            195                 200                 205

Ala Ile Ser Glu Ala Cys Ile Ala Pro Ala Met Pro Ser Thr Thr Ala
210                 215                 220

Arg Ala Gly Gly Val Phe Leu Pro Ile Val Lys Ser Leu Ser Leu Ser
225                 230                 235                 240

Ala Gly Ser Lys Pro Asn Asp Pro Ser Ala Arg Lys Leu Gly Ser Tyr
                245                 250                 255

Leu Val Gln Ser Gln Leu Gln Ala Ser Gly Asn Ser Ser Ala Leu Phe
            260                 265                 270

Leu Thr Ala Ala Ala Gln Asn Leu Leu Cys Leu Lys Leu Ala Glu Glu
            275                 280                 285

Ile Gly Val Lys Ile Ala Asn Pro Trp Ile Ser Trp Phe Lys Val Ala
290                 295                 300

Ser Leu Pro Ala Ile Ile Ser Leu Leu Ala Thr Pro Tyr Leu Leu Tyr
305                 310                 315                 320

Lys Ile Phe Pro Pro Glu Ile Lys Asp Thr Pro Glu Ala Pro Ala Ile
                325                 330                 335

Ala Ala Gln Lys Leu Lys Asn Met Gly Pro Val Thr Arg Asn Glu Trp
            340                 345                 350
```

-continued

```
Ile Met Val Ala Thr Met Ile Leu Ala Val Ser Leu Trp Ile Phe Gly
            355                 360                 365

Asp Thr Ile Gly Val Ser Val Ala Ala Met Ile Gly Leu Ser
    370                 375                 380

Ile Leu Leu Leu Gly Val Leu Asn Trp Glu Asp Cys Leu Asn Glu
385                 390                 395                 400

Lys Ser Ala Trp Asp Thr Leu Ala Trp Phe Ala Ile Leu Val Gly Met
                405                 410                 415

Ala Gly Gln Leu Thr Asn Leu Gly Ile Val Ser Trp Met Ser Asn Cys
            420                 425                 430

Val Ala Lys Val Leu Gln Ser Phe Ser Leu Ser Trp Pro Ala Ala Phe
            435                 440                 445

Gly Val Leu Gln Ala Ser Tyr Phe Phe Ile His Tyr Leu Phe Ala Ser
            450                 455                 460

Gln Thr Ala His Val Gly Ala Leu Tyr Ser Ala Phe Leu Ala Met His
465                 470                 475                 480

Leu Ala Ala Gly Val Pro Ala Ile Leu Ser Ala Leu Ala Leu Thr Tyr
                485                 490                 495

Asn Ser Asn Leu Phe Gly Ala Leu Thr His Tyr Ser Ser Gly Gln Ser
            500                 505                 510

Ala Val Tyr Tyr Gly Ala Gly Tyr Val Asp Leu Pro Asp Val Phe Lys
            515                 520                 525

Leu Gly Phe Thr Thr Ala Ala Ile Asn Ala Val Ile Trp Gly Val Val
            530                 535                 540

Gly Thr Phe Trp Trp Lys Phe Leu Gly Leu Tyr
545                 550                 555

<210> SEQ ID NO 40
<211> LENGTH: 378
<212> TYPE: PRT
<213> ORGANISM: Oryza sativa
<220> FEATURE:
<221> NAME/KEY: MISC_FEATURE
<222> LOCATION: (1)..(378)
<223> OTHER INFORMATION: MEP3a

<400> SEQUENCE: 40

Met Ala Phe Pro Ser Pro Asn Ser Leu Ser Ala Ser His Pro Thr
1               5                   10                  15

Ser Ser Ser Ser Ser Phe His Leu His Leu Gln Leu Gln Gln Pro Val
                20                  25                  30

Pro His Leu Pro Phe Pro Arg Ser Leu Pro Leu Asn Leu Pro Val Leu
            35                  40                  45

Arg Leu Ala Arg Pro Leu Leu Pro Pro Ala Pro Leu Ala Ser Ser Gly
    50                  55                  60

Ser Gly Gly Ile Gly Ile Gly Gly Gly Asp Asp Glu Gly Arg
65                  70                  75                  80

Asp Asn Ala Gly Gly Gly Asp Gly Asp Asp Ala Ser Val Asn
                85                  90                  95

Arg Arg Glu Ala Leu Phe Val Leu Ala Gln Leu Gly Arg Lys Leu Glu
                100                 105                 110

Ser Leu Pro Ala Asp Leu Ala Ala Ile Glu Gly Arg Val Pro
            115                 120                 125

Gly Glu Ile Val Gln Arg Phe Ala Asp Leu Glu Lys Ser Gly Leu Phe
    130                 135                 140
```

```
Arg Trp Leu Leu Gln Phe Gly Gly Phe Lys Glu Arg Leu Leu Ala Asp
145                 150                 155                 160

Asp Leu Phe Leu Ala Lys Val Ala Met Glu Cys Gly Val Gly Ile Phe
                165                 170                 175

Thr Lys Thr Ala Ala Glu Tyr Glu Arg Arg Arg Glu Asn Phe Val Lys
            180                 185                 190

Glu Leu Asp Phe Val Ile Ala Asp Val Val Met Ala Ile Val Ala Asp
        195                 200                 205

Phe Met Leu Val Trp Leu Pro Ala Pro Thr Val Ser Leu Gln Pro Pro
210                 215                 220

Leu Ala Val Asn Ala Gly Ser Ile Ala Lys Phe Phe His Asn Cys Pro
225                 230                 235                 240

Asp Asn Ala Phe Gln Val Ala Leu Ala Gly Thr Ser Tyr Ser Leu Leu
                245                 250                 255

Gln Arg Val Gly Ala Ile Met Arg Asn Gly Ala Lys Leu Phe Ala Val
            260                 265                 270

Gly Thr Ser Ala Ser Leu Ile Gly Thr Gly Val Thr Asn Ala Leu Ile
        275                 280                 285

Lys Ala Arg Lys Ala Val Ser Lys Asp Phe Glu Gly Glu Ser Glu Asp
290                 295                 300

Ile Pro Ile Val Ser Thr Ser Val Ala Tyr Gly Val Tyr Met Ala Val
305                 310                 315                 320

Ser Ser Asn Leu Arg Tyr Gln Ile Leu Ala Gly Val Ile Glu Gln Arg
                325                 330                 335

Met Leu Glu Pro Leu Leu His His His Lys Leu Val Leu Ser Ala Leu
            340                 345                 350

Cys Phe Ala Val Arg Thr Gly Asn Thr Phe Leu Gly Ser Leu Leu Trp
        355                 360                 365

Val Asp Tyr Ala Lys Trp Ile Gly Ile Gln
370                 375

<210> SEQ ID NO 41
<211> LENGTH: 723
<212> TYPE: PRT
<213> ORGANISM: Oryza sativa
<220> FEATURE:
<221> NAME/KEY: MISC_FEATURE
<222> LOCATION: (1)..(723)
<223> OTHER INFORMATION: MEP3b

<400> SEQUENCE: 41

Met Leu Pro Pro Ala Pro Thr Arg Asn Pro Gly Ala Cys Arg Phe Ile
1               5                   10                  15

Pro Leu Leu Pro Pro Lys Pro Leu Leu Ser Pro Ala Ala Ala Ala Ala
                20                  25                  30

Ser Ser Arg Gly Gly Leu Cys Val Ala Ala Ser Arg Arg Asp Phe
            35                  40                  45

Leu Leu Leu Val Pro Ser Ile Ala Ala Ser Thr Val Leu Gln Ser
        50                  55                  60

Leu Pro Leu Ser Ala Ser Ala Ala Asp Glu Lys Gln Ala Ala Ser
65                  70                  75                  80

Pro Ala Pro Gly Pro Ala Ala Pro Ala Pro Thr Ser Ala Gly Glu
                85                  90                  95

Pro Glu Ala Glu Ala Leu Ser Arg Val Tyr Asp Ala Thr Val Ile Gly
                100                 105                 110

Glu Pro Gln Ala Val Gly Lys Asp Ala Arg Arg Arg Val Trp Glu Lys
```

```
              115                 120                 125
Leu Met Ala Arg Val Val Tyr Leu Gly Glu Ala Glu Leu Val Pro
        130                 135                 140
Asp Arg Asp Arg Val Leu Glu Leu Glu Val Val Arg Lys Leu Ala
145                 150                 155                 160
Ala Arg Cys Ala Glu Ala Gly Arg Ser Ile Ser Leu Ala Leu Glu Ala
                165                 170                 175
Phe Pro Cys Asn Leu Gln Glu Gln Leu Asn Gln Phe Met Asp Arg Arg
                180                 185                 190
Ile Asp Gly Asn Asn Leu Arg Leu Tyr Thr Ser His Trp Ala Pro Glu
                195                 200                 205
Arg Trp Gln Glu Tyr Glu Pro Leu Leu Asn Tyr Cys Arg Asp Asn Gly
        210                 215                 220
Val Lys Leu Val Ala Cys Gly Thr Pro Leu Glu Val Ser Arg Thr Val
225                 230                 235                 240
Gln Ala Glu Gly Ile Arg Gly Leu Ser Lys Ala Gln Arg Lys Leu Tyr
                245                 250                 255
Ala Pro Pro Ala Gly Ser Gly Phe Ile Ser Gly Phe Thr Ser Ile Ser
                260                 265                 270
Gly Arg Ser Leu Ile Asp Lys Ile Ser Ala Ile His Gly Ser Pro Phe
        275                 280                 285
Gly Pro Ser Ser Tyr Leu Ser Ala Gln Ala Arg Val Val Asp Asp Tyr
        290                 295                 300
Thr Met Ser Gln Lys Ile Met Lys Glu Ile Thr Asn Gly Tyr Pro Ser
305                 310                 315                 320
Gly Met Leu Val Val Val Thr Gly Ser Ser His Val Ile Tyr Gly Ser
                325                 330                 335
Arg Gly Ile Gly Val Pro Ala Arg Ile Ser Lys Lys Met Gln Lys Lys
                340                 345                 350
Lys Gln Val Val Val Leu Leu Asn Pro Glu Arg Gln Gly Ile Arg Arg
        355                 360                 365
Glu Gly Glu Ile Pro Val Ala Asp Phe Leu Trp Tyr Ser Ala Ala Lys
        370                 375                 380
Pro Cys Ser Arg Asn Cys Phe Asp Arg Ala Glu Ile Ala Arg Val Met
385                 390                 395                 400
Asn Ala Ala Gly Arg Arg Glu Ala Leu Pro Gln Asp Leu Gln Lys
                405                 410                 415
Gly Ile Asp Leu Gly Val Val Ser Pro Glu Ile Leu Gln Asn Phe Phe
                420                 425                 430
Asp Leu Glu Lys Tyr Pro Val Met Ala Glu Leu Ile His Arg Phe Gln
        435                 440                 445
Gly Phe Arg Glu Arg Leu Leu Ala Asp Pro Lys Phe Leu His Arg Leu
        450                 455                 460
Ala Ile Glu Glu Gly Ile Ser Ile Thr Thr Leu Ile Ala Gln Tyr
465                 470                 475                 480
Glu Lys Arg Lys Gly Arg Phe Leu Glu Glu Ile Asp Tyr Val Leu Thr
                485                 490                 495
Asp Thr Ile Arg Gly Ser Val Val Asp Phe Phe Thr Val Trp Leu Pro
                500                 505                 510
Ala Pro Thr Ile Ser Leu Leu Ser Leu Gly Asp Asn Gly Ser Gly Glu
                515                 520                 525
Ser Leu Glu Leu Leu Lys Gly Leu Leu Gly Ser Leu Pro Asp Asn Ala
        530                 535                 540
```

-continued

Phe Gln Lys Gly Ile Met Gly Gln Ser Trp Asn Thr Asn Gln Arg Phe
545                 550                 555                 560

Ala Ser Val Leu Met Gly Gly Ile Lys Leu Ala Gly Val Gly Phe Ile
            565                 570                 575

Ser Ser Ile Gly Ala Gly Val Ala Ser Asp Val Leu Tyr Ala Ala Arg
            580                 585                 590

Arg Val Leu Arg Pro Ser Thr Ser Val Glu Thr Ala Arg Arg Arg Thr
        595                 600                 605

Pro Ile Trp Lys Ser Ala Thr Val Tyr Ser Cys Phe Leu Gly Thr Ser
        610                 615                 620

Ala Asn Leu Arg Tyr Gln Val Ile Ala Gly Leu Val Glu His Arg Leu
625                 630                 635                 640

Gly Glu Tyr Leu Met Ala Tyr Tyr Asn Gln Pro Leu Leu Ala Asn Leu
            645                 650                 655

Leu Ser Phe Val Ser Arg Thr Ile Asn Ser Tyr Trp Gly Thr Gln Gln
            660                 665                 670

Trp Ile Asp Leu Ala Arg Ala Thr Gly Leu Gln Thr Ser Lys Lys Glu
        675                 680                 685

Leu Pro Ser Pro Glu Ile Ser Asn Leu Pro Asp Met Pro Leu Leu Glu
        690                 695                 700

Cys Gly Thr Thr Glu Val Gln Asn Met Asp Asp Ser Asn Lys Gln Gln
705                 710                 715                 720

Pro Met Lys

<210> SEQ ID NO 42
<211> LENGTH: 389
<212> TYPE: PRT
<213> ORGANISM: Oryza sativa
<220> FEATURE:
<221> NAME/KEY: MISC_FEATURE
<222> LOCATION: (1)..(389)
<223> OTHER INFORMATION: MEP3c

<400> SEQUENCE: 42

Met Ala Phe His Tyr Ala Ala Met Pro Ser Ser Ser Ser Ser Ser Leu
1               5                   10                  15

Ser Gly Val Ser Ser Gln Pro Pro Leu His Leu Pro Arg Leu Arg Ser
            20                  25                  30

Pro His Gln Ala Ser Arg Arg Leu Ser Ala Leu Pro Phe Ser Arg Ala
        35                  40                  45

Leu Pro Leu Pro Leu Arg Leu Arg Leu Arg Ile Pro Arg Pro Gln Leu
    50                  55                  60

Pro Pro Leu Pro Leu Ala Phe Ser His Gly Gly Gly Asp Asn Asp
65                  70                  75                  80

Gly Asp Asp Asn Asn Asn Asn Gly Gly Gly Asp Gly Glu Gly Asp Gly
                85                  90                  95

Gly Ala Pro Asp Asn Arg Arg Glu Ala Leu Phe Val Leu Ala Gln Leu
            100                 105                 110

Gly Arg Lys Leu Glu Ser Leu Pro Ser Asp Leu Ala Ala Ala Val Glu
        115                 120                 125

Gly Gly Arg Val Thr Gly Glu Ile Val Arg Arg Phe Ala Glu Met Glu
    130                 135                 140

Gly Ser Ala Leu Leu Arg Trp Leu Leu Gln Phe Gln Gly Phe Arg Glu
145                 150                 155                 160

Arg Leu Leu Ala Asp Asp Leu Phe Leu Ala Lys Leu Ala Met Glu Cys

```
            165                 170                 175
Gly Val Gly Val Ile Ala Lys Thr Ala Ala Glu Tyr Glu Lys Arg Arg
            180                 185                 190

Glu Asn Phe Val Lys Glu Ile Asp Ile Val Ile Ala Asp Val Val Met
            195                 200                 205

Ala Ile Val Ala Asp Phe Met Leu Val Tyr Leu Pro Ala Pro Thr Val
            210                 215                 220

Ser Leu Gln Pro Pro Leu Ala Thr Asn Ala Gly His Ile Ala Asn Phe
225                 230                 235                 240

Phe His Asn Cys Pro Asp Asn Ala Phe Gln Ile Ala Leu Ala Gly Arg
            245                 250                 255

Ser Tyr Ser Ile Leu Gln Arg Leu Gly Ala Ile Leu Arg Asn Gly Ala
            260                 265                 270

Lys Leu Phe Thr Val Gly Thr Ser Ala Ser Leu Ile Gly Thr Gly Val
            275                 280                 285

Thr Asn Ala Leu Ile Lys Ala Arg Lys Ala Val Asp Lys Glu Leu Asp
            290                 295                 300

Asp Glu Val Glu Asp Ile Pro Val Leu Ser Thr Ser Val Ala Tyr Gly
305                 310                 315                 320

Val Tyr Met Ala Val Ser Ser Asn Leu Arg Tyr Gln Ile Leu Ala Gly
            325                 330                 335

Val Ile Glu Gln Arg Met Leu Glu Pro Leu Leu His Asn His Lys Leu
            340                 345                 350

Leu Leu Ser Ala Leu Cys Phe Ala Val Arg Thr Gly Asn Thr Phe Leu
            355                 360                 365

Gly Ser Leu Leu Trp Val Asp Tyr Ala Arg Trp Val Gly Val Gln Lys
            370                 375                 380

Val Gln Glu Glu Ala
385

<210> SEQ ID NO 43
<211> LENGTH: 569
<212> TYPE: PRT
<213> ORGANISM: Oryza sativa
<220> FEATURE:
<221> NAME/KEY: MISC_FEATURE
<222> LOCATION: (1)..(569)
<223> OTHER INFORMATION: NHD

<400> SEQUENCE: 43

Met Ala Ala Leu Ser Ser Cys Leu Leu Ala Ala Val Arg Pro His Pro
1               5                   10                  15

Pro Pro Pro Pro Arg Pro Leu Ser Pro Ser Phe Ile Pro Ser Ala Leu
            20                  25                  30

Arg His Arg His Arg Leu Ser Gln Ala Pro Pro Leu Ala Thr Ser Leu
            35                  40                  45

Pro Arg Pro Arg Pro Pro Trp Cys Arg Phe Ser Ala Ser Ser Pro Pro
        50                  55                  60

Pro Pro Pro Asp Asp Pro Asp Tyr Glu Leu Leu Asp Thr Thr Gly
65                  70                  75                  80

Asn Cys Asp Pro Leu Cys Ser Val Asp Glu Val Ser Ser Gln Tyr Phe
            85                  90                  95

Glu Ala Asn Tyr Lys Pro Lys Asn Asp Leu Leu Lys Ala Leu Thr Ile
            100                 105                 110

Ile Ala Thr Ala Leu Ala Gly Ala Ala Ile Asn His Ser Trp Val
            115                 120                 125
```

-continued

```
Ala Glu His Gln Asp Ile Ala Met Val Leu Val Phe Ala Leu Gly Tyr
    130                 135                 140

Ala Gly Ile Ile Phe Glu Glu Ser Leu Ala Phe Asn Lys Ser Gly Val
145                 150                 155                 160

Gly Leu Leu Met Ala Val Cys Leu Trp Val Ile Arg Ser Ile Gly Ala
                165                 170                 175

Pro Ser Thr Asp Val Ala Val Gln Glu Leu Ser His Thr Thr Ala Glu
            180                 185                 190

Val Ser Glu Ile Val Phe Phe Leu Leu Gly Ala Met Thr Ile Val Glu
        195                 200                 205

Ile Val Asp Ala His Gln Gly Phe Lys Leu Val Thr Asp Asn Ile Ser
    210                 215                 220

Thr Arg Asn Pro Arg Thr Leu Leu Trp Val Ile Gly Phe Val Thr Phe
225                 230                 235                 240

Phe Leu Ser Ser Ile Leu Asp Asn Leu Thr Ser Thr Ile Val Met Val
                245                 250                 255

Ser Leu Leu Arg Lys Leu Val Pro Pro Ser Glu Tyr Arg Lys Leu Leu
            260                 265                 270

Gly Ala Val Val Val Ile Ser Ala Asn Ala Gly Gly Ala Trp Thr Pro
        275                 280                 285

Ile Gly Asp Val Thr Thr Thr Met Leu Trp Ile His Gly Gln Ile Thr
    290                 295                 300

Thr Leu Asn Thr Met Gln Gly Leu Phe Leu Pro Ser Val Val Ser Leu
305                 310                 315                 320

Ala Val Pro Leu Ala Leu Met Ser Leu Thr Ser Glu Ala Asn Gly Ser
                325                 330                 335

Ser Gln Lys Ser Ser Ser Leu Leu Ser Ser Glu Gln Met Ala Pro Arg
            340                 345                 350

Gly Gln Leu Val Phe Ala Val Gly Leu Gly Ala Leu Val Phe Val Pro
        355                 360                 365

Val Phe Lys Ala Leu Thr Gly Leu Pro Pro Phe Met Gly Met Met Leu
    370                 375                 380

Gly Leu Ala Ile Leu Trp Ile Leu Thr Asp Ala Ile His Tyr Gly Asp
385                 390                 395                 400

Ser Gly Arg Gln Arg Leu Lys Val Pro Gln Ala Leu Ser Arg Ile Asp
                405                 410                 415

Thr Gln Gly Val Leu Phe Phe Leu Gly Ile Leu Met Ser Val Gly Ser
            420                 425                 430

Leu Glu Ser Ala Gly Ile Leu Arg Gln Leu Ala Asn Tyr Leu Asp Ala
        435                 440                 445

Asn Ile Pro Asn Ala Asp Leu Ile Ala Ser Ala Ile Gly Val Ala Ser
    450                 455                 460

Ala Ile Ile Asp Asn Val Pro Leu Val Ala Ala Thr Met Gly Met Tyr
465                 470                 475                 480

Asp Leu Thr Ser Phe Pro Gln Asp Ala Asp Phe Trp Gln Leu Ile Ala
                485                 490                 495

Phe Cys Ala Gly Thr Gly Gly Ser Met Leu Ile Ile Gly Ser Ala Ala
            500                 505                 510

Gly Val Ala Phe Met Gly Met Glu Lys Val Asp Phe Phe Trp Tyr Phe
        515                 520                 525

Arg Lys Val Ser Gly Phe Ala Leu Ala Gly Tyr Ala Ala Gly Ile Ile
    530                 535                 540
```

-continued

```
Thr Tyr Leu Ala Ala Gln Asn Leu Pro Leu Ser Leu Pro Thr Ser Leu
545                 550                 555                 560

Ala Glu Ile Pro Phe Ile Ser Gly Ser
                565

<210> SEQ ID NO 44
<211> LENGTH: 419
<212> TYPE: PRT
<213> ORGANISM: Oryza sativa
<220> FEATURE:
<221> NAME/KEY: MISC_FEATURE
<222> LOCATION: (1)..(419)
<223> OTHER INFORMATION: BASS2

<400> SEQUENCE: 44

Met Ala Ala Ser Thr Thr Cys Pro Ala Arg Ser Met Ala Ser Val Ser
1               5                   10                  15

Arg Ala Leu Arg Pro Arg Pro His Ala Ala Ile Ala Ser Ala Ala Val
                20                  25                  30

Arg Thr Ala Ala Arg Leu Gly Gly Gly Leu Gly Ile Val Cys Ser Met
            35                  40                  45

Pro Ser Tyr Gly Arg Lys Glu Lys Glu Trp Gly Leu Thr Ile Ala
50                  55                  60

Ser Ala Pro Ala Thr Thr Ala Ala Pro Ala Leu Arg Ser Cys Gln Leu
65                  70                  75                  80

Leu Cys Lys Ala Glu Ala Asn Ile Ser Ser Asn Leu Pro Glu Ser Ile
                85                  90                  95

Pro Ser Glu Ala Asn Gln Tyr Glu Lys Ile Val Glu Leu Leu Thr Thr
            100                 105                 110

Leu Phe Pro Val Trp Val Ile Leu Gly Thr Ile Ile Gly Ile Tyr Lys
        115                 120                 125

Pro Ser Met Val Thr Trp Leu Glu Thr Asp Leu Phe Thr Val Gly Leu
130                 135                 140

Gly Phe Leu Met Leu Ser Met Gly Leu Thr Leu Thr Phe Glu Asp Phe
145                 150                 155                 160

Arg Arg Cys Met Arg Asn Pro Trp Thr Val Gly Val Gly Phe Leu Ala
                165                 170                 175

Gln Tyr Leu Ile Lys Pro Met Leu Gly Phe Ala Ile Ala Met Thr Leu
            180                 185                 190

Lys Leu Ser Ala Pro Leu Ala Thr Gly Leu Ile Leu Val Ser Cys Cys
        195                 200                 205

Pro Gly Gly Gln Ala Ser Asn Val Ala Thr Tyr Ile Ser Lys Gly Asn
210                 215                 220

Val Ala Leu Ser Val Leu Met Thr Thr Cys Ser Thr Ile Gly Ala Ile
225                 230                 235                 240

Val Met Thr Pro Leu Leu Thr Lys Leu Leu Ala Gly Gln Leu Val Pro
                245                 250                 255

Val Asp Ala Ala Gly Leu Ala Ile Ser Thr Phe Gln Val Val Leu Leu
            260                 265                 270

Pro Thr Ile Val Gly Val Leu Ala His Glu Tyr Phe Pro Lys Phe Thr
        275                 280                 285

Glu Arg Ile Ile Ser Ile Thr Pro Leu Ile Gly Val Leu Leu Thr Thr
            290                 295                 300

Leu Leu Cys Ala Ser Pro Ile Gly Gln Val Ser Glu Val Leu Lys Ala
305                 310                 315                 320

Gln Gly Gly Gln Leu Ile Ile Pro Val Ala Leu Leu His Val Ala Ala
```

325                 330                 335
Phe Ala Leu Gly Tyr Trp Leu Ser Lys Val Ser Ser Phe Gly Glu Ser
                340                 345                 350

Thr Ser Arg Thr Ile Ser Ile Glu Cys Gly Met Gln Ser Ser Ala Leu
            355                 360                 365

Gly Phe Leu Leu Ala Gln Lys His Phe Thr Asn Pro Leu Val Ala Val
        370                 375                 380

Pro Ser Ala Val Ser Val Val Cys Met Ala Leu Gly Ser Ala Leu
385                 390                 395                 400

Ala Val Phe Trp Arg Asn Arg Gly Leu Pro Ala Asn Asp Lys Asp Asp
                405                 410                 415

Phe Lys Glu

<210> SEQ ID NO 45
<211> LENGTH: 393
<212> TYPE: PRT
<213> ORGANISM: Oryza sativa
<220> FEATURE:
<221> NAME/KEY: MISC_FEATURE
<222> LOCATION: (1)..(393)
<223> OTHER INFORMATION: PPT2

<400> SEQUENCE: 45

Met Gln Arg Ala Ala Ala Ala Ser Arg Ala Thr Ala Trp Ser Thr Ala
1               5                   10                  15

Arg His Gly Ala Ala Arg Val Thr Ala Ser Ala Ser Phe Ser Gly Gly
            20                  25                  30

Gly Gly Ile Val Ala Gly Ala Leu Pro Leu Arg Val Arg Gly Gly
        35                  40                  45

Gln Leu Met Ser Leu Pro Leu Leu Ser Gly Gly Arg Ala Val Thr Ala
    50                  55                  60

Arg Val Ala Ala Ala Glu Ala Pro Leu Pro Ala Asp Asp Ala Asp Ala
65                  70                  75                  80

Ala Ala Gly Arg Glu Arg Gly Ala Leu Ala Glu Thr Ala Gln Leu Gly
                85                  90                  95

Ala Met Ile Val Ala Trp Tyr Leu Leu Asn Ile Tyr Phe Asn Ile Tyr
            100                 105                 110

Asn Lys Gln Val Leu Gln Pro Leu Pro Phe Pro Tyr Thr Ile Thr Ala
        115                 120                 125

Phe Gln Leu Ala Phe Gly Ser Phe Val Ile Phe Leu Met Trp Ala Leu
    130                 135                 140

Lys Leu His Pro Ala Pro Arg Ile Ser Ile Ser Gln Leu Ala Lys Ile
145                 150                 155                 160

Ala Pro Leu Ala Ala Gly His Met Leu Gly Thr Val Phe Thr Asn Met
                165                 170                 175

Ser Leu Ser Lys Val Ala Val Ser Phe Thr His Thr Ile Lys Ala Ser
            180                 185                 190

Glu Pro Phe Phe Thr Val Leu Leu Ser Ala Phe Phe Leu Gly Glu Thr
        195                 200                 205

Pro Ser Leu Leu Val Leu Gly Ser Leu Val Pro Ile Val Gly Gly Val
    210                 215                 220

Ala Leu Ala Ser Leu Thr Glu Leu Ser Phe Asn Trp Ile Gly Phe Trp
225                 230                 235                 240

Ser Ala Met Ala Ser Asn Leu Leu Tyr Gln Ser Arg Asn Val Leu Ser
                245                 250                 255

```
Lys Lys Leu Leu Gly Gly Glu Glu Ala Leu Asp Asp Ile Asn Leu
            260                 265                 270
Phe Ser Ile Leu Thr Ile Leu Ser Phe Leu Leu Ser Leu Pro Leu Met
        275                 280                 285
Leu Phe Ser Glu Gly Val Lys Phe Ser Pro Gly Tyr Leu Arg Ser Thr
    290                 295                 300
Gly Leu Asn Leu Gln Glu Leu Cys Val Arg Ala Ala Leu Ala Gly Phe
305                 310                 315                 320
Cys Phe His Gly Tyr Gln Lys Leu Ser Tyr Leu Ile Leu Ala Arg Val
                325                 330                 335
Ser Pro Val Thr His Ser Val Ala Asn Cys Val Lys Arg Val Val Val
            340                 345                 350
Ile Val Ala Ser Val Leu Phe Phe Arg Thr Pro Ile Ser Pro Val Asn
            355                 360                 365
Ala Leu Gly Thr Gly Val Ala Leu Gly Gly Val Phe Leu Tyr Ser Arg
        370                 375                 380
Leu Lys Arg Thr Lys Pro Lys Asn Ala
385                 390

<210> SEQ ID NO 46
<211> LENGTH: 417
<212> TYPE: PRT
<213> ORGANISM: Oryza sativa
<220> FEATURE:
<221> NAME/KEY: MISC_FEATURE
<222> LOCATION: (1)..(417)
<223> OTHER INFORMATION: TPT

<400> SEQUENCE: 46

Met Pro Ala Leu Gly Thr Leu Ser Gly Gly Ala Ala Gly Val Ala Gly
1               5                   10                  15
Leu Leu Arg Leu Arg Arg Ala Thr Pro Ser Pro Ala Val Ala Thr Pro
            20                  25                  30
Phe Pro Ala Ala Ala Ala Arg Cys Ala Ala Ala Ala Ala Ala Ala Val
        35                  40                  45
Val Pro Asp Gly Gly Gln Leu Val Trp Gly Arg Gln Leu Arg Pro Ala
    50                  55                  60
Leu Leu Leu Pro Ala Ala Gly Gly Leu Leu Gln Pro Pro Thr Ser Pro
65                  70                  75                  80
Ser Ser Ser Gln Ala Gly Arg Arg Gln Ala Leu Arg Pro Pro Ala Ala
                85                  90                  95
Ala Thr Ser Gly Glu Ala Lys Pro Ala Gly Phe Leu Glu Lys Tyr Pro
            100                 105                 110
Ala Leu Ile Thr Gly Phe Phe Phe Met Trp Tyr Phe Leu Asn Val
        115                 120                 125
Ile Phe Asn Ile Leu Asn Lys Lys Ile Tyr Asn Tyr Phe Pro Tyr Pro
    130                 135                 140
Tyr Phe Val Ser Val Ile His Leu Leu Val Gly Val Tyr Cys Leu
145                 150                 155                 160
Val Ser Trp Thr Val Gly Leu Pro Lys Arg Ala Pro Ile Asn Ser Thr
                165                 170                 175
Leu Leu Lys Leu Leu Phe Pro Val Ala Leu Cys His Ala Leu Gly His
            180                 185                 190
Val Thr Ser Asn Val Ser Phe Ala Thr Val Ala Val Ser Phe Ala His
        195                 200                 205
Thr Ile Lys Ala Leu Glu Pro Phe Phe Asn Ala Ala Ala Thr Gln Phe
```

```
                    210                 215                 220
Val Leu Gly Gln Gln Val Pro Leu Pro Leu Trp Leu Ser Leu Ala Pro
225                 230                 235                 240

Val Val Leu Gly Val Ser Met Ala Ser Leu Thr Glu Leu Ser Phe Asn
                245                 250                 255

Trp Thr Gly Phe Ile Asn Ala Met Ile Ser Asn Ile Ser Phe Thr Tyr
                260                 265                 270

Arg Ser Ile Tyr Ser Lys Lys Ala Met Thr Asp Met Asp Ser Thr Asn
                275                 280                 285

Val Tyr Ala Tyr Ile Ser Ile Ile Ala Leu Ile Val Cys Ile Pro Pro
                290                 295                 300

Ala Val Ile Ile Glu Gly Pro Gln Leu Leu Gln His Gly Phe Asn Asp
305                 310                 315                 320

Ala Ile Ala Lys Val Gly Leu Thr Lys Phe Val Ser Asp Leu Phe Phe
                325                 330                 335

Val Gly Leu Phe Tyr His Leu Tyr Asn Gln Val Ala Thr Asn Thr Leu
                340                 345                 350

Glu Arg Val Ala Pro Leu Thr His Ala Val Gly Asn Val Leu Lys Arg
                355                 360                 365

Val Phe Val Ile Gly Phe Ser Ile Ile Val Phe Gly Asn Arg Ile Thr
                370                 375                 380

Thr Gln Thr Gly Ile Gly Thr Cys Ile Ala Ile Ala Gly Val Ala Ile
385                 390                 395                 400

Tyr Ser Tyr Ile Lys Ala Lys Ile Glu Glu Lys Arg Ala Lys Ser
                405                 410                 415

Ala

<210> SEQ ID NO 47
<211> LENGTH: 561
<212> TYPE: PRT
<213> ORGANISM: Brachypodium distachyon
<220> FEATURE:
<221> NAME/KEY: MISC_FEATURE
<222> LOCATION: (1)..(561)
<223> OTHER INFORMATION: OMT

<400> SEQUENCE: 47

Met Ala Ser Ser Thr Pro Ala Ala Ser Pro Leu Thr Cys His His Leu
1               5                   10                  15

Gly Leu Arg Leu Arg Pro His Leu Pro Ser Phe Ser Leu Arg Arg Arg
                20                  25                  30

Ser Thr Leu Ser Ser Lys Pro Ile Ser Leu Ser His Ser His Ser Leu
                35                  40                  45

Pro Lys Pro Leu Ala Leu Pro Pro Ser Ala Thr Ala Arg Arg His Leu
                50                  55                  60

Leu Pro Pro Val Ser Ala Ala Ser Pro Ala Ser Thr Pro Ala Pro Val
65                  70                  75                  80

Ser Pro Pro Ala Lys Pro Ala Leu Lys Gly Ala Ala Ile Lys Pro Leu
                85                  90                  95

Leu Ala Ser Ile Ala Thr Gly Leu Leu Ile Trp Phe Ile Pro Ala Pro
                100                 105                 110

Ala Gly Val Ala Arg Asn Ala Trp Gln Leu Leu Ala Val Phe Leu Ala
                115                 120                 125

Thr Ile Val Gly Ile Ile Thr Gln Pro Leu Pro Leu Gly Ala Val Ala
                130                 135                 140
```

```
Leu Leu Gly Leu Gly Ala Ala Val Leu Thr Arg Thr Leu Thr Phe Ala
145                 150                 155                 160

Ala Ala Phe Ser Ala Phe Gly Asp Pro Ile Pro Trp Leu Ile Gly Arg
            165                 170                 175

Ala Phe Phe Phe Ala Arg Gly Val His Gln Asp Arg Ala Arg Gln Pro
            180                 185                 190

Arg Arg Leu Arg Leu Arg Leu Arg Ile Arg Trp Ile His Ala Arg Pro
        195                 200                 205

Arg Leu Leu Ala Arg Leu Arg Arg Gly Arg Ser Ser Pro Pro Pro Asn
    210                 215                 220

Pro Pro Pro Val Ser Arg Ala Gly Pro Ala Ala Ser Ser Leu Pro Val
225                 230                 235                 240

Val Lys Ser Leu Cys Glu Ala Cys Gly Ser Arg Thr Asp Asp Gly Thr
                245                 250                 255

Glu Arg Lys Leu Gly Ser Trp Leu Met Leu Thr Cys Phe Gln Thr Ser
            260                 265                 270

Val Ile Ser Ser Ala Met Phe Leu Thr Ala Met Ala Ala Asn Pro Leu
        275                 280                 285

Ala Ala Asn Leu Thr Ala Ser Thr Ile Gly Gln Gly Ile Gly Trp Thr
    290                 295                 300

Leu Trp Ala Lys Ala Ala Ile Val Pro Gly Leu Leu Ser Leu Ile Ile
305                 310                 315                 320

Val Pro Leu Val Leu Tyr Val Ile Tyr Pro Pro Glu Val Lys Ser Ser
                325                 330                 335

Pro Asp Ala Pro Arg Leu Ala Lys Glu Lys Leu Ala Thr Met Gly Pro
            340                 345                 350

Met Ser Lys Glu Glu Ile Ile Met Ala Gly Thr Leu Leu Leu Thr Val
        355                 360                 365

Gly Leu Trp Ile Phe Gly Gly Met Leu Ser Val Asp Ala Val Ser Ala
    370                 375                 380

Ala Ile Leu Gly Leu Ser Val Leu Leu Ile Thr Gly Val Val Thr Trp
385                 390                 395                 400

Lys Glu Cys Leu Ala Glu Ser Val Ala Trp Asp Thr Leu Thr Trp Phe
                405                 410                 415

Ala Ala Leu Ile Ala Met Ala Gly Tyr Leu Asn Lys Tyr Gly Leu Ile
            420                 425                 430

Ala Trp Phe Ser Glu Thr Val Val Lys Phe Val Gly Leu Gly Leu
        435                 440                 445

Ser Trp Gln Leu Ser Phe Gly Val Leu Val Leu Leu Tyr Phe Tyr Ser
    450                 455                 460

His Tyr Phe Phe Ala Ser Gly Ala Ala His Ile Gly Ala Met Phe Thr
465                 470                 475                 480

Ala Phe Leu Ser Val Ser Ser Ala Leu Gly Thr Pro Pro Leu Phe Ala
                485                 490                 495

Ala Met Val Leu Ser Phe Leu Ser Asn Ile Met Gly Gly Leu Thr His
            500                 505                 510

Tyr Gly Ile Gly Ser Ala Pro Val Phe Tyr Gly Ala Gly Tyr Val Pro
        515                 520                 525

Leu Ala Gln Trp Trp Gly Tyr Gly Phe Val Ile Ser Val Val Asn Ile
    530                 535                 540

Ile Ile Trp Leu Gly Ala Gly Gly Phe Trp Trp Lys Met Ile Gly Leu
545                 550                 555                 560

Trp
```

-continued

<210> SEQ ID NO 48
<211> LENGTH: 550
<212> TYPE: PRT
<213> ORGANISM: Brachypodium distachyon
<220> FEATURE:
<221> NAME/KEY: MISC_FEATURE
<222> LOCATION: (1)..(550)
<223> OTHER INFORMATION: DCT1

<400> SEQUENCE: 48

```
Met Glu His Leu Arg Ile Ala Val Ser His Arg Pro Leu Leu Leu
1               5                   10                  15

Pro Ala Pro Gln Thr Leu Arg Arg Arg Leu His Leu Ser Ala Pro
                20                  25                  30

Leu Thr Leu Pro Pro Ala Ser Arg Ser Leu Ser Ser Arg His His Leu
            35                  40                  45

Phe Pro Val Pro Arg Arg His Ile Ile Arg Pro Leu Leu Ala Ser Gln
    50                  55                  60

Thr Pro Ile Pro Asp Ser Glu Thr Glu Ser Gly Val Pro Pro Ala Gly
65                  70                  75                  80

Ala Lys Leu Val Pro Leu Leu Val Ser Leu Ala Leu Gly Leu Ala Val
                85                  90                  95

Arg Phe Leu Ala Pro Arg Pro Leu Glu Val Ser Leu Gln Ala Trp Gln
                100                 105                 110

Leu Leu Ser Ile Phe Leu Ser Thr Ile Ala Gly Leu Val Leu Gly Pro
            115                 120                 125

Leu Pro Val Gly Ala Trp Ala Phe Leu Gly Leu Thr Val Ala Val Ala
    130                 135                 140

Thr Arg Thr Leu Pro Phe Gly Val Ala Phe Ser Ala Phe Thr Asn Glu
145                 150                 155                 160

Val Ile Trp Leu Ile Val Ile Ser Phe Phe Ala Arg Gly Phe Val
                165                 170                 175

Lys Thr Gly Leu Gly Asp Arg Ile Ala Thr Tyr Phe Ile Lys Trp Leu
                180                 185                 190

Gly Gly Ser Thr Leu Gly Leu Ser Tyr Gly Leu Thr Ile Ser Glu Ala
            195                 200                 205

Cys Ile Ala Pro Ala Met Pro Ser Thr Thr Ala Arg Ala Gly Gly Val
    210                 215                 220

Phe Leu Pro Ile Ile Lys Ser Leu Ser Leu Ser Ala Glu Ser Met Pro
225                 230                 235                 240

Asn Asp Pro Ser Ser Arg Lys Leu Gly Ser Tyr Leu Val Met Thr Gln
                245                 250                 255

Phe Gln Ala Gly Ser Asn Ser Ser Ala Leu Phe Leu Thr Ala Ala Ala
            260                 265                 270

Gln Asn Leu Leu Cys Leu Lys Leu Ala Glu Glu Leu Gly Ile Ile Val
    275                 280                 285

Ala Asn Pro Trp Val Ser Trp Phe Thr Ala Ala Ser Leu Pro Ala Ile
    290                 295                 300

Val Ser Leu Leu Ala Thr Pro Tyr Leu Leu Tyr Lys Ile Phe Pro Pro
305                 310                 315                 320

Asp Met Lys Asp Thr Pro Asp Ala Pro Ala Leu Ala Ala Glu Lys Leu
                325                 330                 335

Lys Cys Met Gly Pro Val Thr Lys Asn Glu Trp Val Met Ile Gly Thr
                340                 345                 350
```

```
Met Val Leu Ala Val Ser Leu Trp Ile Phe Gly Glu Ala Ile Gly Val
            355                 360                 365

Ser Ser Val Val Ala Ala Met Leu Gly Leu Ser Ile Leu Leu Leu Leu
        370                 375                 380

Gly Val Leu Asp Trp Asp Asp Cys Leu Ser Glu Lys Ser Ala Trp Asp
385                 390                 395                 400

Thr Leu Ser Trp Phe Ala Val Leu Val Ala Met Ala Gly Gln Leu Thr
                405                 410                 415

Asn Leu Gly Ile Val Ser Trp Met Ser Asn Ser Val Ala Asn Met Leu
            420                 425                 430

Gln Ser Phe Ser Leu Ser Trp Pro Ala Ala Phe Val Ala Leu Glu Ser
        435                 440                 445

Ser Tyr Phe Leu Ile His Tyr Leu Phe Ala Ser Gln Thr Gly His Val
450                 455                 460

Gly Ala Leu Tyr Ser Ala Phe Leu Ala Met His Val Ala Ala Gly Ala
465                 470                 475                 480

Pro Pro Val Leu Ser Ala Leu Ala Leu Ala Phe Asn Thr Asn Leu Phe
                485                 490                 495

Gly Ala Leu Thr His Tyr Ser Ser Gly Gln Ala Ala Val Tyr Phe Gly
            500                 505                 510

Ala Gly Tyr Leu Glu Leu Pro Asp Ile Phe Lys Met Gly Phe Val Thr
        515                 520                 525

Ala Leu Leu Asn Ala Leu Ile Trp Gly Val Val Gly Thr Leu Trp Trp
530                 535                 540

Lys Phe Leu Gly Leu Tyr
545                 550

<210> SEQ ID NO 49
<211> LENGTH: 556
<212> TYPE: PRT
<213> ORGANISM: Brachypodium distachyon
<220> FEATURE:
<221> NAME/KEY: MISC_FEATURE
<222> LOCATION: (1)..(556)
<223> OTHER INFORMATION: DCT2

<400> SEQUENCE: 49

Met Glu Arg Leu Arg Leu Ala Val Ser His Arg Pro Ala Leu Pro Leu
1               5                   10                  15

Pro Ala Pro His Asn His Leu Arg Arg His Leu Gln Leu Gln Ser
            20                  25                  30

Ser Pro Asn Ser Leu Ser Leu Ser Arg Pro Ile Ser Pro His Leu Ser
        35                  40                  45

Pro Thr Pro Arg Arg His Leu His Pro Leu Leu Ala Ser Ala Ser Ala
50                  55                  60

Thr Gln Ala Ala Ser Ser Ser Pro Glu Pro Thr Pro Ala Pro Val Ala
65                  70                  75                  80

Ala Val Ser Ser Ala Gly Ala Lys Leu Ile Pro Leu Ile Ala Ser Val
                85                  90                  95

Ala Val Gly Leu Ala Val Arg Phe Leu Ala Pro Arg Pro Ala Glu Val
            100                 105                 110

Thr Pro Glu Ala Trp Gln Leu Leu Ser Ile Phe Leu Ser Thr Ile Ala
        115                 120                 125

Gly Leu Val Leu Gly Pro Leu Pro Val Gly Ala Trp Ala Phe Leu Gly
130                 135                 140

Leu Thr Ala Thr Val Ala Thr Arg Thr Leu Pro Phe Thr Ala Ala Phe
```

```
               145                 150                 155                 160
        Gly Ala Phe Thr Asn Glu Val Ile Trp Leu Ile Val Ile Ser Phe Phe
                        165                 170                 175

Phe Ala Arg Gly Phe Val Lys Thr Gly Leu Gly Asp Arg Val Ala Thr
                        180                 185                 190

Tyr Phe Val Lys Trp Leu Gly Ser Thr Leu Gly Leu Ser Tyr Gly
                    195                 200                 205

Leu Thr Ile Ser Glu Ala Cys Ile Ala Pro Ala Met Pro Ser Thr Thr
        210                 215                 220

Ala Arg Ala Gly Gly Val Phe Leu Pro Ile Val Lys Ser Leu Ser Leu
        225                 230                 235                 240

Ser Ala Gly Ser Lys Pro Asn Asp Pro Ser Ala Lys Lys Leu Gly Ala
                        245                 250                 255

Tyr Leu Val Gln Ser Gln Leu Gln Ala Ser Gly Asn Ser Ser Ala Leu
                        260                 265                 270

Phe Leu Thr Ala Ala Ala Gln Asn Leu Leu Cys Leu Lys Leu Ala Glu
                        275                 280                 285

Glu Ala Gly Val Lys Ile Ala Ser Pro Trp Ile Leu Trp Phe Lys Val
                290                 295                 300

Ala Ser Leu Pro Ala Ile Ile Ala Leu Leu Ala Thr Pro Tyr Leu Leu
        305                 310                 315                 320

Tyr Lys Ile Phe Pro Pro Glu Ile Lys Asp Thr Pro Asp Ala Pro Ala
                        325                 330                 335

Leu Ala Ala Gln Lys Leu Glu Lys Met Gly Pro Val Thr Lys Asn Glu
                        340                 345                 350

Trp Val Met Val Ala Thr Met Val Leu Ala Val Ser Leu Trp Ile Phe
                    355                 360                 365

Gly Asp Ile Ile Gly Val Ser Ser Val Ala Ala Met Ile Gly Leu
                370                 375                 380

Ser Ile Leu Leu Leu Leu Gly Val Met Asn Trp Asp Asp Cys Leu Asn
        385                 390                 395                 400

Glu Lys Ser Ala Trp Asp Thr Leu Ala Trp Phe Ala Ile Leu Val Gly
                        405                 410                 415

Met Ala Gly Gln Leu Thr Asn Leu Gly Ile Val Ser Trp Met Ser Asn
                        420                 425                 430

Cys Val Ala Lys Val Leu Gln Ser Phe Ser Leu Ser Trp Pro Ala Ala
                        435                 440                 445

Phe Gly Val Leu Gln Ala Ser Tyr Phe Leu Ile His Tyr Leu Phe Ala
                450                 455                 460

Ser Gln Thr Ala His Val Gly Ala Leu Tyr Ser Ala Phe Leu Ala Met
        465                 470                 475                 480

His Leu Ala Ala Gly Val Pro Ala Leu Leu Ser Ala Leu Ala Leu Thr
                        485                 490                 495

Tyr Asn Ser Asn Leu Phe Gly Ala Leu Thr His Tyr Ser Ser Gly Gln
                        500                 505                 510

Ser Ala Val Tyr Tyr Gly Ala Gly Tyr Val Asp Leu Pro Asp Val Phe
                    515                 520                 525

Lys Leu Gly Phe Ala Ser Ala Ile Asn Ala Ala Ile Trp Gly Val
                    530                 535                 540

Val Gly Thr Phe Trp Trp Lys Phe Leu Gly Leu Tyr
        545                 550                 555

<210> SEQ ID NO 50
```

```
<211> LENGTH: 384
<212> TYPE: PRT
<213> ORGANISM: Brachypodium distachyon
<220> FEATURE:
<221> NAME/KEY: MISC_FEATURE
<222> LOCATION: (1)..(384)
<223> OTHER INFORMATION: MEP3a

<400> SEQUENCE: 50
```

| | | | | | | | | | | | | | | |
|---|---|---|---|---|---|---|---|---|---|---|---|---|---|---|
| Met | Ala | Phe | Ser | Ser | Pro | Asn | Ser | Leu | Ser | Ala | Ser | Ser | Thr | |
| 1 | | | | 5 | | | | | 10 | | | | | 15 |
| Ala | Ala | Ser | Pro | Phe | His | Leu | Arg | Leu | Gln | Pro | Gln | Gln | Pro | Leu | Leu |
| | | | 20 | | | | | 25 | | | | | 30 | | |
| Arg | Leu | Pro | Thr | Leu | Pro | Phe | His | Arg | Ser | Leu | Pro | Ala | Leu | Arg | Leu |
| | | | | 35 | | | | | 40 | | | | | 45 | |
| Thr | Arg | Pro | Leu | Leu | Pro | Pro | Leu | Pro | Leu | Ala | Ser | Ser | Gly | Gly | Gly |
| 50 | | | | | | 55 | | | | | 60 | | | | |
| Gly | Ser | Ser | Ile | Gly | Gly | Gly | Asp | Asp | Leu | Pro | Ser | Gly | Gly | Gly |
| 65 | | | | | 70 | | | | | 75 | | | | | 80 |
| Gly | Gly | Gly | Gly | Gly | Asp | Lys | Asp | Glu | Gly | Asn | Glu | Asp | Gly | Asp |
| | | | | | 85 | | | | | 90 | | | | | 95 |
| Asp | Asp | Ser | Ser | Val | Asn | Arg | Arg | Glu | Ala | Leu | Phe | Val | Leu | Ala | Gln |
| | | | | 100 | | | | | 105 | | | | | 110 | |
| Leu | Gly | Arg | Lys | Leu | Glu | Ser | Leu | Pro | Ala | Asp | Met | Ala | Ala | Ala | Val |
| | | | 115 | | | | | 120 | | | | | 125 | | |
| Asp | Gly | Gly | Arg | Leu | Pro | Gly | Glu | Ile | Val | Arg | Arg | Phe | Ala | Asp | Leu |
| 130 | | | | | | 135 | | | | | 140 | | | | |
| Glu | Lys | Ser | Pro | Met | Phe | Arg | Trp | Leu | Leu | Gln | Phe | Gly | Gly | Phe | Arg |
| 145 | | | | | 150 | | | | | 155 | | | | | 160 |
| Glu | Arg | Leu | Leu | Ala | Asp | Asp | Leu | Phe | Leu | Ala | Lys | Val | Ala | Met | Glu |
| | | | | 165 | | | | | 170 | | | | | 175 | |
| Cys | Gly | Val | Gly | Ile | Phe | Thr | Lys | Thr | Ala | Ala | Glu | Tyr | Glu | Arg | Arg |
| | | | 180 | | | | | 185 | | | | | 190 | | |
| Arg | Glu | Asn | Phe | Val | Lys | Glu | Leu | Asp | Phe | Val | Ile | Ala | Asp | Val | Val |
| | | | 195 | | | | | 200 | | | | | 205 | | |
| Met | Ala | Ile | Val | Ala | Asp | Phe | Met | Leu | Val | Trp | Leu | Pro | Ala | Pro | Thr |
| 210 | | | | | 215 | | | | | 220 | | | | | |
| Val | Ser | Leu | Gln | Pro | Ala | Leu | Ala | Val | Asn | Ala | Gly | Ser | Leu | Ala | Lys |
| 225 | | | | | 230 | | | | | 235 | | | | | 240 |
| Phe | Phe | His | Asn | Cys | Pro | Asp | Asn | Ala | Phe | Gln | Ile | Ala | Leu | Ala | Gly |
| | | | | 245 | | | | | 250 | | | | | 255 | |
| Arg | Ser | Tyr | Thr | Phe | Leu | Gln | Arg | Phe | Gly | Ala | Ile | Met | Arg | Asn | Gly |
| | | | 260 | | | | | 265 | | | | | 270 | | |
| Ala | Lys | Leu | Phe | Ala | Val | Gly | Thr | Ser | Ala | Ser | Leu | Ile | Gly | Thr | Gly |
| | | | 275 | | | | | 280 | | | | | 285 | | |
| Val | Thr | Asn | Ala | Ile | Ile | Lys | Ala | Arg | Asn | Thr | Val | Asn | Lys | Asp | Asp |
| 290 | | | | | 295 | | | | | 300 | | | | | |
| Ala | Gly | Glu | Val | Glu | Asp | Ile | Pro | Ile | Val | Ser | Thr | Ser | Ile | Ala | Tyr |
| 305 | | | | | 310 | | | | | 315 | | | | | 320 |
| Gly | Val | Tyr | Met | Ala | Val | Ser | Ser | Asn | Leu | Arg | Tyr | Gln | Val | Leu | Ala |
| | | | | 325 | | | | | 330 | | | | | 335 | |
| Gly | Val | Ile | Glu | Gln | Arg | Met | Leu | Glu | Pro | Leu | Leu | His | Arg | His | Lys |
| | | | 340 | | | | | 345 | | | | | 350 | | |
| Leu | Ala | Leu | Ser | Ala | Leu | Cys | Phe | Ala | Val | Arg | Thr | Gly | Asn | Thr | Phe |
| | | | 355 | | | | | 360 | | | | | 365 | | |

-continued

```
Leu Gly Ser Leu Leu Trp Val Asp Tyr Ala Lys Trp Ile Gly Ile Gln
    370                 375                 380

<210> SEQ ID NO 51
<211> LENGTH: 720
<212> TYPE: PRT
<213> ORGANISM: Brachypodium distachyon
<220> FEATURE:
<221> NAME/KEY: MISC_FEATURE
<222> LOCATION: (1)..(720)
<223> OTHER INFORMATION: MEP3b

<400> SEQUENCE: 51

Met Leu Pro His Ala Pro Cys Arg Asn Pro Gly Ala Phe Lys Phe Lys
1               5                   10                  15

Pro Leu Leu Pro Thr Lys Pro Pro Leu Ala Ala Ala Ser Ser Arg
            20                  25                  30

Gly Ser Leu Cys Thr Ala Ala Ala Ser Arg Arg Asp Phe Leu Leu Leu
            35                  40                  45

Ala Pro Ser Leu Ala Ala Ala Ser Thr Ala Ile Gln Tyr Phe Pro Leu
    50                  55                  60

Ser Ala Ser Ala Ala Asp Asp Glu Lys Pro Ala Pro Gln Pro Pro Ala
65                  70                  75                  80

Ala Pro Ala Pro Thr Pro Pro Ala Pro Ala Gly Glu Pro Glu Glu Ala
                85                  90                  95

Ala Leu Ser Arg Met Tyr Asp Ala Thr Val Ile Gly Glu Pro Gln Ala
            100                 105                 110

Val Gly Lys Asp Ala Arg Gly Arg Val Trp Glu Lys Leu Met Ala Ala
        115                 120                 125

Arg Val Val Tyr Leu Gly Glu Ala Glu Leu Val Pro Asp Arg Asp Asp
    130                 135                 140

Arg Val Leu Glu Leu Glu Ile Ala Arg Lys Leu Ser Asp Arg Cys Ala
145                 150                 155                 160

Asp Ala Gly Arg Arg Leu Ser Leu Ala Leu Glu Ala Phe Pro Cys Asp
                165                 170                 175

Leu Gln Glu Gln Leu Asn Gln Phe Met Asp Gly Arg Ile Asp Gly Asn
            180                 185                 190

Asn Leu Arg Leu Tyr Thr Ser His Trp Ala Pro Gln Arg Trp Gln Glu
        195                 200                 205

Tyr Glu Pro Leu Leu Asn Tyr Cys Arg Asp Asn Gly Ile Asn Leu Ile
    210                 215                 220

Ala Cys Gly Thr Pro Leu Glu Val Val Arg Thr Val Gln Ala Glu Gly
225                 230                 235                 240

Ile Arg Gly Leu Ser Lys Ala His Arg Lys Leu Tyr Ala Pro Pro Ala
                245                 250                 255

Gly Ser Gly Phe Ile Ser Gly Phe Thr Ser Ile Ser Gly Arg Ser Leu
            260                 265                 270

Ile Asp Lys Thr Ser Ser Thr His Ile Ser Pro Phe Gly Pro Ser Ser
        275                 280                 285

Tyr Leu Ser Ala Gln Ala Arg Val Asp Asp Tyr Thr Met Ser Arg
    290                 295                 300

Ile Ile Met Lys Glu Ile Thr Asn Gly Asp Pro Ser Gly Met Leu Val
305                 310                 315                 320

Val Val Thr Gly Ala Ser His Val Met Tyr Gly Ser Arg Gly Ile Gly
                325                 330                 335

Val Pro Ala Arg Ile Ser Lys Lys Met Gln Lys Lys Lys Gln Val Val
```

```
                340                 345                 350
Ile Leu Leu Asp Pro Glu Arg Gln Gly Ile Arg Arg Glu Gly Glu Ile
            355                 360                 365

Pro Val Ala Asp Ile Leu Trp Tyr Ser Ala Ala Lys Pro Cys Ser Arg
        370                 375                 380

Asn Cys Phe Asp Arg Ala Glu Ile Ala Arg Val Met Asn Ala Ala Gly
385                 390                 395                 400

Arg Arg Arg Glu Ala Leu Pro Gln Asp Ile Gln Lys Gly Ile Asp Leu
                405                 410                 415

Gly Val Val Ser Pro Glu Ile Leu Gln Asn Phe Phe Asp Leu Glu Lys
            420                 425                 430

Tyr Pro Val Val Asp Glu Leu Ile His Arg Phe Gln Gly Phe Arg Glu
        435                 440                 445

Arg Leu Leu Ala Asp Pro Lys Phe Leu Asn Arg Leu Ala Ile Glu Glu
    450                 455                 460

Ala Ile Ser Ile Thr Thr Ala Val Leu Ala Gln Tyr Glu Lys Arg Lys
465                 470                 475                 480

Gly Arg Phe Phe Glu Glu Ile Asp Tyr Val Leu Thr Asp Thr Ile Arg
                485                 490                 495

Gly Ser Val Val Asp Phe Phe Thr Val Trp Leu Pro Ala Pro Thr Ile
            500                 505                 510

Ser Leu Leu Ser Ile Ala Asp Asp Gly Ser Gly Glu Ser Leu Glu Leu
        515                 520                 525

Leu Arg Gly Leu Leu Gly Ser Leu Pro Asp Asn Ala Phe Gln Lys Gly
    530                 535                 540

Ile Val Gly Gln Asn Trp Asp Ile Asn Gln Arg Phe Ala Ser Val Leu
545                 550                 555                 560

Met Gly Gly Ile Lys Leu Ala Gly Val Gly Tyr Val Ser Ser Ile Gly
                565                 570                 575

Ala Gly Val Ala Ser Asp Ile Leu Tyr Ala Ala Arg Arg Val Leu Arg
            580                 585                 590

Pro Ser Ala Ser Ala Glu Ala Val Gln Ile Arg Ser Pro Ile Trp Lys
        595                 600                 605

Ser Ala Ala Val Tyr Ser Gly Phe Leu Gly Thr Ser Ala Asn Leu Arg
    610                 615                 620

Tyr Gln Val Ile Ala Gly Leu Val Glu His Arg Leu Gly Glu Tyr Leu
625                 630                 635                 640

Val Ser Tyr Tyr Asn Gln Pro Leu Leu Ala Asn Val Leu Ser Phe Val
                645                 650                 655

Ala Arg Ile Ile Asn Ser Tyr Phe Gly Thr Gln Gln Trp Ile Asp Leu
            660                 665                 670

Ala Arg Ser Thr Gly Ile Gln Thr Ser Glu Glu Pro Pro Ser Pro
        675                 680                 685

Asn Ile Pro Ser Ser Thr Glu Ile Pro Leu Leu Glu Cys Gly Ser Ala
    690                 695                 700

Glu Ala Gln Asn Val Asp Asp Thr Thr Asn Gln Ser Ser Asp Gln Ala
705                 710                 715                 720

<210> SEQ ID NO 52
<211> LENGTH: 387
<212> TYPE: PRT
<213> ORGANISM: Brachypodium distachyon
<220> FEATURE:
<221> NAME/KEY: MISC_FEATURE
<222> LOCATION: (1)..(387)
```

<223> OTHER INFORMATION: MEP3c

<400> SEQUENCE: 52

```
Met Ala Phe His Ser Ser Met Leu Ser Ser Gln Pro Ser Ser Gln
1               5                   10                  15

Phe His Leu Gln His His Pro Arg Pro Ser Pro Arg Leu Pro Leu Leu
            20                  25                  30

Arg Ser Leu Pro Leu His Leu Arg Leu Arg Ile Ala Arg Pro Arg Leu
            35                  40                  45

Pro Pro Leu Pro Leu Ala Ala Leu Ser Asn Thr Asp Asn Ile Ile Asn
50                  55                  60

Gly Gly Gly Gly Ala Gly Asp Asp Gly Asp Asn Asn Asn Asn Asn Gly
65                  70                  75                  80

Gly Gly Gly Gly Glu Gly Glu Gly Ser Asp Asp Asp Gly Gly Gly Gly
                85                  90                  95

Gly Asn Arg Gly Glu Ala Leu Phe Val Leu Ala Gln Ala Gly Arg Lys
            100                 105                 110

Leu Glu Ser Leu Pro Ser Asp Met Ala Ala Ala Val Arg Gly Gly Arg
            115                 120                 125

Val Thr Gly Glu Ile Val Arg Arg Phe Ala Glu Leu Glu Ala Ser Ser
130                 135                 140

Pro Leu Ile Arg Trp Leu Leu Arg Phe Arg Gly Phe Arg Glu Arg Leu
145                 150                 155                 160

Leu Ala Asp Asp Leu Phe Leu Ala Lys Leu Ala Met Glu Cys Gly Ile
            165                 170                 175

Gly Ile Ile Ala Lys Ser Ala Ala Glu Tyr Glu Lys Arg Arg Glu Asn
            180                 185                 190

Phe Val Lys Glu Ile Asp Val Val Ala Asp Val Val Met Ala Ile
            195                 200                 205

Val Ala Asp Phe Met Leu Val Tyr Leu Pro Ala Pro Thr Val Ser Leu
210                 215                 220

Gln Pro Pro Leu Ala Lys Asn Ala Gly Ile Ile Ala Lys Phe Phe His
225                 230                 235                 240

Asn Cys Pro Asp Asn Ala Phe Gln Ile Ala Leu Ala Gly Arg Ser Tyr
            245                 250                 255

Ser Val Leu Gln Arg Leu Gly Ala Ile Leu Arg Asn Gly Ala Lys Leu
            260                 265                 270

Phe Ala Val Gly Thr Gly Ala Ser Leu Val Gly Thr Gly Val Thr Asn
            275                 280                 285

Ala Leu Ile Lys Ala Arg Arg Ala Val Asp Lys Asp Leu Asp Asp Glu
            290                 295                 300

Val Glu Asp Ile Pro Val Val Ser Thr Ser Ile Ala Tyr Gly Ile Tyr
305                 310                 315                 320

Met Ser Val Ser Ser Asn Leu Arg Tyr Gln Val Leu Ser Gly Val Ile
            325                 330                 335

Glu Gln Arg Met Leu Glu Pro Val Leu His Asn His Lys Leu Leu Leu
            340                 345                 350

Ser Ala Leu Cys Phe Ala Ile Arg Gly Gly Asn Thr Phe Leu Gly Ser
            355                 360                 365

Leu Leu Trp Val Asp Tyr Ala Arg Met Ile Gly Val Gln Lys Ala Gln
            370                 375                 380

Glu Glu Ile
385
```

```
<210> SEQ ID NO 53
<211> LENGTH: 578
<212> TYPE: PRT
<213> ORGANISM: Brachypodium distachyon
<220> FEATURE:
<221> NAME/KEY: MISC_FEATURE
<222> LOCATION: (1)..(578)
<223> OTHER INFORMATION: NHD

<400> SEQUENCE: 53

Met Ala Phe Ser Ser Tyr Leu Ile Ala Gly Ser Arg Ala Ala Ser Pro
1               5                   10                  15

Ser Leu Pro Ser Phe Pro Ser Leu Arg Arg Arg Ser His His Arg Pro
            20                  25                  30

Pro Ser Leu Pro Thr Ser Pro Leu Gln Pro Pro Ala Gln Leu Trp
        35                  40                  45

Arg Arg Ser Leu Arg Phe Cys Ala Ser Ser Ser Pro Pro Pro
50                  55                  60

Val Pro Pro Glu Ser Glu Glu Pro Thr Asp Tyr Glu Leu Leu Glu Thr
65                  70                  75                  80

Thr Gly Asn Cys Asp Pro Leu Cys Ser Val Asp Glu Val Ser Ser Gln
                85                  90                  95

Tyr Phe Glu Ala Asn Tyr Lys Pro Lys Asn Asp Ile Leu Lys Ala Leu
            100                 105                 110

Thr Ile Leu Ala Thr Ala Leu Ala Gly Ala Ala Ala Ile Asn His Ser
        115                 120                 125

Trp Val Ala Ala Asn Gln Asp Ile Ala Met Val Leu Val Phe Ala Leu
130                 135                 140

Gly Tyr Ala Gly Ile Ile Phe Glu Glu Ser Leu Ala Phe Asn Lys Ser
145                 150                 155                 160

Gly Val Gly Leu Leu Met Ala Val Cys Leu Trp Val Ile Arg Ser Ile
                165                 170                 175

Gly Ala Pro Ser Thr Asp Val Ala Val Gln Glu Leu Ser His Thr Thr
            180                 185                 190

Ala Glu Val Ser Glu Ile Val Phe Phe Leu Leu Gly Ala Met Thr Ile
        195                 200                 205

Val Glu Ile Ile Asp Ser His Gln Gly Phe Lys Leu Val Thr Asp Asn
210                 215                 220

Ile Ser Thr Arg Asp Ser Arg Ala Leu Leu Trp Val Val Gly Phe Val
225                 230                 235                 240

Thr Phe Phe Leu Ser Ser Val Leu Asp Asn Leu Thr Ser Thr Ile Val
                245                 250                 255

Met Val Ser Leu Leu Arg Lys Leu Val Pro Pro Ser Glu Tyr Arg Lys
            260                 265                 270

Leu Leu Gly Ala Val Val Ile Ala Ala Asn Ala Gly Gly Ala Trp
        275                 280                 285

Thr Pro Ile Gly Asp Val Thr Thr Met Leu Trp Ile His Gly Gln
        290                 295                 300

Ile Thr Thr Leu Lys Ile Met Gln Gly Leu Phe Ile Pro Ser Val Val
305                 310                 315                 320

Ser Leu Ala Ile Pro Leu Ala Leu Met Ser Leu Thr Ser Glu Ala Asn
                325                 330                 335

Gly Ser Ser Gln Thr Ser Ser Ser Leu Leu Ser Ser Glu Gln Met Ala
            340                 345                 350

Pro Arg Gly Gln Leu Val Phe Ala Val Gly Leu Ala Ala Leu Val Phe
```

```
              355                 360                 365
Val Pro Val Phe Lys Ser Leu Thr Gly Leu Pro Pro Phe Met Gly Met
370                 375                 380

Leu Leu Gly Leu Gly Val Leu Trp Ile Leu Thr Asp Ala Ile His Tyr
385                 390                 395                 400

Gly Glu Ser Gly Arg Gln Arg Leu Lys Val Pro Gln Ala Leu Ser Arg
                405                 410                 415

Ile Asp Thr Gln Gly Ile Leu Phe Phe Leu Gly Ile Leu Leu Ser Val
                420                 425                 430

Gly Ser Leu Glu Ser Ala Gly Ile Leu Arg Gln Leu Ala Asn Tyr Leu
                435                 440                 445

Asp Ala Asn Ile Pro Asn Pro Asp Leu Ile Ala Ser Ile Ile Gly Val
                450                 455                 460

Ala Ser Ala Ile Ile Asp Asn Val Pro Leu Val Ala Ala Thr Met Gly
465                 470                 475                 480

Met Tyr Asp Leu Thr Ser Phe Pro Gln Asp Ser Asp Phe Trp Gln Leu
                485                 490                 495

Val Ala Phe Cys Ala Gly Thr Gly Gly Ser Met Leu Ile Ile Gly Ser
                500                 505                 510

Ala Ala Gly Val Ala Phe Met Gly Met Glu Lys Val Asp Phe Phe Trp
                515                 520                 525

Tyr Phe Arg Lys Leu Ser Val Thr Leu Ser Ile Leu Leu Arg Phe Asn
                530                 535                 540

Leu Asn Ser Gly Glu Trp Leu Cys Pro Cys Arg Leu Cys Ser Arg Tyr
545                 550                 555                 560

His His Leu Pro Ser Cys Ser Lys His Pro Ser Ala Ser Ser His Ile
                565                 570                 575

Thr Gly

<210> SEQ ID NO 54
<211> LENGTH: 417
<212> TYPE: PRT
<213> ORGANISM: Brachypodium distachyon
<220> FEATURE:
<221> NAME/KEY: MISC_FEATURE
<222> LOCATION: (1)..(417)
<223> OTHER INFORMATION: BASS2

<400> SEQUENCE: 54

Met Ala Pro Ser Ala Thr Cys Pro Pro His Ser Met Ala Ser Val Ser
1               5                   10                  15

Arg Ala Leu Arg Pro Arg Pro Arg Leu Ala Thr Ala Cys Thr Ala Ala
                20                  25                  30

Pro Arg Leu Gly Cys Gly Ser Arg Val Ala Cys Ser Val Pro Ala Tyr
                35                  40                  45

Gly Gly Ala Thr Glu Lys Thr Glu His Gly Leu Ala Ile Ala Ser Thr
                50                  55                  60

Leu Ala Ala Thr Val Gly Pro Val Val Arg Ser Arg Gln Ile Leu Cys
65                  70                  75                  80

Lys Ala Glu Ala Asn Ile Ser Ser Asn Leu Pro Glu Ser Val Ala Asn
                85                  90                  95

Gly Val Ser Gln Tyr Glu Lys Ile Val Glu Leu Leu Thr Thr Leu Phe
                100                 105                 110

Pro Val Trp Val Ile Leu Gly Thr Val Ile Gly Ile Tyr Lys Pro Ser
                115                 120                 125
```

```
Met Val Thr Trp Leu Glu Thr Asp Leu Phe Thr Val Gly Leu Gly Phe
            130                 135                 140

Leu Met Leu Ser Met Gly Leu Thr Leu Thr Phe Glu Asp Phe Arg Arg
145                 150                 155                 160

Cys Met Lys Asn Pro Trp Thr Val Gly Val Gly Phe Ile Ala Gln Tyr
                165                 170                 175

Phe Ile Lys Pro Leu Leu Gly Tyr Ala Ile Ala Leu Thr Leu Lys Leu
                180                 185                 190

Ser Ala Pro Leu Ala Thr Gly Leu Ile Leu Val Ser Cys Cys Pro Gly
                195                 200                 205

Gly Gln Ala Ser Asn Val Ala Thr Tyr Ile Ser Lys Gly Asn Val Ala
            210                 215                 220

Leu Ser Val Leu Met Thr Thr Cys Ser Thr Ile Gly Ala Ile Val Met
225                 230                 235                 240

Thr Pro Leu Leu Thr Lys Leu Leu Ala Gly Gln Leu Val Pro Val Asp
                245                 250                 255

Ala Ala Gly Leu Ala Ile Ser Thr Phe Gln Val Val Leu Val Pro Thr
                260                 265                 270

Ile Val Gly Val Leu Ala His Glu Tyr Phe Pro Lys Phe Thr Glu Arg
            275                 280                 285

Ile Ile Ser Ile Thr Pro Leu Ile Gly Val Leu Leu Thr Thr Leu Leu
290                 295                 300

Cys Ala Ser Pro Ile Gly Gln Val Ala Asp Val Leu Lys Thr Gln Gly
305                 310                 315                 320

Ala Gln Leu Ile Leu Pro Val Ala Leu Leu His Ala Val Ala Phe Ala
                325                 330                 335

Leu Gly Tyr Trp Leu Ser Lys Leu Ser Ser Phe Gly Glu Ser Thr Ser
                340                 345                 350

Arg Thr Ile Ser Ile Glu Cys Gly Met Gln Ser Ser Ala Leu Gly Phe
            355                 360                 365

Leu Leu Ala Gln Lys His Phe Thr Asn Pro Leu Val Ala Val Pro Ser
370                 375                 380

Ala Val Ser Val Val Cys Met Ala Leu Gly Gly Ser Ala Leu Ala Val
385                 390                 395                 400

Phe Trp Arg Asn Arg Gly Leu Pro Ala Asp Asp Lys Asp Asp Phe Lys
                405                 410                 415

Glu

<210> SEQ ID NO 55
<211> LENGTH: 430
<212> TYPE: PRT
<213> ORGANISM: Brachypodium distachyon
<220> FEATURE:
<221> NAME/KEY: MISC_FEATURE
<222> LOCATION: (1)..(430)
<223> OTHER INFORMATION: PPT2

<400> SEQUENCE: 55

Met Gln Arg Ala Ala Ser Leu Ser Ser Arg Ala Ala Trp
1               5                   10                  15

Ala Ala Ala Ala Ser Ser Arg His Ala Ala Gly Ala Ser Cys Ser Ala
                20                  25                  30

Ala Ala Gly Arg Arg Glu Asn Thr Met Ala Pro Pro Leu Arg Ile
            35                  40                  45

Leu Arg Gly Gln Gln Leu Leu Pro Leu Leu Pro Leu Leu Ser Gly Asn
50                  55                  60
```

Arg Ala Arg Arg Ala Val Thr Ala Ser Ala Ala Ala Ala Glu Leu
65                  70                  75                  80

Pro Ala Gly Asp Asp Ala Ala Gly Gly Ile Ala Gly Ala Val Glu
            85                  90                  95

Leu Gly Ala Met Ile Val Ala Trp Tyr Leu Leu Asn Ile Tyr Phe Asn
        100                 105                 110

Ile Tyr Asn Lys Leu Val Leu Gln Ala Leu Pro Phe Pro Tyr Thr Met
        115                 120                 125

Thr Ala Phe Gln Leu Gly Phe Gly Ser Leu Val Ile Phe Phe Met Trp
130                 135                 140

Ala Ala Arg Leu His Pro Ala Pro Lys Leu Ser Ala Ala Gln Val Ser
145                 150                 155                 160

Gln Gly His Gly Leu Leu Ile Ile Leu Ser Ala Lys Leu Lys Ala
                165                 170                 175

Phe Ser Leu Leu Pro Gly Lys Leu Asn Leu Val Leu Ser Ser Gln Leu
                180                 185                 190

Ala Arg Ile Ala Pro Leu Ala Ala Gly His Met Leu Gly Thr Val Phe
        195                 200                 205

Thr Asn Met Ser Leu Gly Lys Val Ala Val Ser Phe Thr His Thr Val
210                 215                 220

Lys Ala Ser Glu Pro Phe Phe Thr Val Leu Leu Ser Ala Phe Phe Leu
225                 230                 235                 240

Gly Glu Thr Pro Ser Leu Leu Val Leu Gly Ser Leu Val Pro Ile Val
                245                 250                 255

Gly Gly Val Ala Leu Ala Ser Leu Thr Glu Val Ser Phe Asn Trp Val
            260                 265                 270

Gly Phe Trp Ser Ala Met Ala Ser Asn Leu Leu Asn Gln Thr Arg Asn
        275                 280                 285

Val Leu Ser Lys Arg Leu Leu Gly Gly Gln Gln Glu Glu Ser Met
290                 295                 300

Asp Asp Ile Asn Leu Phe Ser Val Ile Thr Val Leu Ser Phe Leu Met
305                 310                 315                 320

Ser Cys Pro Leu Met Leu Leu Ala Glu Gly Val Lys Phe Ser Pro Ala
                325                 330                 335

Tyr Leu Gln Ser Thr Gly Leu Asn Leu Pro Glu Leu Cys Val Arg Ala
            340                 345                 350

Ala Leu Ala Gly Leu Cys Phe His Gly Tyr Gln Lys Ile Ser Tyr Met
        355                 360                 365

Ile Leu Ala Arg Val Ser Pro Val Thr His Ser Val Ala Asn Cys Val
        370                 375                 380

Lys Arg Val Val Val Ile Val Ser Ser Val Leu Phe Phe Arg Thr Pro
385                 390                 395                 400

Ile Ser Ala Val Asn Ala Leu Gly Thr Gly Ala Ala Leu Gly Gly Val
                405                 410                 415

Tyr Leu Tyr Ser Arg Leu Lys Lys Ser Lys Pro Lys Ser Ile
                420                 425                 430

<210> SEQ ID NO 56
<211> LENGTH: 411
<212> TYPE: PRT
<213> ORGANISM: Brachypodium distachyon
<220> FEATURE:
<221> NAME/KEY: MISC_FEATURE
<222> LOCATION: (1)..(411)
<223> OTHER INFORMATION: TPT

<400> SEQUENCE: 56

Met Pro Ala Pro Leu Gly Thr Ile Ser Ala Gly Gly Ala Ala Ala
1               5                   10                  15

Gly Val Ala Gly Leu Leu Arg Leu Arg Arg Gly His Ala Val Ala Ser
            20                  25                  30

Pro Leu Pro Ala Ser Ala Gly Ala Gly Ala Arg Cys Ser Ala Ala Ala
        35                  40                  45

Ala Val His Asp Gly Gly Gln Leu Val Trp Gly Arg Gln Leu Arg Pro
    50                  55                  60

Gly Leu Leu Leu Pro Ala Gly Leu Ile Pro Ser Arg Ala Ser Lys Arg
65                  70                  75                  80

Leu Pro Leu Arg Pro Ala Ala Ser Ala Glu Pro Ala Gly Glu Ala
                85                  90                  95

Lys Ser Pro Gly Leu Leu Glu Lys Tyr Pro Ala Ile Thr Thr Gly Phe
            100                 105                 110

Phe Phe Phe Met Trp Tyr Phe Leu Asn Val Ile Phe Asn Ile Leu Asn
            115                 120                 125

Lys Lys Ile Tyr Asn Tyr Phe Pro Tyr Pro Tyr Phe Val Ser Val Ile
        130                 135                 140

His Leu Leu Val Gly Val Val Tyr Cys Leu Ile Ser Trp Ala Val Gly
145                 150                 155                 160

Leu Pro Lys Arg Ala Pro Ile Asn Ser Thr Leu Leu Lys Leu Leu Phe
                165                 170                 175

Pro Val Ala Leu Cys His Ala Leu Gly His Val Thr Ser Asn Val Ser
            180                 185                 190

Phe Ala Thr Val Ala Val Ser Phe Ala His Thr Ile Lys Ala Leu Glu
        195                 200                 205

Pro Phe Phe Asn Ala Ala Ala Thr Gln Phe Val Leu Gly Gln Thr Val
    210                 215                 220

Pro Leu Ser Leu Trp Leu Ser Leu Ala Pro Val Val Leu Gly Val Ser
225                 230                 235                 240

Met Ala Ser Leu Thr Glu Leu Ser Phe Asn Trp Lys Gly Phe Ile Asn
                245                 250                 255

Ala Met Ile Ser Asn Ile Ser Phe Thr Tyr Arg Ser Ile Tyr Ser Lys
            260                 265                 270

Lys Ala Met Thr Asp Met Asp Ser Thr Asn Val Tyr Ala Tyr Ile Ser
        275                 280                 285

Ile Ile Ala Leu Leu Val Cys Ile Pro Pro Ala Leu Ile Ile Glu Gly
    290                 295                 300

Pro Gln Leu Met Gln Tyr Gly Leu Asn Asp Ala Ile Ala Lys Val Gly
305                 310                 315                 320

Leu Thr Lys Phe Val Ser Asp Leu Phe Leu Val Gly Leu Phe Tyr His
                325                 330                 335

Leu Tyr Asn Gln Leu Ala Thr Asn Thr Leu Glu Arg Val Ala Pro Leu
            340                 345                 350

Thr His Ala Val Gly Asn Val Leu Lys Arg Val Phe Val Ile Gly Phe
        355                 360                 365

Ser Ile Val Ile Phe Gly Asn Thr Ile Thr Thr Gln Thr Gly Ile Gly
    370                 375                 380

Thr Cys Val Ala Ile Ala Gly Val Ala Ile Tyr Ser Tyr Ile Lys Ala
385                 390                 395                 400

Lys Ile Glu Glu Glu Lys Arg Ala Lys Ser Ala

-continued

```
                    405                 410

<210> SEQ ID NO 57
<211> LENGTH: 557
<212> TYPE: PRT
<213> ORGANISM: Dichanthelium oligosanthes
<220> FEATURE:
<221> NAME/KEY: MISC_FEATURE
<222> LOCATION: (1)..(557)
<223> OTHER INFORMATION: OMT
<220> FEATURE:
<221> NAME/KEY: MISC_FEATURE
<222> LOCATION: (36)..(70)
<223> OTHER INFORMATION: Xaa: any amino acid

<400> SEQUENCE: 57

Met Ala Ser Ser Thr Ala Ala Ser Pro Leu Thr Cys His His Leu Gly
1               5                   10                  15

Ser Gly Ala Gly Pro Arg Ser Arg Leu Pro Ser Leu Ser Phe Ser Leu
            20                  25                  30

Arg Arg Arg Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Ser Ala Ala Ala Pro Ala Pro Ala Ala
65                  70                  75                  80

Pro Pro Pro Lys Pro Ala Leu Gln Gly Ala Ala Ile Lys Pro Leu Leu
                85                  90                  95

Ala Thr Ile Ala Thr Gly Val Leu Ile Trp Leu Val Pro Ala Pro Ala
            100                 105                 110

Gly Val Pro Arg Asn Ala Trp Lys Leu Leu Ala Ile Phe Leu Ser Thr
        115                 120                 125

Ile Val Gly Ile Ile Thr Gln Pro Leu Pro Leu Gly Ala Val Ala Leu
130                 135                 140

Leu Gly Leu Gly Ala Ala Val Leu Thr Arg Thr Leu Thr Phe Ala Ala
145                 150                 155                 160

Ala Phe Ser Ala Phe Gly Asp Pro Ile Pro Trp Leu Ile Ala Leu Ala
                165                 170                 175

Phe Phe Phe Ala Arg Gly Phe Ile Lys Thr Gly Leu Gly Ser Arg Val
            180                 185                 190

Ala Tyr Ala Phe Val Ala Ala Phe Gly Ser Ser Leu Gly Leu Gly
        195                 200                 205

Tyr Ala Leu Val Phe Ala Glu Ala Leu Leu Ala Pro Ala Ile Pro Ser
210                 215                 220

Val Ser Ala Arg Ala Gly Gly Ile Phe Leu Pro Leu Val Lys Ser Leu
225                 230                 235                 240

Cys Glu Ala Cys Gly Ser Arg Thr Gly Asp Gly Thr Glu Arg Arg Leu
                245                 250                 255

Gly Ala Trp Leu Met Leu Thr Cys Phe Gln Thr Ser Val Ile Ser Ser
            260                 265                 270

Ala Met Phe Leu Thr Gly Met Ala Ala Asn Pro Leu Ser Ala Asn Leu
        275                 280                 285

Thr Ala Ala Thr Ile Gly Glu Gly Ile Ser Trp Thr Leu Trp Ala Lys
    290                 295                 300

Ala Ala Ile Val Pro Gly Leu Leu Ser Leu Val Leu Pro Leu Ile
305                 310                 315                 320

Leu Tyr Val Ile Tyr Pro Pro Glu Val Lys Ser Ser Pro Asp Ala Pro
```

```
            325                 330                 335
Arg Leu Ala Lys Glu Arg Leu Ala Lys Met Gly Pro Met Ser Lys Glu
        340                 345                 350

Glu Lys Ile Met Ala Gly Thr Leu Leu Thr Val Gly Leu Trp Ile
        355                 360                 365

Phe Gly Gly Met Leu Asn Val Asp Ala Val Ser Ala Ala Ile Leu Gly
370                 375                 380

Leu Ser Val Leu Leu Ile Ser Gly Val Val Thr Trp Lys Glu Cys Leu
385                 390                 395                 400

Ala Glu Ser Val Ala Trp Asp Thr Leu Thr Trp Phe Ala Ala Leu Ile
                405                 410                 415

Ala Met Ala Gly Tyr Leu Asn Lys Tyr Gly Leu Ile Ala Trp Phe Ser
                420                 425                 430

Glu Thr Val Val Lys Phe Val Gly Gly Leu Gly Leu Ser Trp Gln Leu
                435                 440                 445

Ser Phe Gly Val Leu Val Leu Leu Tyr Phe Tyr Ser His Tyr Phe Phe
            450                 455                 460

Ala Ser Gly Ala Ala His Ile Gly Ala Met Phe Thr Ala Phe Leu Ser
465                 470                 475                 480

Val Ala Ser Ala Leu Gly Thr Pro Pro Leu Phe Ala Ala Met Val Leu
                485                 490                 495

Ser Phe Leu Ser Asn Ile Met Gly Gly Leu Thr His Tyr Gly Ile Gly
                500                 505                 510

Ser Ala Pro Val Phe Tyr Gly Ala Gly Tyr Val Pro Leu Ala Gln Trp
            515                 520                 525

Trp Gly Tyr Gly Phe Val Ile Ser Val Val Asn Ile Ile Ile Trp Leu
        530                 535                 540

Gly Ala Gly Gly Phe Trp Trp Lys Met Ile Gly Leu Trp
545                 550                 555

<210> SEQ ID NO 58
<211> LENGTH: 427
<212> TYPE: PRT
<213> ORGANISM: Dichanthelium oligosanthes
<220> FEATURE:
<221> NAME/KEY: MISC_FEATURE
<222> LOCATION: (1)..(427)
<223> OTHER INFORMATION: DCT1

<400> SEQUENCE: 58

Met Glu Ser Leu Arg Leu Ala Val Ala His Arg Pro Leu Pro Val
1               5                   10                  15

Pro Ala Pro Val His Leu Arg His Arg His Pro His His Leu Pro Ala
                20                  25                  30

Pro Leu Ser Leu Pro Asn Thr Ser Leu Ser Leu Ser Ser Pro His His
            35                  40                  45

His Arg Leu Ser Pro Thr Pro Arg Arg Arg Leu Leu Leu Pro Leu Leu
        50                  55                  60

Ala Ser Gln His Pro Asp Ser Asn Pro Glu Pro Ala Glu Pro Glu
65                  70                  75                  80

Pro Ala Ala Ala Gly Ala Lys Leu Val Pro Leu Val Ile Ser Val Ala
                85                  90                  95

Val Gly Leu Ala Val Arg Phe Leu Ala Pro Arg Pro Ala Glu Val Ser
            100                 105                 110

Leu Gln Ala Trp Gln Leu Leu Ser Ile Phe Leu Ser Thr Ile Ala Gly
        115                 120                 125
```

-continued

```
Leu Val Leu Gly Pro Leu Pro Val Gly Ala Trp Ala Phe Leu Gly Leu
        130                 135                 140

Thr Ala Ala Val Ala Thr His Thr Leu Pro Phe Thr Ala Ala Phe Ser
145                 150                 155                 160

Ala Phe Thr Asn Glu Val Ile Trp Leu Ile Val Ile Ser Phe Phe Phe
                165                 170                 175

Ala Arg Gly Phe Val Lys Thr Gly Leu Gly Asp Arg Ile Ala Thr Tyr
                180                 185                 190

Phe Val Lys Trp Leu Gly Ser Ser Thr Leu Gly Leu Ser Tyr Gly Leu
                195                 200                 205

Thr Ile Ser Glu Ala Cys Ile Ala Pro Ala Met Pro Ser Thr Thr Ala
        210                 215                 220

Arg Ala Gly Gly Val Phe Leu Pro Ile Ile Lys Ser Leu Ser Leu Ser
225                 230                 235                 240

Ala Asp Ser Lys Pro Asn His Pro Ser Ser Arg Lys Leu Gly Ser Tyr
                245                 250                 255

Leu Val Met Thr Gln Phe Gln Ala Ala Gly Asn Ser Ser Ala Leu Phe
                260                 265                 270

Leu Thr Ala Ala Ala Gln Asn Leu Leu Cys Leu Lys Leu Ala Glu Glu
        275                 280                 285

Leu Gly Val Ile Ile Ala Asn Pro Trp Val Ala Trp Phe Lys Ala Ala
        290                 295                 300

Ser Leu Pro Ala Ile Val Ser Leu Leu Ala Thr Pro Tyr Leu Leu Tyr
305                 310                 315                 320

Lys Ile Phe Pro Pro Glu Thr Lys Asp Thr Pro Asp Ala Pro Ala Leu
                325                 330                 335

Ala Ala Glu Lys Leu Lys Arg Met Gly Pro Val Thr Lys Asn Glu Trp
                340                 345                 350

Val Met Ile Gly Thr Met Ile Leu Ala Val Ser Leu Trp Val Phe Gly
                355                 360                 365

Asp Ala Ile Gly Val Ser Ser Val Val Ala Ala Met Leu Gly Leu Ser
        370                 375                 380

Ile Leu Leu Leu Leu Ala Gly Tyr Leu Glu Leu Pro Asp Val Phe Arg
385                 390                 395                 400

Leu Gly Phe Val Thr Ala Leu Val Asn Thr Leu Ile Trp Gly Val Val
                405                 410                 415

Gly Thr Ile Trp Trp Lys Phe Leu Gly Leu Tyr
                420                 425
```

<210> SEQ ID NO 59
<211> LENGTH: 552
<212> TYPE: PRT
<213> ORGANISM: Dichanthelium oligosanthes
<220> FEATURE:
<221> NAME/KEY: MISC_FEATURE
<222> LOCATION: (1)..(552)
<223> OTHER INFORMATION: DCT2

<400> SEQUENCE: 59

```
Met Glu Ser Leu Arg Leu Ala Val Ser His Arg Pro Ala Leu Pro Leu
1               5                   10                  15

Pro Thr Pro His Ser His Leu Arg Arg Arg His Leu His Leu His Pro
                20                  25                  30

Ser Pro Asn Ser Leu Ser Leu Ser Leu Pro Ile Ser Pro His Leu Thr
        35                  40                  45
```

```
Pro Thr Thr Arg Arg His Leu Pro Leu Leu Ala Ser Ala Ser Ala
    50                  55                  60

Ser Ala Val Ala Ser Pro Ser Pro Gly Pro Lys Pro Ala Ala Ala
65                  70                  75                  80

Gly Gly Ala Lys Pro Leu Pro Leu Leu Ile Ser Leu Ala Ala Gly Leu
                85                  90                  95

Ala Val Arg Phe Leu Val Pro Arg Pro Ala Glu Val Thr Pro Gln Ala
                100                 105                 110

Trp Gln Leu Leu Ser Ile Phe Leu Ser Thr Ile Ala Gly Leu Val Leu
            115                 120                 125

Gly Pro Leu Pro Val Gly Ala Trp Ala Phe Leu Gly Leu Thr Ala Thr
    130                 135                 140

Val Ala Thr Arg Thr Leu Pro Phe Thr Ala Ala Phe Gly Ala Phe Thr
145                 150                 155                 160

Asn Glu Val Ile Trp Leu Ile Val Ile Ser Phe Phe Ala Arg Gly
                165                 170                 175

Phe Val Lys Thr Gly Leu Gly Asp Arg Val Ala Thr Tyr Phe Val Lys
                180                 185                 190

Trp Leu Gly Arg Ser Thr Leu Gly Leu Ser Tyr Gly Leu Ala Ile Ser
            195                 200                 205

Glu Ala Phe Ile Ser Pro Ala Met Pro Ser Thr Thr Ala Arg Ala Gly
    210                 215                 220

Gly Val Phe Leu Pro Ile Val Lys Ser Leu Ser Leu Ser Ser Gly Ser
225                 230                 235                 240

Lys Pro Asn Asp Pro Ser Ala Lys Lys Leu Gly Ser Tyr Leu Val Gln
                245                 250                 255

Ser Gln Leu Gln Ala Ser Gly Asn Ser Ser Ala Leu Phe Leu Thr Ala
            260                 265                 270

Ala Ala Gln Asn Leu Leu Cys Leu Lys Leu Ala Glu Glu Ile Gly Val
    275                 280                 285

Lys Ile Gly Asn Pro Trp Ile Thr Trp Leu Lys Val Ala Ser Leu Pro
290                 295                 300

Ala Leu Val Gly Leu Leu Val Thr Pro Tyr Leu Leu Tyr Lys Ile Phe
305                 310                 315                 320

Pro Pro Glu Ile Lys Asp Thr Pro Glu Ala Pro Ala Leu Ala Ala Gln
                325                 330                 335

Lys Leu Lys Asn Met Gly Pro Val Thr Arg Asn Glu Trp Val Met Ile
            340                 345                 350

Gly Thr Met Leu Leu Ala Val Ser Leu Trp Ile Phe Gly Glu Thr Ile
    355                 360                 365

Gly Val Ser Ser Val Val Ala Ala Met Ile Gly Leu Ser Ile Leu Leu
370                 375                 380

Leu Leu Gly Val Leu Asn Trp Glu Asp Cys Leu Asn Glu Lys Ser Ala
385                 390                 395                 400

Trp Asp Thr Leu Ala Trp Phe Ala Ile Leu Val Gly Leu Ala Gly Gln
                405                 410                 415

Leu Thr Ser Leu Gly Ile Val Ser Trp Met Ser Asn Cys Val Ala Lys
            420                 425                 430

Val Leu Gln Ser Phe Ser Leu Ser Trp Pro Ala Ala Phe Gly Val Leu
    435                 440                 445

Gln Ala Ser Tyr Phe Phe Ile His Tyr Leu Phe Ala Ser Gln Thr Ala
    450                 455                 460

His Val Gly Ala Leu Tyr Ser Ala Phe Leu Ala Met His Leu Ala Ala
```

|     |     |     |     |     |     |     |     |     |     |     |     |
| --- | --- | --- | --- | --- | --- | --- | --- | --- | --- | --- | --- |
| 465 |     |     |     |     | 470 |     |     |     | 475 |     | 480 |

Gly Val Pro Ala Val Met Ala Ala Leu Ala Leu Thr Tyr Asn Ser Asn
                           485                 490                 495

Leu Phe Gly Ala Leu Thr His Tyr Ser Ser Gly Gln Ser Ala Val Tyr
          500                   505                 510

Tyr Gly Ala Gly Tyr Val Asp Leu Pro Asp Val Phe Lys Leu Gly Phe
             515                 520            525

Thr Thr Ala Ala Ile Asn Ala Val Ile Trp Gly Val Val Gly Ala Phe
        530                   535               540

Trp Trp Lys Phe Leu Gly Leu Tyr
545            550

<210> SEQ ID NO 60
<211> LENGTH: 389
<212> TYPE: PRT
<213> ORGANISM: Dichanthelium oligosanthes
<220> FEATURE:
<221> NAME/KEY: MISC_FEATURE
<222> LOCATION: (1)..(389)
<223> OTHER INFORMATION: MEP3a

<400> SEQUENCE: 60

Met Ala Phe Pro Pro Thr Ser Leu Ser Ser Gly Tyr Pro Ala
1            5                10              15

Pro Ile His Leu Arg Leu Gln Pro Leu Pro Ser Ile Ile Pro Pro Leu
        20                 25               30

His Pro Thr Val Leu Pro Phe Pro Arg Ser Leu Pro Leu Asn Leu Thr
          35                 40             45

Ser Leu Arg Leu Ala Arg Pro Arg Leu Pro Pro Leu Pro Leu Ala Ser
50                 55                60

Thr Gly Ser Gly Ser Ile Gly Gly Gly Arg Asp Gly Asp Leu Pro Ser
65               70              75              80

Gly Gly Gly Gly Gly Gly Gly Gly Asp Glu Gly Asp Gly Ser
             85                 90            95

Ala Asp Gly Asp Gly Asp Asp Ala Ser Val Asn Arg Arg Glu Ala Leu
        100                105             110

Phe Val Leu Ala Gln Leu Gly Arg Lys Leu Glu Thr Leu Pro Ala Asp
          115              120            125

Leu Ala Ala Val Glu Gly Gly Arg Val Pro Gly Glu Ile Val Arg
130               135              140

Arg Phe Ala Asp Leu Glu Ala Ser Pro Val Phe Arg Trp Leu Leu Gln
145              150             155           160

Phe Gly Gly Phe Lys Glu Arg Leu Leu Ala Asp Asp Leu Phe Leu Thr
          165              170            175

Lys Val Ala Ile Glu Cys Gly Val Gly Ile Phe Thr Lys Thr Ala Ala
        180                185             190

Glu Tyr Glu Lys Arg Arg Glu Asn Phe Val Lys Glu Leu Asp Phe Val
          195              200            205

Val Ala Asp Val Ile Met Ala Ile Val Ala Asp Phe Met Leu Val Trp
210               215              220

Leu Pro Ala Pro Thr Val Ser Leu Arg Pro Pro Leu Ala Val Asn Ser
225              230             235           240

Gly Ala Ile Ala Lys Phe Phe Tyr Ser Cys Pro Asp Asn Ala Phe Gln
          245              250            255

Val Ala Leu Ala Gly Thr Ser Tyr Ser Leu Leu Gln Arg Val Gly Ala
        260                265             270

```
Ile Ala Arg Asn Gly Ala Lys Leu Phe Ala Val Gly Thr Ser Ala Ser
        275                 280                 285

Leu Ile Gly Thr Gly Val Thr Asn Ala Leu Ile Lys Ala Arg Gln Ala
    290                 295                 300

Val Ser Lys Asp Phe Ala Gly Glu Val Glu Asn Ile Pro Ile Leu Ser
305                 310                 315                 320

Thr Ser Val Ala Tyr Gly Val Tyr Met Ala Val Ser Ser Asn Leu Arg
                325                 330                 335

Tyr Gln Val Leu Ala Gly Val Ile Glu Gln Arg Met Leu Glu Pro Leu
                340                 345                 350

Leu His Arg His Lys Leu Ala Leu Thr Ala Val Cys Phe Ala Val Arg
                355                 360                 365

Thr Gly Asn Thr Phe Leu Gly Ser Leu Leu Trp Val Asp Tyr Ala Arg
370                 375                 380

Trp Ile Gly Ile Gln
385

<210> SEQ ID NO 61
<211> LENGTH: 1296
<212> TYPE: PRT
<213> ORGANISM: Dichanthelium oligosanthes
<220> FEATURE:
<221> NAME/KEY: MISC_FEATURE
<222> LOCATION: (1)..(1296)
<223> OTHER INFORMATION: MEP3b

<400> SEQUENCE: 61

Met Ala Thr Glu Pro Leu Ser Pro Gly Lys Ser Pro Ala Asp Glu Asp
1               5                   10                  15

Leu Glu Thr Leu Pro Leu Asp Thr Ser Ser Ser Ser Ser Val Ala Ala
                20                  25                  30

Thr Thr Asp Pro Leu Leu Arg Pro Pro Ser Pro Ser Ser Ala Ser
            35                  40                  45

Ser Ser Pro Thr Ala Gly Ala Asp His Gly Pro Phe Val Asp Asp Val
    50                  55                  60

Asp Glu Glu Asp Glu Ala Asp Asp Val Thr Pro Val Pro Ala Pro
65                  70                  75                  80

Arg Ala Ala Ala Ala Thr Ser His Glu Ala Ser Pro Pro Val Phe
                85                  90                  95

Ala Glu Ile Thr Val Ser Glu Pro Arg Lys His Ala Glu Pro Ala Thr
                100                 105                 110

Gly Ala Val Gly Val Ile Pro Gly Ser Ala Ser Tyr Val Ser Tyr Leu
            115                 120                 125

Ile Ala Thr Arg Ala Ser Asp Gly Gly Glu Phe Arg Val Arg Arg Arg
    130                 135                 140

Phe Arg Asp Val Val Ala Leu Ala Asp Arg Leu Gly Glu Ala His Arg
145                 150                 155                 160

Gly Leu Phe Ile Pro Ala Arg Pro Asp Lys Ser Val Val Glu Gly Gln
                165                 170                 175

Val Met Gln Arg His Asp Phe Val Asn Gln Arg Cys Val Thr Leu Gln
                180                 185                 190

Arg Tyr Leu Arg Arg Leu Ala Ala His Pro Val Val Gly Arg Ser Ala
            195                 200                 205

Asp Leu His Ala Phe Leu Thr Glu Pro Ser Gly Ile Pro Ile Ser Asp
    210                 215                 220
```

-continued

Gly Glu Ser Pro Arg Trp Ser Pro Ala Met Ser Ala Thr Ser Met
225                 230                 235                 240

Ala Ala Ala Ala Pro Ala Thr Pro Thr Lys Ser Gly Arg Asp Phe Phe
            245                 250                 255

Gly Val Leu Lys Asp Leu Lys Gln Thr Val Thr Asn Gly Trp Val Ala
        260                 265                 270

Val Arg Pro Pro Val Glu Glu Thr Asp Thr Lys Tyr Leu Ser
    275                 280                 285

His Lys Ala Lys Leu Glu Asp Leu Glu Gln Tyr Leu Val Thr Ala Ser
    290                 295                 300

Gln Gln Ala Asp Ala Leu Val Lys Ser Tyr Asp Asp Leu Arg Ala Thr
305                 310                 315                 320

Thr Gly Leu Leu Gly Met Ser Phe Ile Lys Leu Ala Lys Phe Glu Lys
                325                 330                 335

Glu Gln Ala Thr Cys Asn Ser Gln Lys Arg Arg Ala Ala Asp Ile Ser
            340                 345                 350

Asn Phe Ala Asn Ala Val Val Arg Val Ser Arg Ser Gln Thr Lys Leu
        355                 360                 365

Asn Ala Glu Ile Val Lys His Val Gly Ile Ile His Glu Tyr Met Glu
    370                 375                 380

Thr Met Ala Ala Val His Asn Ala Phe Thr Asp Arg Ser Asn Ala Leu
385                 390                 395                 400

Leu Arg Val Gln Asn Leu Ser Ala Asp Leu Tyr Phe Leu His Thr Arg
                405                 410                 415

Ala Glu Lys Leu Glu Ala Val Ser Ser Arg Gly Met Asp Gln Glu Arg
            420                 425                 430

Ser Arg Tyr Gln Lys Ile Glu Glu Leu Lys Glu Thr Ile Arg Ala Thr
        435                 440                 445

Glu Asp Ala Lys Thr Arg Ala Leu Lys Glu Leu Glu Leu Ile Lys Glu
    450                 455                 460

Asn Asn Met Asn Glu Ile Lys Arg Phe Asn Lys Glu Arg Arg His Asp
465                 470                 475                 480

Leu Val Glu Met Leu Lys Gly Phe Val Ser Asp Gln Val Glu Ser Leu
                485                 490                 495

Asn Phe Ile Thr Trp Ile Ala Ala Lys Glu Leu Glu Thr Ser Lys Ser
            500                 505                 510

Leu Leu Leu Pro Thr Thr Thr Asn Cys Ser Val Ser Leu Arg Pro Ala
        515                 520                 525

His Phe Thr Pro Ser Pro Gly Thr Gly Ala Arg Ser Arg Arg Ala Pro
    530                 535                 540

Pro Ala Ser Cys Gln Arg Gly Arg Met Leu Pro Gln Ala Pro Ser Arg
545                 550                 555                 560

Ala Pro Gly Val Phe Thr Phe Gln Pro His Leu Pro Ala Lys Pro Pro
                565                 570                 575

Leu Leu Ala Cys Thr Ser Ala Ser Thr Arg Gly Ser Val Cys Ala Ala
            580                 585                 590

Ala Ala Thr Thr Arg Arg Asn Leu Leu Val Leu Pro Ser Leu Val
        595                 600                 605

Ala Ala Ser Thr Val Leu Gln Ser Leu Pro Leu Gly Ala Ser Ala Ala
    610                 615                 620

Ala Gly Asp Asp Lys Pro Ala Pro Pro Ala Pro Ala Pro Ala
625                 630                 635                 640

Ala Pro Ala Pro Ala Pro Pro Ala Ala Glu Pro Ala Leu Ser Arg

-continued

```
                645                 650                 655
Val Tyr Asp Ala Thr Val Ile Gly Glu Pro Gln Ala Val Gly Lys Asp
                660                 665                 670

Ala Arg Arg Arg Val Trp Glu Lys Leu Met Ala Ala Arg Leu Val Tyr
                675                 680                 685

Leu Gly Glu Ala Glu Leu Val Pro Asp Arg Asp Arg Ala Leu Glu
            690                 695                 700

Leu Glu Ile Phe Lys Lys Leu Ala Thr Ser Cys Ser Glu Ala Gly Arg
705                 710                 715                 720

Asn Ile Ser Leu Ala Leu Glu Ala Phe Pro Cys Asp Leu Gln Glu Gln
                725                 730                 735

Leu Asn Arg Phe Met Asp Arg Arg Ile Asp Gly Asn Thr Leu Arg Leu
                740                 745                 750

Tyr Thr Ser His Trp Ala Pro Glu Arg Trp Gln Glu Tyr Glu Pro Leu
                755                 760                 765

Leu Asn Tyr Cys Arg Asp Cys Gln Ile Lys Leu Val Ala Cys Gly Thr
                770                 775                 780

Pro Leu Glu Val Val Arg Thr Val Gln Ala Glu Gly Ile Arg Gly Leu
785                 790                 795                 800

Ser Lys Ala Gln Arg Lys Leu Tyr Ala Pro Pro Ala Gly Ser Gly Phe
                805                 810                 815

Ile Ser Gly Phe Thr Ser Ile Ser Gly Arg Ser Leu Ile Asp Lys Ile
                820                 825                 830

Ser Ser Asn Arg Gly Ser Pro Phe Gly Pro Ser Ser Tyr Leu Ser Ala
                835                 840                 845

Gln Ala Arg Val Val Asp Asp Tyr Thr Met Ser Gln Thr Ile Met Lys
850                 855                 860

Glu Ile Thr Asn Gly Asp Pro Ser Gly Met Leu Val Val Thr Gly
865                 870                 875                 880

Ala Ser His Val Met Tyr Gly Pro Arg Gly Ile Gly Val Pro Ala Arg
                885                 890                 895

Ile Ser Lys Lys Met Gln Lys Lys Gln Val Val Ile Leu Leu Asp
                900                 905                 910

Pro Glu Arg Gln Ser Ile Arg Arg Glu Gly Glu Ile Pro Val Ala Asp
                915                 920                 925

Phe Leu Trp Tyr Ser Ala Ala Lys Pro Cys Ser Arg Asn Cys Phe Asp
                930                 935                 940

Arg Ala Glu Ile Ala Arg Val Met Asn Ala Ala Gly Arg Arg Arg Glu
945                 950                 955                 960

Ala Leu Pro Gln Asp Leu Gln Lys Gly Ile Asp Leu Gly Val Ser
                965                 970                 975

Pro Glu Ile Leu Gln Asn Phe Phe Asp Leu Glu Lys Tyr Pro Val Met
                980                 985                 990

Ala Glu Leu Leu His Arg Phe Gln Gly Phe Arg Glu Arg Leu Leu Ala
                995                 1000                1005

Asp Pro Lys Phe Leu His Arg Leu Ala Ile Glu Glu Gly Ile Ser
            1010                1015                1020

Ile Thr Thr Thr Leu Leu Ala Gln Tyr Glu Lys Arg Lys Gly Arg
            1025                1030                1035

Phe Phe Glu Glu Ile Asp Tyr Val Leu Thr Asp Thr Ile Arg Gly
            1040                1045                1050

Ser Val Val Asp Phe Phe Thr Val Trp Leu Pro Ala Pro Thr Ile
            1055                1060                1065
```

```
Ser Leu Leu Ser Phe Ala Asp Asp Gly Ser Gly Glu Ser Val Glu
        1070            1075                1080

Leu Leu Lys Gly Leu Leu Gly Thr Leu Pro Asp Asn Ala Phe Gln
        1085            1090                1095

Lys Gly Ile Val Gly Gln Asn Trp Ser Ile Asn Gln Arg Phe Ala
        1100            1105                1110

Ser Val Leu Met Gly Gly Ile Lys Leu Ala Gly Val Gly Phe Ile
        1115            1120                1125

Ser Ser Ile Gly Ala Gly Val Ala Ser Asp Val Leu Tyr Gly Ala
        1130            1135                1140

Arg Gln Ile Leu Lys Pro Ser Ala Ser Met Glu Val Gly Arg Lys
        1145            1150                1155

Arg Ser Pro Ile Trp Lys Ser Ala Thr Val Tyr Ser Cys Phe Leu
        1160            1165                1170

Gly Thr Ser Ala Asn Leu Arg Tyr Gln Val Ile Ala Gly Leu Ile
        1175            1180                1185

Glu His Arg Leu Gly Glu Asp Leu Met Ala Tyr Asn Gln Pro
        1190            1195                1200

Phe Leu Ala Asn Leu Leu Ser Phe Val Ser Arg Ile Ile Asn Ser
        1205            1210                1215

Tyr Trp Gly Thr Gln Thr Tyr Cys Met Val Ala Leu Ala Leu Arg
        1220            1225                1230

Phe Ala Leu Leu Thr Pro Cys Phe Leu Gln Gln Trp Ile Asp Leu
        1235            1240                1245

Ala Arg Ala Thr Gly Val Gln Ser Thr Lys Lys Glu Leu Pro Ser
        1250            1255                1260

Pro Glu Val Ser Asn Ala Thr Glu Met Pro Leu Leu Glu Cys Gly
        1265            1270                1275

Thr Ala Asp Val Gln Asn Val Asp Asp Ser Ser Asn Gln Pro Asn
        1280            1285                1290

Asp Phe Thr
        1295

<210> SEQ ID NO 62
<211> LENGTH: 389
<212> TYPE: PRT
<213> ORGANISM: Dichanthelium oligosanthes
<220> FEATURE:
<221> NAME/KEY: MISC_FEATURE
<222> LOCATION: (1)..(389)
<223> OTHER INFORMATION: MEP3c

<400> SEQUENCE: 62

Met Ala Phe Pro Pro Pro Thr Ser Leu Ser Ser Ser Gly Tyr Pro Ala
1               5                   10                  15

Pro Ile His Leu Arg Leu Gln Pro Leu Pro Ser Ile Ile Pro Pro Leu
            20                  25                  30

His Pro Thr Val Leu Pro Phe Pro Arg Ser Leu Pro Leu Asn Leu Thr
        35                  40                  45

Ser Leu Arg Leu Ala Arg Pro Arg Leu Pro Leu Pro Leu Ala Ser
    50                  55                  60

Thr Gly Ser Gly Ser Ile Gly Gly Arg Asp Gly Asp Leu Pro Ser
65              70                  75                  80

Gly Gly Gly Gly Gly Gly Gly Gly Asp Glu Gly Asp Gly Gly Ser
                85                  90                  95
```

```
Ala Asp Gly Asp Gly Asp Ala Ser Val Asn Arg Arg Glu Ala Leu
            100                 105                 110

Phe Val Leu Ala Gln Leu Gly Arg Lys Leu Glu Thr Leu Pro Ala Asp
        115                 120                 125

Leu Ala Ala Ala Val Glu Gly Gly Arg Val Pro Gly Glu Ile Val Arg
    130                 135                 140

Arg Phe Ala Asp Leu Glu Ala Ser Pro Val Phe Arg Trp Leu Leu Gln
145                 150                 155                 160

Phe Gly Gly Phe Lys Glu Arg Leu Leu Ala Asp Asp Leu Phe Leu Thr
                165                 170                 175

Lys Val Ala Ile Glu Cys Gly Val Gly Ile Phe Thr Lys Thr Ala Ala
            180                 185                 190

Glu Tyr Glu Lys Arg Arg Glu Asn Phe Val Lys Glu Leu Asp Phe Val
        195                 200                 205

Val Ala Asp Val Ile Met Ala Ile Val Ala Asp Phe Met Leu Val Trp
    210                 215                 220

Leu Pro Ala Pro Thr Val Ser Leu Arg Pro Pro Leu Ala Val Asn Ser
225                 230                 235                 240

Gly Ala Ile Ala Lys Phe Phe Tyr Ser Cys Pro Asp Asn Ala Phe Gln
                245                 250                 255

Val Ala Leu Ala Gly Thr Ser Tyr Ser Leu Leu Gln Arg Val Gly Ala
            260                 265                 270

Ile Ala Arg Asn Gly Ala Lys Leu Phe Ala Val Gly Thr Ser Ala Ser
        275                 280                 285

Leu Ile Gly Thr Gly Val Thr Asn Ala Leu Ile Lys Ala Arg Gln Ala
    290                 295                 300

Val Ser Lys Asp Phe Ala Gly Glu Val Glu Asn Ile Pro Ile Leu Ser
305                 310                 315                 320

Thr Ser Val Ala Tyr Gly Val Tyr Met Ala Val Ser Ser Asn Leu Arg
                325                 330                 335

Tyr Gln Val Leu Ala Gly Val Ile Glu Gln Arg Met Leu Glu Pro Leu
            340                 345                 350

Leu His Arg His Lys Leu Ala Leu Thr Ala Val Cys Phe Ala Val Arg
        355                 360                 365

Thr Gly Asn Thr Phe Leu Gly Ser Leu Leu Trp Val Asp Tyr Ala Arg
    370                 375                 380

Trp Ile Gly Ile Gln
385

<210> SEQ ID NO 63
<211> LENGTH: 563
<212> TYPE: PRT
<213> ORGANISM: Dichanthelium oligosanthes
<220> FEATURE:
<221> NAME/KEY: MISC_FEATURE
<222> LOCATION: (1)..(563)
<223> OTHER INFORMATION: NHD

<400> SEQUENCE: 63

Met Ala Leu Phe Gly Cys Leu Leu Ala Gly Ala Arg Ala Ala Ala Ser
1               5                   10                  15

Pro Ser Leu Pro Ser Ser Ala Ala Leu Leu Arg Arg His Cys Pro
            20                  25                  30

Leu Ala Val Ala Val Gly Pro Leu Ser His Ala Gln Arg Trp Arg Arg
        35                  40                  45

Gly Leu Arg Phe Cys Cys Val Ser Ser Ser Ser Ser Pro Pro Pro
```

-continued

```
            50                  55                  60
Pro Pro Val Pro Pro Glu Glu Thr Glu Asp Tyr Glu Leu Leu Asp Thr
 65                  70                  75                  80

Thr Gly Asn Cys Asp Pro Leu Cys Ser Val Asp Glu Val Ser Ser Gln
                 85                  90                  95

Tyr Phe Glu Ala Asn Tyr Lys Pro Lys Asn Asp Leu Leu Lys Ala Leu
            100                 105                 110

Thr Ile Phe Ala Thr Ala Leu Val Gly Ala Ala Ile Asn His Ser
            115                 120                 125

Trp Val Ala Ala Asn Gln Asp Ile Ala Met Val Leu Val Phe Ala Leu
            130                 135                 140

Gly Tyr Ala Gly Ile Ile Phe Glu Glu Ser Leu Ala Phe Asn Lys Ser
145                 150                 155                 160

Gly Val Gly Leu Leu Met Ala Val Cys Leu Trp Val Ile Arg Ser Ile
                165                 170                 175

Gly Ala Pro Ser Thr Asp Val Ala Val Gln Glu Leu Ser Gln Thr Thr
                180                 185                 190

Ala Gly Val Ser Glu Ile Val Phe Phe Leu Leu Gly Ala Met Thr Ile
                195                 200                 205

Val Glu Ile Val Asp Ala His Gln Gly Phe Lys Leu Val Thr Asp Asn
210                 215                 220

Ile Ser Thr Arg Asn Ser Lys Thr Leu Leu Trp Val Ile Gly Ile Val
225                 230                 235                 240

Thr Phe Phe Leu Ser Ser Ile Leu Asp Asn Leu Thr Ser Thr Ile Val
                245                 250                 255

Met Val Ser Leu Leu Arg Lys Leu Val Pro Pro Ser Glu Tyr Arg Lys
                260                 265                 270

Leu Leu Gly Ala Val Val Ile Ser Ala Asn Ala Gly Gly Ala Trp
                275                 280                 285

Thr Pro Ile Gly Asp Val Thr Thr Thr Met Leu Trp Ile His Gly Gln
            290                 295                 300

Ile Thr Thr Leu Lys Ile Met Gln Gly Val Met Val Leu Thr Val Thr
305                 310                 315                 320

Asp Leu Thr Leu Cys Ile Ile Ala Asn Ser Glu Ala Asn Gly Ala Ser
                325                 330                 335

Gln Lys Ser Ser Ser Leu Leu Ser Ser Glu Gln Met Ala Pro Arg Gly
                340                 345                 350

Gln Leu Val Leu Ala Val Gly Val Gly Ala Leu Val Phe Val Pro Ile
            355                 360                 365

Phe Lys Ala Leu Thr Gly Leu Pro Pro Phe Met Gly Met Leu Leu Gly
            370                 375                 380

Leu Gly Ile Leu Trp Ile Leu Thr Asp Ala Ile His Tyr Gly Asp Ser
385                 390                 395                 400

Glu Arg Gln Arg Leu Lys Val Pro Gln Ala Leu Ser Arg Ile Asp Thr
                405                 410                 415

Gln Gly Ile Leu Phe Phe Leu Gly Ile Leu Leu Ser Val Gly Ser Leu
            420                 425                 430

Val His Tyr Gln Ser Asp Val Leu His Leu Leu Ile Val Phe Leu Ser
            435                 440                 445

Phe Gly Thr Ser Leu Glu Ser Ala Gly Ile Leu Arg Gln Leu Ala Asn
            450                 455                 460

Tyr Leu Asp Ala Asn Ile Pro Asn Ala Asp Leu Ile Ala Ser Ala Ile
465                 470                 475                 480
```

```
Gly Val Ala Ser Ala Val Ile Asp Asn Val Pro Leu Val Ala Ala Thr
                485                 490                 495

Met Gly Met Tyr Asp Leu Thr Ser Tyr Pro Gln Asp Ser Asp Phe Trp
            500                 505                 510

Gln Leu Val Ala Phe Cys Ala Gly Thr Gly Gly Ser Met Leu Ile Ile
        515                 520                 525

Gly Ser Ala Ala Gly Val Ala Phe Met Gly Met Glu Lys Val Asp Phe
    530                 535                 540

Phe Trp Tyr Phe Arg Lys Val Ile Phe Cys Phe Val Gln Ile Gln Arg
545                 550                 555                 560

Gly Ala Arg

<210> SEQ ID NO 64
<211> LENGTH: 350
<212> TYPE: PRT
<213> ORGANISM: Dichanthelium oligosanthes
<220> FEATURE:
<221> NAME/KEY: MISC_FEATURE
<222> LOCATION: (1)..(350)
<223> OTHER INFORMATION: BASS2

<400> SEQUENCE: 64

Met Ala Ser Val Ser Arg Ala Leu Leu Pro Arg Pro Arg Ala Ala Val
1               5                   10                  15

Cys Ser Ala Ala Arg Leu Gly Cys Gly Gly Leu Gly Asn Gly Ile Gly
            20                  25                  30

Arg Ser Met Pro Ser Tyr Arg Thr Arg Asn Glu Asn His Glu Leu Gly
        35                  40                  45

Leu Ala Val Ala Ser Ala Pro Val Ala Thr Val Thr Pro Val Leu Arg
    50                  55                  60

Ser Arg Gln Ile Leu Cys Lys Ser Glu Ala Asn Ile Ser Ser Asn Leu
65                  70                  75                  80

Pro Glu Ser Leu Pro Thr Gly Val Ser Gln Tyr Glu Lys Ile Val Glu
                85                  90                  95

Leu Leu Thr Thr Leu Phe Pro Val Trp Val Ile Leu Gly Thr Val Ile
            100                 105                 110

Gly Ile Tyr Arg Pro Ser Met Val Thr Trp Leu Glu Thr Asp Leu Phe
        115                 120                 125

Thr Val Gly Leu Gly Phe Leu Met Leu Ser Met Gly Leu Thr Leu Thr
    130                 135                 140

Phe Glu Asp Phe Arg Arg Cys Met Arg Asn Pro Trp Thr Val Tyr Met
145                 150                 155                 160

His Phe Leu Leu Asp Arg Ala Leu His Leu Ser Ile Thr Leu Lys Leu
                165                 170                 175

Ser Ala Pro Leu Ala Thr Gly Leu Ile Leu Val Ser Cys Cys Pro Gly
            180                 185                 190

Gly Gln Ala Ser Asn Val Ala Thr Tyr Ile Ser Lys Gly Asn Val Ala
        195                 200                 205

Leu Ser Val Leu Met Thr Thr Cys Ser Thr Ile Gly Ala Ile Val Met
    210                 215                 220

Thr Pro Leu Leu Thr Lys Leu Leu Ala Gly Gln Leu Val Pro Val Asp
225                 230                 235                 240

Ala Ala Gly Leu Ala Ile Ser Thr Phe Gln Val Val Leu Val Pro Thr
                245                 250                 255

Ile Val Gly Val Leu Ala His Glu Tyr Phe Pro Lys Phe Thr Glu Arg
```

```
              260                 265                 270
Ile Ile Thr Val Thr Pro Leu Ile Gly Val Leu Leu Thr Thr Leu Leu
            275                 280                 285

Cys Ala Ser Pro Ile Gly Gln Val Ser Glu Val Leu Lys Thr Gln Gly
        290                 295                 300

Ala Gln Leu Ile Ile Pro Val Ala Leu Leu His Val Ala Ala Phe Ala
305                 310                 315                 320

Leu Gly Tyr Trp Leu Ser Lys Leu Ser Thr Phe Gly Glu Ser Thr Ser
                325                 330                 335

Arg Thr Ile Ser Ile Glu Cys Gly Met Gln Val Lys Ile Cys
            340                 345                 350

<210> SEQ ID NO 65
<211> LENGTH: 422
<212> TYPE: PRT
<213> ORGANISM: Dichanthelium oligosanthes
<220> FEATURE:
<221> NAME/KEY: MISC_FEATURE
<222> LOCATION: (1)..(422)
<223> OTHER INFORMATION: PPT1
<220> FEATURE:
<221> NAME/KEY: MISC_FEATURE
<222> LOCATION: (148)..(148)
<223> OTHER INFORMATION: Xaa: any amino acid

<400> SEQUENCE: 65

Met Gln Ser Ala Ala Ala Phe Arg Pro Cys Pro Ala Gln Pro Leu Val
1               5                   10                  15

Ser Arg Asn Pro Ser Arg Pro Leu Leu Pro Ala Arg Pro Leu Arg Val
            20                  25                  30

Ser Ser Ala Gly Ile Val Ala Ala Ala Thr Thr Arg Cys Gly Ala
        35                  40                  45

Val Gly Pro Arg Gly Leu Gly Leu Gly Leu Leu Pro Val Ser Pro Asp
    50                  55                  60

Leu Glu Arg Lys Ala His Gln Arg Pro Val Ala Cys Gly Ala Ala Gly
65                  70                  75                  80

Asp Ala Ala Ala Gly Asn Ala Glu Glu Ser Gly Gly Leu Val Lys
                85                  90                  95

Thr Leu Gln Leu Gly Ala Leu Phe Gly Leu Trp Tyr Leu Phe Asn Ile
            100                 105                 110

Phe Phe Asn Ile Tyr Asn Lys Gln Val Leu Lys Val Phe Pro Tyr Pro
        115                 120                 125

Ile Asn Ile Thr Thr Val Gln Phe Ala Val Gly Thr Ala Val Ala Leu
    130                 135                 140

Phe Met Trp Xaa Cys Ile Trp Gln Val Leu Lys Val Phe Pro Tyr Pro
145                 150                 155                 160

Ile Asn Ile Thr Thr Val Gln Phe Ala Val Gly Thr Ala Val Ala Leu
                165                 170                 175

Phe Met Trp Ile Thr Gly Ile Leu Lys Arg Pro Lys Ile Ser Gly Ala
            180                 185                 190

Gln Leu Leu Ala Ile Leu Pro Leu Ala Val Val His Thr Met Gly Asn
        195                 200                 205

Leu Phe Thr Asn Met Ser Leu Gly Lys Val Ala Val Ser Phe Thr His
    210                 215                 220

Thr Ile Lys Ala Met Glu Pro Phe Phe Ser Val Leu Leu Ser Ala Ile
225                 230                 235                 240

Phe Leu Gly Glu Leu Pro Thr Val Trp Val Val Leu Ser Leu Leu Pro
```

```
                    245                 250                 255
Ile Val Gly Gly Val Ala Leu Ala Ser Leu Thr Glu Ala Ser Phe Asn
            260                 265                 270

Cys Cys Ala Leu Pro Ser Leu Ile Pro Asn Pro Ile His Met Phe Pro
            275                 280                 285

Phe Ala Gln Glu Ser Leu Asp Asn Ile Asn Leu Phe Ser Ile Ile Thr
            290                 295                 300

Val Met Ser Phe Phe Leu Leu Ala Pro Val Ala Phe Phe Thr Glu Gly
305                 310                 315                 320

Val Lys Ala Thr Pro Ala Phe Leu Gln Ser Ala Gly Leu Asn Val Asn
            325                 330                 335

Gln Val Leu Thr Arg Ser Leu Leu Ala Ala Leu Cys Phe His Ala Tyr
            340                 345                 350

Gln Gln Val Ser Tyr Met Ile Leu Ala Arg Val Ser Pro Val Thr His
            355                 360                 365

Ser Val Gly Asn Cys Val Lys Arg Val Val Ile Val Thr Ser Val
370                 375                 380

Leu Phe Phe Lys Thr Pro Val Ser Pro Ile Asn Ser Leu Gly Thr Ala
385                 390                 395                 400

Ile Ala Leu Ala Gly Val Phe Leu Tyr Ser Gln Leu Lys Arg Leu Lys
            405                 410                 415

Pro Lys Pro Lys Thr Ala
            420

<210> SEQ ID NO 66
<211> LENGTH: 425
<212> TYPE: PRT
<213> ORGANISM: Dichanthelium oligosanthes
<220> FEATURE:
<221> NAME/KEY: MISC_FEATURE
<222> LOCATION: (1)..(425)
<223> OTHER INFORMATION: PPT2

<400> SEQUENCE: 66

Met Met Gln Gly Ala Ala Ala Ala Thr Thr Ser Val Ser Gly Ala
1               5                   10                  15

Ser Trp Thr Arg Ala Thr Arg Gly Arg Ala Ser Ala Leu Ala Ser Arg
            20                  25                  30

His Val Gly Leu Ala Ala Ala Ser Ser Ser Ser Ser Phe Gly Pro
            35                  40                  45

Arg Gly Ala His Ala Ala Ala Pro Pro Pro Ser Pro Leu Leu Arg Val
    50                  55                  60

Arg Gly Gly Cys Arg Leu Arg Pro Leu Ser Leu Leu Ser Asp Lys Gly
65                  70                  75                  80

Arg Asn Gly Asp Val Ala Lys Ala Ala Ala Ala Ala Ala Ser
            85                  90                  95

Val Pro Ala Asp Asp Ala Ser Ala Ala Ala Arg Gly Glu Asp Ala Gly
            100                 105                 110

Ala Gly Gly Ile Ala Ala Thr Val Gln Leu Gly Ala Met Ile Val Ala
            115                 120                 125

Trp Tyr Leu Leu Asn Ile Tyr Phe Asn Ile Tyr Asn Lys Gln Val Leu
    130                 135                 140

Gly Val Leu Pro Leu Pro Leu Pro Tyr Thr Ile Thr Ala Phe Gln Leu
145                 150                 155                 160

Ala Phe Gly Ser Leu Leu Ile Phe Leu Met Trp Ala Thr Arg Leu His
            165                 170                 175
```

```
Pro Ala Pro Arg Leu Ser Ala Ala Gln Leu Gly Lys Ile Ala Pro Leu
            180                 185                 190

Ala Leu Gly His Met Leu Gly Thr Val Phe Thr Asn Met Ser Leu Gly
        195                 200                 205

Lys Val Ala Val Ser Phe Thr His Thr Ile Lys Ala Ser Glu Pro Phe
    210                 215                 220

Phe Thr Val Val Leu Ser Ala Leu Phe Leu Gly Glu Val Pro Ser Leu
225                 230                 235                 240

Pro Val Leu Gly Ser Leu Val Pro Ile Val Gly Val Ala Leu Ala
                245                 250                 255

Ser Phe Thr Glu Val Ser Phe Asn Trp Thr Gly Phe Trp Ser Ala Met
        260                 265                 270

Ala Ser Asn Leu Thr Asn Gln Ser Arg Asn Val Leu Ser Lys Lys Leu
        275                 280                 285

Leu Ala Gly Asp Lys Asp Val Met Asp Asp Ile Asn Leu Phe Ser Val
        290                 295                 300

Ile Thr Ile Leu Ser Phe Leu Leu Ser Cys Pro Leu Met Phe Leu Ala
305                 310                 315                 320

Glu Gly Val Lys Phe Thr Pro Gly Tyr Leu Gln Ser Thr Gly Leu Asn
                325                 330                 335

Leu Gln Glu Leu Cys Val Arg Ala Val Leu Ala Gly Phe Cys Phe His
        340                 345                 350

Gly Tyr Gln Lys Leu Ser Tyr Leu Ile Leu Ser Arg Val Ser Pro Val
        355                 360                 365

Thr His Ser Val Ala Asn Cys Val Lys Arg Val Val Ile Val Ser
        370                 375                 380

Ser Val Leu Phe Phe Ser Thr Pro Ile Ser Pro Val Asn Thr Leu Gly
385                 390                 395                 400

Thr Gly Ala Ala Leu Gly Gly Val Phe Leu Tyr Ser Arg Leu Thr Arg
                405                 410                 415

Ser Lys Lys Pro Lys Asn Lys Glu Gly
            420                 425

<210> SEQ ID NO 67
<211> LENGTH: 423
<212> TYPE: PRT
<213> ORGANISM: Dichanthelium oligosanthes
<220> FEATURE:
<221> NAME/KEY: MISC_FEATURE
<222> LOCATION: (1)..(423)
<223> OTHER INFORMATION: TPT

<400> SEQUENCE: 67

Met Ser Ala Leu Gly Thr Leu Ser Gly Gly Ala Ala Gly Val Ala Gly
1               5                   10                  15

Leu Leu Arg Leu Arg Arg Cys Ala Ala Pro Ala Pro Ser Ala Leu Ala
            20                  25                  30

Ser Ser Pro Asn Leu Pro Pro Leu Lys Cys Ala Ala Val Thr Asp Ala
        35                  40                  45

Arg Gln Leu Val Trp Gly Arg Gln Leu Arg Pro Ala Leu Leu Pro Ala
    50                  55                  60

Ala Leu Leu Leu Pro Ser Gln Gln Gln Ala Ala Ala Arg Arg Asn Thr
65                  70                  75                  80

Leu Arg Pro Pro Ala Ala Ala Glu Glu Ala Lys Pro Ala Gly Phe
                85                  90                  95
```

Leu Asp Lys Asn Pro Ala Leu Val Thr Gly Phe Phe Phe Met Trp
            100                 105                 110

Tyr Phe Leu Asn Val Ile Phe Asn Ile Leu Asn Lys Lys Ile Tyr Asn
        115                 120                 125

Tyr Phe Pro Tyr Pro Tyr Phe Val Ser Val Ile His Leu Ala Val Gly
    130                 135                 140

Val Val Tyr Cys Leu Ile Ser Trp Ala Val Gly Leu Pro Lys Arg Ala
145                 150                 155                 160

Pro Ile Asn Ser Thr Leu Leu Lys Leu Leu Phe Pro Val Ala Leu Cys
                165                 170                 175

His Ala Leu Gly His Val Thr Ser Asn Val Ser Phe Ala Ala Val Ala
            180                 185                 190

Val Ser Phe Ala His Thr Ile Lys Ala Leu Glu Pro Phe Phe Asn Ala
        195                 200                 205

Ala Ala Thr Gln Phe Val Leu Gly Gln Gln Val Pro Leu Ser Leu Trp
    210                 215                 220

Leu Ser Leu Ala Pro Val Val Leu Gly Val Ser Met Ala Ser Leu Thr
225                 230                 235                 240

Glu Leu Ser Phe Asn Trp Thr Gly Phe Ile Asn Ala Met Ile Ser Asn
                245                 250                 255

Ile Ser Phe Thr Tyr Arg Ser Ile Tyr Ser Lys Lys Ala Met Thr Asp
            260                 265                 270

Met Asp Ser Thr Asn Val Tyr Ala Tyr Ile Ser Ile Ala Leu Ile
        275                 280                 285

Val Cys Ile Pro Pro Ala Leu Ile Ile Glu Gly Pro Gln Leu Met Gln
    290                 295                 300

His Gly Phe Asn Glu Ala Ile Thr Lys Val Gly Leu Gln Lys Phe Val
305                 310                 315                 320

Thr Asp Leu Phe Leu Val Gly Leu Phe Tyr His Leu Tyr Asn Gln Val
                325                 330                 335

Ala Thr Asn Thr Leu Glu Arg Val Ala Pro Leu Thr His Ala Val Gly
            340                 345                 350

Asn Val Leu Lys Arg Val Phe Val Ile Gly Phe Ser Ile Ile Ala Phe
        355                 360                 365

Gly Asn Arg Ile Thr Thr Gln Thr Gly Ile Gly Thr Cys Ile Ala Ile
    370                 375                 380

Ala Gly Val Ala Val Tyr Ser Tyr Ile Lys Ala Lys Ile Glu Glu Glu
385                 390                 395                 400

Lys Arg Val Ala Arg Ser Ile Ser Leu Leu Thr Ile Arg Thr Asp Asp
                405                 410                 415

His Gly Val Ser Met Asn Val
            420

<210> SEQ ID NO 68
<211> LENGTH: 731
<212> TYPE: PRT
<213> ORGANISM: Setaria italica
<220> FEATURE:
<221> NAME/KEY: MISC_FEATURE
<222> LOCATION: (1)..(731)
<223> OTHER INFORMATION: MEP3b

<400> SEQUENCE: 68

Met Leu Pro His Ala Pro Ser Arg Ala Pro Gly Ala Phe Arg Phe Lys
1               5                   10                  15

Pro His Leu Pro Ala Lys Pro Pro Leu Leu Ala Ser Thr Ser Thr Pro

-continued

```
                20                  25                  30
Ala Ser Ala Ser Ala Ser Thr Arg Gly Ser Val Cys Thr Ala Ala Ala
            35                  40                  45
Ala Thr Thr Arg Arg Asn Leu Leu Val Leu Val Pro Ser Leu Val Ala
        50                  55                  60
Ala Ser Thr Ala Leu Gln Ser Leu Pro Leu Ala Ala Ser Ala Ala Ala
65                  70                  75                  80
Gly Asp Asp Lys Pro Ala Pro Pro Ala Ala Pro Ala Pro Ala Ala
                85                  90                  95
Pro Ala Pro Pro Pro Pro Ala Asp Glu Pro Ala Leu Ser Arg Val
            100                 105                 110
Tyr Asp Ala Thr Val Ile Gly Glu Pro Gln Ala Val Gly Lys Asp Ala
            115                 120                 125
Arg Arg Arg Val Trp Glu Lys Leu Met Ala Ala Arg Val Val Tyr Leu
        130                 135                 140
Gly Glu Ala Glu Leu Val Pro Asp Arg Asp Arg Ala Leu Glu Leu
145                 150                 155                 160
Glu Ile Val Arg Lys Leu Ala Ala Gly Cys Ala Glu Ala Gly Arg Ser
                165                 170                 175
Ile Ser Leu Ala Leu Glu Ala Phe Pro Cys Asp Leu Gln Glu Gln Leu
            180                 185                 190
Asn Arg Phe Met Asp Gly Arg Ile Asn Gly Asp Asn Leu Arg Leu Tyr
            195                 200                 205
Thr Ser His Trp Ala Pro Glu Arg Trp Gln Glu Tyr Glu Pro Leu Leu
        210                 215                 220
Asn Tyr Cys Arg Asp Asn Gly Ile Lys Leu Val Ala Cys Gly Thr Pro
225                 230                 235                 240
Leu Glu Val Val Arg Thr Val Gln Ala Glu Gly Ile Arg Gly Leu Ser
                245                 250                 255
Lys Ala Glu Arg Lys Met Tyr Ala Pro Pro Ala Gly Ser Gly Phe Ile
                260                 265                 270
Ser Gly Phe Thr Ser Ile Ser Gly Arg Ser Leu Ile Asp Lys Ile Ser
            275                 280                 285
Ser Thr Arg Gly Ser Pro Phe Gly Pro Ser Ser Tyr Leu Ser Ala Gln
        290                 295                 300
Ala Arg Val Val Asp Asp Tyr Thr Met Ser Gln Thr Ile Leu Lys Glu
305                 310                 315                 320
Ile Ala Ser Gly Asp Pro Ser Gly Met Leu Val Val Thr Gly Ala
                325                 330                 335
Ser His Val Met Tyr Gly Pro Arg Gly Ile Gly Val Pro Ala Arg Ile
            340                 345                 350
Ser Lys Lys Met Gln Lys Lys Lys Gln Val Val Val Leu Leu Asp Pro
            355                 360                 365
Glu Arg Gln Ser Ile Arg Arg Glu Gly Glu Ile Pro Val Ala Asp Phe
        370                 375                 380
Leu Trp Tyr Ser Ala Ala Lys Pro Cys Ser Arg Asn Cys Phe Asp Arg
385                 390                 395                 400
Ala Glu Ile Ala Arg Val Met Asn Ala Ala Gly Arg Arg Glu Ala
                405                 410                 415
Leu Pro Gln Asp Leu Gln Lys Gly Ile Asp Leu Gly Val Val Ser Pro
            420                 425                 430
Glu Ile Leu Gln Asn Phe Phe Asp Leu Glu Lys Tyr Pro Val Met Ala
            435                 440                 445
```

```
Glu Leu Ile His Arg Phe Gln Gly Phe Arg Glu Arg Leu Leu Ala Asp
    450                 455                 460
Pro Lys Phe Leu His Arg Leu Ala Ile Glu Glu Gly Ile Ser Ile Thr
465                 470                 475                 480
Thr Thr Leu Leu Ala Gln Tyr Glu Lys Arg Lys Gly Arg Phe Phe Glu
                485                 490                 495
Glu Ile Asp Tyr Val Leu Thr Asp Thr Ile Arg Gly Ser Val Val Asp
                500                 505                 510
Phe Phe Thr Val Trp Leu Pro Ala Pro Thr Ile Ser Leu Leu Ser Phe
            515                 520                 525
Ala Asp Asp Gly Ser Gly Asp Ser Val Glu Leu Leu Lys Gly Leu Leu
        530                 535                 540
Gly Thr Leu Pro Asp Asn Ala Phe Gln Lys Gly Ile Val Gly Gln Asn
545                 550                 555                 560
Trp Ser Ile Lys Gln Arg Phe Ala Ser Val Leu Met Gly Gly Leu Lys
                565                 570                 575
Leu Ala Gly Val Gly Phe Ile Ser Ser Ile Gly Ala Gly Val Ala Ser
                580                 585                 590
Asp Val Leu Tyr Gly Ala Arg Gln Ile Leu Lys Pro Ser Ala Ser Met
            595                 600                 605
Glu Val Gly Arg Lys Arg Ser Pro Ile Trp Lys Ser Ala Thr Val Tyr
        610                 615                 620
Ser Cys Phe Leu Gly Thr Ser Ala Asn Leu Arg Tyr Gln Val Ile Ala
625                 630                 635                 640
Gly Leu Ile Glu His Arg Leu Gly Glu His Leu Met Ala Tyr Tyr Asn
                645                 650                 655
Gln Pro Leu Leu Ala Ser Leu Leu Ser Phe Val Ser Arg Ile Ile Asn
            660                 665                 670
Ser Tyr Trp Gly Thr Gln Gln Trp Ile Asp Leu Ala Arg Ala Thr Gly
        675                 680                 685
Val Gln Ser Thr Lys Lys Glu Leu Ala Ser Pro Glu Val Ser Asn Ala
    690                 695                 700
Thr Glu Met Pro Leu Leu Glu Cys Gly Thr Thr Asp Val Gln Asn Val
705                 710                 715                 720
Asp Asp Ser Asn Lys Gln Pro Asn Asp Leu Thr
                725                 730
```

<210> SEQ ID NO 69
<211> LENGTH: 974
<212> TYPE: DNA
<213> ORGANISM: Zea mays
<220> FEATURE:
<221> NAME/KEY: misc_feature
<222> LOCATION: (1)..(974)
<223> OTHER INFORMATION: RbcS_promoter

<400> SEQUENCE: 69

```
gagctcccctt taatctggcg ctagatctgc atccgcggct tgcaaagata aatggcacat    60
ttagtgtgtt attttgcaat acctttcata gtagatatcc ttaaatgcag ttttaggcat   120
gtttgggtaa ttaaataaca ttttaggag gagttttaga tttacctttc tttcgtgatg    180
actgatgaca gacgtgggga attcaaatgc aactctagcg aaagttcata tattttcat    240 aaatagctga ggctggggta attatttttt ttgtagaaaa atagaatagg tggaatggtt    300
ggggaaggcg taggcgctcg tggacgacgc ccgataaaag acaagaggcg gaattgccat    360
```

| | |
|---|---|
| gaattcgagg tagctaagta aggcgcatat atatgccaaa aaattctact gtcactttcc | 420 |
| aatttcaatg cgctgccaaa caagccatcc tggaaactga cttgaattca gcccaattct | 480 |
| gtagatccaa acagggccgg cgtcagtgcc tcaggtgaga gagcagcaga cgatgcaaag | 540 |
| agccaaaact gcaagcagac gcagccgaag ccgaagccga agcccaagcc caaaactgtt | 600 |
| ttgtctttgc ccagaaccgc gacgagccta aactgcgctt cctcctatct acaagtccct | 660 |
| ggcacatcac gcatagtcca accatggcgc gcaggcgata aggcgcgcca cggggacgcg | 720 |
| acatgtggtg gcggacgcga tcaggatagg gccaggctgg ccgggcgcgg ccacgggaga | 780 |
| acggtggcca ctcgtcccac atccgcttcg tcctgtcctg tactgcgtcc tgcccccaac | 840 |
| gagagccgga gccggccatc ccgtcgcaca ctctccccct ctatatatgc cgtcggtgtg | 900 |
| ggggagccta ctacaggacg acccaagcaa gcaagcaagc agcgagtaca tacatactag | 960 |
| gcagccaggc agcc | 974 |

<210> SEQ ID NO 70
<211> LENGTH: 439
<212> TYPE: DNA
<213> ORGANISM: Zea mays
<220> FEATURE:
<221> NAME/KEY: misc_feature
<222> LOCATION: (1)..(439)
<223> OTHER INFORMATION: RbcS_3_UTR

<400> SEQUENCE: 70

| | |
|---|---|
| accgcgcccg ccggccgccc ccgccggct agctagctag ctagctcctg cgtgagctag | 60 |
| tagctagtgc catgcgtcgt ctctgtcgtt cggttttgct tcgggtcacc gtgtaccctt | 120 |
| tgcttgcttg gtttcttctt tcctttttc ctttttttt cttctttcc ccggccatgg | 180 |
| ttcctttgct ttccagcagt tctctgctgg atgtgatgta tccattgttg caatcatggc | 240 |
| cttgcattgg ctacctctat acctgctaca aaactactgc aacgcctata tatacttggg | 300 |
| gtgaggaaca tgtgaatgca agctccggct atcatataca tgtaatatgg atacaaacta | 360 |
| tatatataaa tccgccgagg cgccgacaat actatacgac accgtgttaa gttaatatat | 420 |
| aactggtgct tttattta | 439 |

<210> SEQ ID NO 71
<211> LENGTH: 2000
<212> TYPE: DNA
<213> ORGANISM: Setaria italica
<220> FEATURE:
<221> NAME/KEY: promoter
<222> LOCATION: (1)..(2000)
<223> OTHER INFORMATION: Si035016m promoter

<400> SEQUENCE: 71

| | |
|---|---|
| ccctgaggat tactccatat ccatattgga tcctattgaa ttacggatag cagaaggctt | 60 |
| cattccacgt acaacgaagc acaagttgga aaaagtagca cataagtacg taaccgagct | 120 |
| ggctcaaaga agcttagtac caattgttag cataagcgag gtgcatatgg gtggagcgaa | 180 |
| caaataagga tccatgatat tttacgtgat tggtgcatag aagaagcaag atatgctggt | 240 |
| tttgttgatg tcgtcgccaa cactgcaggt caggcttccc gcttcctctc cattctctgt | 300 |
| atacggttcg ttcatttggg aagtacttca taactgttgg ctccttagtg acctatcatg | 360 |
| cactccaaaa aattgcaggc catgttggcg aataccatgg tacccatcg ctcttctttg | 420 |
| caaaactacc ttgatggtat agcatgttcc cagaaatgcc gaacctccag actttggttg | 480 |
| gctttgaact ttcatcattc tatctacgta agctatggta tctaagagtg ctccatgtag | 540 |

```
aaaacacgag cctgacgaat ttctctaggg caatcagtgt gtgcattcac ttaagatatc    600
tcatgctcag aaagtgtggg caggtcacgc tcccttcttc aattggacaa ttccttcact    660
tgcaaactat agacctgaac aacacagaat tgaattcagt ggtgccaaac tctatatggg    720
acactacaac tctaaggcac gtttaccttg aaagggatt ttctgcaccg aggaatcgac     780
cacaaaagca gctccagtcc ttgtacttat ctgtcccaga tgaggacagt aagtatttcc    840
agagtaagaa catggtggcc ttttttagcc aaatgaccca accaactact ctctccttgg    900
atgttgaaaa cctatactac ccgcaaagat gattcatata ctaacaaact tagatgacct    960
ttctggttga ggtttacctt aataagttgc ctgagagccg actcttacca caaggcctac   1020
gggagcttca tttgtttgct gatgccatta agaagaccc catgccgatc ctggagaaac    1080
ttccctgcct ggtattgctc gagtcatcgg ggccgaacca tgttctgctc tgctcaaggg   1140
ttcaattccc tcggctgcta gagttggacc tgtattactt caacagtcag gagtggagaa   1200
tgcctaccgg ggcaatgcca aggctctcac gcctgaagct ttatcgttgc cggaacatga   1260
agaagctccc agagggcgc acctgccgtc cctcgaggta ggtgactggt tttcctcccg    1320
tcctgacctt agttatctct ttcctcctat caatctttaa acggttgggc aaatgtaggc   1380
tcctgctagc atagatcatt ttattacttt taatgaattg gatgagtagc ttgatccgta   1440
actggaagac aatttatctt gtgcaaaaca tagtgcaggt gtgacgttca gtgaatgtaa   1500 ttaactttg tgtcgctctc ttgagtattt ctggtgtgtt ctaagttata accaccaact    1560
gtactgtgtt tgcctgaatg agatttcagc gaactcgtgc tttcgaaaag aacgataagt   1620
tgccattaaa gaacagccaa tgccgatatc gatcctggag aaactgccat gcctagtggt   1680
gctcgagtta ccaaggccga accatgttct gctccgccca agggttccct cggctgctct   1740
cttcttatct ttccatcgag gagtggatga tggaggttga ggcaagagct ctcttctttc   1800
tgcgaccagt cgaccaccaa ggcaccaacc gcccagcggc ccaggcctct ggctgccact   1860
catctgtgtc gtaaccacca aggcacaatc ggcccagcag cccaggcctc aagctgccgc   1920
tcatctgtgt cgtaactcat acgcatcgac attgccccca cttatgcact tcaaaatggt   1980
cactctcccg tcctgaacca                                               2000
```

<210> SEQ ID NO 72
<211> LENGTH: 400
<212> TYPE: DNA
<213> ORGANISM: Setaria italica
<220> FEATURE:
<221> NAME/KEY: misc_feature
<222> LOCATION: (1)..(400)
<223> OTHER INFORMATION: Si035016m 3'UTR
<400> SEQUENCE: 72

```
gaaaaagaaa acaagcaac aagttgcatg gatgtcacat gctaacgtgc tcatgtatcc     60
tctctcaagc atgtacatgg ctgatcagct aataaccggc cgccaggaga ataatcatgc    120
atggatgggc catgcattgt attagcacca tgccaccaag atacacacgc gctatgttct    180
gccgccggcc gcaagcacgc gcggtacctg ctggcgcgct ctggcccaga cattacggga    240
gggagccaga atgtagcccc acaattctga agatatgcat cgtcagacgg tcaacgcgtg    300
atgataagag cagctgcacg attatcagac cggccttctc tcgagccgat taaggcctcg    360
ttcgttttca ccggattagc tcggaatgag gtccattcct                          400
```

<210> SEQ ID NO 73

<211> LENGTH: 1814
<212> TYPE: DNA
<213> ORGANISM: Zea mays
<220> FEATURE:
<221> NAME/KEY: promoter
<222> LOCATION: (1)..(1814)
<223> OTHER INFORMATION: CA1_promoter

<400> SEQUENCE: 73

```
ccccgcccat gtcagcaggc ctccgaggct tttggttgcc caaccagccc atgggctgaa      60
ttcataacag tgttggcaca cagtttcctc ttcactcgga agcttattat tatcgatcct     120
gaaccagaga ctagcagagc tagcatttcg acgacgcgtc tcaactctca acctccaagt     180
ccacctcgtg tacgtgctgc cttgccagtt gccactgggc actgctggcc cagtgaccaa     240
ccatgcgtta gatctgacag caccaccgaa ccatcctccc cggtgatcaa caaacgacgg     300
cagccacatc ttgcacccaa cgtgatgatg aatgatgcct agaacttttg acaacaaaac     360
gcagcacagg tagcaggttt aattcaacaa gactttctac tatatagagc cacaccatag     420
agataactaa tctgtgcgca aagccaaagt gctgacggca actgtggtgc agccttttca     480
tctccgtttt taagttttttt gcccctcctt ttgttttctg tttttctggg aactctttaa     540
accgccgtgg cgccgtgtaa actttgctgt agccttttcg cgtgcaatgg cagagcgccc     600
tgttcttttc ctgctaaaga aaaaaaaaaa ggagcacctg atcgctggca ggcccacggc     660
ccacccaact gtgtctgtaa cgctcggcgt ccctgcattg catgccaagt gccaaccacc     720
agtccatagc agggtcaggg agaccgcaga tgaggccggg caacggtga tgccgcaaag     780
aggattcaga atccttttc ttttcttttc ttttaccacc gggctggcat cacagattac     840
acgcgcagta gagtaagcac gtctctctcg tagccaagaa caacagtcta cacagctcgc     900
tttctccgcc cttgtctggg cgttacggca ggcaagcccc ctcgttttct tctgctcgcg     960
ttctccttcc atgtccacat ctcctgtgcc accgcacgca aggtgccaac gctccctcgc    1020
cgcagtagca tcgcgtccac acaaactgca cctccactag atacggcggt gatccggcga    1080
gagagcgcga cacgcacagg ccagctagcg tttctccgac gccgcgcgtt tcatcatttc    1140
ccgcttcccc tgccccggcc cgcgcgcgcg cgcccgtgtg gtccagacca ggacgcgcgc    1200
ggatgtgcat ccggcgcgcg cccgtcggcc acacggtgcc gccgcgcgtt atcccgagcc    1260
ctgtcctgtc ctgtcctgtt ccatctcgcg cgcgaggggg ggaggggagg gcagcgagtg    1320
gcgcgctggc ggatgaggcg ccgagtggcc cgcatccacc ggcgcaggcg agccgcacga    1380
cgccgccgcg ctcgcggaac gccgccgcca cacatgcgca ccccggccc gcggggctgt     1440
aacggccttg tcgccacgcg tgcgccccgt gtgtataagg aggcagcgcg tacagggggc    1500
gacaacgata agcggcactc gcacgatcaa tgtacacatt gcccgtccgc gccaccacat    1560
ccagcatcgt cgccagcctc gccaccccg cgccgtcctc ctcctccggc tccggctccg    1620
gccgccccag gcccaggctc atccggaacg ccccgtctt cgccgccccc gccaccgtcg    1680
tgtaaacggg acggcgggca gctgaggagt caaacgagag agatcgagag aaagaaaggg    1740
agggcatcca ccagccgccg gcgataagag gggaggagag agaggccaga gaagaggagg    1800
agaagaagaa gaaa                                                       1814
```

<210> SEQ ID NO 74
<211> LENGTH: 283
<212> TYPE: DNA
<213> ORGANISM: Zea mays
<220> FEATURE:
<221> NAME/KEY: misc_feature

<222> LOCATION: (1)..(283)
<223> OTHER INFORMATION: CA_3_UTR

<400> SEQUENCE: 74

```
aaaactaggg ctacggcaat tctaccggcc cgccgactcc tgcatcatca taaatatata    60
tactatacta tactactacg tacctaccga tatgcacccg agcaatgtga atgcgtcgag   120
tactatatat ctgttttctg catctacata tataccgg atcaatcgcc caatgtgaat    180
gtaataagca atatcatttt ctaccacttt tcattcctaa cgctgagctt tttatgtact   240
atatcttata tgatgaataa taatatgacc gccttgtgat cta                    283
```

<210> SEQ ID NO 75
<211> LENGTH: 1584
<212> TYPE: DNA
<213> ORGANISM: Zea mays
<220> FEATURE:
<221> NAME/KEY: promoter
<222> LOCATION: (1)..(1584)
<223> OTHER INFORMATION: PepC_Promoter

<400> SEQUENCE: 75

```
gggggggggg gggggagggt cgtcgtctcc ctatctgacc tctcttctgc attggattgc    60 cttttcggt actctattta aaacttaaaa gtacaaatga ggtgccggat tgatggagtg   120
atatataagt ttgatgtgtt tttcacataa gtgacaagta ttattgaaag agaacatttg   180
cattgctact gtttgcatat gggaaaattg agaattgtat catgccatgg ccgatcagtt   240
ctttacttag ctcgatgtaa tgcacaatgt tgatagtatg tcgaggatct agcgatgtaa   300
tggtgttagg acacgtggtt agctactaat ataaatgtaa ggtcattcga tggttttttct   360 atttcaatt acctagcatt atctcatttc taattgtgat aacaaatgca ttagaccata   420
attctgtaaa tatgtacatt taagcacaca gtctatattt taaaattctt cttttgtgt   480 ggatatccca acccaaatcc acctctctct tcaatccgtg catgttcacc gctgccaagt   540
gccaacaaca catcgcatcg tgcatatctt tgttggcttg tgcacggtcg cgccaatgg   600 aggagacacc tgtacggtgc ccttggtaga caacatcct tatccctata tgtatggtgc   660
ccttcgtaga atgacacccc ttatccctac aatagccatg tatgcatacc aagaattaaa   720 tatactttt cttgaaccac aataattat tatagcggca cttcttgttc aggttgaaca   780
cttatttgga acaataaaat gccgagttcc taaccacagg ttcacttttt tttttccttta   840 tcctcctagg aaactaaatt ttaaaatcat aaatttaatt taaatgttaa tggaaacaaa   900
aaattatcta caaagacgac tcttagccac agccgcctca ctgcaccctc aaccacatcc   960
tgcaaacaga caccctcgcc acatccctcc agattcttca ctccgatgca gcctacttgc  1020
taacagacgc cctctccaca tcctgcaaag cattcctcca aattcttgcg atccccgaa   1080 tccagcatta actgctaagg gacgccctct ccacatcctg ctacccaatt agccaacgga  1140
ataacacaag aaggcaggtg agcagtgaca agcacgtca acagcaccga gccaagccaa  1200
aaaggagcaa ggaggagcaa gcccaagccg cagccgcagc tctccaggtc cccttgcgat  1260
tgccgccagc agtagcagac acccctctcc catccccctc cggccgctaa cagcagcaag  1320
ccaagccaaa aaggagcctc agccgcagcc ggttccgttg cggttaccgc cgatcacatg  1380
cccaaggccg cgcctttccg aacgccgagg gccgcccgtt cccgtgcaca gccacacaca  1440 caccccgcccg ccaacgactc cccatcccta tttgaaccca cccgcgcact gcattgatca  1500
gacaccaatc gcatcgcagc agcacgagca gcacgccgtg ccgctccaac catctcgctt  1560
```
ccgtgcttag cttcccgccg cgcc                                          1584

<210> SEQ ID NO 76
<211> LENGTH: 291
<212> TYPE: DNA
<213> ORGANISM: Zea mays
<220> FEATURE:
<221> NAME/KEY: misc_feature
<222> LOCATION: (1)..(291)
<223> OTHER INFORMATION: PepC_3_UTR

<400> SEQUENCE: 76
gcggcttctc ttcactcacc tgcagagtgc accgcaataa tcagcttccg gatggtggcg    60
ttttgtcagt tttggatgga aatgccgaac tggcagcgtc tgttttccct atgcatatgt   120
aatttcctgc ctctttatat tcactcttgt tgtcaagtcc aagtggaaaa tcttggcata   180
ttatacatat tgtaataata aacatcgtac aatctgcatg ctgttttgta ataattaatt   240
aatatcccag cccattggat ggacttgttt accatggtgt tacttcagcc a            291

<210> SEQ ID NO 77
<211> LENGTH: 2000
<212> TYPE: DNA
<213> ORGANISM: Setaria italica
<220> FEATURE:
<221> NAME/KEY: promoter
<222> LOCATION: (1)..(2000)
<223> OTHER INFORMATION: NHD_promoter

<400> SEQUENCE: 77
gtggtggccg ttcactggtg gaaaagtgag cattagtccc ggttggagag acgcataggt    60
ctcgaaaatt caaccaggac taatcttttg agactaaagg cccccatctt tagtcccggg   120
tatttcaccc aggactaaag accttcttta gtcccggacc aaccgggact aaaaaggtta   180
aaaaaataaa aaaatggacc accccccacct acggcagctc gcccgtgcca gccgcctgcc   240
cgccccagct cgcctgctcg caccggccgc cgagagctgc gccagctcgc ccgcccgcgt   300
cggccgctcg ctcgtgtcgg ccaaccgcct acccacgctg gcgctcgccc gcccgcccca   360
gcttgcccgc ccacatcggc cgccgggagc gcgctagct cacccgcccg aggccggcc    420 gcaccgctcg tggcccccgt cactccgctt ggaagaaagg gagtggagga ggagagaaga   480
taaggaagaa gagaaagagt gctgcctgcg caagataagg gaaaaatgga gaggaggaga   540
gaagataagg tggagagaaa gggggactgc gtgaaaagat tagtcccgat tggtaaaggg   600
aagcctttag tcccggttgg tgttttcaac cgggactaaa aggcctacca gattttctca   660
tcccactacc ctttagtcct agttgatatt accaaccgag actaaagctc ccgtcatcgg   720
tggctatcgg tggtggccgt ttgatccggg actaaaggcc ctttagttcc gggtccagaa   780
acgatcggga ctaaaaatgc tggatggaag gtctcttctc tactagtggc ctgacccgtc   840
ccaggtccaa aaagcgtcga gacatgttac gctggatgga gctttagtcc cgatcaaaaa   900
gcatcgagac atattacgct ggatggaagg tctattgtct accggtgttt cccaacccaa   960
ctcaactcag ctgttcattg ttttgacagt aggggtgttg cacaaagcta cttggttttg   1020
ctagttttct gaaagctaat tgatcactac agtctctcgt tcgtgcatta acgttctcat   1080
tgtttctttc tcatttcgct catgtatgcg cgaagcagat cctttgtttg aggattcttg   1140
ttgataaatt gggctgcttc gttgtgtggt gtgtgtgtg tgtggtgtgt gtggtgtgtg   1200
tgtttgtttg tttttttgtg tgttgatagc tttgttccat ggatcggagt gccaagttgg   1260
cgaaactagg ctaggccagt gaagttcgat tcagagattg aaaacgtagt ccgatgctag   1320

```
gctagtaacg ttctgaactc ttttctttct ttcccttgac cttacaaatt ggctcagccg    1380
ttttattttc attttctttt ccttgccttt ttaaattagc ttagccgttt ttcatttctt    1440
tcttctttca cactttgctt ttcttatttt agaaagcccc gcaaatattt tcaaagcaag    1500
aatccaatgt tctagcacag ctttgacatt cacaacaatc caacaaattc tcgtttggct    1560
ggagaaatgg aatgtgttcc atgtttcgtc accccatctc tcatatgcat aaacgtaagg    1620
atttggaatc atcgtataaa agttcacggg atgggatcaa ctcaagatac cgagatctct    1680
ctccttaaat catacaattc ttattttcag aacttggttg gttagcttcc aattttttgtc   1740 tagccaaaat caaagtatgt caaaattaag ataagaaatt tagatgttca cttgatttaa    1800
actaaaatac gacgaccaat acttttttca caaccaaatg tccccaacgt gctcacagct    1860
ccgcctttca aaggttatca ttatcattgt ttctttctag gtttattcaa aaaaggtttc    1920
ttttctagga aagagattgc tgccacaagt tattgtaaag gcctccagta acggaatgcc    1980
ctggaccgct acacgctact                                                2000

<210> SEQ ID NO 78
<211> LENGTH: 400
<212> TYPE: DNA
<213> ORGANISM: Setaria italica
<220> FEATURE:
<221> NAME/KEY: misc_feature
<222> LOCATION: (1)..(400)
<223> OTHER INFORMATION: SiNHD_3_UTR

<400> SEQUENCE: 78
atggacgttt gctctgcatc tttgcgaagc tcgggaatca acacgcatag caatcaacaa     60
acgttagata tcgtcatctt tctcacacat ggagtagaaa tacttaaaag taacctcata    120
cgcatgaatg ttttatgttt gtaatatatt tcatactaaa taagaattct aaagagacat    180
attctatcca aaatcattca tcaaacatgc aattgaccaa gaactggcag gtcaggcgct    240
ctctaaccac aacgctccct gcagcgttac actatcaata tatttctatg cttccaacac    300
gtccttatac acaatgttct tagttctctt accaggagga tcggcatcaa tgttaggttt    360
ggccaaaacc cacgtagtat ttcgtgcaac acctctagac                           400

<210> SEQ ID NO 79
<211> LENGTH: 741
<212> TYPE: DNA
<213> ORGANISM: Sorghum bicolor
<220> FEATURE:
<221> NAME/KEY: promoter
<222> LOCATION: (1)..(741)
<223> OTHER INFORMATION: 4x_RGCGR_promoter
<220> FEATURE:
<221> NAME/KEY: misc_feature
<222> LOCATION: (1)..(63)
<223> OTHER INFORMATION: RGCGR_unit
<220> FEATURE:
<221> NAME/KEY: misc_feature
<222> LOCATION: (253)..(741)
<223> OTHER INFORMATION: S_bicolor_CA_5_UTR

<400> SEQUENCE: 79
gaagcgagtg gcgcgctggc ggatgaggcg gcgagtggcc cggatgcacc ggcgcaggcg     60
agcgaagcga gtggcgcgct ggcggatgag gcggcgagtg gcccggatgc accggcgcag    120
gcgagcgaag cgagtggcgc gctggcggat gaggcggcga gtggcccgga tgcaccggcg    180
caggcgagcg aagcgagtgg cgcgctggcg gatgaggcgg cgagtggccc ggatgcaccg    240
```

| | |
|---|---|
| gcgcaggcga ccgcacgcc gccgcccgcc gcggcgctcg cgcgcgcacc gctgccgcct | 300 |
| gccgccacac aatgcgagcg cgcgcgcaca cacacacaca ccacccgggc gggggggctg | 360 |
| tagtagtaac ggccttgtct tgtcggcacg cgcgcgtccg tgtgtataag gaggcaggcc | 420 |
| cgcgacaacg ataagcggca ctcgcacgat caatgtacac attgcccgtc cgcgccacca | 480 |
| catccagcat cgtcgccagc ctcgccaccc ccgcgccgtc ctcctcctcc ggctccggct | 540 |
| ccggccgccc caggcccagg ctcatccgga acgcccccgt cttcgccgcc ccgccaccg | 600 |
| tcgtgtaaac gggacggcgg gcagctgagg agtcaaacga gagagatcga gagaaagaaa | 660 |
| gggagggcat ccaccagccg ccggcgataa gaggggagga gagagaggcc agagaagagg | 720 |
| aggagaagaa gaagaaatcg a | 741 |

<210> SEQ ID NO 80
<211> LENGTH: 1571
<212> TYPE: DNA
<213> ORGANISM: Flaveria bidentis
<220> FEATURE:
<221> NAME/KEY: promoter
<222> LOCATION: (1)..(1571)
<223> OTHER INFORMATION: GLDC_promoter

<400> SEQUENCE: 80

| | |
|---|---|
| aagctttact cctctcaact ttcaaatcat aacataaaag ttcgtaggtt tgtgttcttc | 60 |
| ccaaaaaaaa agtgattttt tttcatcggt taattcatga ttaacatttc gacattcat | 120 |
| ccactatttc acatcatgtt ttgatgggag attgaaatag cgataaggcg aatgtgaaag | 180 |
| tgtgaaacag gatgagccac accatcacca catcacaatt tacccaaata atatcccaaa | 240 |
| gattcatacg cattttgatc cactgaaacc ccatccaatt ctatccaatg cccaccacat | 300 |
| gttcgacgat ttgcctcagt gaatcaagac caacacatgc cactgctttc tgcttttag | 360 |
| tccctgataa caaacgattg gctttcattg ctcactgtag aaagtggaga cacccaacaa | 420 |
| ctatcatctc cacgtggttc cgtgccgcct ttttgccttt catactgctg gtgcgtcatt | 480 |
| tgtcgtcatc aaagcactca cccactatca ttgatctcga aatcttgaat ctttaggttt | 540 |
| ttatgctttg atacttgaac tctacacaca gtctcgtatc tgacttttg ttatctgtgt | 600 |
| tttgctttac taaagatctc acctttaatc aagttttgaa cttttgatgg atttgtcatg | 660 |
| ataatgaaga acacatagtt attattgatt atattttgac gaatcttttt tcatgatcgt | 720 |
| taaacataat ttgagttctt tttaccttgt cttctttga ggtttaactg tacatgaaga | 780 |
| ctgtattttg agtttattgc ataaatggtc tatatagttt gggttaaaac aactggtttt | 840 |
| aatatcaagt ttgatactag acaaaccaac ttttgatta acttttaaaa aaattaataa | 900 |
| gtctatttgg aaaaaattg aaaatttgat tttaagggt taaagttct ttttgaaaag | 960 |
| ttaataagag taacttttga aatgtaactt ttaaaaaat actgttgata aaaaagaaa | 1020 |
| tcctaatcat gggcttagta ttgtaagtag cttggatatt gaagctaatt tttcactta | 1080 |
| tatttataga aaagttaatg gaagtaagag gtttggatac tttttttctt aatttagacg | 1140 |
| aatgttacac atgaaaaata agcgttgttt tgtaagattt ttttaattcg caagcactaa | 1200 |
| actcctaatc aactttggg gttaaggagt aggcagtaaa ccaaaagcgt ttttgcacga | 1260 |
| tacgatgttc aaacatttga tctataacga taagtccaag tgcgttacaa aatgaaactt | 1320 |
| tggtatccaa tatgaaactg ggtgtgtagt tcagtaccaa aagcataact ttcagcctcc | 1380 |
| ttagtgactt atgactaggc aagagaacat gtgagcccaa tgtactaact ttttacccct | 1440 |
| tttattacca ccaccccagc cccccaccat gaaccgatca gaaaaagaag caagaaaaac | 1500 |

```
agagcattct tgctccttct tcttcatcaa ttcaataaca ttcttcatac cattagaccc   1560
catcttacac t                                                        1571
```

<210> SEQ ID NO 81
<211> LENGTH: 1497
<212> TYPE: DNA
<213> ORGANISM: Oryza sativa
<220> FEATURE:
<221> NAME/KEY: promoter
<222> LOCATION: (1)..(1497)
<223> OTHER INFORMATION: OsRbcS_promoter

<400> SEQUENCE: 81

```
gaaccatacg gaattgacgg accaattgtg catacggact tagctaaaat aattgttgat    60
ttttggcaat aagaaaagcg agtagcacat aaaatctaaa gtggatgagt aaagggacaa   120
aattttatac atgttcaggc cttctcgatg agaagtaata ctatactcct gttttgggga   180
ttatatttgt cagatgttgt atcaatctga cgatcgagtt atggttattg ttggcggctg   240
ttaaatatcg attttatgcc atcaatacct gtataattta tacagaaata ataaaacatt   300
caacatagtg gtaggcttta attctaacat attccataag tgttggtgta tatttggatg   360
caggtaataa accaccgaat taggaggaaa tctagactaa gttgaaggaa attttcatcc   420
atacaagtgt tgggcttttt aactccattt taacaccaaa atgcaagccc aaaaacctgc   480
gaaatggata aggcagactg agaaggaggc ccaggccaaa acttgggcca gttgggccaa   540
gccaggtttc ggccaaatcc tgatcatcgc tgttgatctc agggtttggc atggacgctc   600
ttgatttact cctgatggca gttgcagggc atttccgatc attcgcatgc tctacaacca   660
tcatacctac ttatttaagg agctctcatc ctcacttcat atcacacact ccaatcttga   720
gctgaattat aagaggctct attgtatttt attgtatact agaattaggg aaagattaag   780
gtcgtagaag aaatcggagg aattccggag ttatcggtga tccttttcta tttcttatac   840
tttgttattt gctttaatag aaatatcatt tcaagtaatt aagatttgtt tagtgagaac   900
tattattggc tagttcctaa ttagcgtatg agatcactgt tcactataat ccgttaaaat   960
atagtgattg ctttagtgag ttacaaacac tacagtagtt attgattgct taaacgtggt  1020
gtttagatag ttaatttcta gtggttgctg cgtatcccat agtacgttag aggcgggtgt  1080
agaggtggtg accgccctca agagcactta attcctcctt gtttgtgtac gtggtagagc  1140
gacatctggg aacagtgggt taccagtgcc tgaagtacca tgttaggatt aaaattgtaa  1200
cattgtttct cattagtaaa tcttctctac cctctaccca catttgcttt gtatccttgg  1260
tgaacctgaa gaggaactga acacacacgt tccatgagga agacactcag tactcaagcc  1320
ggaggcagca cactgcaact taagttttc tatagctcct agcaagctag caatggctcc  1380
ctcggtgatg gcttcgtcgg ccacctccgt ggctcccttc caggggctca agtccactgc  1440
gggcctcccg gtgaaccgcc gctccagcag ctcgagcttt ggcaacgtca gcatcga     1497
```

<210> SEQ ID NO 82
<211> LENGTH: 1429
<212> TYPE: DNA
<213> ORGANISM: Oryza sativa
<220> FEATURE:
<221> NAME/KEY: misc_feature
<222> LOCATION: (1)..(1429)
<223> OTHER INFORMATION: OsRbcS_3_UTR

<400> SEQUENCE: 82

```
gttcgcgctt tcgttccttc gtgcatgttc tttctttttc ttttttttt gtgtgtccgt    60 gttaagctgc acgtaattgt tctctcgcgc tccgacctgc cgttgttgca agagtactac   120
tacaactatc ggtctatcgt tcggtgacgg tgagacaggg cacgtgaatg caagatctcc   180
ggctatacac acgtactcat gtaatatgat gcctagagca tatctgaatc cgtcgacaat   240
gaaattttgg ttttgcaaaa tgctggtatt tgtttatcat cctggcacgt gatatttgcc   300
tagagcatct aaatcacttt tacgaaatgt gcgcgtcaac aaactgatac ggcccaaatg   360
ccagaaatta ccagcatata tagccatatc aacttttgat tcgtatatat gaaggttgat   420
ttagttagag aaattcggtt gtgagagaag gaggctagca agattcggt tgatcaagct    480 gtaccgccag gccaggacgt gctgtgcgcg cggctgtgcc gcttgaccgc agaaccatac   540
ggaattgacg gaccaattgt gcatacggac ttagctaaaa taattgttga tttttggcaa   600
taagaaaagc gagtagcaca taaaatctaa agtggatgag taaagggaca aaattttata   660
catgttcagg ccttctcgat gagaagtaat actatactcc tgttttgggg attatatttg   720
tcagatgttg tatcaatctg acgatcgagt tatggttatt gttggcggct gttaaatatc   780
gattttatgc catcaatacc tgtataattt atacagaaat aataaaacat tcaacatagt   840
ggtaggcttt aattctaaca tattccataa gtgttggtgt atatttggat gcaggtaata   900
aaccaccgaa ttaggaggaa atctagacta agttgaagga aattttcatc catacaagtg   960
ttgggctttt taactccatt ttaacaccaa aatgcaagcc caaaacctg cgaaatggat   1020 aaggcagact gagaaggagg cccaggccaa aacttgggcc agttgggcca agccaggttt   1080
cggccaaatc ctgatcatcg ctgttgatct cagggtttgg catggacgct cttgatttac   1140
tcctgatggc agttgcaggg catttccgat cattcgcatg ctctacaacc atcatacctg   1200
cttatttaag gagctctcat cctcacttca tatcacacac tccaatcttg agctgaatta   1260
taagaggctc tattgtattt tattgtatac tagaattagg gaaagattaa ggtcgtagaa   1320
gaaatcggag gaattccgga gttatcggtg atccttttct attcttata ctttgttatt   1380 tgctttaata gaaatatcat ttcaagtaat taagatttgt ttagtgaga                1429
```

<210> SEQ ID NO 83
<211> LENGTH: 1416
<212> TYPE: DNA
<213> ORGANISM: Oryza sativa
<220> FEATURE:
<221> NAME/KEY: promoter
<222> LOCATION: (1)..(1416)
<223> OTHER INFORMATION: OsCA_promoter

<400> SEQUENCE: 83

```
atcttggcta tttcccatgg cttctccgct ctactcttgt ccctgtttgg atgacgccgt    60
ccagaccaag acatcaaaac ggggcgacac tgtgaggtta cggtgtcgcc attcgccaca   120
atgtgctcac catgtcacct tgtcgacatt tcgccgcata caagtcgctg tgcgaccgcc   180
aggtgggccc cactgtgagc agcacgagtg tggcgcgtat ataaatttgt cggatggaga   240
ggcagctgaa ggttttttcgc catggcaact gcgtccttcg acatctgcgc gaaggttggg   300
ctcggaattt cgacaggata ctcacagcga aatcaatact ctgctatggc aaatggtacg   360
cactcgtttc gattgttctg ccttcttctg ttttatttt tttcccgtat gtagctgtag   420
ctgctgataa acgtgccatg tattccatct cgttcttgca agcagtttct tagatgagtt   480
aaaatatgta ttccatgtca actgttcact ttagttaggt agaactttct tacattatga   540
ttagttatct acttactctc tctgtccgat aataattatc gcattgattt tttttataat   600
```

```
gtttgatcat tcgtcttatt aaaaaaaatt atagaattat ttttttttatt ttgtttgtga      660 cttgctttat tatcaaaaaa ataatttaaa tatggcatat cttttttttat atttacaata      720 atttttcaaa aaagatgaat ggtcaaacgt tacacgaaaa aatcaaagcg accactattt      780
tggaatggaa gtagtacctg tagagaaaaa ttaaatatta gttcttaagt gagtgtggac      840
cgaaaaaatt ccttatttat cataaacacg ttttccaaac ttttaaatga tatgtttttt      900
taaatatata aatgaacatg ttcttttcaaa aatcaaataa atcacttttt caagtttgta      960
ctgattaata ctagactaat catttgctaa ttgtttatat tgttttactt gccatcataa     1020
ctcatgccaa attgcttttc caaacccacc attagccgct gtggcaagct cagttgctag     1080
cttgaggagg actatacaaa gttgcacaca cgccatggta ctaacgagaa ctggaaaata     1140
tgttgactgg aaaaattgta tcagttcata ttagaaacaa attactgtca gaatgaggaa     1200
aaactcagtc catgccacta aaggcatcag atgcgaattg gcgctccttt ctcctttcaa     1260
ggagtaggca taaacatagg ctctgcagta gtttcatctg agacagtcgg cacgcggggg     1320
cgcgggcgtc tatttgttgc gcgcgcgggc gcggcggcga gacgcgtgtg tagctactgc     1380
tataaggagc gcgccgtgca ccgcctctca catcga                               1416

<210> SEQ ID NO 84
<211> LENGTH: 315
<212> TYPE: DNA
<213> ORGANISM: Oryza sativa
<220> FEATURE:
<221> NAME/KEY: misc_feature
<222> LOCATION: (1)..(315)
<223> OTHER INFORMATION: OsCA_3_UTR

<400> SEQUENCE: 84
gttcatccga ccgtccgtcc gttcagttcg tcagtttacg ccaacgcttt tgcataagta       60
ctacctgagg atatcgtccc cgatcatcga tgtgaacgcg tggagtacta ctacgtacgt      120
accggatggt tcgatatatg tgaatgctgt attaagtaat aacaagaaat atatctcctc      180 tacttttttcc tgacgcggag ttgtactgcc tatgatgcat aatttgatcg cagtgtgatc      240
aaaagacatc agctataatg tcttaataat attattatga agagtttacc ttttttactac      300 cttttactct ggtaa                                                       315

<210> SEQ ID NO 85
<211> LENGTH: 1418
<212> TYPE: DNA
<213> ORGANISM: Oryza sativa
<220> FEATURE:
<221> NAME/KEY: promoter
<222> LOCATION: (1)..(1418)
<223> OTHER INFORMATION: OsCAB_promoter

<400> SEQUENCE: 85
atgtgatcaa ctgacaattc aagtttgtga tggtttctat tatttatgat gtttcttaag       60
ccagaatagg aaatagcact aaggaggttc gagttcagtt ttggcttcta acttagtacc      120
aatgttgggg gcatatctgg acttttctgt gggaggactc attggagata gggagattcc      180
atacaggata aaactccaaa agcattcttg aggcattcta gtatagtaca agtcaagtaa      240
ttttttcagt gtccaatgat aatttcagga acatttaag ccagttatgt ttgtcatttg      300
gtgaactcaa aatgtaatgt gcactttgat gttacctact tacctcacta atattttcaa      360
tggcttcctt gacagctttg cgctgctcta aacatcaaca aaagaagtgt cgacagggat      420
```

| | |
|---|---|
| ctcgatgttt accggaacat actctccaaa ttggtccagg ctaaggaact tctcaaggaa | 480 |
| tacgtggaaa ggtaaccaac ttatccgctg atttcccact tctcttactg cccaaaccct | 540 |
| gatttgttca atcactgata ttactaacgc acgagggatg ttcctaattt tattttgcaa | 600 |
| caattgtgtg atattaatag ctttatactt gaagtttact gtttagcaca taaatctctc | 660 |
| ctcttttcaat gagcccaggc aaatggatta gtttatattg ccttctcttt acattttgta | 720 |
| tcctccccag ttttctgtg ttaaactgat catctcaacg agttgaactc aactttgttg | 780 |
| gcagggaaaa gaagaagaga gaggaaagat cagagacccc aaaatcgaat gaagctgtta | 840 |
| cgaaatttga cgggagtctc aattccatga ggcattaact caagccttca taggggagt | 900 |
| gagtgctacc gtggataaca gattttaaca gagttctgga tcacgttgag aaactatcaa | 960 |
| ggtcaccttt cactgcacgg acactttggc tgctctcgtg tggttttgta ttctgccgta | 1020 |
| taaaaggatc cagattgttc ttactactga gcattatatt tttttgtaa ttctcctttt | 1080 |
| cagtgttcaa atgtatcgtt ttccttttct ttgacaatat atgaagaggt atgtggggat | 1140 |
| caatgttact cacaagatga aaaatatatt gttcagttat ctcttcatga tgaaaatgaa | 1200 |
| atcggtcaca agttctttct ttggatctgt atgtatcagg aatatcagtg gtggaaacga | 1260 |
| gcaggaagac ttttctgcat tggatcatat gccagaaaat cgcgaagggc agggcattgg | 1320 |
| taacctcctt accttggaca cctgcggatg acagaacccc ccctcaccac cacccacaca | 1380 |
| ttctcgaaga aggagaagaa ggagaggagc agcctcga | 1418 |

<210> SEQ ID NO 86
<211> LENGTH: 368
<212> TYPE: DNA
<213> ORGANISM: Oryza sativa
<220> FEATURE:
<221> NAME/KEY: misc_feature
<222> LOCATION: (1)..(368)
<223> OTHER INFORMATION: OsCAB_3_UTR

<400> SEQUENCE: 86

| | |
|---|---|
| gttctttaag ctctttcgcg cgcaattcaa acgggatcga tgcgttggtg tgcgttcgcg | 60 |
| cgcgctgttt agttttgtga tgacgagcga gctgggaggg tatggagaga ggagaggtca | 120 |
| tccttttgtt gattactact taaattagga aagctgggtt ggtggttaat ggcgacttgc | 180 |
| atggtggtga tttgtaatat aagaacaccc aagatgatga attaatgcat ccacttgtac | 240 |
| atcgatcgat cgatcttggt atttgactaa gtgagtgtga ctgtgaatgc acatatgcac | 300 |
| actgcataga ctttacctga catgtattga tattaataaa gttataacag gtgtctcgct | 360 |
| atcaataa | 368 |

<210> SEQ ID NO 87
<211> LENGTH: 2000
<212> TYPE: DNA
<213> ORGANISM: Setaria italica
<220> FEATURE:
<221> NAME/KEY: promoter
<222> LOCATION: (1)..(2000)
<223> OTHER INFORMATION: SiBASS_promoter

<400> SEQUENCE: 87

| | |
|---|---|
| ggaaagagaa tgcgaggctt caggaccgcc gtcagctcaa tttctcttcc agctgtgcca | 60 |
| atcaaacctc gtcaactccg gtgaacgtgg catctcgtc gccgtggtca aaccccccaa | 120 |
| tcagatcttc actcgtgctg tctactgacc acgcatcaca tcctattcca aaattttctt | 180 |
| cagactgaac aaagttaatc agggcgattg acaacaccat gcattcccaa cattagtgtg | 240 |

| | | | |
|---|---|---|---|
| acattacagt | gcgaataaag | aataggagca ctgtaaatga tgcatatcaa ggaagctgat | 300 |
| cagaagtgaa | aggtggaagt | tctgggacag attattggca gagaatgtcg cgcggtcttg | 360 |
| tggaggaact | cactccctgt | tttgcatcgc accgcaagag gcatagctct ggcgtggagg | 420 |
| actggtcggc | gccgatcatc | tccatctcaa ccttgaactc cagctcgcct cgtgcgcgct | 480 |
| tgtccgacgc | catccggtcg | cgcagtccgg gtgacagtgc cacgccgggg ggcgatacga | 540 |
| ggatcacata | ttcacatcca | cctcgcccgt ggccctcctg ggcacgcaca agcccgacgc | 600 |
| cacgccccag | ccgacgtcca | ggccagcgta gaggatccac acggcggcgg ccccgtgca | 660 |
| ggtctcgtcg | tcccggcggt | tgtccacccg gagtgttagg ttgaaggagg gggtggccgc | 720 |
| tgggttccgc | gcggcgccga | tcatcccctc ggccgccgtg accccgacgt agaattcggc | 780 |
| gcccttttcg | agctcggcgg | acatgaatat gagcatagta aaacggcgaa ggccagtccc | 840 |
| acgcagacga | tgaaagctaa | cgccggtcat gtcaggcagg ggggttcgcc tgatgactct | 900 |
| ggttcgacgc | cgctggcctc | aacgtcaacg ggtaccacgg gtgccatggc gagcaaccga | 960 |
| ggacgcagta | tctaggcaga | acaaaacgat ctaatattag atttctcgtg tagctaatgc | 1020 |
| aagcagatag | caaagtccgt | attcaattcg agtctgtgaa ccgagtcctc ggttacacaa | 1080 |
| aagcttctgc | gatccggatt | ttgtacaatc caaggtctcc ttccaagttc cgttcggagt | 1140 |
| tgcacagtca | cgtaaaatcc | ttgttctata cgctttgcac tttttgccgt cgatcctaat | 1200 |
| ctcgtgctca | ctttttttagc | catgtcctgc tggcgagtgc gtaacgctgc tgacgatctc | 1260 |
| gcgcagcctg | cggcggccgg | acggcgatct gctccacgca acaagataat ggcatgcctg | 1320 |
| tattgtgtgg | tcatcatcct | cggcgttctt ctttgcggtt tcgccgtctt caggttagcc | 1380 |
| gatgacgtag | cggggcacta | cgtcgtgaaa atcagcatcg aggcgtcgga attccgatcc | 1440 |
| atcatggcgg | acgacgggag | cacgatgtca tctccagtaa aggtaaagcc atcgttcaac | 1500 |
| gtcaccgcac | gcgtcgagaa | ccactaccac catcacatac gcttcaggac tggggcggcg | 1560 |
| ccgtgttgca | cgacggagta | ccgctcggcc gggccacttt ccccgacggc ctctgcgcgc | 1620 |
| tgagcatggg | agaaggcaaa | gtgacggcca ccacggcgag cgggttggtg gggctgaccg | 1680 |
| acgaggtgcg | ccgccgcatg | gcgaggcgcg ggcagacttg gggagaggta gatctgcgga | 1740 |
| tcgatatgag | acatcacgtc | ctgctagccg attcaagcgc ggacgagtgg ctccggtgca | 1800 |
| ccgcaaggtt | ggacgggcga | cctacttcag caccgtgcca attcgaaatc tcatcgcgat | 1860 |
| cttaggccac | ttgtttctct | ctctctttcg agacgattta ggccatttgt ttcaagtttg | 1920 |
| tccatatttg | ctcgtctaat | ccggcaatcc caataatatt cccatcgagc agccacagcc | 1980 |
| acagcgcaca | agcgacagag | | 2000 |

<210> SEQ ID NO 88
<211> LENGTH: 400
<212> TYPE: DNA
<213> ORGANISM: Setaria italica
<220> FEATURE:
<221> NAME/KEY: misc_feature
<222> LOCATION: (1)..(400)
<223> OTHER INFORMATION: SiBASS_3_UTR

<400> SEQUENCE: 88

| | | | |
|---|---|---|---|
| aatgctgttt | tttgttcgaa | ctgggccagc caggaaatta attgcctcag aatgagatta | 60 |
| ttcttttta | aaatggaaga | atattctttt ttattaatgc aagaaacgaa cagaatcatt | 120 |
| tgttcattgt | agaatgtaag | taacatgatg aatccagctg gggagttctt tttctgttga | 180 |

| | |
|---|---|
| tttaagtatg tttttttacg cctgcacctg gggggctgtg gcacgctcgg gtattgtata | 240 |
| actcctgcag tcctgctatg tactcctagg tgacaacatt gtactatgaa tagttaatgg | 300 |
| agaagttaca ataatgtagt agtaacgtca aaaccgtggg cagggaaaaa ctcgaacaaa | 360 |
| actggtacgt ctgcgtcgca ggctcgcagc atcagcgcag | 400 |

<210> SEQ ID NO 89
<211> LENGTH: 1656
<212> TYPE: DNA
<213> ORGANISM: Setaria italica
<220> FEATURE:
<221> NAME/KEY: misc_feature
<222> LOCATION: (1)..(1656)
<223> OTHER INFORMATION: DCT4

<400> SEQUENCE: 89

| | |
|---|---|
| atggaaattg gcctggtggt ggcccacagg ccgagcctgc cagtggccgc ggtcccagcc | 60 |
| ccggcgtatc tgcgcaggag gcacctccca ggcctgatct ccctgccgag gaccagccca | 120 |
| agcctcttca gcccacacca ccagcgcctg tccccgaccc cacgccatga cctcctccag | 180 |
| ccgctcaggg cgtccccagc cccggacagc agcccgaagc cggagccgcc agccgcctcc | 240 |
| ggcgccaagc tcgtgccact cgtgatctcc attgcgtgg gctggccgt gcgctttctg | 300 |
| gcgccacgcc cggcggaggt cagcccaaac gcgtggcaga tgctcagcat ttttctcagc | 360 |
| accatcgcgg gcctggtgct ggcccactc ccagtcggcg cggtcgcctt cctgggcctg | 420 |
| accacagtgg tggcgaccaa gaccctcccg ttcgcggcgg cctttgcggc gttcaccaac | 480 |
| gagatcatct ggctgatcgt gatctccttc tttttcgcca ggggctttgt gaagacaggg | 540 |
| ctcggggacc gcattgcgac ctatttcgtg aaatggctcg ggtccagcac cctcgggctg | 600 |
| tcctacgggc tgaccctcgg cgaggcgtgc atcgcgccag cgatgccgtc caccgccgcc | 660 |
| agggcgggcg ggattttcct gccgatcatt aaaagcctca gcatctccgc gggctccaag | 720 |
| ccgaaccacc catccagccg caagctcggc tcctatctcg tcatgaccca gtttcaagcc | 780 |
| gccagcagct cctccgcgct gttcctcaca gccggggccc agaacctcct ctgtctcaac | 840 |
| ctcgcggagg aactcggcgt gatcattgcg aatccatggg tgtcctggtt taaggccgcg | 900 |
| tccctcccag cgattgtcag cctcctcgcc accccatatc tcctctacaa aatttatccg | 960 |
| ccggagacca aggacacccc ggaagcgccg gcgctcgccg ccgagaagca aaaaggatg | 1020 |
| ggcccggtga caaaaaatga atgggtgatg gtggggacca tgatcttcgc cgtcagcctc | 1080 |
| tggattctgg gggacgccat tgggtccca tccgtggtcg ccgcgatgct cggcctcagc | 1140 |
| attctcctgc tcctcggcgt gctcgactgg ggggacattc tgaatgaaaa atccgcgtgg | 1200 |
| gatacattgg cgtggtttag cgtgctcgtc ggcatggccg cccaactcac aaacctcggc | 1260 |
| atcgtcagct ggatgtccaa ctgcattgcg aagctcctcc aaagcttttc cctctcctgg | 1320 |
| ccagccgcct tctgtgtgct gcaagcgagc tactttctca ttcactacct ctttgcctcc | 1380 |
| caaaccggcc atatcggcgc gctctactcc gcctttctgg ccatgcatgt cgcggcgggg | 1440 |
| gtgccaaggg tcctgtccgc gctggccctc gccttcaata ccgacctctt tgggggcatc | 1500 |
| acacactact cctccgggca agccgccgtc tattttgggg cgggctatct cgacctccca | 1560 |
| gatgtgttca ggattgggtt tgtcatcacc atgattaatg cgtgcatctg gggggtgatt | 1620 |
| gggaccatct ggtggaagtt tctggggctc tactga | 1656 |

<210> SEQ ID NO 90
<211> LENGTH: 1542

```
<212> TYPE: DNA
<213> ORGANISM: Zea mays
<220> FEATURE:
<221> NAME/KEY: misc_feature
<222> LOCATION: (1)..(1542)
<223> OTHER INFORMATION: DCT2

<400> SEQUENCE: 90
atggaatccc tccgcctcgc cgtgacacat aggccggccc tcccactgcc aacctcccat      60
agccatctga ggcgcaggca tctgcacctg cacctccatt cctacccaaa tccactgtcc     120
ctcagcccac caatcgcgtc ccacctgagc ccgatcccac gcaggcatct gccaccactg     180
ctggcctccg cctccgcctc ccaagcgagc tccaaaccgg ccgcctccgc ggcgagcggc     240
ggggccaaac cgctgccact ctttctctcc ctcgcggccg ggctcgccgt gcgctttctc     300
gtgccacgcc cggccgaagt caccccagaa gcgtggcaac tgctcagcat tttctctcc     360
acaattgcgg gcctcgtgct ggggccgctg ccagtggggg cgtgggcctt tctcggcctg     420
accgcgacag tggcgacacg caccctcccg tttaccgcgg cgttcgggc cttcaccaat     480
gaggtgatct ggctgatcgt gattagcttc tttttgcga ggggcttcgt gaaaacaggg      540
ctgggcgacc gcgtggcgac atacttcgtc aagtggctgg ggaggtccac actgggcctc     600
agctatgggc tggccattag cgaagccctg attagcccag ccatgccgag caccacagcg     660
cgcgccggcg gcgtgttcct cccgatcgtg aaaagcctca gcctcagcag cgggtccaaa     720
ccaaacgatc cgagcgcgaa aaactcggc agctacctcg tccaaagcca gctccaagcc     780
gccgcgaatt ccagcgcgct cttcctgaca gccgccgccc aaaatctcct ctgcctcaag     840
ctggcggaag aaattgggga cacccagaa gcgccggcgc tcgcggcgga gaaactcaaa     900
aacatgggc cagtgacaaa aaacgaatgg gtcatgattg gcaccatgct gctcgccgtg     960
tccctgtgga ttttggcga aacaattggg gtcagctccg tcgtcgcggc catgattggc    1020
ctgtccatcc tgctggtgct cggggtcctg aattgggaag attgtctcaa tgagaaaagc    1080
gcgtgggata cactcgcgtg gttttgcgatc ctggtcggcc tcgcgggcca gctgacaaat    1140
ctcgggatcg tcagctggat gtccaattgc gtcgcgaagg tcctccaaag cttcagcctc    1200
agctggccag cggccttcgt cgtgctccaa gcgtcctatt ttttcattca ttatatcttc    1260
gcgtcccaaa ccgcccatgt cggggccctg tattccgcct ttctggccat gcacctcgcc    1320
gcggggtcc cggccctgat gtccgcgctc gcgctggcct acaacgccaa cctgttcggg    1380
gcgctcacac attatagctc cgggcaaagc gcggtctact tgggggcggg ctatgtcgat    1440
ctgccagatg tgttcaagct cggcttcatt acagccgcaa tcaatgcggt gatttggggc    1500
gtcgccggcg ccctgtggtg gaaatttctg ggctgtact ga                       1542

<210> SEQ ID NO 91
<211> LENGTH: 1713
<212> TYPE: DNA
<213> ORGANISM: Setaria italica
<220> FEATURE:
<221> NAME/KEY: misc_feature
<222> LOCATION: (1)..(1713)
<223> OTHER INFORMATION: NHD

<400> SEQUENCE: 91
atggcgctgt cctgcgggct gctggcgggg gccagggcgg cggccttccc gagcctcccg      60
tccagcgcgg cgctcctccg caggaggagg tgtccgccgg cggtcgcggt gggcccgctc     120
ccacatgccg aaaggtggag gagggggctc aggttttgtt gcgccagctc cagctcctcc     180
```

| | |
|---|---|
| agcccaccac tcccaccagc cccgccagaa gaaccagagg actacgagct gctcgatacc | 240 |
| acagggaatt gcgacccact ctgcagcgtc gacgaggtga gctcccagta cctgggcgaa | 300 |
| aattacaaac caaaaaatga cctgctcaaa gccttcacca tttttcgccac agcgctcgcg | 360 |
| ggcgcggcgg caataaacca ttcctgggtc gcggccaatc aagacgcggc catggtgctg | 420 |
| gtcttcgcga tcgggtatgc cgggatcatc ttcgaagagt ccctcgcctt taataaaagc | 480 |
| ggggtcgcgc tgctcatggc cgcgtgtctg tgggtgatcc gaagcatcgg ggcgccgtcc | 540 |
| atcgacattg cggtggaaga actgaaccac accaccaccg aagtgagcga aatcgtcttc | 600 |
| ttcctgctgg gggccatgac cattgtcgaa attgtcgatg cccatcaagg ctttaagctg | 660 |
| gtgacagaca atattagcac aaggtcccca aaaaccctcg tctgggtgat cggcattgtg | 720 |
| acctttttg tcagcgcgat tctggacaat ctcacaagca ccatcgtgat ggtgtccctg | 780 |
| ctcaggaaac tcgtcccgcc gtccgaatac aggaaactgc tcggggccgt cgtcgtgatc | 840 |
| gcggcgaacg cgggcggcgc gtggaccccg attggggatg tgaccaccac catgctgtgg | 900 |
| atccacgggc agctgacaac actcaaaata atgcaaggcc tgttcatccc gtccgtggtg | 960 |
| agcctggccg tcccgctggc gctgatgtcc ctcacatccg aagcgaacgg gtcctcccaa | 1020 |
| aaaagctcca gcctctcctc cgagcaaatg gccccacgcg ccagctcgt cctcgccgtg | 1080 |
| ggggtgggg cgctcgtgtt cgtcccagtg tttaagtccc tgacaggcct cccaccgttc | 1140 |
| atgggcatgc tcctcgggct ggggatcctc tggatcctca ccgatgcaat acattatggg | 1200 |
| gattccgaac gccagcgcct gaaggtcccg caggcgctca gccgcatcga ttcccagggc | 1260 |
| atcctgttt tcctggggat cctcctgtcc gtcgggagcc tggagagcgc ggggatcctc | 1320 |
| aggcaactcg ccaactacct cgacgcgaat attccgaacg cggacctcat cgccagcgcc | 1380 |
| atcggggtgg ccagcgcgct catcgataac gtcccactgg tggccgcgac catgggcatg | 1440 |
| tacgatctga cagcgtatcc acaggacagc gacttttggc agctcattgc cttttgcgcc | 1500 |
| ggcacaggcg gtccatgct gattattggc agcgccgcgg gcgtcgcgtt catgggcatg | 1560 |
| gaaaaagtcg actttttctg gtatattagg aaagtgagcg gcttcgccct cgcggggtac | 1620 |
| gcggccggca ttatttccta cctcgtcggc caaaacctca ttttttccct cccgacatcc | 1680 |
| ctggccgaga ttccattcat tccagggtcc tga | 1713 |

<210> SEQ ID NO 92
<211> LENGTH: 1188
<212> TYPE: DNA
<213> ORGANISM: Zea mays
<220> FEATURE:
<221> NAME/KEY: misc_feature
<222> LOCATION: (1)..(1188)
<223> OTHER INFORMATION: PPT1

<400> SEQUENCE: 92

| | |
|---|---|
| atgcagagcg ccgcggcttt ccggccatgc cccactcggc tgctggtgag cagcccttgt | 60 |
| cgccccctcc tctcggcccg cccgcttcgt gcctccgccg ctggcgccgt cgctaccaga | 120 |
| agcagcgccg tgggccctcg cggtctgggg ctcgggctgc tgccagcctc gcccgatcgg | 180 |
| gatggcaagt gccgccagcg acaggtgtca tgcagcgcgg ccggggatgc tgtggcggcc | 240 |
| ccgaaggcgg aagaaggagg cgggctcatg aagacgctgt ggctcggctc gctcttcggc | 300 |
| ctctggtacc tgttcaacat ctacttcaac atctataaca agcaggtact caaggttttc | 360 |
| ccataccccta taaacatcac agaagttcaa tttgctgtcg gaactgtagc agctctgttc | 420 |
| atgtggatca ctggtattat taagaggcca agatttctg gagcacagct tgtagccatc | 480 |

```
ctacctctgg ctattgttca tactatgggc aatctcttca ccaacatgag ccttgggaaa      540
gttgcagtgt catttacgca caccatcaag gctatggagc ctttcttttc tgttattctt      600
tctgcaattt tccttggcga gctacctact atttgggtag tatcttctct tcttccaatt      660
gttggtggtg ttgcattggc atctcttact gaggcatcct ttaactgggc tggcttttgg      720
agtgcaatgg cttcaaatgt tacctttcaa tcccgaaatg tattgagcaa gaagctcatg      780
gttaagaaag aggaatcctt ggacaacctt aatctcttct ctatcattac agtgatgtca      840
ttttttcctt tggcccctgt taccttcttt acagaaggtg tcaaaattac tcctacattt      900
ttgcaatctg ctggtctgaa tgtaaaccaa gtccttacaa ggtgtctttt cgctggactg      960
tgtttccatg cataccaaca ggtgtcttac atgattttgg cgatggtgtc tcctgtcact     1020
cattctgtgg gcaactgtgt taaacgtgtt gtggtcattg taacatcagt gctgttcttc     1080
aggacacctg tttctcctat caactctctc ggtactgcga ttgcacttgc cggagttttc     1140
ctgtactcac agctcaagcg acttaagccc aagccgaaga cggcttaa                  1188
```

<210> SEQ ID NO 93
<211> LENGTH: 1266
<212> TYPE: DNA
<213> ORGANISM: Setaria italica
<220> FEATURE:
<221> NAME/KEY: misc_feature
<222> LOCATION: (1)..(1266)
<223> OTHER INFORMATION: BASS

<400> SEQUENCE: 93

```
atggcgccgt ccgcgaccag ctccatggcg tccgtcagcc gcgccctcag gccaaggcca       60
cgcgccgcgg cgtgctccgc cccacgcctc gggtgcggcc tggggattgc ctgcagcatg      120
ccatccctgg ggctggcggt ggtgaccgcc ccgagcgcca ccgtcacacc agcgctccgc      180
aggcgccaaa tcctgtgcca ggcggaggcg aatatctcca ataatctgcc agagaaactg      240
ccggccaaag tgagccaacc agcgaaggtc tcccagccag ccgaagtctc ccagccagcg      300
gaagtgagcc aatacgagaa gattgtcgaa ctgctgacaa cactgttccc ggtctgggtc      360
attatcggga cagtcattgg gatttataag ccagcgatgg tcacatggct ggataccgat      420
ctgttcacaa tcgggctggg gctcctgatg ctcagcatgg gcctcacact cacattcgag      480
gacttcaggc gctgtctccg caacccatgg accgtgggga ttggcttcct ggcgcagtat      540
tgtgtgaagc cactgctggg gctggccatc gcgaccaccc tgaaactgcc agccccactg      600
gcgaccggcc tcattctggt ctcctgctgt ccaggcgggc aagcatccaa cgtggcgacc      660
tacatctcca aaggcaatgt cgcgctcagc gtcctcatga acatgtag cacaatcggc        720 gccataataa tgaccccgct cctgaccaag ctgctggccg ccagctcgt gccggtcgac       780 gcggcgggcc tggcgatcag cacattccaa gtggtcctgc tgccgacagt gctggggtg      840 ctcgcgcacg agtatttccc gaagttcacc gagcgcatca tcacagtggc cccactcttt      900
ggcgtgctcc tcacaacccct cctctgcgcc tccccgatcg gccaggtcgc ggaggtcctc      960
aaaacccaag gggcccagct gatcattcca gtcgccctgc tccatgtggc ggcctttgcg     1020
ctggggtatt ggctcagccg ctttagcagc tttggggaat caacatcccg cacaattagc     1080
attgaatgcg gcatgcaatc ctccgcgctc gggtttctcc tggcccagaa gcattttacc     1140
aacccgctgg tcgcggtgcc aagcgcggtc tccgtggtcg ccatggcgct gggcggcagc     1200
gcgctggcgg tcttttggag aagcattggg ctcccggcga atgacaaaga tgactttaag     1260
``` gagtga                                                                 1266

<210> SEQ ID NO 94
<211> LENGTH: 1215
<212> TYPE: DNA
<213> ORGANISM: Zea mays
<220> FEATURE:
<221> NAME/KEY: misc_feature
<222> LOCATION: (1)..(1215)
<223> OTHER INFORMATION: TPT

<400> SEQUENCE: 94
atgtcggcgc tcgggacgct ctccggcggg gccgccggtg tctccggcct catccgcctc      60
cgccgtcggg tggcccccgc gctcgcggcg ccgtcgcacc acgccgctgg gacgttgaac     120
tgcgccgcct tgcccgatgc cgccccgctc gtctggggac gccagctccg cccgtcgctc     180
ctcctccccg ccacactgct cccgtcgtcg tcgcagggcg ccaggaggca cacgccacgg     240
cggcccgccg cagccgcagg ggaggccaag tctgtgggtt tcctggagaa gtacccggcc     300
ctggtcactg gcttcttctt cttcatgtgg tacttcctca acgtcatatt caacatcctc     360
aacaagaaga tctacaacta cttcccctat ccatactttg tgtccttgat ccatctagta     420
gtgggtgtcg tatactgcct catcagctgg agtgtcggtc tccccaagcg agcgcctatc     480
aatggcacgc tcctgaagct tctctttcca gtcgccctgt gccatggtat tggtcacatc     540
actagcaatg tgtccttcgc tgctgttgca gtctcatttg cccacactat caaagctctg     600
gagcccttct tcagcgcagc tgctactcag tttatccttg gacagcaagt tcccttctct     660
ctgtggcttt ctcttgcccc tgttgtcatc ggtgtttcaa tggcatccct tactgagctc     720
tcattcaact ggactggctt catcaatgcc atgatatcaa acatctcatt cacctacagg     780
agcatttatt ccaagaaagc catgactgac atggatagca ccaacgtgta tgcttacatt     840
tcaataattg ctctcattgt ttgcattccg cctgcagtga tctttgaagg gccccggcta     900
atgcagcatg gattcagtga tgccattgca aaagtaggct tgacaaagtt tgttagtgac     960
ctattcttgg ttggactgtt ctaccatctg tacaaccaga ttgctacgaa caccttggag    1020
cgagtggctc ctctgacaca tgctgtgggc aatgtgttga agcgtgtgtt tgtcattggc    1080
ttctcaatcg ttgttttttgg caacaaaatt agcacacaaa ctggaattgg cacgtccatt    1140
gccatagctg tgtgttgctat gtactcttac attaaggcta agattgaaga ggagaaaagg    1200
aaaaagagcg catga                                                     1215

<210> SEQ ID NO 95
<211> LENGTH: 1176
<212> TYPE: DNA
<213> ORGANISM: Brachypodium distachyon
<220> FEATURE:
<221> NAME/KEY: misc_feature
<222> LOCATION: (1)..(1176)
<223> OTHER INFORMATION: SBPase

<400> SEQUENCE: 95
atggagaccg tggccgcctc cggctacgcc aggggcgccg ccaccaggtc cccggcctgc      60
tgcgccgcca tgtccttctc ccagtcctac aggccgaagg ccgccaggcc gccgaccacc     120
ttctacggcg agtccgtgag ggccaacacc gccaggaccc tcccgggcag gcagtccaag     180
gccgcctcca gggccgccct caccaccagg tgcgccatcg gcgactccct cgaggagttc     240
ctcaccaagg ccacccccga caagaaccte atcaggctcc tcatctgcat gggcgaggcc     300
atgaggacca tcgccttcaa ggtgaggacc gcctcctgcg gcggcaccgc ctgcgtgaac     360

```
tccttcggcg acgagcagct cgccgtggac atgctcgccg acaagctcct cttcgaggcc    420
ctcgagtact cccacgtgtg caagtacgcc tgctccgagg aggtgccgga gctccaggac    480
atgggcggcc cggtggacgg cggcttctcc gtggccttcg acccgctcga cggctcctcc    540
atcgtggaca ccaacttcac cgtgggcacc atcttcggcg tgtggccggg cgacaagctc    600
accggcgtga ccggcggcga ccaggtggcc gccgccatgg gcatctacgg cccgaggacc    660
accttcgtgg tggccctcaa ggactgcccg ggcacccacg agttcctcct cctcgacgag    720
ggcaagtggc agcacgtgaa ggacaccacc accatcggcg agggcaagat gttctccccg    780
ggcaacctca gggccacctt cgacaacccg gactacgaca gctcgtgaa ctactacgtg     840 aaggagaagt acaccctcag gtacaccggc ggcatggtgc cggacgtgaa ccagatcatc    900
gtgaaggaga agggcatctt caccaacgtg acctccccga ccgccaaggc caagctcagg    960
ctcctcttcg aggtggcccc gctcggcttc ctcatcgaga aggccggcgg ccactcctcc   1020
gacggcaagc agtccgtgct cgacaaggtg atcaccgtgc tcgacgagag gacccaggtg   1080
gcctacggct ccaagaacga gatcatcagg ttcgaggaga ccctctacgg ctcctccagg   1140
ctcgccgccg cgccaccgt gggcgccacc gtgtga                             1176
```

<210> SEQ ID NO 96  
<211> LENGTH: 391  
<212> TYPE: PRT  
<213> ORGANISM: Brachypodium distachyon  
<220> FEATURE:  
<221> NAME/KEY: MISC_FEATURE  
<222> LOCATION: (1)..(391)  
<223> OTHER INFORMATION: SBPase

<400> SEQUENCE: 96

```
Met Glu Thr Val Ala Ala Ser Gly Tyr Ala Arg Gly Ala Ala Thr Arg
1               5                   10                  15

Ser Pro Ala Cys Cys Ala Ala Met Ser Phe Ser Gln Ser Tyr Arg Pro
            20                  25                  30

Lys Ala Ala Arg Pro Pro Thr Thr Phe Tyr Gly Glu Ser Val Arg Ala
        35                  40                  45

Asn Thr Ala Arg Thr Leu Pro Gly Arg Gln Ser Lys Ala Ala Ser Arg
    50                  55                  60

Ala Ala Leu Thr Thr Arg Cys Ala Ile Gly Asp Ser Leu Glu Glu Phe
65                  70                  75                  80

Leu Thr Lys Ala Thr Pro Asp Lys Asn Leu Ile Arg Leu Leu Ile Cys
                85                  90                  95

Met Gly Glu Ala Met Arg Thr Ile Ala Phe Lys Val Arg Thr Ala Ser
            100                 105                 110

Cys Gly Gly Thr Ala Cys Val Asn Ser Phe Gly Asp Glu Gln Leu Ala
        115                 120                 125

Val Asp Met Leu Ala Asp Lys Leu Leu Phe Glu Ala Leu Glu Tyr Ser
    130                 135                 140

His Val Cys Lys Tyr Ala Cys Ser Glu Glu Val Pro Glu Leu Gln Asp
145                 150                 155                 160

Met Gly Gly Pro Val Asp Gly Phe Ser Val Ala Phe Asp Pro Leu
                165                 170                 175

Asp Gly Ser Ser Ile Val Asp Thr Asn Phe Thr Val Gly Thr Ile Phe
            180                 185                 190

Gly Val Trp Pro Gly Asp Lys Leu Thr Gly Val Thr Gly Gly Asp Gln
        195                 200                 205
```

-continued

```
Val Ala Ala Ala Met Gly Ile Tyr Gly Pro Arg Thr Thr Phe Val Val
        210                 215                 220

Ala Leu Lys Asp Cys Pro Gly Thr His Glu Phe Leu Leu Leu Asp Glu
225             230                 235                 240

Gly Lys Trp Gln His Val Lys Asp Thr Thr Thr Ile Gly Glu Gly Lys
                245                 250                 255

Met Phe Ser Pro Gly Asn Leu Arg Ala Thr Phe Asp Asn Pro Asp Tyr
            260                 265                 270

Asp Lys Leu Val Asn Tyr Tyr Val Lys Glu Lys Tyr Thr Leu Arg Tyr
        275                 280                 285

Thr Gly Gly Met Val Pro Asp Val Asn Gln Ile Ile Val Lys Glu Lys
        290                 295                 300

Gly Ile Phe Thr Asn Val Thr Ser Pro Thr Ala Lys Ala Lys Leu Arg
305             310                 315                 320

Leu Leu Phe Glu Val Ala Pro Leu Gly Phe Leu Ile Glu Lys Ala Gly
                325                 330                 335

Gly His Ser Ser Asp Gly Lys Gln Ser Val Leu Asp Lys Val Ile Thr
                340                 345                 350

Val Leu Asp Glu Arg Thr Gln Val Ala Tyr Gly Ser Lys Asn Glu Ile
            355                 360                 365

Ile Arg Phe Glu Glu Thr Leu Tyr Gly Ser Ser Arg Leu Ala Ala Gly
        370                 375                 380

Ala Thr Val Gly Ala Thr Val
385             390
```

EXPRESSION OF DICARBOXYLATE TRANSPORTER FROM SETARIA ITALICA IN TRANSGENIC PLANTS TO INCREASE YIELD

CROSS-REFERENCE TO RELATED APPLICATIONS

This application is a continuation of U.S. application Ser. No. 15/769,870, filed Apr. 20, 2018, which is a national stage filing under 35 U.S.C. 371 of PCT/US2016/058091, filed Oct. 21, 2016, which International Application was published by the International Bureau in English on Apr. 27, 2017, and claims priority from U.S. Provisional Application 62/245,348, filed Oct. 23, 2015, which applications are hereby incorporated by reference in their entirety in this application.

FIELD OF THE INVENTION

The invention is drawn to compositions and methods for increasing plant growth and yield through expression of one or more metabolite transporter genes in a plant of interest. Additionally, the invention is drawn to methods for identifying genes under positive selection in C4 plants.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on many factors, for example, the number and size of the organs, plant architecture (for example, the number of branches), seed production, leaf senescence, photosynthetic carbon assimilation and more. Root development, nutrient uptake, stress tolerance and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn, forage sorghum, and hay as well as for biomass crops like switchgrass, Miscanthus, biomass sorghum, and energycane.

As described above, crop yield is a trait that is controlled by many factors. One contributing factor is the rate of photosynthetic carbon assimilation by the plant. By increasing the rate of carbon assimilation, plant growth and ultimately plant yield may be increased. Therefore, methods for increasing photosynthetic carbon assimilation are desired. One aspect of photosynthetic regulation that is of interest is the intercellular and intracellular transport of photosynthetic metabolites, particularly of the metabolites produced in the C4 photosynthetic pathway.

SUMMARY OF THE INVENTION

Compositions and methods for increasing plant growth for higher crop yield are provided. The methods involve the expression in a plant of interest of at least one C4 transporter coding sequence. Plants showing increased expression of one or more C4 transporter coding sequence of interest are encompassed by the invention. It is recognized that any method for increasing the expression of the C4 transporter coding sequences in a plant of interest can be used in the practice of the methods disclosed herein. Such methods include transformation, breeding and the like. Increased expression of the C4 transporter coding sequences in the plant of interest results in yield gains. Expression cassettes and vectors comprising the C4 transporter sequences disclosed herein are also provided herein. Methods for identifying genes under positive in C4 plants are also provided herein.

Embodiments of the invention include:
1. A method of expressing a nucleic acid sequence encoding a C4 transporter protein comprising:
   introducing into a plant cell a DNA construct comprising a promoter sequence operably linked to a first nucleic acid sequence encoding a first C4 transporter protein, said first C4 transporter protein having an amino acid sequence with at least 80% identity to an amino acid sequence selected from the group consisting of SEQ ID NOs: 1-68, and
   regenerating a plant comprising the DNA construct.
2. The method of embodiment 1 wherein said first C4 transporter protein has an amino acid sequence selected from the group consisting of SEQ ID NOs: 1-68.
3. The method of embodiment 1 further comprising introducing into a plant cell a DNA construct comprising a promoter sequence operably linked to a second nucleic acid sequence encoding a second C4 transporter protein.
4. The method of embodiment 3, wherein said first C4 transporter protein has an amino acid sequence with at least 80% identity to an amino acid sequence selected from the group consisting of SEQ ID NO: 1, 22, 33, 43, 53, and 63.
5. The method of any one of embodiments 3 or 4, wherein said second C4 transporter protein has an amino acid sequence with at least 80% identity to an amino acid sequence selected from the group consisting of SEQ ID NO: 2, 34, 44, 54, and 64.
6. The method of any one of embodiments 1-5 where the transformed plant is a monocotyledonous plant.
7. The method of any one of embodiments 1-5 where the transformed plant is a dicotyledonous plant.
8. The method of any one of embodiments 1-7, wherein said plant is a C4 photosynthetic plant.
9. An expression cassette for the expression of at least one C4 transporter protein comprising in operable linkage:
    a. a promoter that functions in a plant cell, and
    b. a nucleic acid sequence encoding a C4 transporter protein having an amino acid sequence with at least 80% identity to an amino acid sequence selected from the group consisting of SEQ ID NOs: 1-68.
10. The expression cassette of embodiment 9, wherein said C4 transporter protein is selected from the group consisting of SEQ ID NOs: 1-68.
11. A vector comprising the expression cassette of embodiment 9 or 10.
12. A transformed plant comprising the expression cassette of embodiment 9 or 10.
13. The plant of embodiment 12, wherein said expression cassette is stably incorporated into the plant genome.
14. The transformed plant of embodiment 12 or 13, wherein said plant has higher yield than a control plant not transformed with said expression cassette.
15. The transformed plant of any one of embodiments 12-14, wherein said plant comprises an expression cassette comprising a nucleic acid sequence encoding a C4 transporter protein having an amino acid sequence with at least 80% identity to an amino acid sequence selected from the group consisting of SEQ ID NO: 1, 22, 33, 43, 53, and 63, and an expression cassette comprising a nucleic acid sequence encoding a C4 transporter protein having an amino acid sequence with at least 80% identity to an amino acid sequence selected from the group consisting of SEQ ID NO: 2, 34, 44, 54, and 64.
16. Transformed seed of any one of the plants of embodiments 11-15.
17. A method of modulating the growth of a plant comprising inserting into the nuclear genome of a plant cell a transcriptional enhancer sequence to alter the expression of a plant gene encoding a C4 transporter polypeptide wherein said C4 transporter polypeptide is selected from the group of SEQ ID NOs: 1-68.
18. A method of modulating the growth of a plant comprising modulating the expression of a plant gene encoding a C4 transporter polypeptide by modulating the expression of a transcription factor or transcription factors known to interact with said gene encoding a C4 transporter polypeptide wherein said C4 transporter polypeptide is selected from the group of SEQ ID NOs: 1-68.
19. A method of modulating the growth of a plant comprising modulating the expression of a plant gene encoding C4 transporter polypeptide wherein said C4 transporter polypeptide is selected from the group of SEQ ID NOs: 1-68 and wherein said expression is modulated by inserting a transposable element DNA sequence at a location in the plant genomic DNA within 2 kb of said gene encoding a C4 transporter polypeptide.
20. A method of modulating the growth of a plant comprising modulating the chromatin content or structure of a particular region of a plant's genome within 2 kb of a plant gene encoding a C4 transporter polypeptide wherein said C4 transporter polypeptide is selected from the group of SEQ ID NOs: 1-68.
21. A method of modulating the growth of a plant comprising altering the DNA methylation status within 2 kb of a particular region of a plant's genome such that the expression of a plant gene encoding a C4 transporter polypeptide is altered, wherein said C4 transporter polypeptide is selected from the group of SEQ ID NOs: 1-68.
22. A method for identifying genes under positive selection in C4 plants comprising
    a. identifying syntenic orthologs through comparisons of the genomes, exomes, or transcriptomes of C3 and C4 plant species that evolved from a common ancestor,
    b. calculating the rate of synonymous mutation ($d_S$) for each gene by dividing the number of synonymous mutations in a given coding sequence as compared with the coding sequence of the ancestral gene by the total number of codons in the coding sequence of the evolved gene,
    c. calculating the rate of non-synonymous mutation ($d_N$) for each gene by dividing the number of non-synonymous mutations in a given coding sequence as compared with the coding sequence of the ancestral gene by the total number of codons in the coding sequence of the evolved gene,
    d. calculating the ratio of adaptive evolution, ω, from the ratio $d_N/d_S$ for each gene,
    e. comparing the ratios of adaptive evolution for each pair of syntenic orthologs in the C3 and C4 plant genomes identified in part a, and
    f. identifying genes under positive selection by finding examples where ω is greater for the gene in the C4 plant than for the corresponding syntenic ortholog in the C3 plant.
23. The method of embodiment 1 wherein said nucleic acid sequence encoding a C4 transporter protein has at least 70% identity to a sequence selected from the group of SEQ ID NOs:89-94.
24. The method of embodiment 1 wherein said nucleic acid sequence encoding a C4 transporter protein comprises a sequence selected from the group of SEQ ID NOs:89-94.
25. The expression cassette of embodiment 9 wherein said nucleic acid sequence encoding a C4 transporter protein has at least 70% identity to a sequence selected from the group of SEQ ID NOs:89-94.
26. The expression cassette of embodiment 9 wherein said nucleic acid sequence encoding a C4 transporter comprises a sequence selected from the group of SEQ ID NOs:89-94.
27. The method of embodiment 1 further comprising introducing into a plant cell a DNA construct comprising a promoter sequence operably linked to a second nucleic acid sequence encoding a photosynthetic protein.
28. The method of embodiment 27 wherein said nucleic acid sequence encoding a photosynthetic protein has at least 70% identity to SEQ ID NO:95.
29. The method of embodiment 27 wherein said nucleic acid sequence encoding a photosynthetic protein comprises SEQ ID NO:95.
30. The method of embodiment 27 wherein said photosynthetic protein has at least 80% identity to SEQ ID NO:96.
31. The method of embodiment 27 wherein said photosynthetic protein comprises SEQ ID NO:96.
32. The method of embodiment 1 wherein said promoter sequence comprises a sequence selected from the group of SEQ ID NOs:69, 71, 73, 75, 77, 79-81, 83, 85, and 87.

33. The expression cassette of embodiment 9 wherein said promoter that functions in a plant cell comprises a sequence selected from the group of SEQ ID NOs:69, 71, 73, 75, 77, 79-81, 83, 85, and 87.

DETAILED DESCRIPTION OF THE INVENTION

Compositions and methods for increasing plant yield are provided. The methods disclosed herein involve the production of a plant that expresses one or more coding sequences encoding a C4 transporter protein of interest. As used herein, the term "C4 transporter" or "C4 photosynthesis transporter" or "C4 transporter protein" refers to any protein that transports or contributes to the transport of molecules during the C4 photosynthesis process. For example, C4 transporters can transport molecules between mesophyll and bundle sheath cells. Molecules transported by C4 transporters include but are not limited to malate, pyruvate, aspartate, alanine, 3-phosphate glycerate, triose-phosphate, phosphoenolpyruvate (PEP), and oxaloacetate. Examples of C4 transporters include but are not limited to, OMT (mitochondrial oxaloacetate/malate transporter), DCT1 (dicarboxylic acid transporter 1), DCT4 (dicarboxylic acid transporter 4), DCT2 (dicarboxylic acid transporter 2), MEP3a (protein/pyruvate symporter 3a), MEP3b (protein/pyruvate symporter 3b), MEP3c (protein/pyruvate symporter 3c), NHD (sodium proton antiporter), BASS2 (pyruvate transporter 2), PPT1 (phosphoenolpyruvate phosphate translocator), and TPT (triose-phosphate phosphate translocator).

While not bound by any theory, it is believed that expression of these C4 transporter coding sequences will improve transport of key photosynthetic metabolites across membranes of cells and organelles. Improving metabolite transport is predicted to relieve feedback inhibition of photosynthetic processes to improve photosynthetic metabolism. Therefore, expression of the transporter coding sequences is expected to increase carbon assimilation for plant growth and to ultimately result in improved yield.

Methods of the invention include the manipulation of photosynthesis through altering the expression of genes encoding proteins involved in photosynthesis. Specifically, the methods disclosed herein encompass any method for increasing expression of C4 transporter sequences. That is, any plant may be manipulated to increase the expression of a native C4 transporter sequence or the C4 transporter sequence may be introduced into a plant via a C4 transporter expression construct.

Polynucleotides, genes, and coding regions of the invention can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat. No. 6,015,891, and the references cited therein.

In one embodiment, the methods and compositions disclosed herein describe strategies to modulate the expression of genes encoding C4 transporter proteins. Recombinant nucleotide sequences encoding the C4 transporter proteins of interest are provided. Methods to alter the expression level and/or profile of native plant genes in order to improve plant growth are described. By increasing or decreasing the expression of C4 transporter proteins in a plant or plant cell, the plant can have a resulting increase or decrease in plant growth rate, plant height, or plant yield.

By "yield" or "crop yield" is intended the measurement of the amount of a crop that was harvested per unit of land area. Crop yield is the measurement often used for grains or cereals and is typically measured as the amount of plant harvested per unit area for a given time, i.e., metric tons per hectare or kilograms per hectare. Crop yield can also refer to the actual seed or biomass produced or generated by the plant. In specific embodiments, increasing the level of C4 transporter expression in a plant can increase the yield of the plant by at least 1%, 2%, 3%, 4%, 5%, 6%, 7%, 8%, 9%, 10%, 12%, 15%, 20%, 25%, 30%, 40%, 50%, 60%, 70%, 80%, 90%, 100%, or more when compared to the same plant without an increased level of C4 transporter expression. Methods to measure yield are commonly known in the art.

The C4 transporters disclosed herein can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) Biotechniques 4:320 334), electroporation (Riggs et al. (1986) Proc. Natl. Acad. Sci. USA 83:5602 5606, Agrobacterium-mediated transformation (U.S. Pat. Nos. 5,563,055 and 5,981,840), direct gene transfer (Paszkowski et al. (1984) EMBO J. 3:2717 2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6:923 926); and Lec1 transformation (WO 00/28058). Also see Weissinger et al. (1988) Ann. Rev. Genet. 22:421 477; Sanford et al. (1987) Particulate Science and Technology 5:27 37 (onion); Christou et al. (1988) Plant Physiol. 87:671 674 (soybean); McCabe et al. (1988) Bio/Technology 6:923 926 (soybean); Finer and McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8:736 740 (rice); Klein et al. (1988) Proc. Natl. Acad. Sci. USA 85:4305 4309 (maize); Klein et al. (1988) Biotechnology 6:559 563 (maize); U.S. Pat. Nos. 5,240,855; 5,322,783; and, 5,324,646; Klein et al. (1988) Plant Physiol. 91:440 444 (maize); Fromm et al. (1990) Biotechnology 8:833 839 (maize); Hooykaas-Van Slogteren et al. (1984) Nature (London) 311:763-764; U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505

(electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional methods. See, for example, McCormick et al. (1986) Plant Cell Reports 5:81-84. In this manner, the present invention provides transformed seed (also referred to as "transgenic seed") having a polynucleotide of the invention, for example, an expression cassettes disclosed herein, stably incorporated into their genome.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers. In particular embodiments, the C4 transporter sequences disclosed herein are introduced into C4 photosynthetic plants. A C4 photosynthetic plant is a plant that carries out C4 photosynthesis. Examples of C4 photosynthetic plants include but are not limited to: corn, sugarcane, millet, and sorghum.

The C4 transporter sequences disclosed herein can be any transporter that contributes to the transport of any molecule in the C4 photosynthesis process. For example, the OMT gene encodes a mitochondrial oxaloacetate/malate transporter as provided in SEQ ID NOs: 3, 15, 26, 37, 47, 57, and variants and fragments thereof having mitochondrial oxaloacetate/malate transporter activity. The DCT1 gene encodes a dicarboxylic acid transporter as provided in SEQ ID NOs: 12, 17, 27, 38, 48, and 58, and variants and fragments thereof having dicarboxylic acid transporter activity. The DCT4 gene encodes a dicarboxylic acid transporter as provided in SEQ ID NOs: 8 and 28, and variants and fragments thereof having dicarboxylic acid transporter activity. The DCT2 gene encodes a dicarboxylic acid transporter as provided in SEQ ID NOs: 7, 18, 29, 39, 49, and 59, and variants and fragments thereof having dicarboxylic acid transporter activity. The MEP3a gene encodes protein/pyruvate symporter as provided in SEQ ID NOs: 4, 19, 30, 40, 50, and 60, and variants and fragments thereof having protein/pyruvate symporter activity. The MEP3b gene encodes protein/pyruvate symporter as provided in SEQ ID NOs: 20, 31, 41, 51, 61, and 68, and variants and fragments thereof having protein/pyruvate symporter activity. The MEP3c gene encodes protein/pyruvate symporter as provided in SEQ ID NOs: 9, 10, 21, 32, 42, 52, and 62, and variants and fragments thereof having protein/pyruvate symporter activity. The NHD gene encodes a sodium proton antiporter as provided in SEQ ID NOs: 1, 22, 33, 43, 53, and 63, and variants and fragments thereof having sodium proton antiporter activity. The BASS2 gene encodes a pyruvate transporter as provided in SEQ ID NOs: 2, 34, 44, 54, and 64, and variants and fragments thereof having pyruvate transporter activity. The PPT1 gene encodes a phosphoenolpyruvate phosphate translocator as provided in SEQ ID NOs: 11, 23, and 65, and variants and fragments thereof having phosphoenolpyruvate phosphate translocator activity. The PPT2 gene encodes a phosphoenolpyruvate phosphate translocator as provided in SEQ ID NOs: 13, 14, 24, 35, 45, 55, and 66, and variants and fragments thereof having phosphoenolpyruvate phosphate translocator activity. The TPT gene encodes a triose-phosphate phosphate translocator as provided in SEQ ID NOs: 5, 6, 25, 36, 46, 56, and 67, and variants and fragments thereof having triose-phosphate phosphate translocator activity.

C4 transporters can be identified from any C4 photosynthetic organism. For example, certain C4 transporters such as SEQ ID NOs: 1-14 and SEQ ID NO: 68 can be isolated from *S. italica*. C4 transporters such as SEQ ID NOs: 15-25 can be isolated from *Z. mays*. C4 transporters such as SEQ ID NOs: 26-36 can be isolated from *S. bicolor*. Additionally, orthologs of C4 transporters can be identified in C3 photosynthetic organisms, as the proteins required for C4 photosynthesis are present in C3 photosynthetic organisms, often with similar activities (Aubry et al (2011) *J Exp Bot* 62:3049-3059). "Orthologs" is intended to mean genes derived from a common ancestral gene and which are found in different species as a result of speciation. Genes found in different species are considered orthologs when their nucleotide sequences and/or their encoded protein sequences share at least about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. C4 transporters such as SEQ ID NOs: 37-46 can be isolated from *O. sativa*. C4 transporters such as SEQ ID NOs: 47-56 can be isolated from *B. distachyon*. C4 transporters such as SEQ ID NOs: 57-67 can be isolated from *D. oligosanthes*. Additional C4 transporter orthologs can be identified, e.g., by BLAST searches to identify proteins with significant similarity to one or more of the polypeptides included in the group of SEQ ID NOs: 1-68.

The C4 transporter sequences can be provided in DNA constructs or expression cassettes for expression of C4 transporters in a plant of interest. The expression cassette will include a promoter sequence active in a plant cell operably linked to a C4 transporter sequence. The cassette may additionally contain at least one additional gene to be co-transformed into the organism. Multiple C4 transporter sequences can be provided on a single expression cassette under the control of a single promoter or on a single expression cassette under the control of multiple promoters. Alternatively, C4 transporter sequences can be provided on multiple expression cassettes. Such an expression cassette is provided with a plurality of restriction sites and/or recombination sites for insertion of the C4 transporter sequence to be under the transcriptional regulation of the operably linked promoter. The expression cassette may additionally contain selectable marker genes. In certain embodiments, polynucleotide sequences encoding C4 transporters that transport the same molecule or similar molecules are expressed together in a plant. For example, C4 transporter sequences encoding NHD (SEQ ID NOs: 1, 22, 33, 43, 53, and 63) and BASS2 (SEQ ID NOs: 2, 34, 44, 54, and 64) can be provided together to act in concert in the transport of pyruvate. Thus, polynucleotides encoding different C4 transporters can be provide on the same expression cassette or different expression cassettes. Likewise, polynucleotides encoding different C4 transporters can be operably linked to the same promoter or different promoters.

The expression cassette will include in the 5'-3' direction of transcription, a transcriptional and translational initiation region (i.e., a promoter), a polynucleotide encoding a C4 transporter protein, and a transcriptional and translational termination region (i.e., termination region) functional in plants.

The C4 transporter sequences disclosed herein, when assembled within a promoter such that the promoter is operably linked to a nucleotide sequence encoding a C4 transporter protein, enable expression of the C4 transporter sequence in the cells of a plant stably transformed with this DNA construct. "Operably linked" is intended to mean a functional linkage between two or more elements. For example, an operable linkage between a promoter and a heterologous C4 transporter sequence is a functional link that allows for expression of the C4 transporter sequence. Operably linked elements may be contiguous or non-contiguous. When used to refer to the joining of two protein coding regions, by operably linked is intended that the coding regions are in the same reading frame.

A number of promoters may be used in the practice of the compositions and methods disclosed herein. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Tissue-preferred promoters include Yamamoto et al. (1997) *Plant J.* 12 (2):255-265; Kawamata et al. (1997) *Plant Cell Physiol.* 38 (7):792-803; Hansen et al. (1997) *Mol. Gen Genet.* 254 (3):337-343; Russell et al. (1997) *Transgenic Res.* 6 (2):157-168; Rinehart et al. (1996) *Plant Physiol.* 112 (3):1331-1341; Van Camp et al. (1996) *Plant Physiol.* 112 (2):525-535; Canevascini et al. (1996) *Plant Physiol.* 112 (2):513-524; Yamamoto et al. (1994) *Plant Cell Physiol.* 35 (5):773-778; Lam (1994) *Results Probl. Cell Differ.* 20:181-196; Orozco et al. (1993) *Plant Mol Biol.* 23 (6):1129-1138; Matsuoka et al. (1993) *Proc Natl. Acad. Sci. USA* 90 (20):9586-9590; and Guevara-Garcia et al. (1993) *Plant J.* 4 (3):495-505. Leaf-preferred promoters are also known in the art. See, for example, Yamamoto et al. (1997) *Plant J.* 12 (2):255-265; Kwon et al. (1994) *Plant Physiol.* 105:357-67; Yamamoto et al. (1994) *Plant Cell Physiol.* 35 (5):773-778; Gotor et al. (1993) *Plant J.* 3:509-18; Orozco et al. (1993) *Plant Mol. Biol.* 23 (6):1129-1138; and Matsuoka et al. (1993) *Proc. Natl. Acad. Sci. USA* 90 (20):9586-9590.

Developmentally-regulated promoters may be desirable for the expression of some genes of interest. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of some genes of interest. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of some genes of interest. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be highly important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta include (Vandepoele et al. (2009) *Plant Physiol* 150: 535-546; Rushton et al. (2002) *Plant Cell* 14: 749-762). Cis-regulatory elements may also be used to alter promoter expression profiles. See, Venter (2007) *Trends Plant Sci* 12: 118-124. The rapid development of new technologies for transcriptomic studies and of new methods to analyze such datasets has enabled the discovery of new cis-regulatory elements. It is well understood that microarray datasets used previously did not have the same resolution as transcriptomic data generated using RNA-Seq. The use of these newer technologies to generate transcriptomic data and the development of new software algorithms for the analysis of transcriptomic data has enabled the discovery of novel cis-regulatory elements including those described herein.

Plant terminators are known in the art and include those available from the Ti-plasmid of *A. tumefaciens*, such as the octopine synthase and nopaline synthase termination regions. See, for example, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

A "recombinant polynucleotide construct" comprises two or more operably linked nucleic acid segments that are not found operably linked in nature. Non-limiting examples of recombinant polynucleotide constructs include a C4 transporter sequence or active variant or fragment thereof operably linked to heterologous sequences which aid in the expression, autologous replication, and/or genomic insertion of the sequence of interest. Such heterologous and operably linked sequences include, for example, promoters, termination sequences, enhancers, etc, or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 1, 2, 3, 4, 5, 6, 7, 8, 9, 10, 15, 20 or amino acids.

The compositions disclosed herein comprise synthetic oligonucleotides or nucleotide sequences encoding C4 transporters. A synthetic sequence is one that is produced or reproduced in a laboratory setting. While the nucleotide sequence may have an altered nucleotide sequence relative to the parent sequence, the synthetic sequence may be identical to the naturally occurring sequence. In both instances, however, the structure of the synthetic sequence is altered or different from that found in the sequence that is directly isolated from its natural setting.

By "altering" or "modulating" the expression level of a C4 transporter is intended that the expression is upregulated or downregulated relative to the expression level of said C4 transporter in a wild-type or control plant. It is recognized that in some instances, plant growth and yield are increased by increasing the expression levels of one or more of the C4 transporters disclosed herein, i.e. upregulating expression. Likewise, in some instances, plant growth and yield may be increased by decreasing the expression levels of one or more of the C4 transporters disclosed herein, i.e. downregulating expression. Thus, the invention encompasses the upregulation or downregulation of one or more of the C4 transporters disclosed herein. By modulating the concentration and/or activity of at least one of the C4 transporters in a transgenic plant is intended that the concentration and/or activity is increased or decreased by at least 1%, 5%, 10%, 20%, 30%, 40%, 50%, 60%, 70%, 80%, or 90% relative to a native control plant, plant part, or cell which did not have the sequence of the invention introduced. The expression level of a plant gene may be measured directly, for example, by assaying for the level of the RNA transcript encoded by the plant gene of interest in the plant cells of interest.

The compositions of the invention are used to alter expression of genes of interest in a plant, particularly genes encoding transporter proteins involved in the inter- and/or intra-cellular transport of metabolites produced from photosynthetic reactions. Therefore, the expression of a plant gene encoding a C4 transporter protein of interest may be modulated as compared to a control plant. A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The invention encompasses simultaneous modulation of the expression of more than one gene in a plant of interest (e.g., more than one C4 transporter sequence). A person skilled in the art will recognize that there are many ways to achieve such simultaneous modulation. A plant cell may be transformed with a vector containing more than one gene cassette. Alternatively, multiple transformation vectors may be used for co-transformation of a plant cell in order to modulate multiple gene targets. Alternatively, transformation approaches or breeding approaches may be used to produce a first plant line wherein the expression of a first gene has been modulated. This plant line may be crossed with a second plant line wherein a second gene of interest has been modulated through a breeding approach or through a transformation approach. The plants resulting from such a cross may be expected to show the desired modulation of both genes of interest. Modulation of the genes of interest is assayed through the use of molecular approaches including RT-PCR, Northern blotting, or quantitative RT-PCR. A person skilled in the art will recognize that these transformation and breeding approaches to achieve the simultaneous modulation of the expression of two genes may also be used to simultaneously modulate more than two genes through the use of the appropriate transformation and/or breeding techniques and the appropriate screening methods to identify plant lines in which the expression of the genes of interest has been modulated as desired. These approaches may be used to simultaneously modulate the expression of three, four, five, six, seven, eight, or more than eight genes in a plant of interest.

The invention encompasses isolated or substantially purified C4 transporter polynucleotides or amino acid compositions. An "isolated" or "purified" C4 transporter polynucleotide or protein, or biologically active portion thereof, is substantially or essentially free from components that normally accompany or interact with the C4 transporter polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived.

Fragments and variants of the disclosed C4 transporter polynucleotides and amino acid sequences encoded thereby are also encompassed by the present invention. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular C4 transporter disclosed herein will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired C4 transporter biological activity of the native plant protein. Biologically active variants of a native C4 transporter protein disclosed herein will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. A biologically active variant of a C4 transporter protein disclosed herein may differ from that protein by as few as 1-15 amino acid residues, as few as 1-10, such as 6-10, as few as 5, as few as 4, 3, 2, or even 1 amino acid residue. Biologically active variants of C4 transporters retain C4 transporter activity. As used herein, "C4 transporter activity" refers to the ability of the C4 transporter to transport or contributes to the transport of molecules during the C4 photosynthesis process.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding gene sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci. USA* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) CABIOS 5:151-153; Corpet et al. (1988) *Nucleic Acids Res.* 16:10881-90; Huang et al. (1992) CABIOS 8:155-165; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

As indicated, the C4 transporter polynucleotides disclosed herein are modulated, i.e., upregulated or downregulated, in a plant of interest. It may be desirable to upregulate at least one plant gene while simultaneously downregulating at least one different plant gene. Methods for increasing the expression or upregulating a gene are known in the art and any can be used in the methods of the invention. In one embodiment, upregulation can be achieved by transforming a plant with an expression cassette comprising a promoter that drives expression in the plant operably linked to at least one plant gene of the invention. Alteration of the expression of one or more of the genes listed in Table 1 may be achieved through the use of precise genome-editing technologies to modulate the expression of the endogenous plant gene sequence. In this manner, a nucleic acid sequence will be inserted proximal to a native plant sequence encoding the C4 transporter protein of interest through the use of methods available in the art. Such methods include, but are not limited to, meganucleases designed against the plant genomic sequence of interest (D'Halluin et al. (2013) *Plant Biotechnol J* 11: 933-941); CRISPR-Cas9, TALENs, and other technologies for precise editing of genomes (Feng, et al. (2013) *Cell Research* 23:1229-1232, Podevin, et al. (2013) *Trends Biotechnol* 31: 375-383, Wei et al. (2013) *J Gen Genomics* 40: 281-289, Zhang et al (2013) WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta, H. (2002) *Plant Mol Biol* 48:173-182). The insertion of said nucleic acid sequences will be used to achieve the desired result of overexpression of one or more genes encoding one or more of the polypeptides listed in Table 1.

Enhancers include any molecule capable of enhancing gene expression when inserted into the genome of a plant. Thus, an enhancer can be inserted in a region of the genome upstream or downstream of at least one gene of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy, M. and Hannah, L. C. (2002) *Plant Physiol.* 130 (2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi, S. (2011) *Methods Mol. Biol.* 701:285-300). In some embodiments, the present invention comprises a subdomain, fragment, or duplicated enhancer element (Benfrey et al. (1990) *EMBO J* 9:1677-1684).

The invention further provides methods for modulating gene expression in a plant by inserting a promoter or enhancer into a plant genome such that it modulates expression of an endogenous or exogenous C4 transporter sequence. Methods for determining an insertion site for a promoter or enhancer using the C4 transporter sequences provided herein and methods for inserting a promoter or enhancer sequence into a plant genome at a given insertion site are known in the art.

Alteration of C4 transporter gene expression may also be achieved through the modification of DNA in a way that does not alter the sequence of the DNA. Such changes could include modifying the chromatin content or structure of the C4 transporter gene of interest and/or of the DNA surrounding the C4 transporter gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the C4 transporter gene of interest and/or of the DNA surrounding the C4 transporter gene. It is well known that such changes in DNA methylation can alter transcription (Hsieh (1994) *Mol Cell Biol* 14: 5487-5494). It will be obvious to those skilled in the art that other similar alterations (collectively termed "epigenetic alterations") to the DNA that regulates transcription of the C4 transporter gene of interest may be applied in order to achieve the desired result of an altered C4 transporter gene expression profile.

Alteration of C4 transporter gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding C4 transporter in a photosynthetic organism may be achieved by inserting a transposable element upstream of the C4 transporter gene of interest, causing the expression of said gene to be altered.

Alteration of C4 transporter gene expression may also be achieved through mis-expression of a transcription factor or transcription factors that regulate the expression of the C4 transporter gene of interest. It is well understood that alteration of transcription factor expression can in turn alter the expression of the target gene(s) of said transcription factor (Hiratsu et al. (2003) *Plant J* 34:733-739). Alteration of C4 transporter gene expression may be achieved by altering the expression of transcription factor(s) that are known to interact with the C4 transporter gene of interest.

Downregulation or reduction of the activity of a plant gene (also known as gene silencing or gene suppression) is also encompassed by the methods of the invention. Many techniques for gene silencing are well known to one of skill in the art, including, but not limited to, antisense technology (see, e.g., Sheehy et al. (1988) *Proc. Natl. Acad. Sci. USA* 85:8805-8809; and U.S. Pat. Nos. 5,107,065; 5,453,566; and 5,759,829); cosuppression (e.g., Taylor (1997) *Plant Cell* 9:1245; Jorgensen (1990) *Trends Biotech.* 8 (12):340-344; Flavell (1994) *Proc. Natl. Acad. Sci. USA* 91:3490-3496; Finnegan et al. (1994) *Bio/Technology* 12:883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *Proc. Natl. Acad. Sci. USA* 95:15502-15507), virus-induced gene silencing (Burton et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; WO 02/00904; WO 98/53083; Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. (2003) *BMC Biotechnology* 3:7, U.S. Patent Publication No. 20030175965; Panstruga et al. (2003) *Mol. Biol. Rep.* 30:135-140; Wesley et al. (2001) *Plant J.* 27:581-590; Wang and Waterhouse (2001) *Curr. Opin. Plant Biol.* 5:146-150; U.S. Patent Publication No. 20030180945; and, WO 02/00904, all of which are herein incorporated by reference); ribozymes (Steinecke et al. (1992) *EMBO J.* 11:1525; and Perriman et al. (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes et al. (1999) *Trends Plant Sci.* 4:90-96; Dharmapuri and Sonti (1999) *FEMS Microbiol. Lett.* 179:53-59; Meissner et al. (2000) *Plant J.* 22:265-274; Phogat et al. (2000) *J. Biosci.* 25:57-63; Walbot (2000) *Curr. Opin. Plant Biol.* 2:103-107; Gai et al. (2000) *Nucleic Acids Res.* 28:94-96; Fitzmaurice et al. (1999) *Genetics* 153:1919-1928; Bensen et al. (1995) *Plant Cell* 7:75-84; Mena et al. (1996) *Science* 274:1537-1540; and U.S. Pat. No. 5,962,764); each of which is herein incorporated by reference; and other methods or combinations of the above methods known to those of skill in the art.

It is recognized that with the polynucleotides of the invention, antisense constructs, complementary to at least a portion of the messenger RNA (mRNA) for the gene sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructs having 70%, optimally 80%, more optimally 85% or greater and up to 100% sequence identity to the corresponding sequences to be silenced may be used. Furthermore, portions of the antisense nucleotides may be used to disrupt the expression of the target gene.

The polynucleotides of the present invention may also be used in the sense orientation to suppress the expression of endogenous genes in plants. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference. Such methods may be used to reduce the expression of at least one plant gene.

In addition to genes encoding the C4 transporter proteins of the invention, it is recognized that the identification of additional genes involved in C4 photosynthesis may provide opportunities to further improve the operation of the C4 photosynthetic pathway. Accordingly, the present invention provides methods for identifying genes under positive selection in C4 plants through an analysis of "synonymous" mutations and "non-synonymous" mutations in syntenic ortholog gene pairs in C4 plants and C3 plants that diverged from a common ancestor. By "synonymous" mutations is intended mutations that result in a codon change but that does not alter the encoded amino acid of the codon. It is recognized that more than one codon can be used to encode a given amino acid for all but methionine, which is encoded by ATG (or AUG in the RNA strand following transcription of the DNA). For example, lysine may be encoded by the codons AAA or AAG; either codon will produce the equivalent amino acid following transcription and translation. A mutation that results in a codon change from AAA to AAG, then, would be classified as a "synonymous" mutation. By "non-synonymous" mutations is intended mutations that result in a codon change that alters the encoded amino acid of the codon. A mutation that results in a codon change from AAA to AGG, for example, would result in a mutation at the amino acid level from lysine to arginine. This mutation would therefore be classified as a "non-synonymous" mutation. It is recognized that these mutations are offered merely as examples and that many other synonymous and non-synonymous mutations may be analyzed based on the standard genetic code with 64 codons encoding 20 standard amino acids.

Methods for identifying syntenic orthologs through the examination of genome sequences are known in the art. For example, Schnable et al. (2012) *Genome Biol Evol* 4: 265-277 determined synteny among genes in grass genomes using the SynMap utility of CoGe. The SynMap utility is described by Lyons et al. (2008) *Trop Plant Biol* 1:181-190.

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1: Method for Identifying Genes Involved in C4 Photosynthesis

The C4 photosynthetic pathway has been shown to be more productive than the C3 photosynthetic pathway in a range of environmental conditions. Since optimizing photosynthesis has been identified as a promising route to improve crop yields, and since many important crop plants utilize C4 photosynthesis, it is desirable to identify genes involved in C4 photosynthesis. The expression of such genes may be modulated to improve C4 photosynthetic metabolism, leading to improved crop yields. Genes involved in C4 photosynthesis may be identified by analyzing "synonymous" mutations (i.e., mutations in a coding sequence that do not result in an altered amino acid sequence of the encoded protein) and "non-synonymous" mutations (i.e., mutations in a coding sequence that result in an altered amino acid sequence of the encoded protein). Genes that are under positive selection in plants using C4 photosynthesis may be identified through the following method:

1. Syntenic orthologs are identified through comparisons of the genomes of C3 and C4 plant species that evolved from a common ancestor.
2. The rate of synonymous mutation ($d_S$) is calculated for each gene by dividing the number of synonymous mutations in a given coding sequence as compared with the coding sequence of the ancestral gene by the total number of codons in the coding sequence of the evolved gene.
3. The rate of non-synonymous mutation ($d_N$) is calculated for each gene by dividing the number of non-synonymous mutations in a given coding sequence as compared with the coding sequence of the ancestral gene by the total number of codons in the coding sequence of the evolved gene.
4. The ratio of adaptive evolution, ω, is calculated from the ratio $d_N/d_S$ for each gene.
5. The ratios of adaptive evolution are compared for each pair of syntenic orthologs in the C3 and C4 plant genomes identified in Step 1.
6. In those cases where ω is greater for the gene in the C4 plant than for the corresponding syntenic ortholog in the C3 plant, it is concluded that the gene is under positive selection in the C4 plant.

Example 2: Identification of Transporter Genes of Interest

C4 photosynthesis is differentiated from C3 photosynthesis by the spatial separation of $CO_2$ diffusion into plant leaves, which occurs primarily in mesophyll cells, and $CO_2$ fixation by the Calvin-Benson cycle, which occurs primarily in bundle sheath cells (Taiz and Zeiger, eds. (2002) Plant Physiology, Sinauer Associates, Sunderland, Mass.). For C4 photosynthesis to operate effectively and maintain this spatial separation, intercellular and intracellular transport of metabolites must occur. Specialized transporter proteins are used in C4 plants to transport metabolites such as malate, pyruvate, aspartate, alanine, 3-phosphate glycerate, triose-phosphate, phosphoenolpyruvate (PEP), and oxaloacetate within bundle sheath and mesophyll cells as well as between bundle sheath and mesophyll cells. C4 photosynthesis has evolved multiple times independently and thus the transporter proteins used by C4 plants differ somewhat; even orthologous genes may differ in their transport rates and/or specificity for different metabolites. Transporter genes were identified that are likely to play important roles in the transport of key metabolites produced by C4 photosynthesis. Transporter genes were identified in the C4 plants *Setaria italica*, maize (*Zea mays*), and sorghum (*Sorghum bicolor*). Putative orthologs of these transporter genes were identified in the C3 plants rice (*Oryza sativa*), *Brachypodium distachyon*, and *Dichanthelium oligosanthes*. While C4-specific genes often perform specialized functions in C4 plants, orthologs of these genes are present in C3 plants (Aubry et al (2011) *J Exp Bot* 62:3049-3059). Expression of transporter genes derived from C3 plants in a C4 host plant may therefore result in a similar phenotype as expression of a transporter gene derived from a C4 plant in a C4 host plant. The genes listed in Table 1 were identified as transporter genes that may be of interest for engineering approaches to improve C4 photosynthesis.

TABLE 1

Transporter genes of interest for improving C4 photosynthesis

| Gene name | S. italica | Z. mays | S. bicolor | O. sativa | B. distachyon | D. oligosanthes |
|---|---|---|---|---|---|---|
| OMT | Si024403m (SEQ ID NO: 3) | GRMZM2G383088 (SEQ ID NO: 15) | Sobic.008G112300 (SEQ ID NO: 26) | LOC_Os12g33080 (SEQ ID NO: 37) | Bradi4g06300 (SEQ ID NO: 47) | Do017525.1 (SEQ ID NO: 57) |
| DCT1 | Si029415m (SEQ ID NO: 12) | GRMZM2G040933, GRMZM2G515874 (SEQ ID NOs: 16-17) | Sobic.002G233700 (SEQ ID NO: 27) | LOC_Os09g29430 (SEQ ID NO: 38) | Bradi4g32730 (SEQ ID NO: 48) | Do013844.1 (SEQ ID NO: 58) |
| DCT4 | Si035016m (SEQ ID NO: 8) | N.A. | Sobic.004G035500 (SEQ ID NO: 28) | N.A. | N.A. | N.A. |
| DCT2 | Si013503m (SEQ ID NO: 7) | GRMZM2G086258 (SEQ ID NO: 18) | Sobic.007G226800 (SEQ ID NO: 29) | LOC_Os08g37600 (SEQ ID NO: 39) | Bradi3g38580 (SEQ ID NO: 49) | Do011021.1 (SEQ ID NO: 59) |
| MEP3a | Si024315m (SEQ ID NO: 4) | GRMZM2G305851 (SEQ ID NO: 19) | Sobic.009G124000 (SEQ ID NO: 30) | LOC_Os05g32230 (SEQ ID NO: 40) | Bradi2g26950 (SEQ ID NO: 50) | Do020718.1 (SEQ ID NO: 60) |
| MEP3b | Si000451m (SEQ ID NO: 68) | GRMZM2G099036 (SEQ ID NO: 20) | Sobic.003G341300 (SEQ ID NO: 31) | LOC_Os01g61120 (SEQ ID NO: 41) | Bradi2g53780 (SEQ ID NO: 51) | Do007926.1 (SEQ ID NO: 61) |
| MEP3c | Si005376m (SEQ ID NOs: 9-10) | GRMZM2G138258 (SEQ ID NO: 21) | Sobic.003G431900 (SEQ ID NO: 32) | LOC_Os01g72710 (SEQ ID NO: 42) | Bradi2g61270 (SEQ ID NO: 52) | Do020718.1 (SEQ ID NO: 62) |
| NHD | Si029362m (SEQ ID NO: 1) | GRMZM2G053927 (SEQ ID NO: 22) | Sobic.002G141900 (SEQ ID NO: 33) | LOC_Os09g02214 (SEQ ID NO: 43) | Bradi4g08260 (SEQ ID NO: 53) | Do023727.1 (SEQ ID NO: 63) |

TABLE 1-continued

Transporter genes of interest for improving C4 photosynthesis

| Gene name | S. italica | Z. mays | S. bicolor | O. sativa | B. distachyon | D. oligosanthes |
|---|---|---|---|---|---|---|
| BASS2 | Si001591m (SEQ ID NO: 2) | N.A. | Sobic.003G236800 (SEQ ID NO: 34) | LOC_Os01g45750 (SEQ ID NO: 44) | Bradi2g45100 (SEQ ID NO: 54) | Do010383.1 (SEQ ID NO: 64) |
| PPT1 | Si013874m (SEQ ID NO: 11) | GRMZM2G174107 (SEQ ID NO: 23) | N.A. | N.A. | N.A. | Do023872.1 (SEQ ID NO: 65) |
| PPT2 | Si005351m (SEQ ID NOs: 13-14) | GRMZM2G066413 (SEQ ID NO: 24) | Sobic.003G050800 (SEQ ID NO: 35) | LOC_Os01g07730 (SEQ ID NO: 45) | Bradi2g04447 (SEQ ID NO: 55) | Do025241.1 (SEQ ID NO: 66) |
| TPT | Si001693m (SEQ ID NOs: 5-6) | GRMZM2G070605 (SEQ ID NO: 25) | Sobic.003G002300 (SEQ ID NO: 36) | LOC_Os01g13770 (SEQ ID NO: 46) | Bradi2g08340 (SEQ ID NO: 56) | Do017690.1 (SEQ ID NO: 67) |

Expression of the genes listed in Table 1 in a plant may cause improved growth and yield. In some cases, multiple genes from Table 1 may be co-expressed. Co-expression of genes encoding NHD (SEQ ID NOs: 1, 22, 33, 43, 53, and 63) and BASS2 (SEQ ID NOs: 2, 34, 44, 54, and 64) is of particular interest, as these two proteins act in concert to transport pyruvate. Additionally, co-expression of one or more of the genes listed in Table 1 with genes encoding enzymes involved in photosynthesis may be of interest, as this has the potential to relieve multiple bottlenecks simultaneously. Of particular interest is co-expression of one or more of the genes listed in Table 1 with genes encoding rate-limiting enzymes of the Calvin-Benson cycle pathway. In certain constructs a gene encoding SBPase (SEQ ID NO:96) is included along with one or more of the genes listed in Table 1.

Example 3: Building Plant Transformation Constructs

Plant transformation vectors were constructed in plasmid backbones containing sequences for maintenance in both *E. coli* and *Agrobacterium tumefaciens*. These transformation vectors contained one or more expression cassettes for one or more of the transporter genes listed in Table 1. Each expression cassette contained a promoter that is operable in plant cells, operably linked to a coding region that encodes one or more of the transporter proteins listed in Table 1, operably linked to a terminator region. Table 2 summarizes the plant transformation constructs that were built. In this table, the SEQ ID NOs are listed for the promoters, 5'UTRs, and 3'UTRs included in the transformation constructs. Two SEQ ID NOs are listed for each open reading frame (ORF); the first SEQ ID NO refers to the DNA sequence listing and the second SEQ ID NO refers to the encoded protein.

TABLE 2

Plant Transformation Constructs

| | Cassette One | | | Cassette Two | | |
|---|---|---|---|---|---|---|
| Construct | Promoter + 5'UTR | ORF (DNA/Protein) | 3'UTR | Promoter '5'UTR2 | ORF (DNA/Protein) | 3'UTR2 |
| 131017 | ZmRbcS (SEQ ID NO: 69) | DCT4 (89/8) | ZmRbcS (SEQ ID NO: 70) | | | |
| 131018 | Si035016m (SEQ ID NO: 71) | DCT4 (89/8) | Si035016m (SEQ ID NO: 72) | | | |
| 131183 | GLDC (SEQ ID NO: 80) | DCT4 (89/8) | ZmRbcS (SEQ ID NO: 70) | | | |
| 131019 | ZmRbcS (SEQ ID NO: 69) | DCT2 (90/18) | ZmRbcS (SEQ ID NO: 70) | | | |
| 131678 | ZmRbcS (SEQ ID NO: 69) | DCT2 (90/18) | ZmRbcS (SEQ ID NO: 70) | | | |
| 131182 | GLDC (SEQ ID NO: 80) | DCT2 (90/18) | ZmRbcS (SEQ ID NO: 70) | | | |
| 131033 | ZmCA (SEQ ID NO: 73) | NHD (91/1) | ZmCA (SEQ ID NO: 74) | | | |
| 131034 | ZmPepC (SEQ ID NO: 75) | NHD (91/1) | ZmPepC (SEQ ID NO: 76) | | | |
| 131035 | SiNHD (SEQ ID NO: 77) | NHD (91/1) | SiNHD (SEQ ID NO: 78) | | | |
| 131036 | 4xRGCGR (SEQ ID NO: 79) | NHD (91/1) | ZmCA (SEQ ID NO: 74) | | | |
| 131222 | OsRbcS (SEQ ID NO: 81) | PPT1 (92/23) | OsRbcS (SEQ ID NO: 82) | | | |
| 131225 | OsCA (SEQ ID NO: 83) | PPT1 (92/23) | OsCA (SEQ ID NO: 84) | | | |
| 131284 | ZmCA (SEQ ID NO: 73) | PPT1 (92/23) | ZmCA (SEQ ID NO: 74) | | | |

TABLE 2-continued

Plant Transformation Constructs

| | Cassette One | | | Cassette Two | | | |
|---|---|---|---|---|---|---|---|
| Construct | Promoter + 5'UTR | ORF (DNA/ Protein) | 3'UTR | Promoter '5'UTR2 | ORF (DNA/ Protein) | 3'UTR2 | |
| 131457 | OsCAB (SEQ ID NO: 85) | TPT (94/25) | OsCAB (SEQ ID NO: 86) | | | | |
| 131532 | OsCAB (SEQ ID NO: 85) | TPT (94/25) | OsCAB (SEQ ID NO: 86) | | | | |
| 131028 | ZmPepC (SEQ ID NO: 75) | BASS (93/2) | ZmPepC (SEQ ID NO: 76) | ZmCA (SEQ ID NO: 73) | NHD (91/1) | ZmCA (SEQ ID NO: 74) | |
| 131029 | ZmCA (SEQ ID NO: 73) | BASS (93/2) | ZmCA (SEQ ID NO: 74) | ZmPepC (SEQ ID NO: 75) | NHD (91/1) | ZmPepC (SEQ ID NO: 76) | |
| 131030 | SiBASS (SEQ ID NO: 87) | BASS (93/2) | SiBASS (SEQ ID NO: 88) | SiNHD (SEQ ID NO: 77) | NHD (91/1) | SiNHD (SEQ ID NO: 78) | |
| 131031 | 4xRGCGR (SEQ ID NO: 79) | BASS (93/2) | ZmCA (SEQ ID NO: 74) | SiNHD (SEQ ID NO: 77) | NHD (91/1) | SiNHD (SEQ ID NO: 78) | |
| 131032 | SiBASS (SEQ ID NO: 87) | BASS (93/2) | SiBASS (SEQ ID NO: 88) | 4xRGCGR (SEQ ID NO: 79) | NHD (91/1) | ZmCA (SEQ ID NO: 74) | |
| 131665 | ZmPepC (SEQ ID NO: 75) | BASS (93/2) | ZmPepC (SEQ ID NO: 76) | ZmCA (SEQ ID NO: 73) | NHD (91/1) | ZmCA (SEQ ID NO: 74) | |
| 131666 | SiBASS (SEQ ID NO: 87) | BASS (93/2) | SiBASS (SEQ ID NO: 88) | SiNHD (SEQ ID NO: 77) | NHD (91/1) | SiNHD (SEQ ID NO: 78) | |
| 131667 | 4xRGCGR (SEQ ID NO: 79) | BASS (93/2) | ZmCA (SEQ ID NO: 74) | SiNHD (SEQ ID NO: 77) | NHD (91/1) | SiNHD (SEQ ID NO: 78) | |
| 131281 | ZmCA (SEQ ID NO: 73) | PPT1 (92/23) | ZmCA (SEQ ID NO: 74) | OsCA (SEQ ID NO: 83) | SBPase (95/96) | OsCA (SEQ ID NO: 84) | |
| 131282 | OsRbcS (SEQ ID NO: 81) | PPT1 (92/23) | ZmRbcS (SEQ ID NO: 70) | OsCA (SEQ ID NO: 83) | SBPase (95/96) | OsCA (SEQ ID NO: 84) | |

Example 4: Plant Transformation

Plant transformation vectors are transformed into *A. tumefaciens* for plant transformation. The plant tissue of interest is contacted with *A. tumefaciens* cells containing the plant transformation vectors. Following contact with the *A. tumefaciens* cells, the plant tissue is placed on a suitable tissue culture medium for regeneration of fertile plants. Alternatively, the plant transformation vector is coated onto beads for biolistic bombardment of transformable plant tissue. PCR, Southern blotting, or other suitable molecular assays are performed in order to verify the presence of the transporter gene(s) of interest in the genome of the transformed plants. Expression of the transporter gene(s) of interest is verified through the use of RT-PCR, Northern blotting, or other suitable assays to detect the encoded transcripts. The regenerated plants are grown to maturity. Following the maturation of the plants, above-ground biomass is harvested, dried, and weighed. The seeds are harvested, weighed, and counted.

Example 5: Plant Characterization and Yield Measurement

Plants expressing one or more genes encoding one or more of the transporter genes listed in Table 1 are cultivated and grown alongside control plants in order to assess the effects of the expression of these genes on photosynthesis and yield. Expression of the genes of interest is assessed through reverse transcriptase PCR (RT-PCR) experiments that use primers designed to specifically amplify the genes of interest. Carbon assimilation by the plants expressing the gene(s) of interest is assessed through the use of gas exchange instruments such as the LI6400XT (Li-Cor). The gas exchange measurements show the rate of $CO_2$ assimilation at the leaf level. Gas exchange measurements are taken at multiple timepoints during the plants' development and at multiple timepoints through the circadian cycle.

Following the maturation of the plants, yield is assessed by harvesting the mature tissue. In some cases yield measurements may focus on grains (e.g., in crops such as maize and soybean that are cultivated for their seeds). In other cases yield measurements may include all of the above-ground material (e.g., in crops such as biomass sorghum, energy grasses, alfalfa, and poplar that are cultivated for their total biomass). The yields of the plants expressing the transporter gene(s) of interest and of the control plants are calculated on a per-plant (i.e., grams of biomass per plant or grams of seed per plant) and on a per-area (i.e., kilograms of biomass per hectare or kilograms of seed per hectare) basis. Appropriate statistical analyses are performed to determine whether the plants expressing the gene(s) of interest show increased yield relative to the control plants.

Example 6: *Setaria viridis* Transformation

Plant transformation vectors were transformed into *Agrobacterium tumefaciens* for transformation of *Setaria viridis*. *A. tumefaciens* cells harboring the transformation vectors listed in Table 3 were used to transform *S. viridis*. Following transformation, the *S. viridis* tissue that was contacted with the appropriate *A. tumefaciens* cells was transferred to tissue culture medium for regeneration of shoots. Newly generated shoots were transferred to rooting medium, and rooted shoots were subsequently transferred to soil. Leaf samples were collected from *S. viridis* plants in soil and DNA was extracted from these leaf samples for analysis. Initially, PCR assays were performed to identify positive transformants comprising the transgene cassette(s) in the transformation construct of interest. Table 3 lists the number of plants to soil following transformation with each of the vectors listed in this table along with the number of those plants that were PCR-positive based on these initial assays. Taqman® assays were performed to quantify the number of copies of the transgene cassettes that were inserted from these transformations. Table 3 lists the number of single copy and number of multi-copy events resulting from transformation with each of the constructs listed in this table.

TABLE 3

Constructs used for S. viridis transformation, along with the number of plants transferred to soil, number of plants identified as PCR-positive transgenic events, and the number of single- and multi-copy insertion events.

| Construct | # Plants to Soil | PCR-positive | # Multi-Copy | # Single Copy |
|---|---|---|---|---|
| 131225 | 34 | 31 | 23 | 8 |
| 131281 | 35 | 33 | 23 | 10 |
| 131282 | 30 | 28 | 23 | 5 |
| 131284 | 39 | 37 | 31 | 6 |
| 131665 | 32 | 32 | 11 | 21 |
| 131666 | 26 | 16 | 14 | 2 |
| 131667 | 32 | 32 | 26 | 6 |
| 131678 | 18 | 18 | 4 | 14 |

Example 7: Maize Transformation

Plant transformation vectors were transformed into *Agrobacterium tumefaciens* for transformation of maize (*Zea mays*). *A. tumefaciens* cells harboring the transformation vectors listed in Table 4 were used to transform maize. Following transformation, the maize tissue that was contacted with the appropriate *A. tumefaciens* cells was transferred to tissue culture medium for regeneration of shoots. Newly generated shoots were transferred to rooting medium, and rooted shoots were subsequently transferred to soil. Leaf samples were collected from maize plants in soil and DNA was extracted from these leaf samples for analysis. Initially, PCR assays were performed to identify positive transformants comprising the transgene cassette(s) in the transformation construct of interest. Table 4 lists the number of plants to soil following transformation with each of the vectors listed in this table along with the number of those plants that were PCR-positive based on these initial assays. Taqman® assays were performed to quantify the number of copies of the transgene cassettes that were inserted from these transformations. Table 4 lists the number of single copy and number of multi-copy events resulting from transformation with each of the constructs listed in this table.

TABLE 4

Constructs used for maize transformation, along with the number of plants transferred to soil, number of plants identified as PCR-positive transgenic events, and the number of single- and multi-copy insertion events.

| Construct | # Plants to Soil | PCR-positive | # Multi-Copy | # Single Copy |
|---|---|---|---|---|
| 131018 | 13 | 12 | 3 | 9 |
| 131030 | 11 | 7 | 0 | 7 |
| 131182 | 8 | 4 | 4 | 4 |
| 131032 | 2 | 1 | 1 | 0 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. A method of expressing a nucleic acid sequence encoding a C4 transporter protein comprising:
   introducing into a plant cell a DNA construct comprising a promoter sequence operably linked to a first nucleic acid sequence encoding a first C4 transporter protein, wherein said first nucleic acid sequence comprises a sequence with at least 90% identity to the nucleic acid sequence set forth in SEQ ID NO: 90 or wherein said first nucleic acid sequence encodes a first C4 transporter protein comprising an amino acid sequence with at least 90% identity to the amino acid sequence set forth in SEQ ID NO: 18, wherein said promoter sequence is heterologous to said first nucleic acid sequence encoding a first C4 transporter protein and wherein said plant cell is from a C4 plant species and regenerating a plant comprising the DNA construct.

2. The method of claim 1 wherein said first nucleic acid sequence comprises the nucleic acid sequence set forth in SEQ ID NO: 90 or wherein said first nucleic acid sequence encodes a first C4 transporter protein comprising the amino acid sequence set forth in SEQ ID NO: 18.

3. The method of claim 1 further comprising introducing into a plant cell a DNA construct comprising a promoter sequence operably linked to a second nucleic acid sequence encoding a second C4 transporter protein.

4. The method of claim 3, wherein said second C4 transporter protein has an amino acid sequence with at least 90% identity to the amino acid sequence selected from the group consisting of SEQ ID NOs: 1, 22, 33, 43, 53, and 63.

5. The method of claim 3, wherein said second C4 transporter protein has an amino acid sequence with at least 90% identity to the amino acid sequence selected from the group consisting of SEQ ID NOs: 2, 34, 44, 54, and 64.

6. A C4 plant comprising an expression cassette for the expression of at least one C4 transporter protein, wherein said expression cassette comprises in operable linkage:
   a. a promoter that functions in a plant cell, and
   b. a nucleic acid sequence encoding a C4 transporter protein wherein said nucleic acid sequence shares at least 90% identity with the nucleic acid sequence set forth in SEQ ID NO: 90 or wherein said nucleic acid sequence encodes a C4 transporter protein comprising an amino acid sequence with at least 90% identity to the amino acid sequence set forth in SEQ ID NO: 18, wherein the promoter is heterologous to the nucleic acid sequence encoding the C4 transporter protein.

7. The C4 plant of claim 6, wherein said nucleic acid sequence comprises the nucleic acid sequence set forth in SEQ ID NO: 90 or wherein said nucleic acid sequence encodes a C4 transporter protein comprising the amino acid sequence set forth in SEQ ID NO: 18.

8. The C4 plant of claim 6, wherein said expression cassette is located on a vector.

9. The C4 plant of claim 6, wherein said C4 plant has higher yield than a control plant not transformed with said expression cassette.

10. Seed of the C4 plant of claim 6, wherein said seed comprises said expression cassette.

11. The method of claim 1 wherein said promoter sequence comprises the sequence set forth in SEQ ID NO: 71.

12. The C4 plant of claim 6 wherein said promoter that functions in a plant cell comprises the sequence set forth in SEQ ID NO: 71.

13. The C4 plant of claim 6, wherein said expression cassette is stably integrated into the plant genome.

14. Seed of the plant of claim 13, wherein said seed comprises said expression cassette integrated into the plant genome.

* * * * *